(12) United States Patent
Qi et al.

(10) Patent No.: US 11,634,450 B2
(45) Date of Patent: Apr. 25, 2023

(54) DOT1L DEGRADERS AND USES THEREOF

(71) Applicant: DANA-FARBER CANCER INSTITUTE, INC., Boston, MA (US)

(72) Inventors: Jun Qi, Sharon, MA (US); Scott Armstrong, Mayland, MA (US); Paul M. Park, Waltham, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 17/252,842

(22) PCT Filed: Jun. 27, 2019

(86) PCT No.: PCT/US2019/039368
§ 371 (c)(1),
(2) Date: Dec. 16, 2020

(87) PCT Pub. No.: WO2020/006157
PCT Pub. Date: Jan. 2, 2020

(65) Prior Publication Data
US 2021/0130386 A1    May 6, 2021

Related U.S. Application Data

(60) Provisional application No. 62/690,791, filed on Jun. 27, 2018.

(51) Int. Cl.
*C07H 19/16* (2006.01)
*A61P 35/02* (2006.01)
(52) U.S. Cl.
CPC .............. *C07H 19/16* (2013.01); *A61P 35/02* (2018.01)
(58) Field of Classification Search
CPC .................................................. C07H 19/16
See application file for complete search history.

(56) References Cited

FOREIGN PATENT DOCUMENTS

WO    2015/017311 A1    2/2015

OTHER PUBLICATIONS

Yi, J., et al., "Structure-Guided DOT1L Probe Optimization by Label-Free Ligand Displacement", ACS Chemical Biology, 2015, 10(3):667-674.
Gross, Stefan, et al., "Targeting Cancer with Kinase Inhibitors", J. Clin. Invest., 2015, vol. 125, No. 5, pp. 1780-1789.
Medves, Sandrine, et al., "Tyrosine Kinase Gene Fusions in Cancer: Translating Mechanisms into Targeted Therapies", J. Cell. Mol. Med., 2012, vol. 16, No. 2, pp. 237-248.
Simpson, David L., et al., "Killing of Human Myelomonocytic Leukemia and Lymphocytic Cell Lines by Actinobacillus Actinomycetemcomitans Leukotoxin", Infect & Immunity, 1988, vol. 56, No. 5, pp. 1162-1166.
Stransky, Nicolas, et al., "The Landscape of Kinase Fusions in Cancer", Nat. Commun., 2014, vol. 5, Article No. 4846.

*Primary Examiner* — Traviss C McIntosh, III
(74) *Attorney, Agent, or Firm* — Burns & Levinson, LLP; Daniel W. Clarke; Shawn P. Foley

(57) ABSTRACT

Provided herein are bifunctional compounds with a moiety (e.g., lenalidomide, thalidomide) that is a binder of an E3 ubiquitin ligase (e.g., Cereblon) and another moiety that is a binder of a target protein DOT1L to induce degradation of DOT1L. Also provided are pharmaceutical compositions comprising the bifunctional compounds, and methods of treating and/or preventing diseases (e.g., proliferative diseases, such as cancers). Provided also are methods of inducing the degradation of DOT1L by administering a bifunctional compound or composition described herein, wherein one component of the bifunctional compound is a binder of an E3 ubiquitin ligase (e.g., lenalidomide, thalidomide) and another component of the compound is a binder of the target protein DOT1L in a subject.

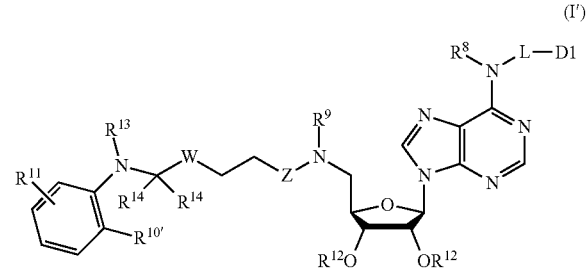

28 Claims, 38 Drawing Sheets
Specification includes a Sequence Listing.

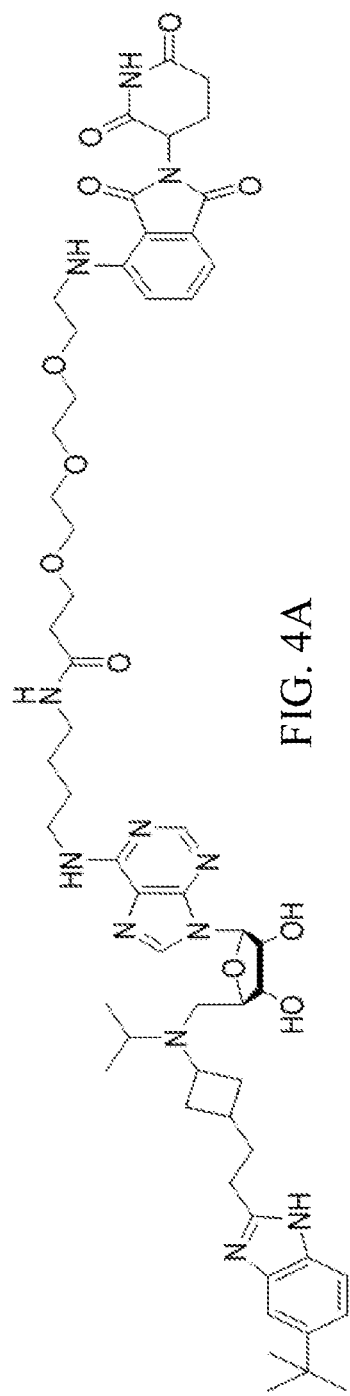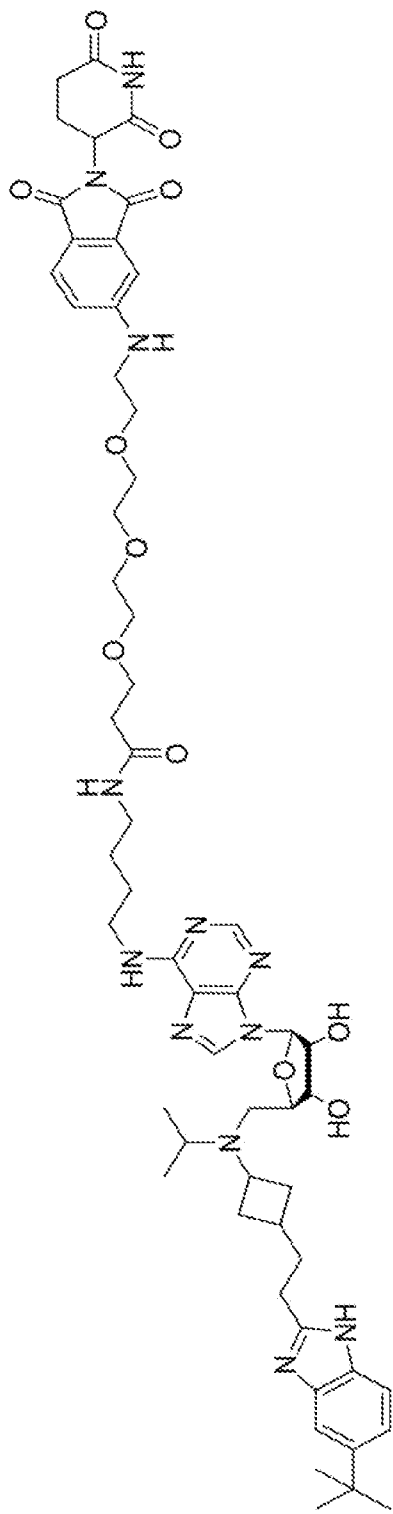
FIG. 4A
FIG. 4B

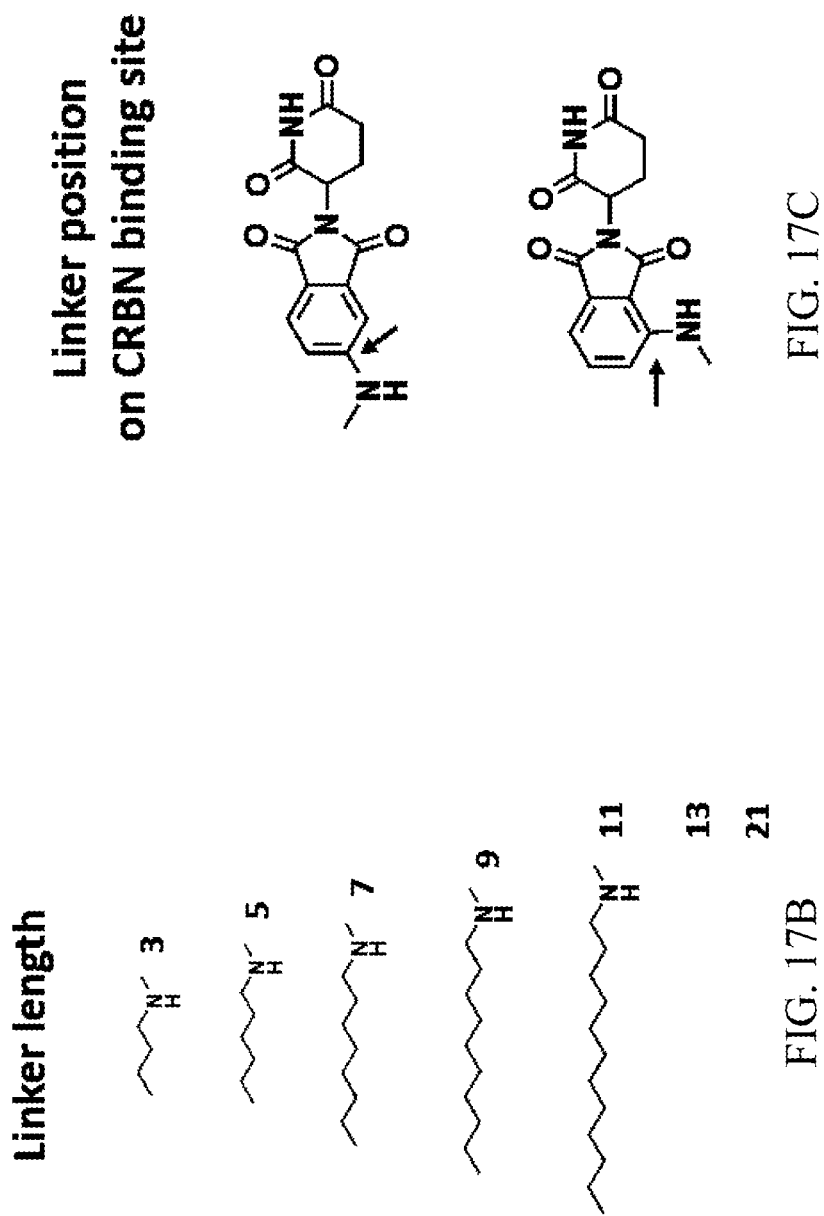

SEQUENCE LISTING

```
<160> NUMBER OF SEQ ID NOS: 3

<210> SEQ ID NO 1
<211> LENGTH: 352
<212> TYPE: PRT
<213> ORGANISM: Homo sapiens

<400> SEQUENCE: 1

Met Glu Ser Gly Gly Arg Pro Ser Leu Cys Gln Phe Ile Leu Leu Gly
1               5                   10                  15

Thr Thr Ser Val Val Thr Ala Ala Leu Tyr Ser Val Tyr Arg Gln Lys
            20                  25                  30

Ala Arg Val Ser Gln Glu Leu Lys Gly Ala Lys Lys Val His Leu Gly
        35                  40                  45

Glu Asp Leu Lys Ser Ile Leu Ser Glu Ala Pro Gly Lys Cys Val Pro
    50                  55                  60

Tyr Ala Val Ile Glu Gly Ala Val Arg Ser Val Lys Glu Thr Leu Asn
65                  70                  75                  80

Ser Gln Phe Val Glu Asn Cys Lys Gly Val Ile Gln Arg Leu Thr Leu
                85                  90                  95

Gln Glu His Lys Met Val Trp Asn Arg Thr Thr His Leu Trp Asn Asp
            100                 105                 110

Cys Ser Lys Ile Ile His Gln Arg Thr Asn Thr Val Pro Phe Asp Leu
        115                 120                 125

Val Pro His Glu Asp Gly Val Asp Val Ala Val Arg Val Leu Lys Pro
    130                 135                 140
```

```
Leu Asp Ser Val Asp Leu Gly Leu Glu Thr Val Tyr Glu Lys Phe His
145                 150                 155                 160

Pro Ser Ile Gln Ser Phe Thr Asp Val Ile Gly His Tyr Ile Ser Gly
                165                 170                 175

Glu Arg Pro Lys Gly Ile Gln Glu Thr Glu Glu Met Leu Lys Val Gly
            180                 185                 190

Ala Thr Leu Thr Gly Val Gly Glu Leu Val Leu Asp Asn Asn Ser Val
        195                 200                 205

Arg Leu Gln Pro Pro Lys Gln Gly Met Gln Tyr Tyr Leu Ser Ser Gln
    210                 215                 220

Asp Phe Asp Ser Leu Leu Gln Arg Gln Glu Ser Ser Val Arg Leu Trp
225                 230                 235                 240

Lys Val Leu Ala Leu Val Phe Gly Phe Ala Thr Cys Ala Thr Leu Phe
                245                 250                 255

Phe Ile Leu Arg Lys Gln Tyr Leu Gln Arg Gln Glu Arg Leu Arg Leu
                260                 265                 270

Lys Gln Met Gln Glu Glu Phe Gln Glu His Glu Ala Gln Leu Leu Ser
            275                 280                 285

Arg Ala Lys Pro Glu Asp Arg Glu Ser Leu Lys Ser Ala Cys Val Val
    290                 295                 300

Cys Leu Ser Ser Phe Lys Ser Cys Val Phe Leu Glu Cys Gly His Val
305                 310                 315                 320

Cys Ser Cys Thr Glu Cys Tyr Arg Ala Leu Pro Glu Pro Lys Lys Cys
                325                 330                 335

Pro Ile Cys Arg Gln Ala Ile Thr Arg Val Ile Pro Tyr Asn Ser
                340                 345                 350

<210> SEQ ID NO 2
<211> LENGTH: 923
<212> TYPE: PRT
<213> ORGANISM: Homo sapiens

<400> SEQUENCE: 2

Met Glu Glu Gly Asn Asn Asn Glu Val Ile His Leu Asn Asn Phe
1               5                   10                  15

His Cys His Arg Gly Gln Glu Trp Ile Asn Leu Arg Asp Gly Pro Ile
                20                  25                  30

Thr Ile Ser Asp Ser Ser Asp Glu Glu Arg Ile Pro Met Leu Val Thr
            35                  40                  45

Pro Ala Pro Gln Gln His Glu Glu Glu Asp Leu Asp Asp Asp Val Ile
        50                  55                  60

Leu Thr Glu Thr Asn Lys Pro Gln Arg Ser Arg Pro Asn Leu Ile Lys
65                  70                  75                  80

Pro Ala Ala Gln Trp Gln Asp Leu Lys Arg Leu Gly Glu Glu Arg Pro
                85                  90                  95

Lys Lys Ser Arg Ala Ala Phe Glu Ser Asp Lys Ser Ser Tyr Phe Ser
                100                 105                 110

Val Cys Asn Asn Pro Leu Phe Asp Ser Gly Ala Gln Asp Asp Ser Glu
            115                 120                 125

Asp Asp Tyr Gly Glu Phe Leu Asp Leu Gly Pro Gly Ile Ser Glu
        130                 135                 140

Phe Thr Lys Pro Ser Gly Gln Thr Glu Arg Glu Pro Lys Pro Gly Pro
145                 150                 155                 160

Ser His Asn Gln Ala Ala Asn Asp Ile Val Asn Pro Arg Ser Glu Gln
                165                 170                 175
```

```
Lys Val Ile Ile Leu Glu Gly Ser Leu Tyr Thr Glu Ser Asp
            180                 185                 190

Pro Leu Glu Thr Gln Asn Gln Ser Glu Asp Ser Glu Thr Glu Leu
        195                 200                 205

Leu Ser Asn Leu Gly Glu Ser Ala Ala Leu Ala Asp Asp Gln Ala Ile
    210                 215                 220

Glu Glu Asp Cys Trp Leu Asp His Pro Tyr Phe Gln Ser Leu Asn Gln
225                 230                 235                 240

Gln Pro Arg Glu Ile Thr Asn Gln Val Val Pro Gln Glu Arg Gln Pro
                245                 250                 255

Glu Ala Glu Leu Gly Arg Leu Leu Phe Gln His Glu Phe Pro Gly Pro
            260                 265                 270

Ala Phe Pro Arg Pro Glu Pro Gln Gln Gly Gly Ile Ser Gly Pro Ser
        275                 280                 285

Ser Pro Gln Pro Ala His Pro Leu Gly Glu Phe Glu Asp Gln Gln Leu
    290                 295                 300

Ala Ser Asp Asp Glu Glu Pro Gly Pro Ala Phe Pro Met Gln Glu Ser
305                 310                 315                 320

Gln Glu Pro Asn Leu Glu Asn Ile Trp Gly Gln Glu Ala Ala Glu Val
                325                 330                 335

Asp Gln Glu Leu Val Glu Leu Leu Val Lys Glu Thr Glu Ala Arg Phe
            340                 345                 350

Pro Asp Val Ala Asn Gly Phe Ile Glu Glu Ile Ile His Phe Lys Asn
        355                 360                 365

Tyr Tyr Asp Leu Asn Val Leu Cys Asn Phe Leu Leu Glu Asn Pro Asp
    370                 375                 380

Tyr Pro Lys Arg Glu Asp Arg Ile Ile Ile Asn Pro Ser Ser Ser Leu
385                 390                 395                 400

Leu Ala Ser Gln Asp Glu Thr Lys Leu Pro Lys Ile Asp Phe Phe Asp
                405                 410                 415

Tyr Ser Lys Leu Thr Pro Leu Asp Gln Arg Cys Phe Ile Gln Ala Ala
            420                 425                 430

Asp Leu Leu Met Ala Asp Phe Lys Val Leu Ser Ser Gln Asp Ile Lys
        435                 440                 445

Trp Ala Leu His Glu Leu Lys Gly His Tyr Ala Ile Thr Arg Lys Ala
    450                 455                 460

Leu Ser Asp Ala Ile Lys Lys Trp Gln Glu Leu Ser Pro Glu Thr Ser
465                 470                 475                 480

Gly Lys Arg Lys Arg Lys Gln Met Asn Gln Tyr Ser Tyr Ile Asp
                485                 490                 495

Phe Lys Phe Glu Gln Gly Asp Ile Lys Ile Glu Lys Arg Met Phe Phe
            500                 505                 510

Leu Glu Asn Lys Arg Arg His Cys Arg Ser Tyr Asp Arg Arg Ala Leu
        515                 520                 525

Leu Pro Ala Val Gln Gln Gln Glu Phe Tyr Glu Gln Lys Ile Lys
    530                 535                 540

Glu Met Ala Glu His Glu Asp Phe Leu Leu Ala Leu Gln Met Asn Glu
545                 550                 555                 560

Glu Gln Tyr Gln Lys Asp Gly Gln Leu Ile Glu Cys Arg Cys Cys Tyr
                565                 570                 575

Gly Glu Phe Pro Phe Glu Glu Leu Thr Gln Cys Ala Asp Ala His Leu
            580                 585                 590
```

-continued

```
Phe Cys Lys Glu Cys Leu Ile Arg Tyr Ala Gln Glu Ala Val Phe Gly
            595                 600                 605

Ser Gly Lys Leu Glu Leu Ser Cys Met Glu Gly Ser Cys Thr Cys Ser
        610                 615                 620

Phe Pro Thr Ser Glu Leu Glu Lys Val Leu Pro Gln Thr Ile Leu Tyr
625                 630                 635                 640

Lys Tyr Tyr Glu Arg Lys Ala Glu Glu Val Ala Ala Ala Tyr Ala
                645                 650                 655

Asp Glu Leu Val Arg Cys Pro Ser Cys Ser Phe Pro Ala Leu Leu Asp
            660                 665                 670

Ser Asp Val Lys Arg Phe Ser Cys Pro Asn Pro His Cys Arg Lys Glu
        675                 680                 685

Thr Cys Arg Lys Cys Gln Gly Leu Trp Lys Glu His Asn Gly Leu Thr
    690                 695                 700

Cys Glu Glu Leu Ala Glu Lys Asp Asp Ile Lys Tyr Arg Thr Ser Ile
705                 710                 715                 720

Glu Glu Lys Met Thr Ala Ala Arg Ile Arg Lys Cys His Lys Cys Gly
                725                 730                 735

Thr Gly Leu Ile Lys Ser Glu Gly Cys Asn Arg Met Ser Cys Arg Cys
            740                 745                 750

Gly Ala Gln Met Cys Tyr Leu Cys Arg Val Ser Ile Asn Gly Tyr Asp
        755                 760                 765

His Phe Cys Gln His Pro Arg Ser Pro Gly Ala Pro Cys Gln Glu Cys
    770                 775                 780

Ser Arg Cys Ser Leu Trp Thr Asp Pro Thr Glu Asp Asp Glu Lys Leu
785                 790                 795                 800

Ile Glu Glu Ile Gln Lys Glu Ala Glu Glu Gln Lys Arg Lys Asn
                805                 810                 815

Gly Glu Asn Thr Phe Lys Arg Ile Gly Pro Pro Leu Glu Lys Pro Val
            820                 825                 830

Glu Lys Val Gln Arg Val Glu Ala Leu Pro Arg Pro Val Pro Gln Asn
        835                 840                 845

Leu Pro Gln Pro Gln Met Pro Pro Tyr Ala Phe Ala His Pro Pro Phe
    850                 855                 860

Pro Leu Pro Pro Val Arg Pro Val Phe Asn Asn Phe Pro Leu Asn Met
865                 870                 875                 880

Gly Pro Ile Pro Ala Pro Tyr Val Pro Pro Leu Pro Asn Val Arg Val
                885                 890                 895

Asn Tyr Asp Phe Gly Pro Ile His Met Pro Leu Glu His Asn Leu Pro
            900                 905                 910

Met His Phe Gly Pro Gln Pro Arg His Arg Phe
        915                 920

<210> SEQ ID NO 3
<211> LENGTH: 866
<212> TYPE: PRT
<213> ORGANISM: Homo sapiens

<400> SEQUENCE: 3

Met Glu Glu Gly Asn Asn Glu Glu Val Ile His Leu Asn Asn Phe
1               5                   10                  15

His Cys His Arg Gly Gln Glu Trp Ile Asn Leu Arg Asp Gly Pro Ile
                20                  25                  30

Thr Ile Ser Asp Ser Ser Asp Glu Glu Arg Ile Pro Met Leu Val Thr
            35                  40                  45
```

-continued

Pro Ala Pro Gln Gln His Glu Glu Asp Leu Asp Asp Val Ile
    50                  55                  60

Leu Thr Glu Asp Asp Ser Glu Asp Tyr Gly Glu Phe Leu Asp Leu
65                  70                  75                  80

Gly Pro Pro Gly Ile Ser Glu Phe Thr Lys Pro Ser Gly Gln Thr Glu
                    85                  90                  95

Arg Glu Pro Lys Pro Gly Pro Ser His Asn Gln Ala Ala Asn Asp Ile
                100                 105                 110

Val Asn Pro Arg Ser Glu Gln Lys Val Ile Ile Leu Glu Glu Gly Ser
            115                 120                 125

Leu Leu Tyr Thr Glu Ser Asp Pro Leu Glu Thr Gln Asn Gln Ser Ser
        130                 135                 140

Glu Asp Ser Glu Thr Glu Leu Leu Ser Asn Leu Gly Glu Ser Ala Ala
145                 150                 155                 160

Leu Ala Asp Asp Gln Ala Ile Glu Glu Asp Cys Trp Leu Asp His Pro
                165                 170                 175

Tyr Phe Gln Ser Leu Asn Gln Gln Pro Arg Glu Ile Thr Asn Gln Val
            180                 185                 190

Val Pro Gln Glu Arg Gln Pro Glu Ala Glu Leu Gly Arg Leu Leu Phe
        195                 200                 205

Gln His Glu Phe Pro Gly Pro Ala Phe Pro Arg Pro Glu Pro Gln Gln
    210                 215                 220

Gly Gly Ile Ser Gly Pro Ser Ser Pro Gln Pro Ala His Pro Leu Gly
225                 230                 235                 240

Glu Phe Glu Asp Gln Gln Leu Ala Ser Asp Asp Glu Pro Gly Pro
                245                 250                 255

Ala Phe Pro Met Gln Glu Ser Gln Glu Pro Asn Leu Glu Asn Ile Trp
                260                 265                 270

Gly Gln Glu Ala Ala Glu Val Asp Gln Glu Leu Val Glu Leu Leu Val
            275                 280                 285

Lys Glu Thr Glu Ala Arg Phe Pro Asp Val Ala Asn Gly Phe Ile Glu
        290                 295                 300

Glu Ile Ile His Phe Lys Asn Tyr Tyr Asp Leu Asn Val Leu Cys Asn
305                 310                 315                 320

Phe Leu Leu Glu Asn Pro Asp Tyr Pro Lys Arg Glu Asp Arg Ile Ile
                325                 330                 335

Ile Asn Pro Ser Ser Ser Leu Leu Ala Ser Gln Asp Glu Thr Lys Leu
            340                 345                 350

Pro Lys Ile Asp Phe Phe Asp Tyr Ser Lys Leu Thr Pro Leu Asp Gln
        355                 360                 365

Arg Cys Phe Ile Gln Ala Ala Asp Leu Leu Met Ala Asp Phe Lys Val
    370                 375                 380

Leu Ser Ser Gln Asp Ile Lys Trp Ala Leu His Glu Leu Lys Gly His
385                 390                 395                 400

Tyr Ala Ile Thr Arg Lys Ala Leu Ser Asp Ala Ile Lys Lys Trp Gln
                405                 410                 415

Glu Leu Ser Pro Glu Thr Ser Gly Lys Arg Lys Lys Arg Lys Gln Met
            420                 425                 430

Asn Gln Tyr Ser Tyr Ile Asp Phe Lys Phe Glu Gln Gly Asp Ile Lys
        435                 440                 445

Ile Glu Lys Arg Met Phe Phe Leu Glu Asn Lys Arg Arg His Cys Arg
450                 455                 460

-continued

```
Ser Tyr Asp Arg Arg Ala Leu Leu Pro Ala Val Gln Gln Glu Gln Glu
465                 470                 475                 480

Phe Tyr Glu Gln Lys Ile Lys Glu Met Ala Glu His Glu Asp Phe Leu
            485                 490                 495

Leu Ala Leu Gln Met Asn Glu Glu Gln Tyr Gln Lys Asp Gly Gln Leu
        500                 505                 510

Ile Glu Cys Arg Cys Cys Tyr Gly Glu Phe Pro Phe Glu Glu Leu Thr
    515                 520                 525

Gln Cys Ala Asp Ala His Leu Phe Cys Lys Glu Cys Leu Ile Arg Tyr
530                 535                 540

Ala Gln Glu Ala Val Phe Gly Ser Gly Lys Leu Glu Leu Ser Cys Met
545                 550                 555                 560

Glu Gly Ser Cys Thr Cys Ser Phe Pro Thr Ser Glu Leu Glu Lys Val
            565                 570                 575

Leu Pro Gln Thr Ile Leu Tyr Lys Tyr Tyr Glu Arg Lys Ala Glu Glu
            580                 585                 590

Glu Val Ala Ala Ala Tyr Ala Asp Glu Leu Val Arg Cys Pro Ser Cys
        595                 600                 605

Ser Phe Pro Ala Leu Leu Asp Ser Asp Val Lys Arg Phe Ser Cys Pro
610                 615                 620

Asn Pro His Cys Arg Lys Glu Thr Cys Arg Lys Cys Gln Gly Leu Trp
625                 630                 635                 640

Lys Glu His Asn Gly Leu Thr Cys Glu Glu Leu Ala Glu Lys Asp Asp
            645                 650                 655

Ile Lys Tyr Arg Thr Ser Ile Glu Glu Lys Met Thr Ala Ala Arg Ile
            660                 665                 670

Arg Lys Cys His Lys Cys Gly Thr Gly Leu Ile Lys Ser Glu Gly Cys
        675                 680                 685

Asn Arg Met Ser Cys Arg Cys Gly Ala Gln Met Cys Tyr Leu Cys Arg
690                 695                 700

Val Ser Ile Asn Gly Tyr Asp His Phe Cys Gln His Pro Arg Ser Pro
705                 710                 715                 720

Gly Ala Pro Cys Gln Glu Cys Ser Arg Cys Ser Leu Trp Thr Asp Pro
            725                 730                 735

Thr Glu Asp Asp Glu Lys Leu Ile Glu Glu Ile Gln Lys Glu Ala Glu
            740                 745                 750

Glu Glu Gln Lys Arg Lys Asn Gly Glu Asn Thr Phe Lys Arg Ile Gly
        755                 760                 765

Pro Pro Leu Glu Lys Pro Val Glu Lys Val Gln Arg Val Glu Ala Leu
770                 775                 780

Pro Arg Pro Val Pro Gln Asn Leu Pro Gln Pro Gln Met Pro Pro Tyr
785                 790                 795                 800

Ala Phe Ala His Pro Pro Phe Pro Leu Pro Pro Val Arg Pro Val Phe
            805                 810                 815

Asn Asn Phe Pro Leu Asn Met Gly Pro Ile Pro Ala Pro Tyr Val Pro
            820                 825                 830

Pro Leu Pro Asn Val Arg Val Asn Tyr Asp Phe Gly Pro Ile His Met
        835                 840                 845

Pro Leu Glu His Asn Leu Pro Met His Phe Gly Pro Gln Pro Arg His
850                 855                 860

Arg Phe
865
```

DOT1L DEGRADERS AND USES THEREOF

RELATED APPLICATIONS

This application is a national stage application, filed under 35 U.S.C. § 371, of International Application No. PCT/US2019/039368, filed Jun. 27, 2019, which claims priority under 35 U.S.C. § 119(e) to U.S. Provisional Application, U.S. Ser. No. 62/690,791, filed Jun. 27, 2018, the contents of each of which are incorporated herein by reference in their entirety

GOVERNMENT SUPPORT

This disclosure was made with government support under grant R01 CA176745 awarded by the National Institutes of Health (NIH). The government has certain rights in the invention.

SEQUENCE LISTING

The instant application contains a Sequence Listing which has been submitted electronically in ASCII format and is hereby incorporated by reference in its entirety. Said ASCII copy, created on Jun. 27, 2019, is named "D050470149WO00-SEQ-JC.txt," and is 18.2 KB in size.

BACKGROUND OF THE INVENTION

E3 ubiquitin ligases are proteins that, in combination with an E2 ubiquitin-conjugating enzyme, promote the attachment of ubiquitin to a lysine on a target protein via an isopeptide bond (e.g., an amide bond that is not present on the main chain of a protein). The ubiquitination of the target protein results in degradation of the target protein by the proteasome.

There remains a need to identify compounds that effectively promote the degradation of target proteins (e.g., DOT1L) found to be associated with certain pathological states, including proliferative diseases and cancers. DOT1L has been found to be associated with certain pathological states, including proliferative diseases and cancers. In particular, compounds that can take advantage of cellular machinery involved in protein homeostasis (e.g., ubiquitination and proteasome degradation) to target the degradation of certain proteins may find use as therapeutic agents. There is a need for compounds that both target a target protein DOT1L, and also bind the E3 ubiquitin ligase, thereby inducing proteasome degradation of the target protein DOT1L.

SUMMARY OF THE INVENTION

The present disclosure stems from the recognition that selected target proteins (e.g., DOT1L) are associated with certain diseases (e.g., proliferative diseases, cancers). The recognition that is targeting a selected protein, and the use of an E3 ubiquitin ligase binding moiety (e.g., lenalidomide, thalidomide), leads to the ubiquitination of the selected target protein DOT1L, thereby resulting in proteasome degradation of the target protein. DOT1L has been found to be associated with certain pathological states, including proliferative diseases and cancers (e.g., cancers involving particular mutations (e.g., mixed-lineage leukemia (MLL) rearranged acute myelocytic leukemia, acute myelocytic leukemia with a mutation in the nucleophosmin (NPM1) gene, acute myelocytic leukemia with a mutation in the DNMT3A gene); or cancer resistant to proteasome inhibitors). The disclosure therefore provides new compounds, compositions, and methods for the treatment of various diseases (e.g., cancers) based on this discovery. Described herein are compounds of Formula (I'). The compounds described herein include a component that is an E3 ubiquitin ligase binding moiety based on an immunomodulatory imide drug (e.g., lenalidomide, thalidomide), and a component that binds the target protein DOT1L and therefore may be useful in promoting the degradation of DOT1L. The compounds may be useful in treating and/or preventing a disease or condition associated with DOT1L, e.g., in treating and/or preventing a disease (e.g., a proliferative disease (e.g., cancers)) in a subject in need thereof. Also provided are pharmaceutical compositions and kits including a compound described herein.

In one aspect, the present disclosure provides compounds of Formula (I'):

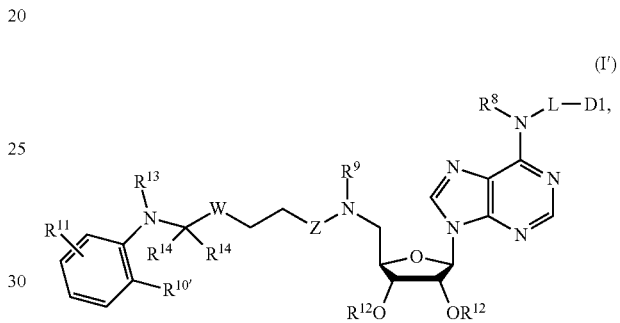

and pharmaceutically acceptable salts, solvates, hydrates, polymorphs, co-crystals, tautomers, stereoisomers, isotopically labeled derivatives, and prodrugs thereof, wherein $R^8$, $R^9$, $R^{10'}$, $R^{11}$, $R^{12}$, $R^{13}$, $R^{14}$, W, Z, L, and D1 are as defined herein. In certain embodiments, a compound of Formula (I') is a compound of Formula (I).

In one aspect, the present disclosure provides compounds of Formula (I):

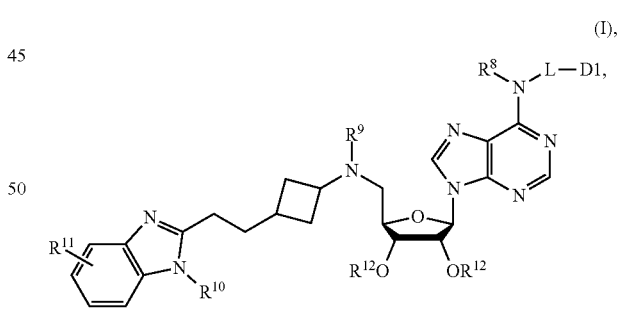

and pharmaceutically acceptable salts, solvates, hydrates, polymorphs, co-crystals, tautomers, stereoisomers, isotopically labeled derivatives, and prodrugs thereof, wherein $R^8$, $R^9$, $R^{10}$, $R^{11}$, $R^{12}$, L, and D1 are as defined herein.

In Formula (I'), D1 is an E3 ubiquitin ligase binding moiety. In certain embodiments, D1 is derived from an immunomodulatory imide drug. In certain embodiments, D1 is derived from lenalidomide. In certain embodiments, D1 is derived from thalidomide. In certain embodiments, D1 is an E3 ubiquitin ligase binding moiety, wherein D1 is of Formula (IA) or (IB).

In certain embodiments, D1 is of Formula (IA):
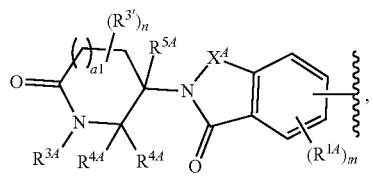
wherein $R^{1A}$, $R^{3A}$, $R^{4A}$, $R^{5A}$, $R^{3'}$, $X^A$, a1, m, and n are as defined herein.
In certain embodiments, D1 is of Formula (IB):
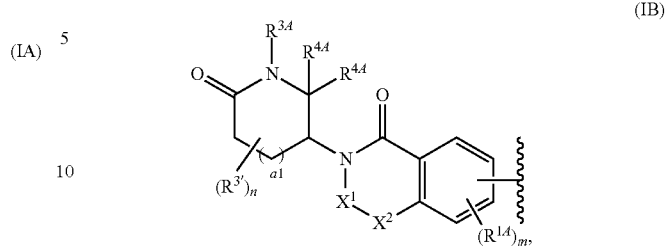
wherein $R^{1A}$, $R^{3A}$, $R^{4A}$, $R^{3'}$, $X^1$, $X^2$, a1, m, and n are as defined herein.
Exemplary compounds of Formula (I') include, but are not limited to:
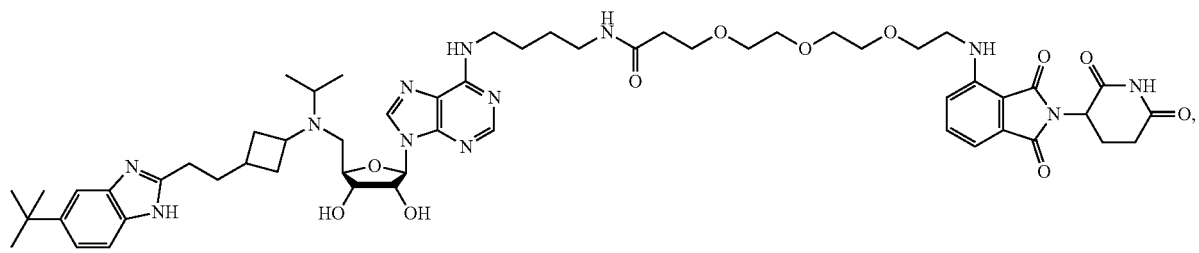
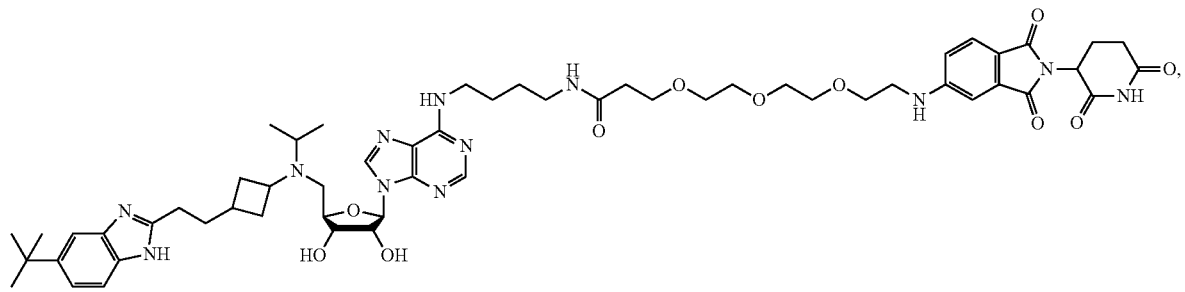
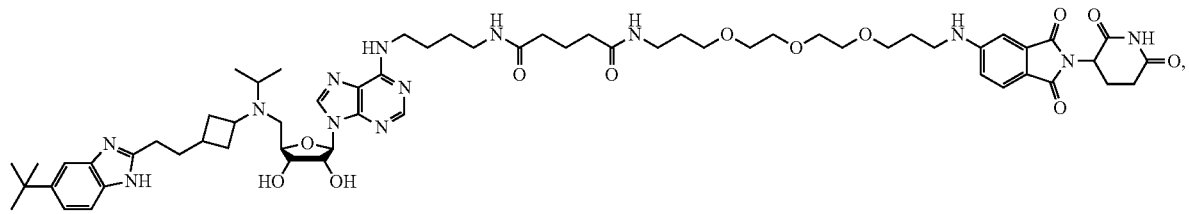
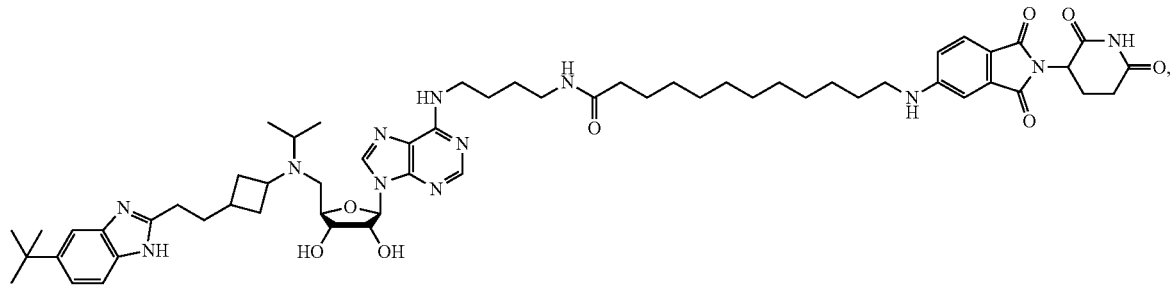
(JQ-DD1)

-continued
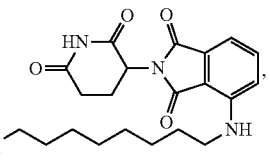
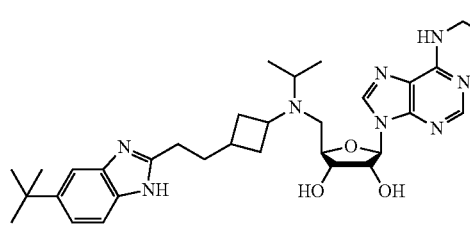
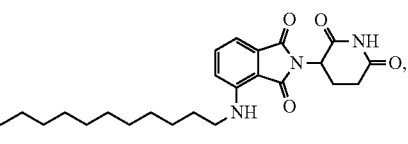
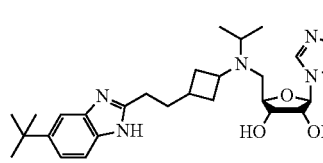
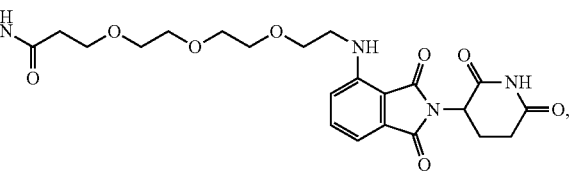
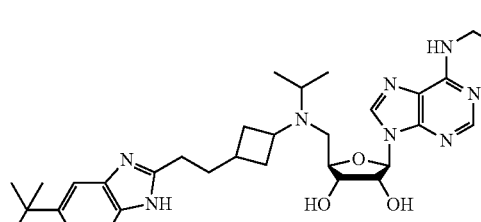
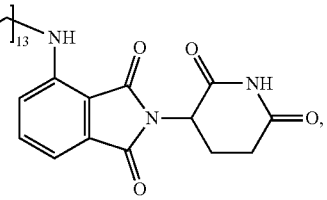
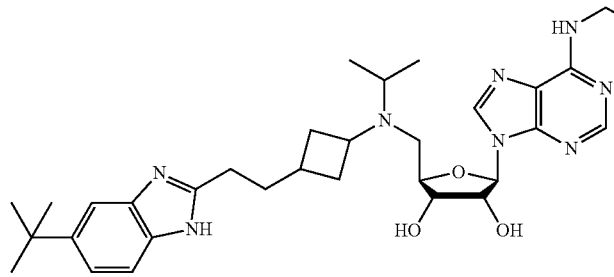
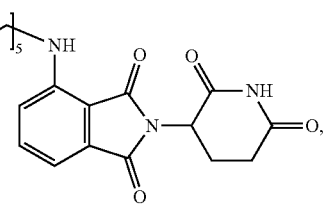
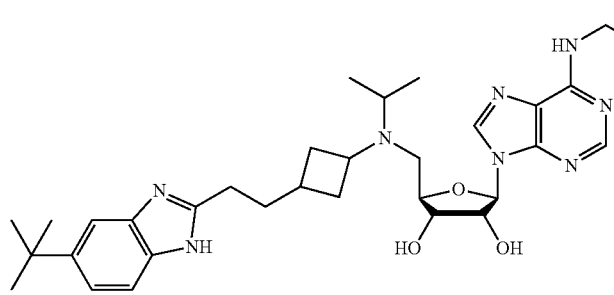
and pharmaceutically acceptable salts, solvates, hydrates, polymorphs, co-crystals, tautomers, stereoisomers, isotopically labeled derivatives, and prodrugs thereof.

Exemplary compounds of Formula (I') include, but are not limited to:
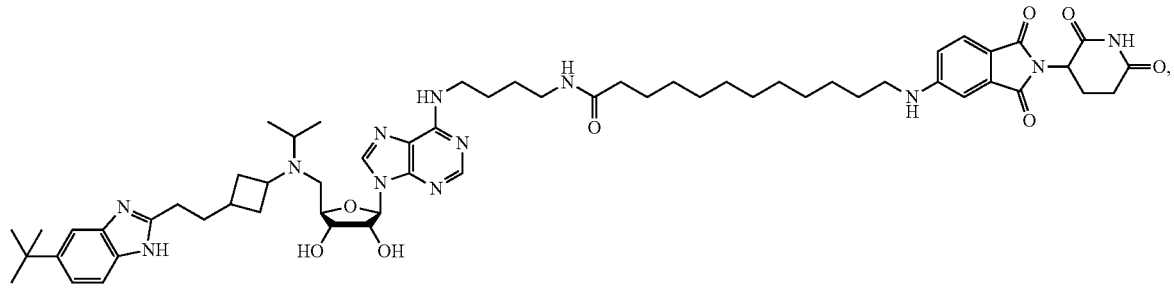
(JQDD1)
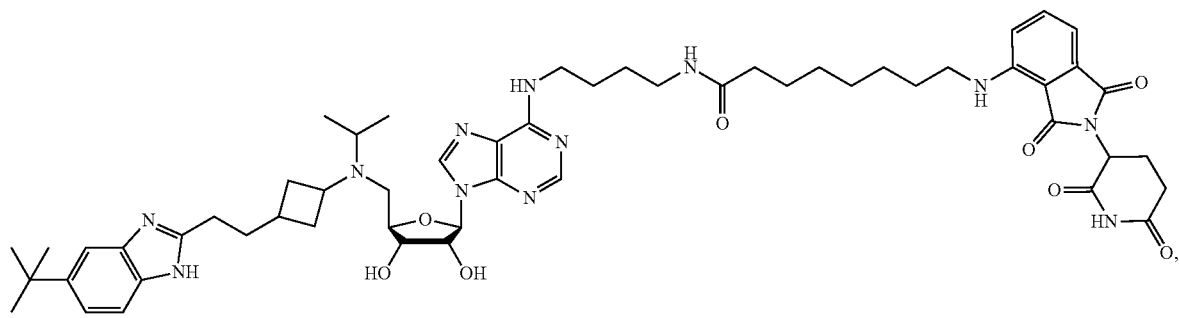
(JQDD2)
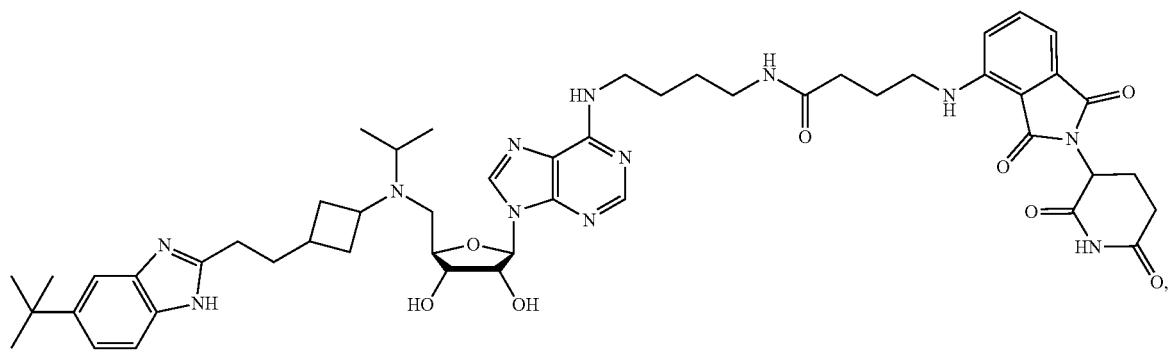
(JQDD3)
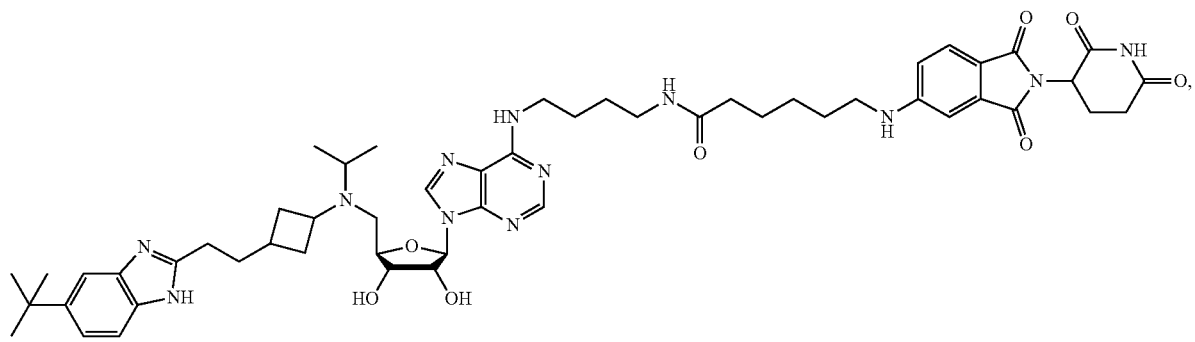
(JQDD4)

-continued
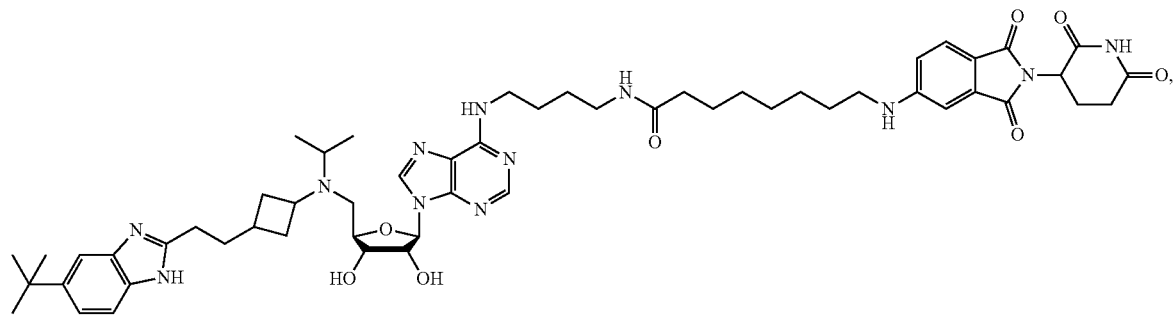
(JQDD5)
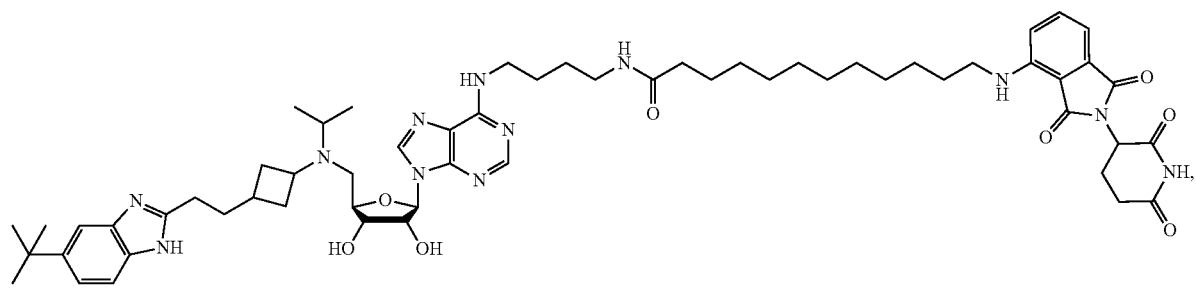
(JQDD6)
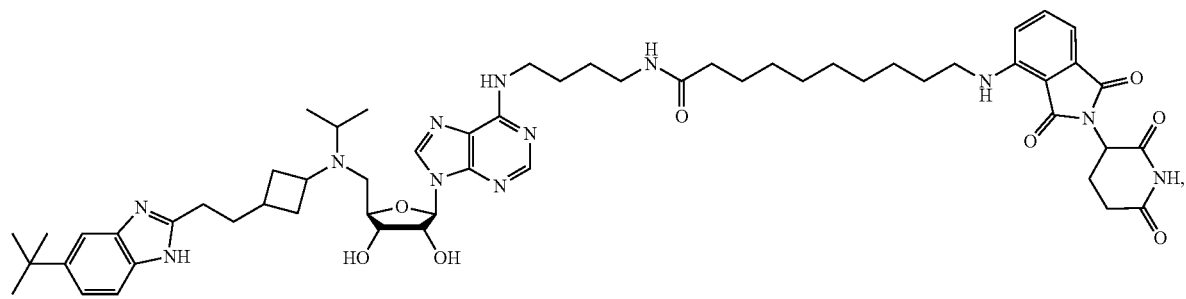
(JQDD7)
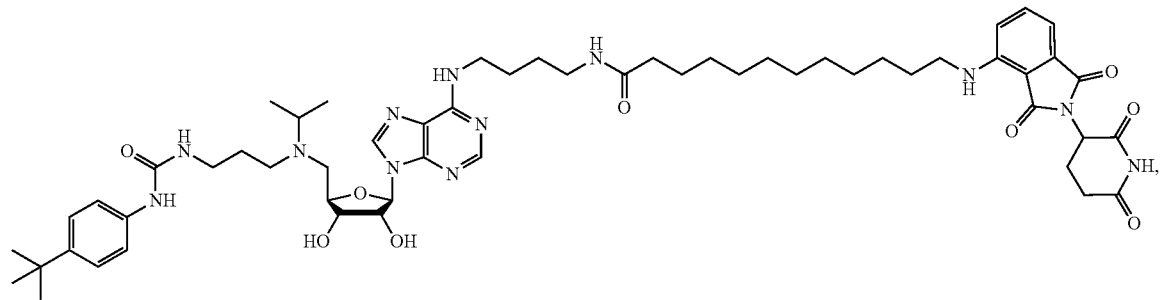
(JQDD8)
and pharmaceutically acceptable salts, solvates, hydrates, polymorphs, co-crystals, tautomers, stereoisomers, isotopically labeled derivatives, and prodrugs thereof.

Exemplary compounds of Formula (I') described herein include, but are not limited to:

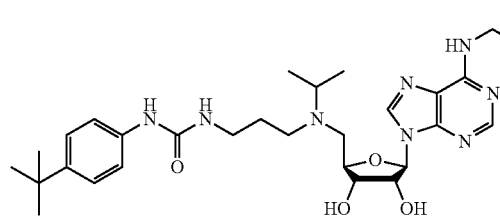 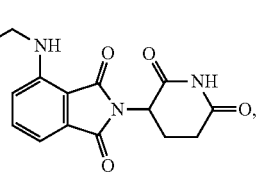

and pharmaceutically acceptable salts, solvates, hydrates, polymorphs, co-crystals, tautomers, stereoisomers, isotopically labeled derivatives, and prodrugs thereof.

Exemplary compounds of Formula (I') described herein include, but are not limited to, compounds of Examples 1-5, and pharmaceutically acceptable salts, solvates, hydrates, polymorphs, co-crystals, tautomers, stereoisomers, isotopically labeled derivatives, and prodrugs thereof. In certain embodiments, exemplary compounds of Formula (I') described herein include, but are not limited to, compounds of Examples 1 and 5.

In another aspect, described herein are pharmaceutical compositions including a compound described herein, and optionally a pharmaceutically acceptable excipient. In certain embodiments, a pharmaceutical composition described herein includes a therapeutically or prophylactically effective amount of a compound described herein. The pharmaceutical compositions may be useful in inducing the degradation of DOT1L in a subject, or biological sample, tissue, or cell, in treating a disease (e.g., a proliferative disease) in a subject in need thereof, or in preventing a disease in a subject in need thereof. In certain embodiments, the compound being administered or used induces the degradation of DOT1L in a subject, biological sample, tissue, or cell, in treating a disease (e.g., a proliferative disease) in a subject in need thereof, or in preventing a disease in a subject in need thereof.

In still another aspect, described herein are kits including a container with a compound or pharmaceutical composition described herein. A kit described herein may include a single dose or multiple doses of the compound or pharmaceutical composition. The described kits may be useful in inducing the degradation of DOT1L. In certain embodiments, a kit described herein further includes instructions for using the compound or pharmaceutical composition included in the kit.

In certain embodiments, the compound being administered or used induce the degradation of DOT1L. Another aspect of the present disclosure relates to methods of treating a disease in a subject in need thereof, the methods comprising administering to the subject a therapeutically effective amount of a compound or pharmaceutical composition described herein. In another aspect, the present disclosure provides methods of preventing a disease in a subject in need thereof, the methods comprises administering to the subject a prophylactically effective amount of a compound or pharmaceutical composition described herein.

In yet another aspect, the present disclosure provides compounds and pharmaceutical compositions described herein for use in a method of the disclosure (e.g., a method of inducing the degradation of DOT1L, a method of treating and/or preventing a disease (e.g., a proliferative disease)).

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., Tetrahedron 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms.

In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —CH$_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —CF$_3$, Bn).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix-ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —S$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —S$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 Rd groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{aa}$, —SO$_2$OR$^{aa}$, —SOR$^{aa}$, —C(=S)N(R$^{cc}$)$_2$, —C(=O)SR$^{cc}$, —C(=S)SR$^{aa}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

each instance of R$^{dd}$ is, independently, selected from hydrogen, C$_{1-10}$ alkyl, C$_{1-10}$ perhaloalkyl, C$_{2-10}$ alkenyl, C$_{2-10}$ alkynyl, heteroC$_1$ alkyl, heteroC$_{2-10}$ alkenyl, hetero C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ee}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O) (OR$^{ee}$)$_2$, —P(=O)(R$^{ee}$)$_2$, —OP(=O)(R$^{ee}$)$_2$, —OP(=O) (OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{99}$ groups, or two geminal R$^{dd}$ substituents can be joined to form =O or =S; wherein X$^-$ is a counterion;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_{2-6}$alkenyl, heteroC$_{2-6}$alkynyl, C$_{3-10}$ carbocyclyl, 3-10 membered heterocyclyl, C$_{6-10}$ aryl and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$ alkyl), —NHC(=O)N(C$_{1-6}$ alkyl)$_2$, —NHC(=O)NH (C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C (=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, heteroC$_{1-6}$alkyl, heteroC$_2$-6 alkenyl, heteroC$_{2-6}$alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S; wherein X$^-$ is a counterion. In some embodiments, an optional substituent is halogen, —NO$_2$, —N$_3$, —SO$_2$H, —SO$_3$H, acyl (e.g., —C(=O)C$_{1-10}$ alkyl), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, 5-14 membered heteroaryl, branched C$_{1-10}$ alkyl, —OH, —O(C$_{1-10}$ alkenyl), —O(C$_{2-10}$ alkynyl), acid (e.g., —COOH), ester (e.g., —COO(C$_{1-10}$ alkyl)), amine (e.g., —NH$_2$, —NH(C$_{1-10}$ alkyl), —N(C$_{1-10}$ alkyl)$_2$), substituted amine, amide (e.g., —C(=O)N(C$_{1-10}$ alkyl)), ureas, imides, —CN, nitriles, cyano groups, or carbamates. In some embodiments, a carbon atom is optionally substituted with halogen, —NO$_2$, —N$_3$, —SO$_2$H, —SO$_3$H, acyl (e.g., —C(=O)C$_{1-10}$ alkyl), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, 5-14 membered heteroaryl, branched C$_{1-10}$ alkyl, —OH, —O(C$_{1-10}$ alkyl), —O(C$_{2-10}$ alkenyl), —O(C$_{2-10}$ alkynyl), acid (e.g., —COOH), ester (e.g., —COO(C$_{1-10}$ alkyl)), amine (e.g., —NH$_2$, —NH(C$_{1-10}$ alkyl), —N(C$_{1-10}$ alkyl)$_2$), substituted amine, amide (e.g., —C(=O)N(C$_{1-10}$ alkyl)), ureas, imides, —CN, nitriles, cyano groups, or carbamates. In some embodiments, a carbon atom is optionally substituted with halogen, acyl (e.g., —C(=O)C$_{1-10}$ alkyl), C$_{1-10}$ alkyl, branched C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, 5-14 membered heteroaryl, —OH, —O(C$_{1-10}$ alkyl), —CN, —NO$_2$, —N$_3$, —SO$_2$H, or amine (e.g., —NH$_2$, —NH(C$_{1-10}$ alkyl). In some embodiments, an optional substituent is halogen, acyl (e.g., —C(=O)C$_{1-10}$ alkyl), C$_{1-10}$ alkyl, branched C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, 5-14 membered heteroaryl, —OH, —O(C$_{1-10}$ alkyl), —CN, —NO$_2$, —N$_3$, —SO$_2$H, or amine (e.g., —NH$_2$, —NH(C$_{1-10}$ alkyl).

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HCO$_3$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, B(C$_6$F$_5$)$_4$$^-$, BPh$_4$$^-$, Al(OC (CF$_3$)$_3$)$_4$$^-$, and carborane anions (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N (R$^{bb}$)$_2$, —C(=NR$^{bb}$)R$^{aa}$, —C(=NR$^{bb}$)OR$^{aa}$, —C(=NR$^{bb}$) N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N (R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide. In certain embodiments, a nitrogen protecting group is formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, or o-(benzoyloxymethyl)benzamide; or.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenz0enesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —C(=O)$SR^{aa}$, —C(=O)$R^{aa}$, —$CO_2R^{aa}$, —C(=O)N($R^{bb})_2$, —C(=$NR^{bb}$)$R^{aa}$, —C(=$NR^{bb}$)$OR^{aa}$, —C(=$NR^{bb}$)N($R^{bb})_2$, —S(=O)$R^{aa}$, —$SO_2R^{aa}$, —Si($R^{aa})_3$, —P($R^{cc})_2$, —P($R^{cc})_3^+X^-$, —P($OR^{cc})_2$, —P($OR^{cc})_3^+X^-$, —P(=O)($R^{aa})_2$, —P(=O)($OR^{cc})_2$, and —P(=O)(N($R^{bb})_2)_2$, wherein $X^-$, $R^{aa}$, $R^{bb}$, and $R^{cc}$ are as defined herein.

Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. In certain embodiments, the oxygen protecting group is methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, or diphenylmethylsilyl (DPMS), t-butylmethoxyphenylsilyl (TBMPS).

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$$^+$X$^-$, —P(OR$^{cc}$)$_2$, —P(OR)$_3$$^+$X$^-$, —P(=O)(R$^{aa}$)$_2$, —P(=O)(OR$^{aa}$)$_2$, and —P(=O)(N(R$^{bb}$)$_2$)$_2$, wherein R$^{aa}$, R$^{bb}$, and R$^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R—, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —C$^A$H(C$^B$H$_2$C$^C$H$_3$)— includes one chain atom C$^A$, one hydrogen atom on C$^A$, and non-chain substituent —(C$^B$H$_2$C$^C$H$_3$). The term "C$_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

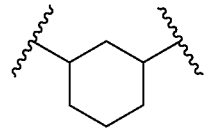 [SMILES: *C1CCCC(*)C1]

is a C$_3$ hydrocarbon chain. When a range of values is used, the meaning of the range is as described herein. For example, a C$_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring. For instance,

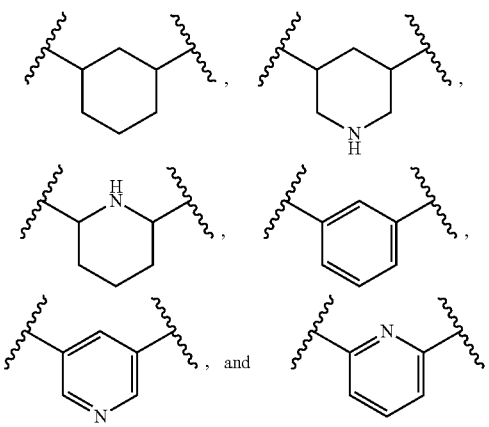

are all examples of a hydrocarbon chain. In contrast, in certain embodiments,

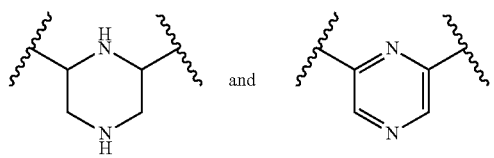 [SMILES: *C1CNCC(*)N1 ; *c1cncc(*)n1]

are not within the scope of the hydrocarbon chains described herein. When a chain atom of a $C_x$ hydrocarbon chain is replaced with a heteroatom, the resulting group is referred to as a $C_x$ hydrocarbon chain wherein a chain atom is replaced with a heteroatom, as opposed to a $C_{x-1}$ hydrocarbon chain. For example,

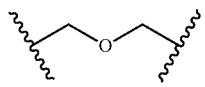 [SMILES: *COC*]

is a $C_3$ hydrocarbon chain wherein one chain atom is replaced with an oxygen atom.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4} \text{ alkyl})_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and claims. The invention is not intended to be limited in any manner by the above exemplary listing of substituents.

Other Definitions

The following definitions are more general terms used throughout the present application.

The term "solvate" refers to forms of the compound, or a salt thereof, that are associated with a solvent, usually by a solvolysis reaction. This physical association may include hydrogen bonding. Conventional solvents that can form solvates include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.x\ H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R.0.5H_2O$)), and polyhydrates (x is a number greater than 1, e.g., dihydrates ($R.2H_2O$) and hexahydrates ($R.6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred. In certain embodiments, a prodrug comprises (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, or $C_7$-$C_{12}$ arylalkyl esters of the compounds described herein. In certain embodiments, a prodrug comprises a glycyl ester derivative of a compound described herein.

As used herein the term "inhibit" or "inhibition" in the context of enzymes, for example, in the context of an enzyme, refers to a reduction in the level of protein by promoting degradation of the protein. The reduction in the level of protein thus reduces the level of the activity of the protein. As used herein the term "inhibit" or "inhibition" in the context of the proteasome, for example, refers to a reduction in the level of activity by the proteasome, for example, reducing the level of proteasome degradation. In some embodiments, the term refers to a reduction of the level of proteasome activity to a level that is statistically significantly lower than an initial level, which may, for example, be a baseline level of proteasome activity. In some embodiments, the term refers to a reduction of the level of proteasome activity to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of proteasome activity.

When a compound, pharmaceutical composition, method, use, or kit is referred to as "selectively," "specifically," or "competitively" binding or inhibiting a target (e.g., enzyme, E3 ligase), the compound, pharmaceutical composition, method, use, or kit inhibits the target enzyme, to a greater extent (e.g., not less than 2-fold, not less than 5-fold, not less than 10-fold, not less than 30-fold, not less than 100-fold, not less than 1,000-fold, or not less than 10,000-fold; and/or: not more than 2-fold, not more than 5-fold, not more than 10-fold, not more than 30-fold, not more than 100-fold, not more than 1,000-fold, or not more than 10,000-fold) than binding or inhibiting a different target (e.g., enzyme, DOT1L).

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments, or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a biological sample.

The term "tissue" refers to any biological tissue of a subject (including a group of cells, a body part, or an organ) or a part thereof, including blood and/or lymph vessels, which is the object to which a compound, particle, and/or composition of the invention is delivered. A tissue may be an abnormal or unhealthy tissue, which may need to be treated. A tissue may also be a normal or healthy tissue that is under a higher than normal risk of becoming abnormal or unhealthy, which may need to be prevented. In certain embodiments, the tissue is the central nervous system. In certain embodiments, the tissue is the brain.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms, signs, or causes of the condition, and/or enhances the therapeutic efficacy of another therapeutic agent. In certain embodiments, a therapeutically effective amount is an amount sufficient for binding a target (e.g., a protein (e.g., DOT1L) (and/or inducing the degradation of the target (e.g., a protein (e.g., DOT1L)).

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for binding a target (e.g., a protein (e.g., DOT1L). In certain embodiments, a prophylactically effective amount is an amount sufficient for treating a disease (e.g., a proliferative disease (e.g., cancer)). In certain embodiments, a prophylactically effective amount is an amount sufficient for binding a target (e.g., a protein (e.g., DOT1L) and/or inducing the degradation of the target (e.g., a protein (e.g., DOT1L) and treating a disease (e.g., a proliferative disease (e.g., cancer)).

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism. In certain embodiments, a hematological disease is a hematological malignancy. The term "hematological malignancy" refers to tumors that affect blood, bone marrow, and/or lymph nodes. Exemplary hematological malignancies include, but are not limited to, leukemia, such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma, such as Hodgkin lymphoma (HL) (e.g., B-cell HL, T-cell HL) and non-Hodgkin lymphoma (NHL) (e.g., B-cell NHL, such as diffuse large cell lymphoma (DLCL) (e.g., diffuse large B-cell lymphoma (DLBCL, e.g., activated B-cell (ABC) DLBCL (ABC-DLBCL))), follicular lymphoma, chronic lymphocytic leukemia/small lymphocytic lymphoma (CLL/SLL), mantle cell lymphoma (MCL), marginal zone B-cell lymphoma (e.g., mucosa-associated lymphoid tissue (MALT) lymphoma, nodal marginal zone B-cell lymphoma, splenic marginal zone B-cell lymphoma), primary mediastinal B-cell lymphoma, Burkitt lymphoma, Waldenström's macroglobulinemia (WM, lymphoplasmacytic lymphoma), hairy cell leukemia (HCL), immunoblastic large cell lymphoma, precursor B-lymphoblastic lymphoma, central nervous system (CNS) lymphoma (e.g., primary CNS lymphoma and secondary CNS lymphoma); and T-cell NHL, such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); lymphoma of an immune privileged site (e.g., cerebral lymphoma, ocular lymphoma, lymphoma of the placenta, lymphoma of the fetus, testicular lymphoma); a mixture of one or more leukemia/lymphoma as described above; myelodysplasia; and multiple myeloma (MM).

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans.

Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

The term "E3 ubiquitin ligase" or "E3 ligase" refers to any protein that recruits an E2 ubiquitin-conjugating enzyme that has been loaded with ubiquitin, recognizes a protein substrate, and assists or directly catalyzes the transfer of ubiquitin from the E2 protein to the protein substrate. For E3 ubiquitin ligase, exemplary sequences for GenBank: ACH72645.1 (*Homo sapiens*) include: MESGGRPSLC QFILLGTTSV VTAALYSVYR QKARVSQELK GAKKVHLGED LKSILSEAPG KCVPYAVIEG AVRSVKETLN SQFVENCKGV IQRLTLQEHK MVWNRTTHLW NDCSKIIHQR TNTVPFDLVP HEDGVDVAVR VLKPLDSVDL GLETVYEKFH PSIQSFTDVI GHYISGERPK GIQETEEMLK VGATLTGVGE LVLDNNSVRL QPPKQGMQYY LSSQDFDSLL QRQESSVRLW KVLALVFGFA TCATLF- FILR KQYLQRQERL RLKQMQEEFQ EHEAQLLSRA KPEDRESLKS ACVVCLSSFK SCVFLECGHV CSCTECYRAL PEPKKCPICR QAITRVIPPY NS (SEQ ID NO: 1). FOR E3 UBIQUITIN LIGASE, EXEMPLARY SEQUENCES FOR GENBANK: AAP47175.1 (*Homo sapiens*) INCLUDE: MEEGNNNEEV IHLNNFHCHR GQEWINLRDG PITISDSSDE ERIPMLVTPA PQQHEEEDLD DDVILTETNK PQRSRPNLIK PAAQWQDLKR LGEERPKKSR AAFESDKSSY FSVCNNPLFD SGAQDDSEDD YGEFLDLGPP GISEFTKPSG QTEREPKPGP SHNQAANDIV NPRSE- QKVII LEEGSLLYTE SDPLETQNQS SEDSETELLS NLGESAALAD DQAIEEDCWL DHPYFQSLNQ QPRE- ITNQVV PQERQPEAEL GRLLFQHEFP GPAFPRPEPQ QGGISGPSSP QPAHPLGEFE DQQLASDDEE PGPAFPMQES QEPNLENIWG QEAAEVDQEL VELL- VKETEA RFPDVANGFI EEIIHFKNYY DLNVLCNFLL ENPDYPKRED RIIINPSSSL LASQDETKLP KIDFFDYSKL TPLDQRCFIQ AADLLMADFK VLSSQDIKWA LHELKGHYAI TRKALSDAIK KWQEL- SPETS GKRKKRKQMN QYSYIDFKFE QGDIKIEKRM FFLENKRRHC RSYDRRALLP AVQQEQEFYE QKIKEMAEHE DFLLALQMNE EQYQKDGQLI ECRCCYGEFP FEELTQCADA HLFCKECLIR YAQEAVFGSG KLELSCMEGS CTCSFPTSEL EKVLPQTILY KYYERKAEEE VAAAYADELV RCP- SCSFPAL LDSDVKRFSC PNPHCRKETC RKCQGLWKEH NGLTCEELAE KDDIKYRTSI EEKMTAARIR KCHKCGTGLI KSEGCNRMSC RCGAQMCYLC RVSINGYDHF CQHPRSPGAP CQECSRCSLW TDPTEDDEKL IEEIQKEAEE EQKRKN- GENT FKRIGPPLEK PVEKVQRVEA LPRPVPQNLP QPQMPPYAFA HPPFPLPPVR PVFNNFPLNM GPIPA- PYVPP LPNVRVNYDF GPIHMPLEHN LPMHFGPQPR HRF (SEQ ID NO: 2). For E3 ubiquitin ligase, exemplary sequences for GenBank: AAP47174.1 (*Homo sapiens*) include: MEEGNNNEEV IHLNNFHCHR GQEWINLRDG PITISDSSDE ERIPMLVTPA PQQHEEEDLD DDVILTEDDS EDDYGEFLDL GPPGISEFTK PSGQ-TEREPK PGPSHNQAAN DIVNPRSEQK VIILEEGSLL YTESDPLETQ NQSSEDSETE LLSNLGESAA LADDQAIEED CWLDHPYFQS LNQQPREITN QVVPQERQPE AELGRLLFQH EFPGPAFPRP EPQQG-GISGP SSPQPAHPLG EFEDQQLASD DEEPGPAFPM QESQEPNLEN IWGQEAAEVD QELVELLVKE TEARFPDVAN GFIEEIIHFK NYYDLNVLCN FLLEN-PDYPK REDRIIINPS SSLLASQDET KLPKIDFFDY SKLTPLDQRC FIQAADLLMA DFKVLSSQDI KWAL-HELKGH YAITRKALSD AIKKWQELSP ETSGKRKKRK QMNQYSYIDF KFEQGDIKIE KRMF-FLENKR RHCRSYDRRA LLPAVQQEQE FYEQKIKEMA EHEDFLLALQ MNEEQYQKDG QLIE-CRCCYG EFPFEELTQC ADAHLFCKEC LIRYAQEAVF GSGKLELSCM EGSCTCSFPT SELEKVLPQT ILYKYYERKA EEEVAAAYAD ELVRCPSCSF PALL-DSDVKR FSCPNPHCRK ETCRKCQGLW KEHNGLT-CEE LAEKDDIKYR TSIEEKMTAA RIRKCHKCGT GLIKSEGCNR MSCRCGAQMC YLCRVSINGY DHFCQHPRSP GAPCQECSRC SLWTDPTEDD EKLIEE-IQKE AEEEQKRKNG ENTFKRIGPP LEKPVEKVQR VEALPRPVPQ NLPQPQMPPY AFAHPPFPLP PVRPVFNNFP LNMGPIPAPY VPPLPNVRVN YDFG-PIHMPL EHNLPMHFGP QPRHRF (SEQ ID NO: 3).

The term "binder" refers to a compound that binds to a protein. The binder binds to a protein with a $K_d$ of less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

The term "proteasome" refers to a multisubunit enzyme complex that plays a key role regulating proteins that control cell-cycle progression and apoptosis. The proteasome conducts proteolysis of selected proteins.

The term "DOT1L" or "Disruptor of telomeric silencing 1-like histone H3K79 methyltransferase" refers to an enzyme that is encoded by the DOT1L gene. DOT1L is a histone methyltransferase that methylates lysine-79 of histone H3. DOT1L is inactive against free core histones but shows significant histone methyltransferase activity against nucleosomes.

BRIEF DESCRIPTION OF THE DRAWINGS

FIG. 2A shows a crystal structure of the interaction between the DOT1L protein and an exemplary DOT1L degrader compound. FIG. 2B shows a closer view of the crystal structure of the interaction between the DOT1L protein and an exemplary DOT1L degrader compound. FIG. 2C shows a detailed description of the moieties of an exemplary DOT1L degrader compound.

FIGS. 4A-4F show exemplary DOT1L degrader compounds. FIG. 4A shows an exemplary DOT1L degrader compound (dDOT1L-1). FIG. 4B shows an exemplary DOT1L degrader compound (dDOT1L-2). FIG. 4C shows an exemplary biotinylated probe compound (dDOT1L-3). FIG. 4D shows an exemplary DOT1L degrader compound (dDOT1L-4). FIG. 4E shows an exemplary DOT1L degrader compound (dDOT1L-5). FIG. 4F shows an exemplary DOT1L degrader compound.

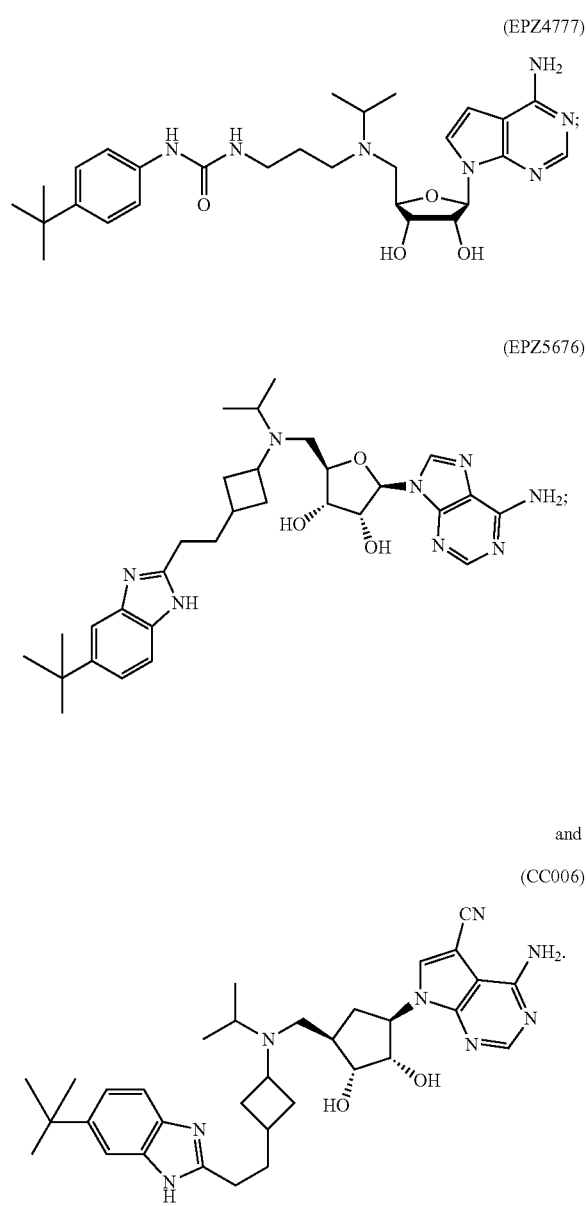

This is another exemplary negative control compound:

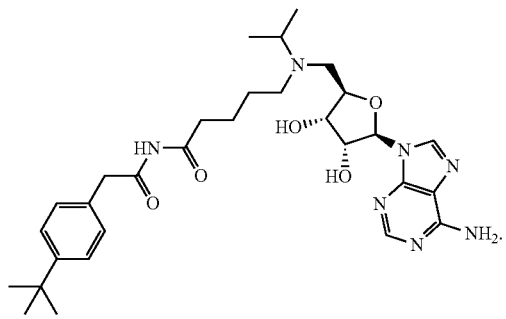 [SMILES: CC(C)N(CCCCC(=O)NC(=O)Cc1ccc(C(C)(C)C)cc1)C[C@H]1O[C@@H](n2cnc3c(N)ncnc32)[C@H](O)[C@@H]1O]

Figure 6:
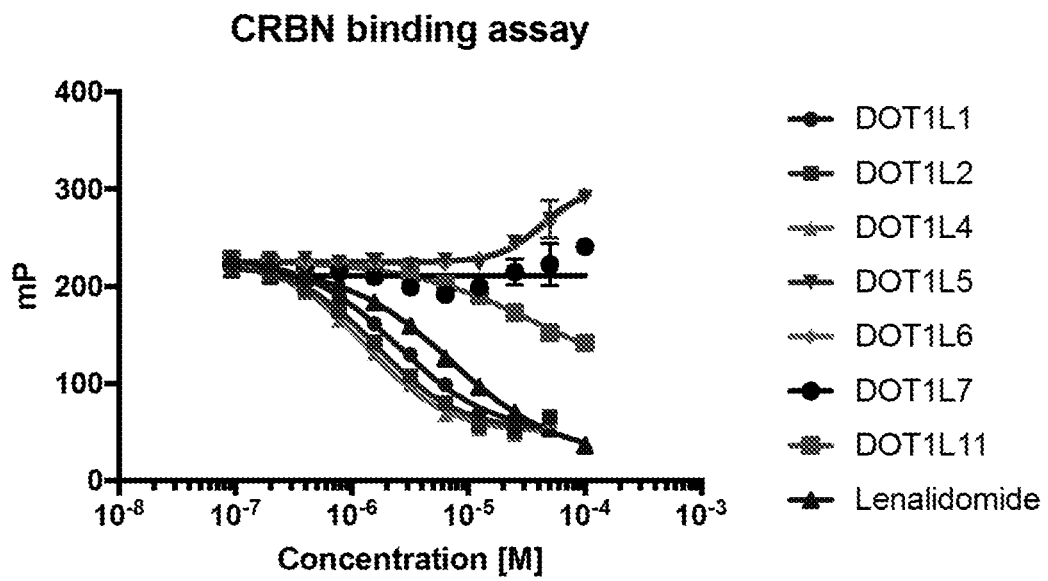

FIG. 6 shows a CRBN binding assay of exemplary DOT1L degrader compounds, a derivative of an inhibitor, and positive control compounds at different concentrations [M], as indicated in concentration [M] versus mP. The compounds include exemplary DOT1L degrader compounds DOT1L-1, DOT1L-2, DOT1L-4, DOT1L-5, DOT1L-6, and DOT1L-7; a derivative of an inhibitor (DOT1L-11); and positive control Lenalidomide.

Figure 7:
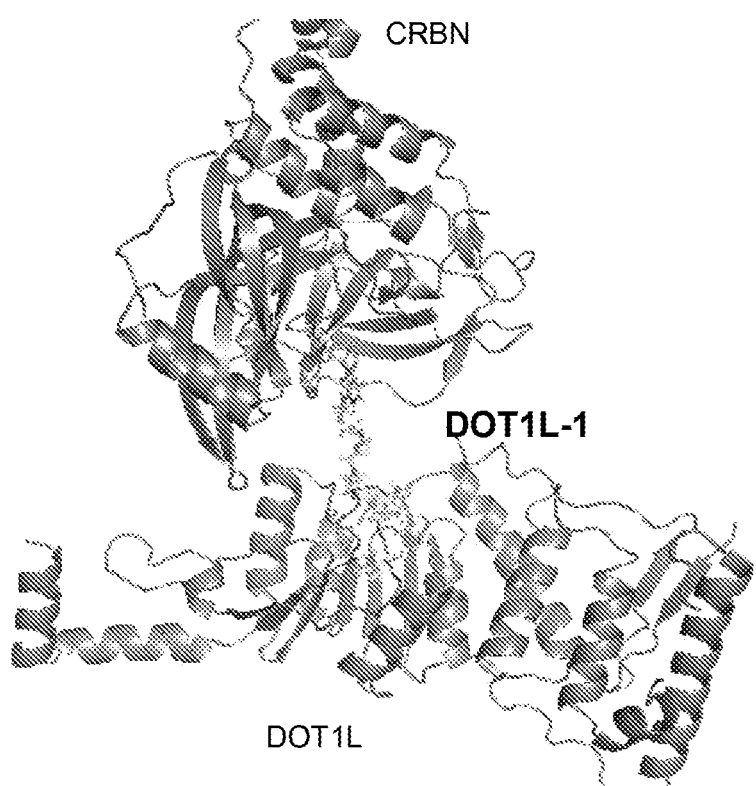

FIG. 7 shows a docking model of the interaction between an exemplary DOT1L degrader compound with a CRBN protein and a DOT1L protein.

Figure 8:
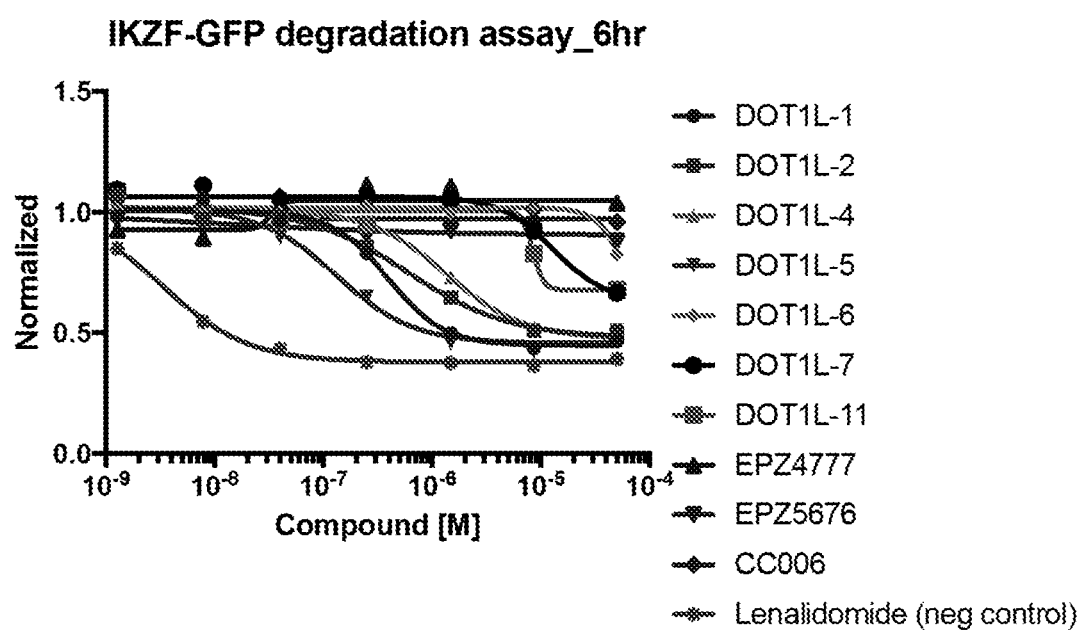

FIG. 8 shows an IKZF-GFP degradation assay of exemplary DOT1L degrader compounds, a derivative of an inhibitor, negative control compounds, and positive control compounds at different concentrations [M], as indicated as concentration of the compounds versus normalized levels over 6 hours. The exemplary compounds include exemplary DOT1L degrader compounds DOT1L-1, DOT1L-2, DOT1L-4, DOT1L-5, DOT1L-6, DOT1L-7; a derivative of an inhibitor DOT1L-11; negative control compounds EPZ4777, EPZ5676, and CC006; and positive control Lenalidomide.

Figure 9A:
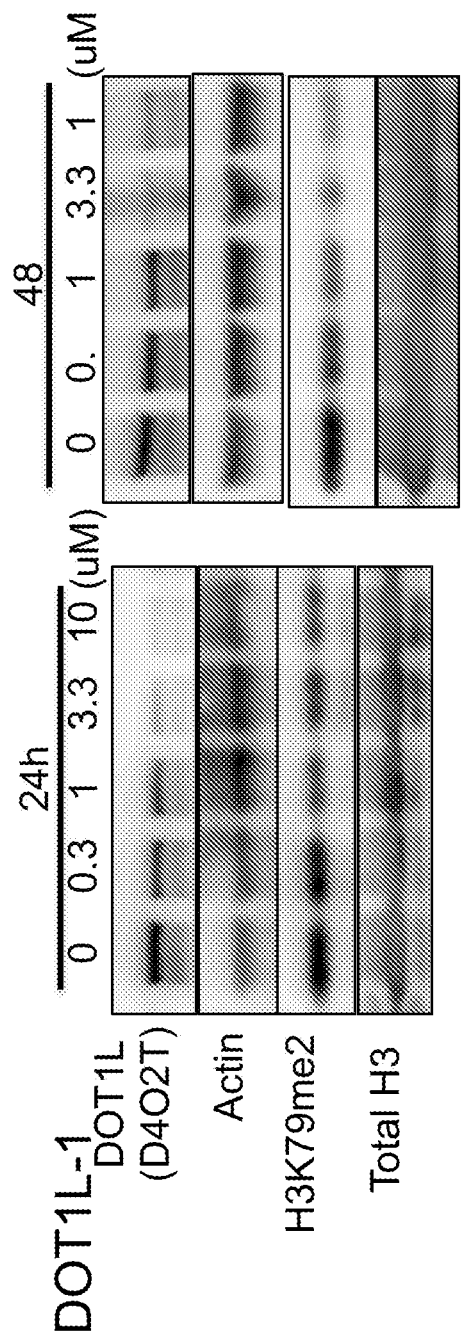
Figure 9B:
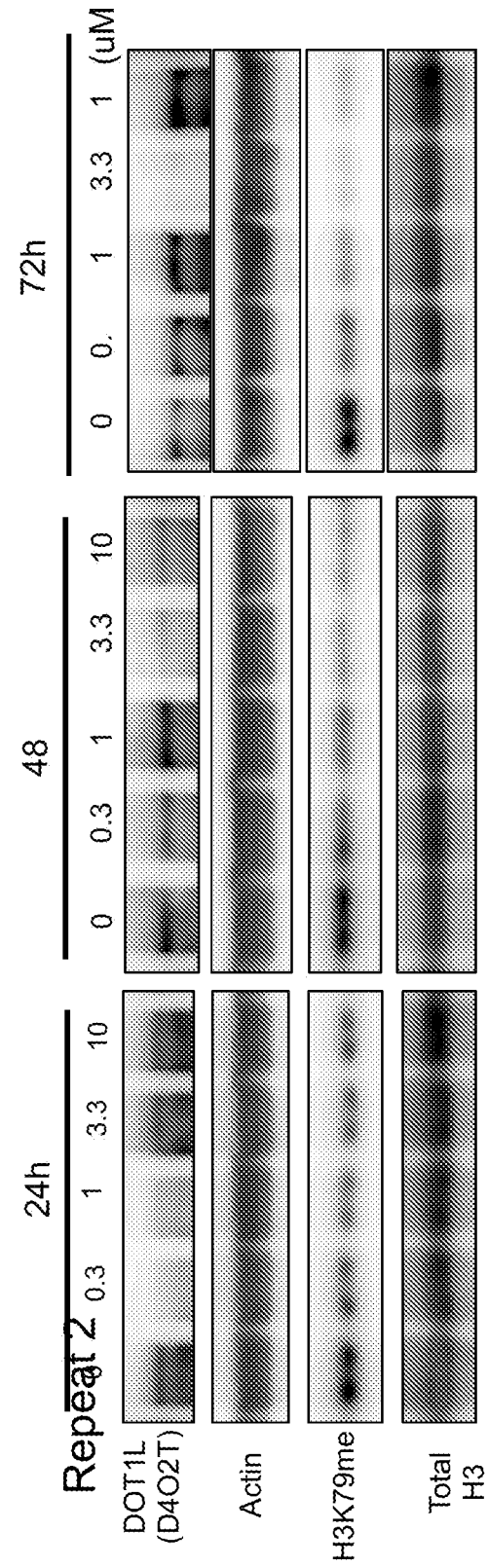

FIGS. 9A-9B show acute myeloid leukemia cells (Molm13 PA) treated with DOT1L-1 at the indicated concentrations for the indicated amount of time. The cells were immunoblotted with DOT1L (D402T), actin, and H3K79me2. FIG. 9A shows the cells were treated with DOT1L-1 at the indicated concentration (0 µM, 0.3 µM, 1 µM, 3.3 µM, and 10 µM) for the indicated amount of time (24 hours and 48 hours). FIG. 9B shows a repeat treatment where the cells were treated with DOT1L-1 at the indicated concentration (0 µM, 0.3 µM, 1 µM, 3.3 µM, and 10 µM) for the indicated amount of time (24 hours, 48 hours, and 72 hours).

Figure 10A:
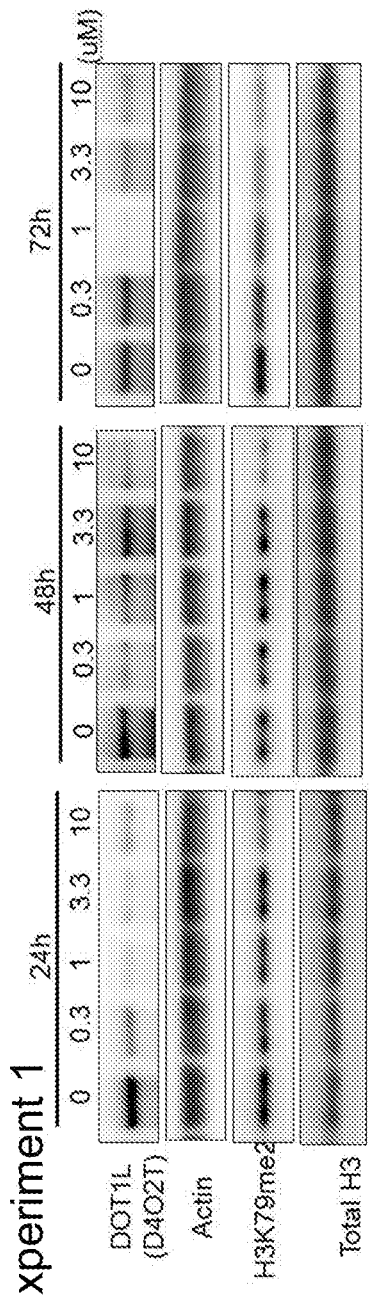
Figure 10B:
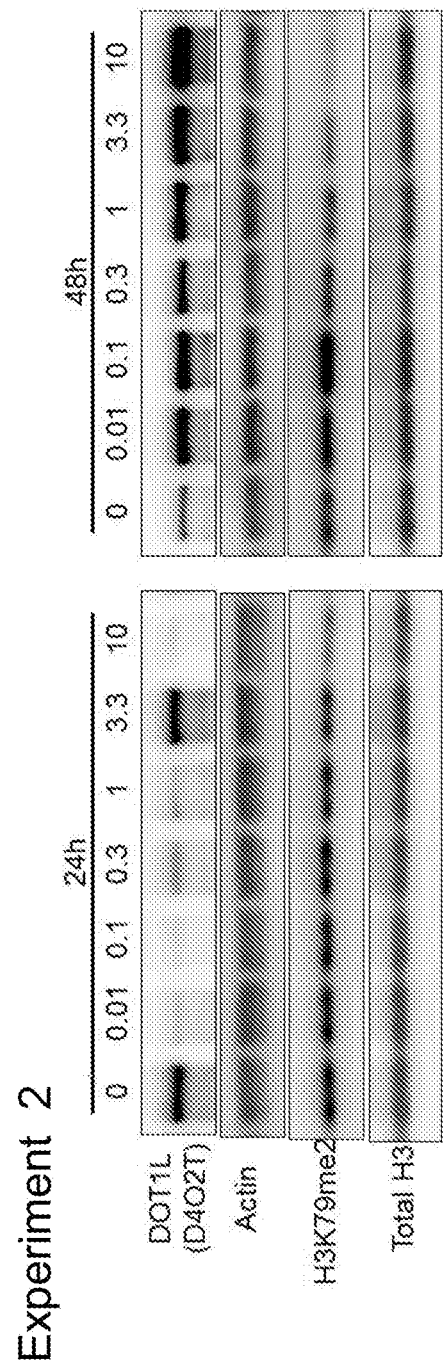

FIGS. 10A-10B show mouse MLL-AF9 PA (Mixed-lineage leukemia (MLL)-AF9 leukemia) cells treated with DOT1L-1 at the indicated concentrations for the indicated amount of time. The cells were immunoblotted with DOT1L (D402T), actin, and H3K79me2.

FIG. 10A shows Experiment 1 where the cells were treated with DOT1L-1 at the indicated concentration (0 µM, 0.3 µM, 1 µM, 3.3 µM, and 10 µM) for the indicated amount of time (24 hours, 48 hours, and 72 hours). FIG. 10B shows Experiment 2 where the cells were treated with DOT1L-1 at the indicated concentration (0 µM, 0.3 µM, 1 µM, 3.3 µM, and 10 µM) for the indicated amount of time (24 hours and 48 hours).

Figure 11:
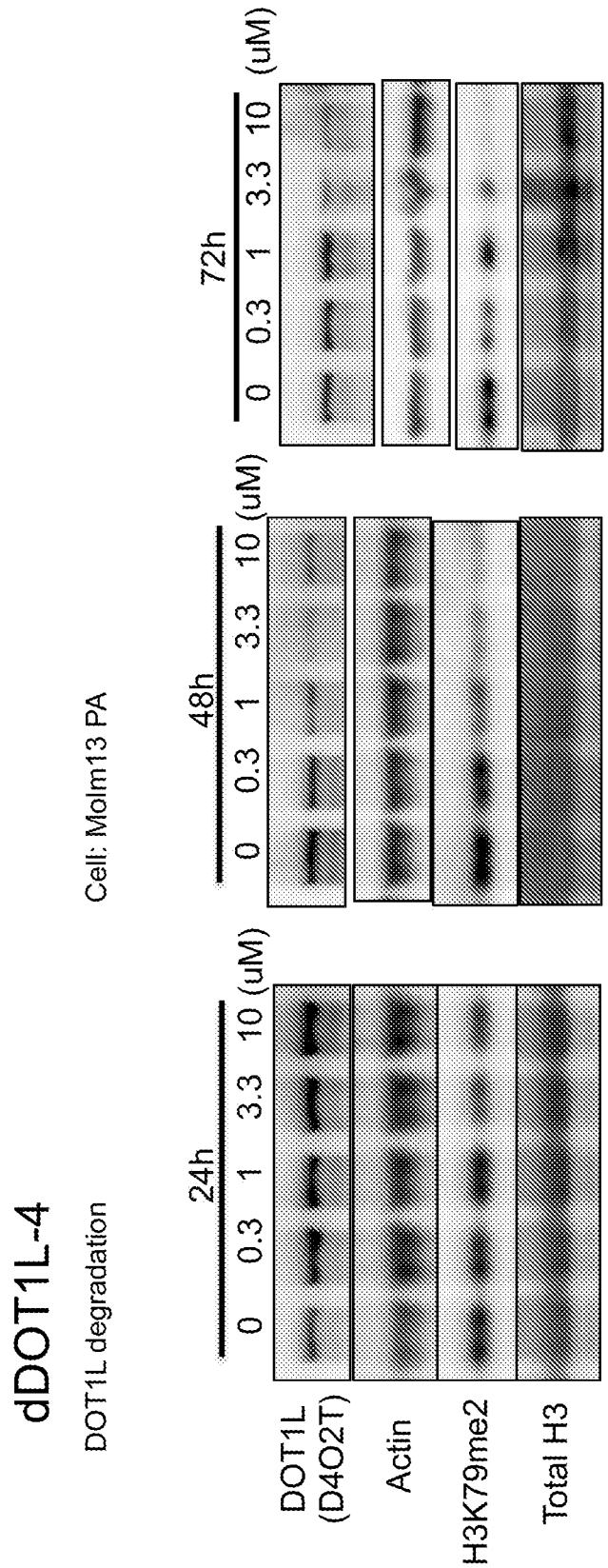

FIG. 11 shows Molm13 PA cells treated with DOT1L-4 at the indicated concentrations (0 µM, 0.3 µM, 1 µM, 3.3 µM, and 10 µM) for the indicated amount of time (24 hours, 48 hours, and 72 hours). The cells were immunoblotted with DOT1L (D402T), actin, and H3K79me2. These cells show DOT1L degradation.

Figure 12A:
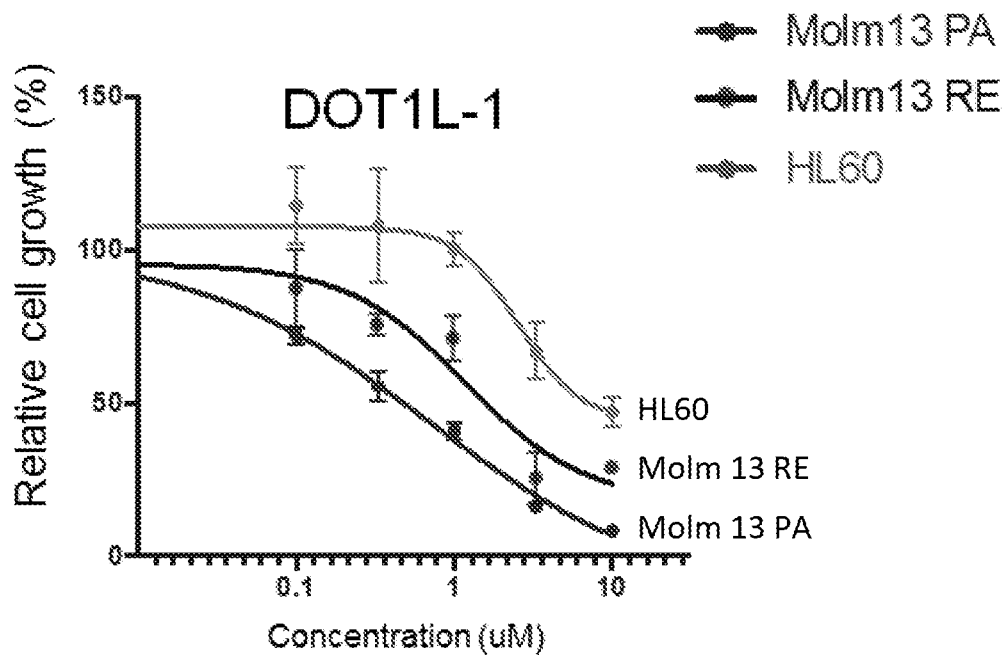
Figure 12B:
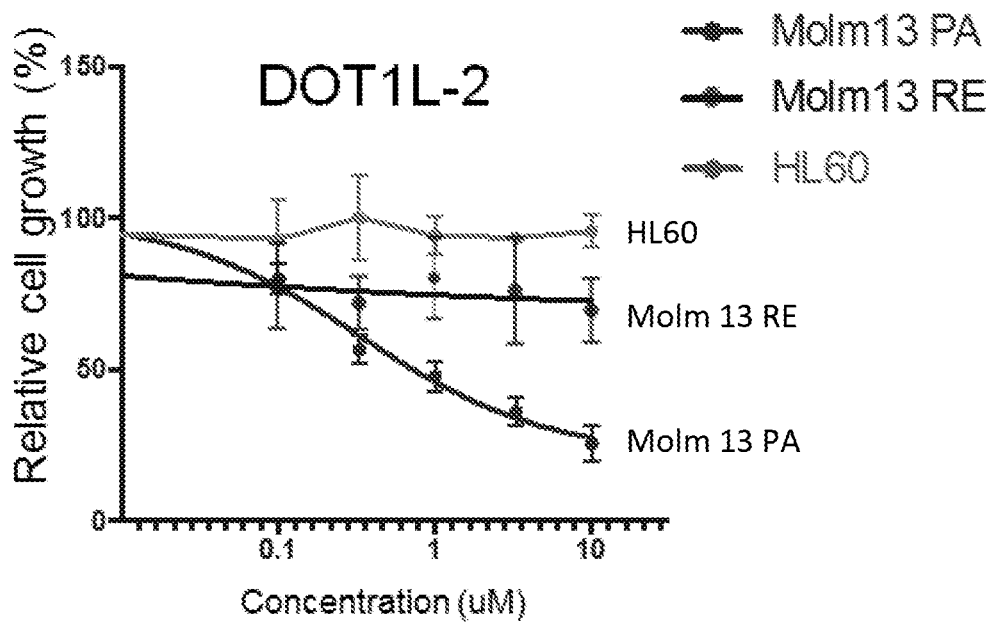
Figure 12C:
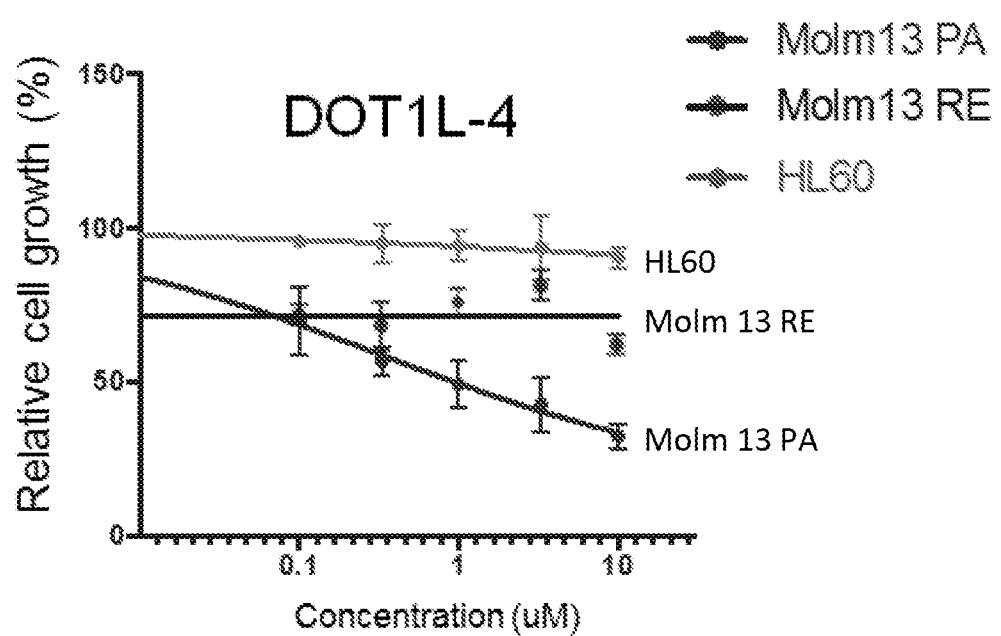
Figure 12D:
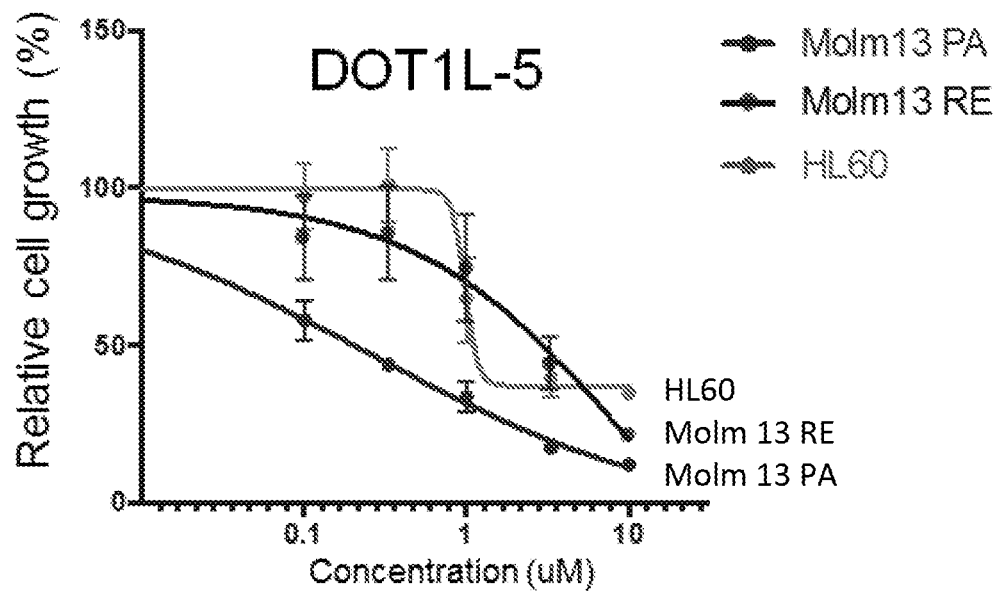
Figure 12E:
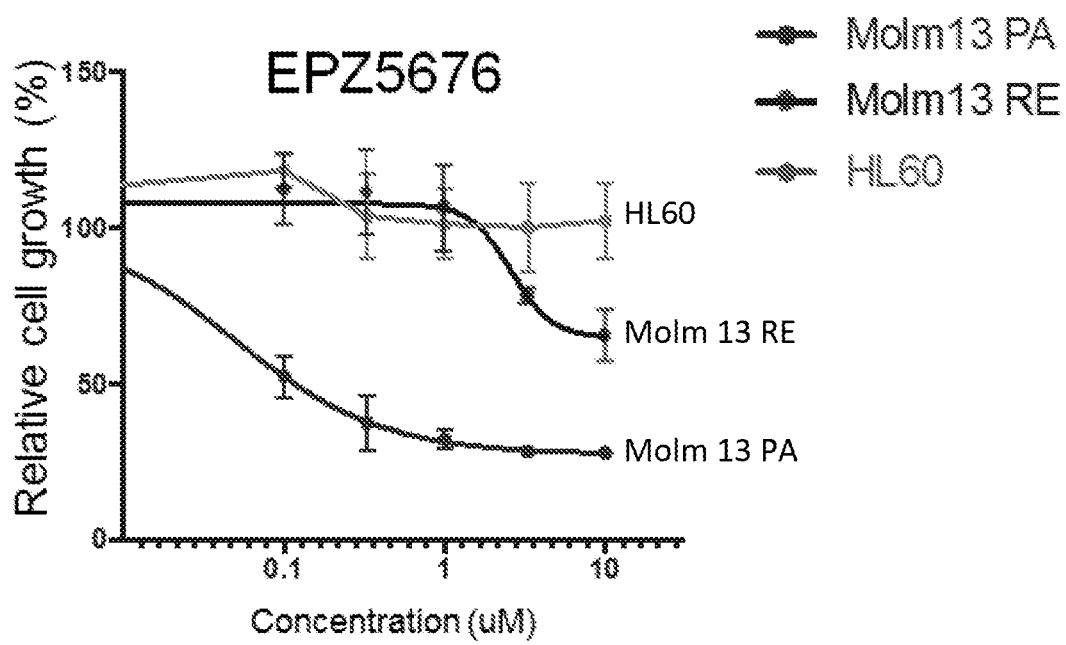

FIGS. 12A-12E show the relative cell growth (%) of acute myeloid leukemia cells, as indicated by the treatment of Molm13 PA cells, Molm13 RE cells, and HL60 (as negative control) cells with exemplary thalidomide-based, DOT1L degrader compounds at various concentrations for 10 days. FIG. 12A shows the results of cells treated with exemplary DOT1L degrader DOT1L-1. FIG. 12B shows the shows the results of cells treated with exemplary DOT1L degrader DOT1L-2. FIG. 12C shows the results of cells treated with exemplary DOT1L degrader DOT1L-4. FIG. 12D shows the results of cells treated with exemplary DOT1L degrader DOT1L-5. FIG. 12E shows the results of cells treated with negative control compound EPZ5676.

Figure 13:
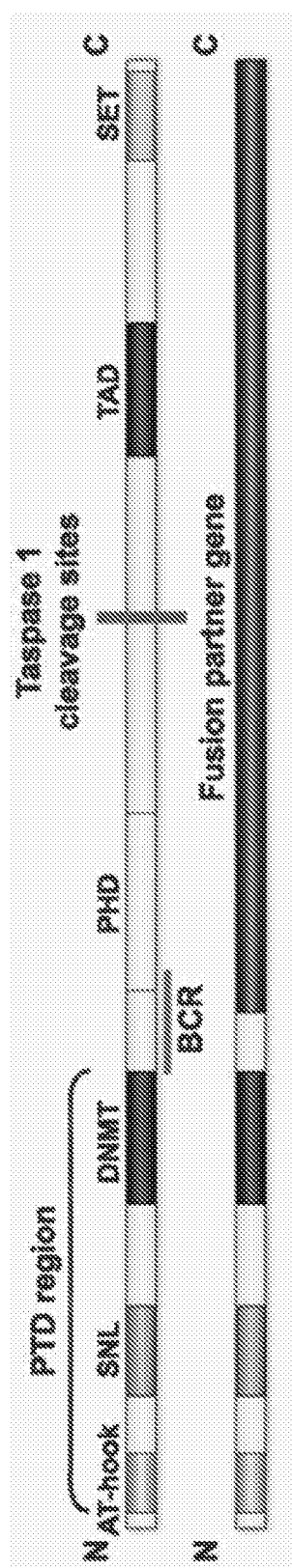

FIG. 13 shows the MLL-rearranged leukemia (Mixed-lineage leukemia-rearranged leukemia) gene. MLL rearranged leukemia constitutes 10% of adult leukemia and 70% of infant leukemia. There is generally a poor prognosis and MLL patients often suffer from early relapse after treatment with current therapies. Rearrangements of the MLL gene located at 11q23 are common chromosomal abnormalities associated with acute leukemia.

Figure 14A:
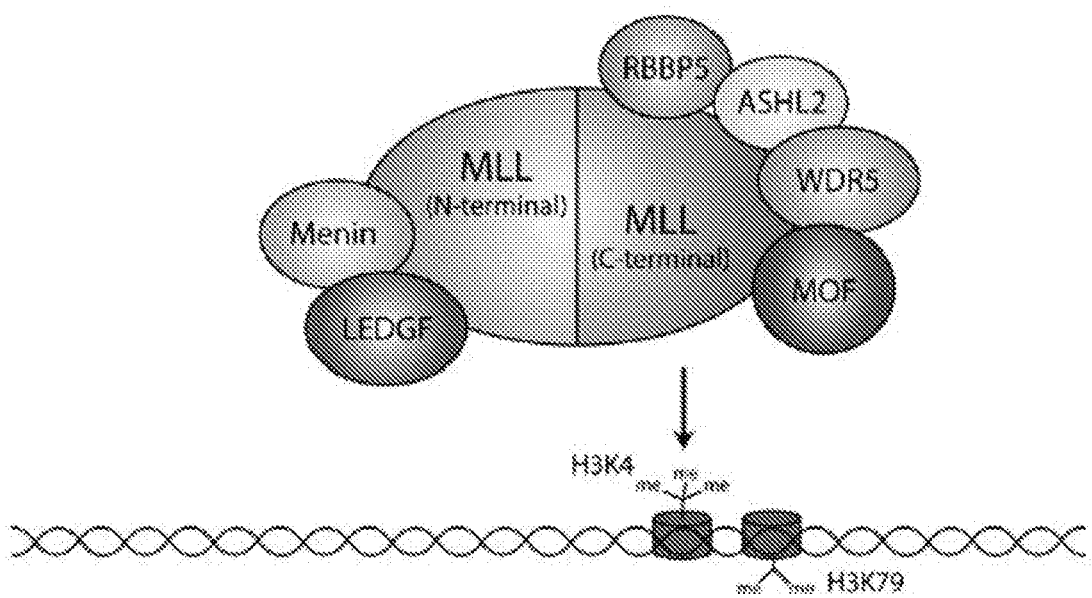
Figure 14B:
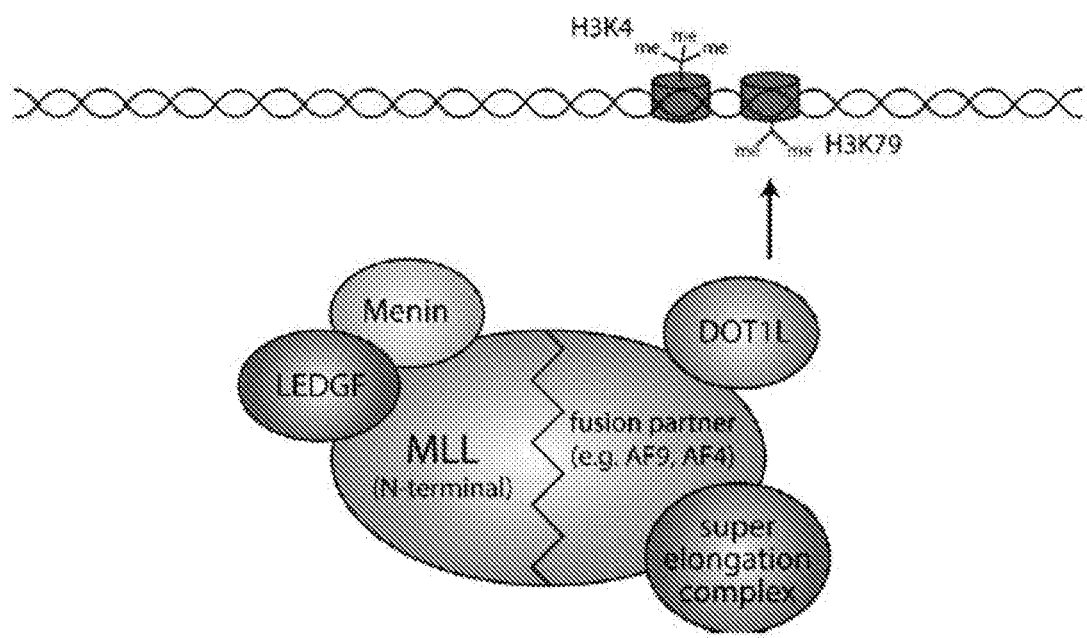

FIG. 14A shows wild-type MLL (Mixed-lineage leukemia) containing a SET domain histone methyltransferase in the C terminus that catalyzes the methylation at lysine 4 of histone 3 (H3K4). FIG. 14B shows MLL-rearrangements with a C-terminal portion that is replaced with over 70 known fusion patterns such as: AF4, AF9, AF6, AF10, ELL, ENL, etc. These fusion partners recruit DOT1L, which methylates lysine 79 of histone 3 (H3K79). H3K79me2 is a mark associated with active transcriptional elongation.

Figure 15:
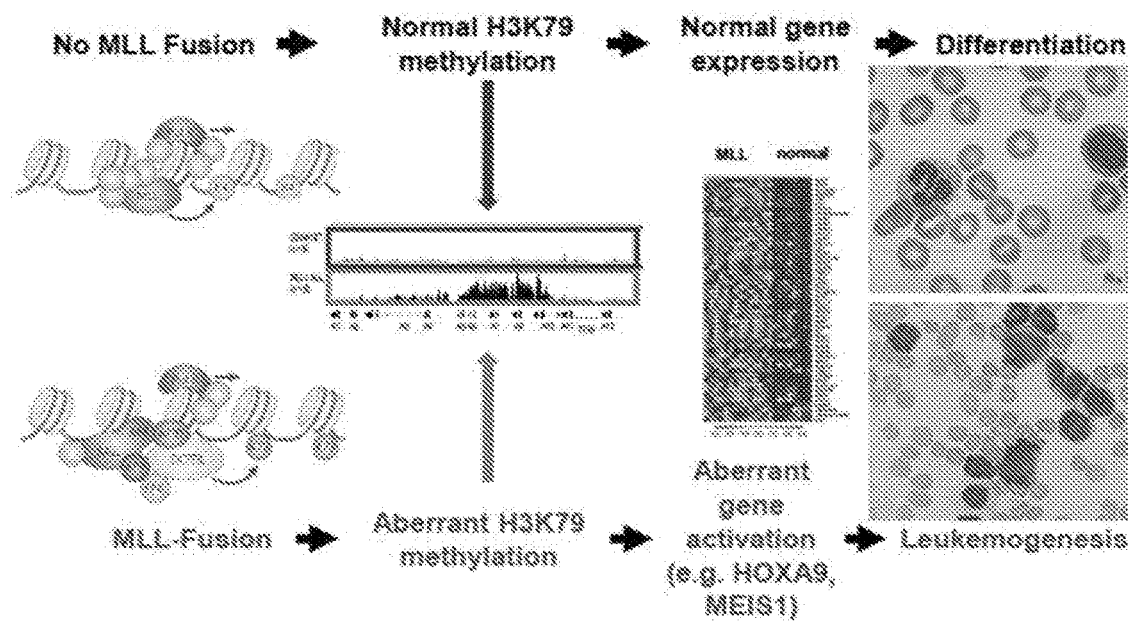

FIG. 15 shows DOT1L promotes MLL-r (Mixed-lineage leukemia-rearrangements) leukemia via Aberrant H3K79 methylation, which results in inappropriately enhanced expression of genes critical for hematopoietic differentiation and leukemogenesis.

Figure 16A:
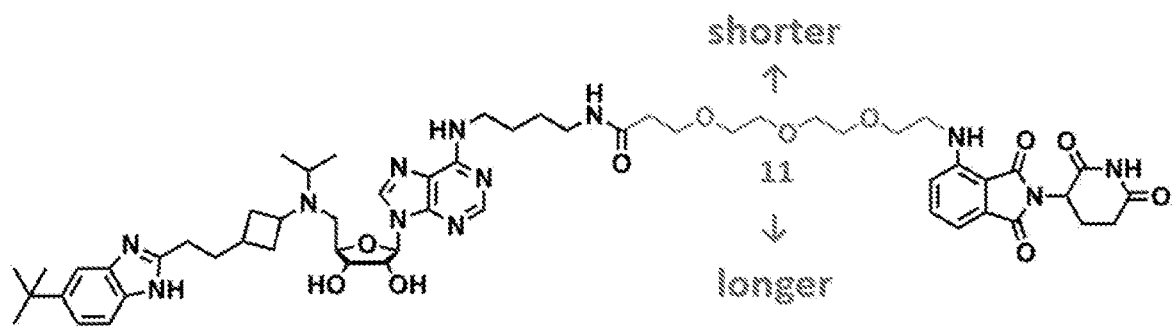
Figure 16B:
Figure 16C:
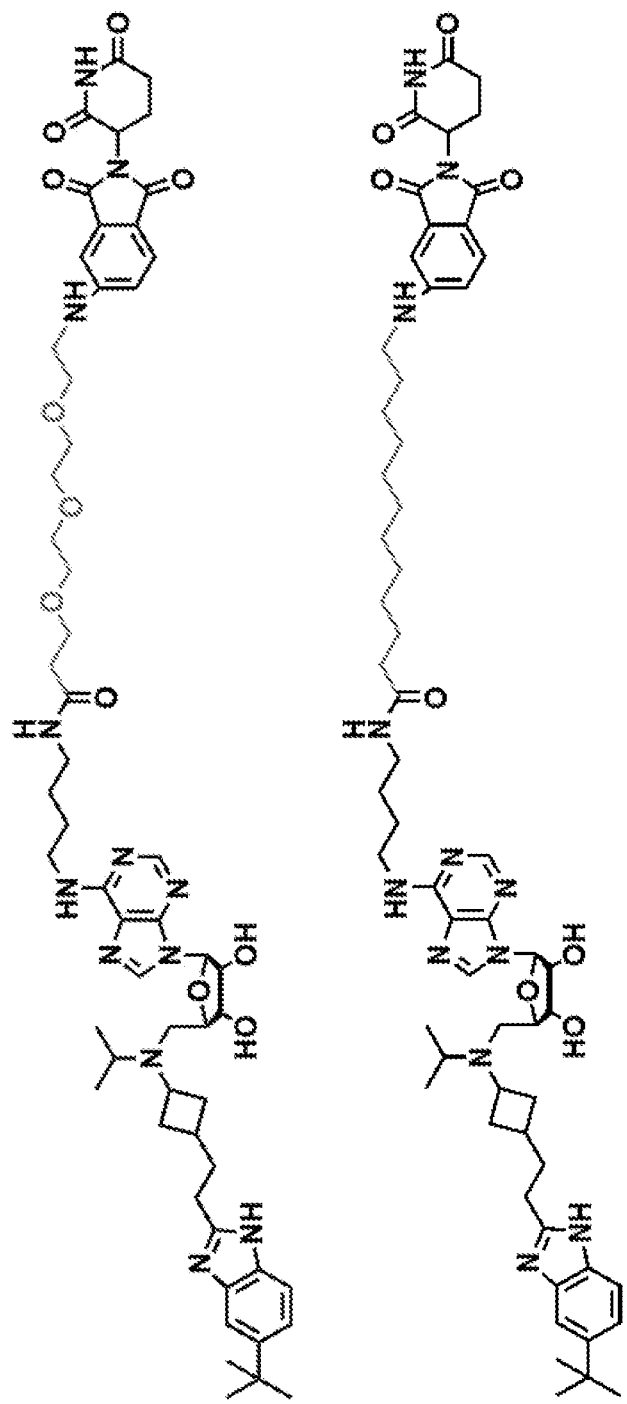

FIGS. 16A-16C shows a first round of exemplary degraders. FIG. 16A shows an exemplary linker length of a first round of exemplary degraders. FIG. 16B shows an exemplary linker position on the CRBN binding side of first round degraders. FIG. 16C shows exemplary degraders with PEG and alkyl linkers.

Figure 17A:
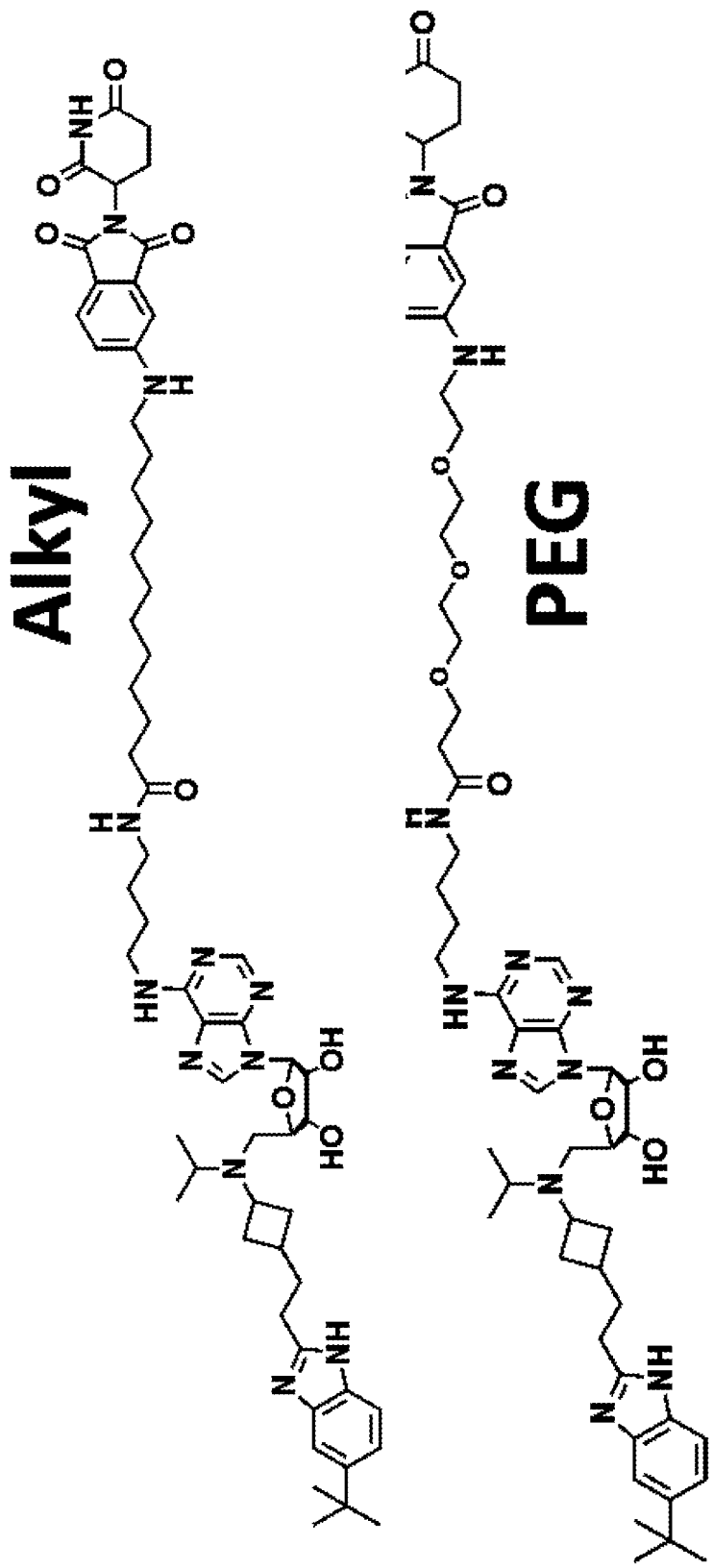
Figure 17D:
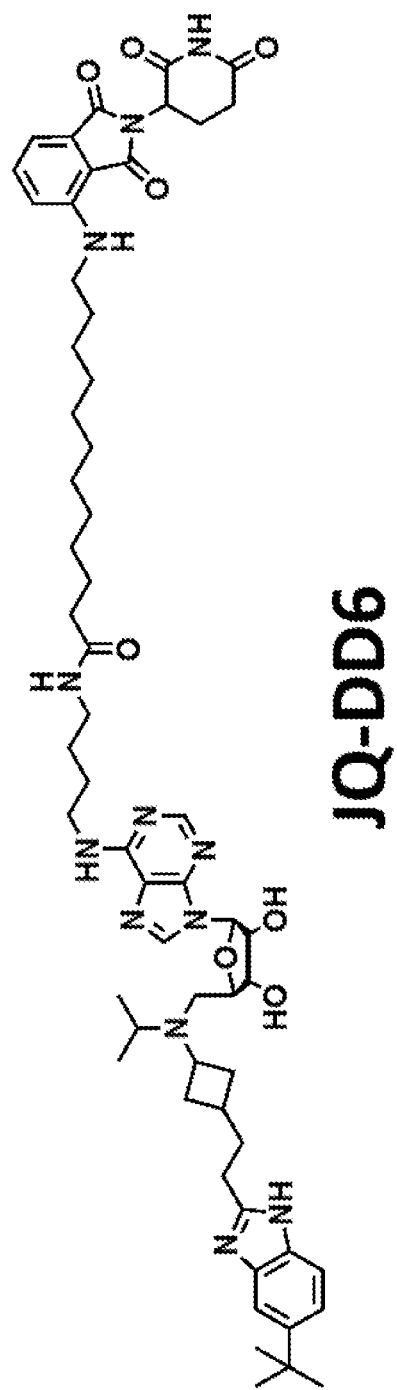

FIGS. 17A-17D show exemplary DOT1L degraders with different combinations of PEG or alkyl groups, varying linker length, and linker position on the CRBN binding site on the iMiDs. FIG. 17A shows exemplary DOT1L degraders with alkyl and PEG linkers, respectively. FIG. 17B shows exemplary DOT1L degraders, including one with linker length 11. FIG. 17C shows exemplary DOT1L degraders, including different linker positions on the CRBN binding site. FIG. 17D shows exemplary DOT1L degrader JQ-DD6.

Figure 18:
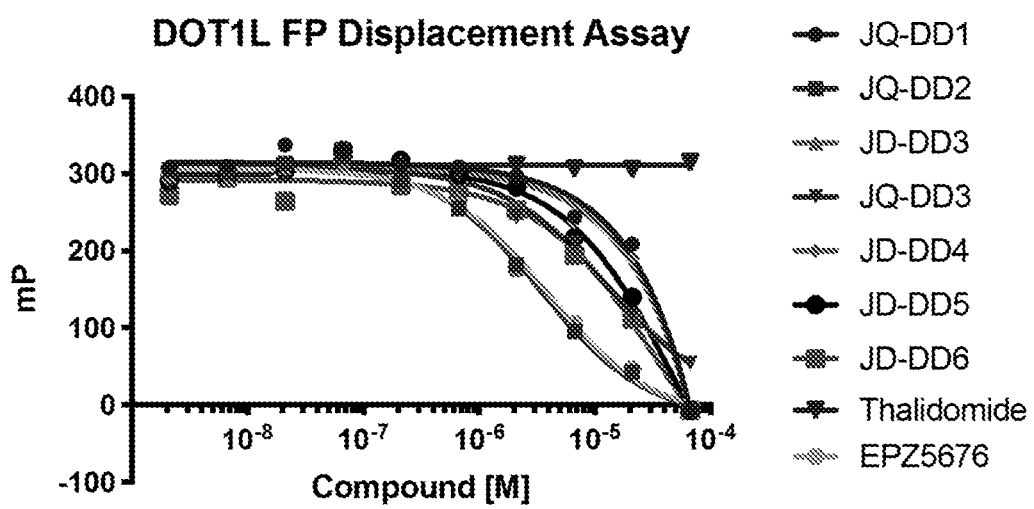

FIG. 18 shows a DOT1L Fluorescence Polarization (FP) displacement assay of tested exemplary DOT1L degrader compounds, and control compounds at different concentrations [M], measured in [M] per mP. The tested compounds include exemplary DOT1L degrader compounds JQ-DD1, JQ-DD2, JQ-DD3, JD-DD4, JD-DD5, JD-DD6, and positive control Thalidomide and negative control EPZ5676. The exemplary compounds show binding to each of DOT1L and CRBN.

Figure 19:
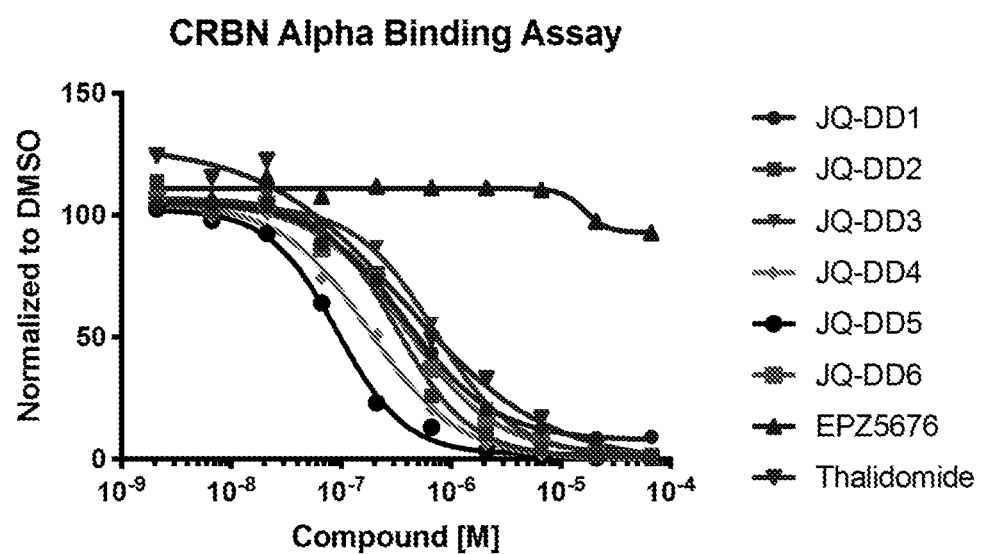

FIG. 19 shows a CRBN binding assay of exemplary DOT1L degrader compounds, negative control compounds, and positive control compounds at different concentrations [M], as indicated in concentration [M] versus mP. The compounds include exemplary DOT1L degrader compounds JQ-DD1, JQ-DD2, JQ-DD3, JQ-DD4, JQ-DD5; JQ-DD6; and positive control thalidomide and negative control EPZ5676.

Figure 20:
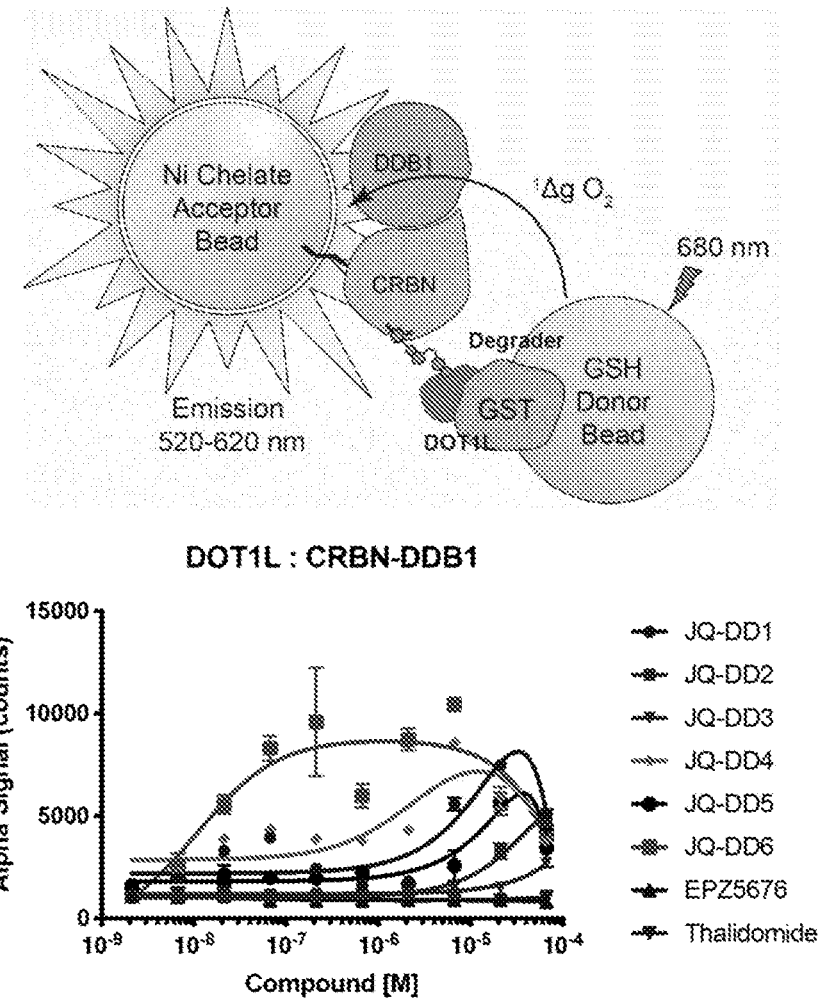

FIG. 20 shows a biochemical assay to determine the dimerization of CRBN with DOT1L induced by the degraders. This new assay checks if the exemplary compounds can dimerize CRBN and DOT1L in a biochemical assay setting. FIG. 20 shows that the exemplary compounds can bind to both proteins simultaneously. The JQ-DD6 gave the strongest signal, means it dimerizes the proteins very well. JQ-DD6 also works very well in the cell.

Figure 21:
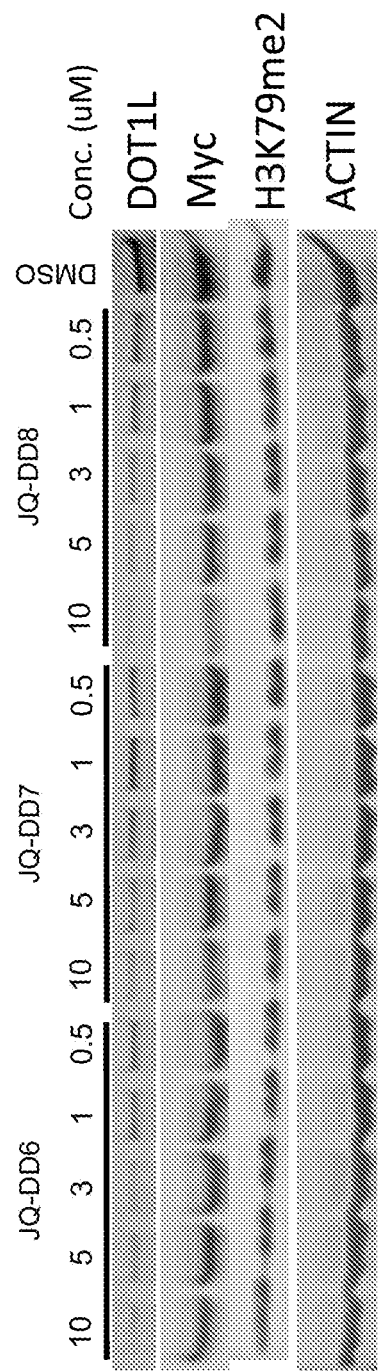

FIG. 21 shows EOL1 cells treated with exemplary DOT1L degrader compounds JQ-DD6, JQ-DD7, and JQ-DD8 with DOT1L, Myc, H3K79me2, and actin at the indicated concentrations for 24 hours and immunoblotted. EOL1 (acute myeloid (eosinophilic) leukemia cell line) has the highest DOT1L levels among all the cell lines, and confirmed JQ-DD6 gave solid degradation. JQ-DD7 and JQ-DD8 also show degradation in EOL1 cell lines. JQ-DD8 shows potential toxicity in EOL1 at 24 hours.

Figure 22:
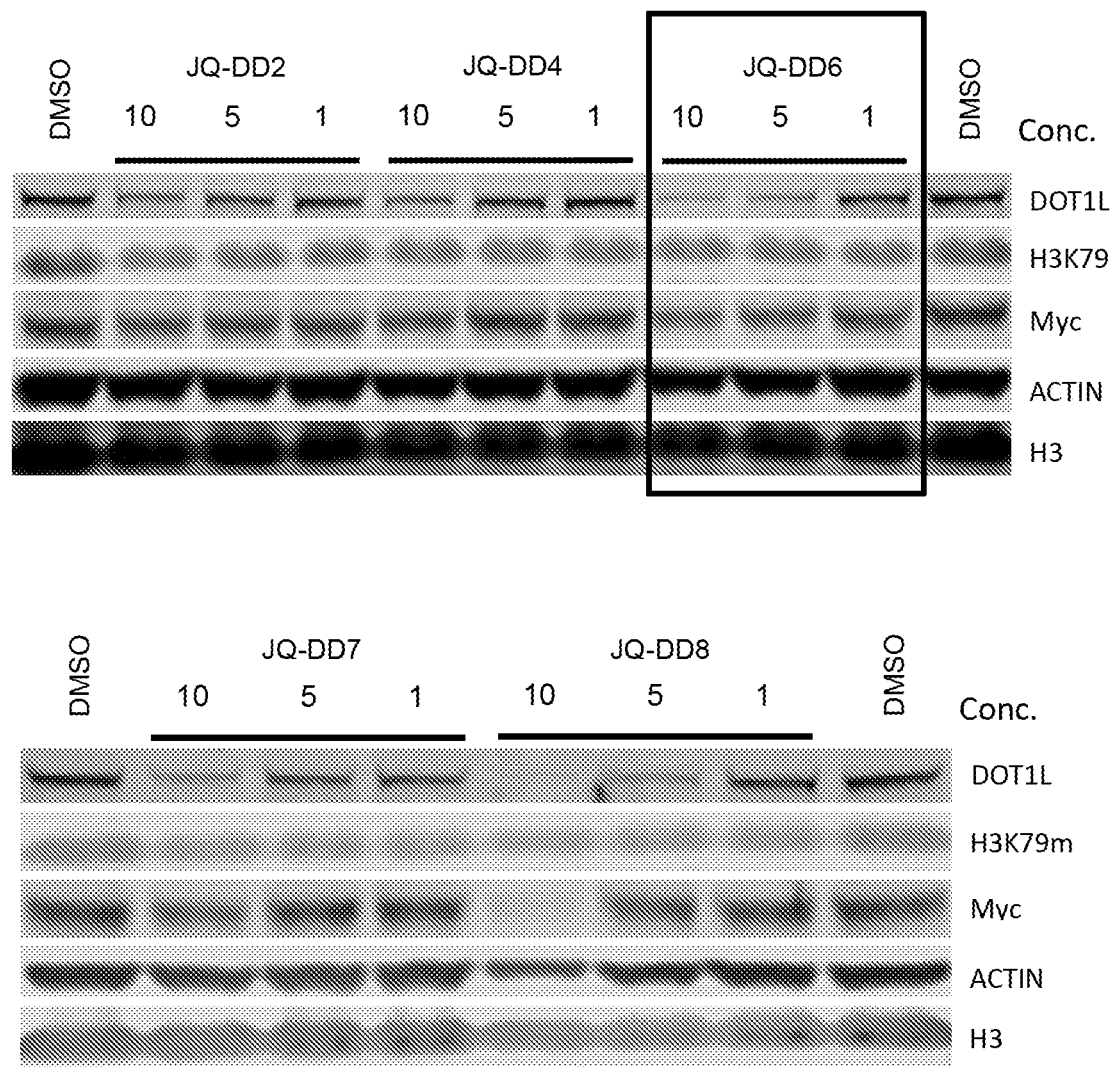

FIG. 22 shows EOL1 cells treated with exemplary DOT1L degrader compounds JQ-DD2, JQ-DD4, JQ-DD6, JQ-DD7, and JQ-DD8 with DOT1L, H3K79me2, Myc, actin, and H3 at the indicated concentrations for 48 hours and immunoblotted.

Figure 23:
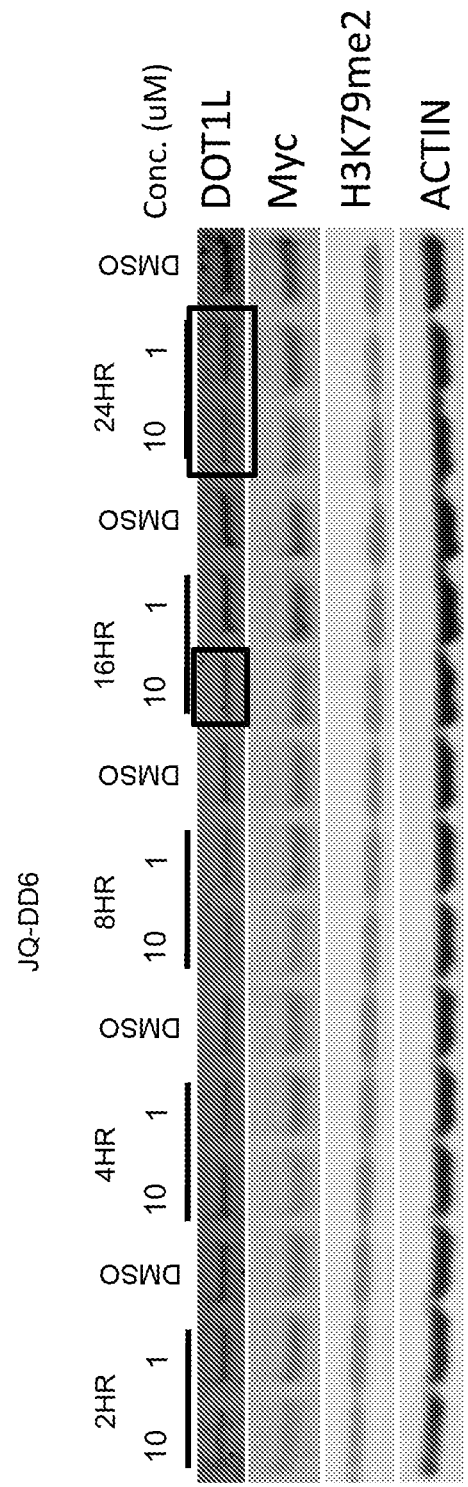

FIG. 23 shows EOL1 cells treated with exemplary DOT1L degrader compounds JQ-DD2, JQ-DD4, JQ-DD6, JQ-DD7, and JQ-DD8 with DOT1L, Myc, H3K79me2, and actin at the indicated concentrations for the indicated times and immunoblotted. This shows a time course of DOT1L degradation. With JQ-DD6, the degradation happened at 16 hours and maximum degradation occurs at 24 hours.

Figure 24:
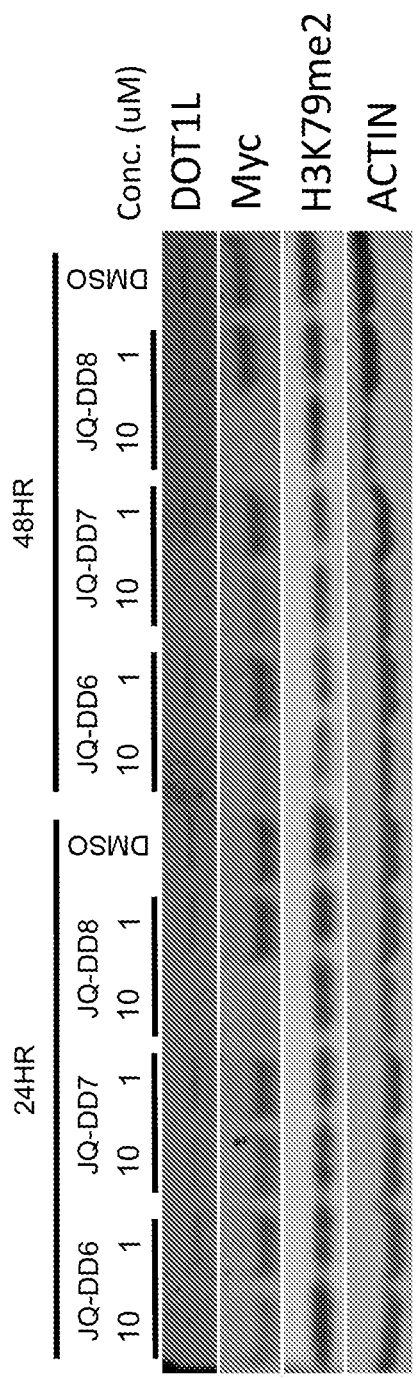

FIG. 24 shows EOL1 cells treated with exemplary DOT1L degrader compounds JQ-DD6, JQ-DD7, and JQ-DD8 with DOT1L, Myc, H3K79me2, and actin at the indicated concentrations for the indicated times and immunoblotted. The structures of compounds JQ-DD6 (JQDD6), JQ-DD7 (JQDD7), and JQ-DD8 (JQDD8) are shown in Table 1 below. FIG. 24 shows a time course of DOT1L degradation. Treatment with JQ-DD6 shows degradation. Treatment with JQ-DD7 and JQ-DD8 also shows degradation in EOL1 cell lines. Treatment with JQ-DD8 shows potential toxicity in EOL1 at 24 hours.

Figure 25:
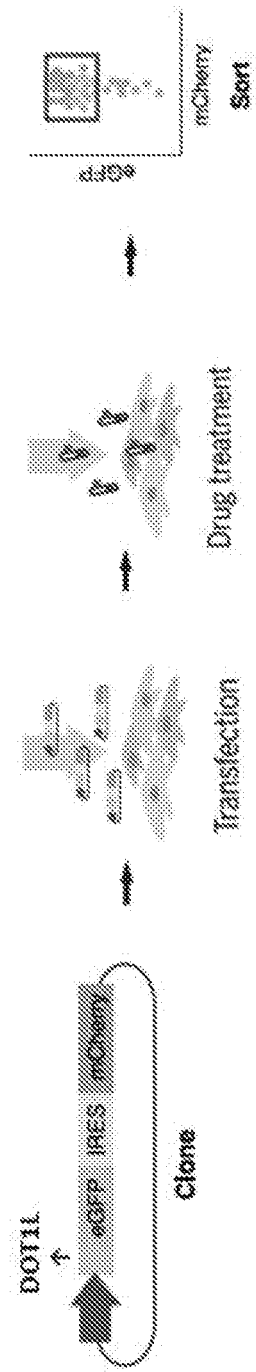

FIG. 25 shows the development of a DOT1L degradation reporting cell line with DOT1L tagged GFP and mcherry. This can directly report the targeted protein degradation. (See Sievers et al., *Science*, 2018).

Figure 26:
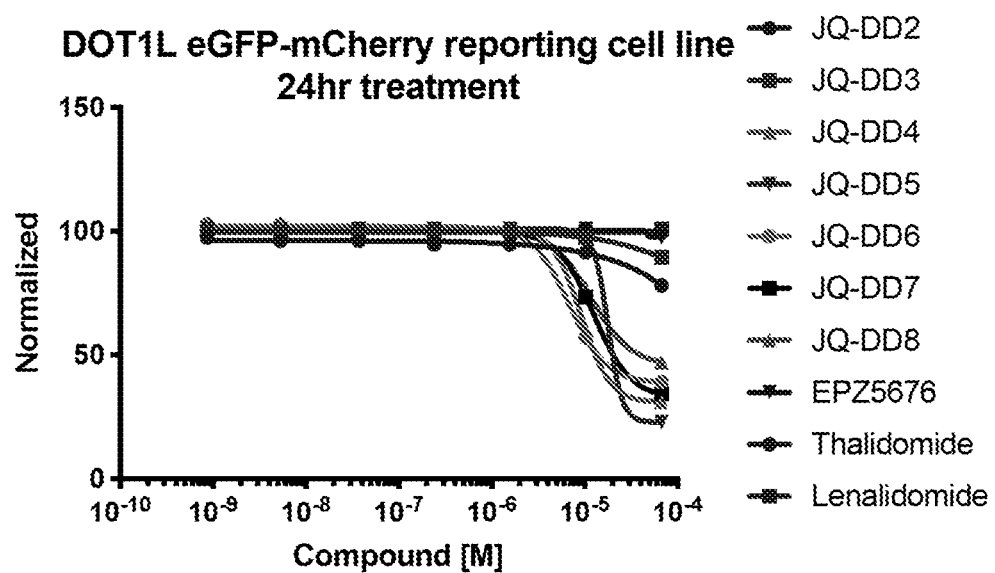

FIG. 26 shows a DOT1L degradation using eGFP-mCherry reporting cell line assay of tested exemplary DOT1L degrader compounds, and negative and positive control compounds at different concentrations [M], measured in [M] per mP upon the indicated 24 hour treatment. The tested compounds include exemplary DOT1L degrader compounds JQ-DD2, JQ-DD3, JQ-DD4, JQ-DD5, JQ-DD6, JQ-DD7, JQ-DD8, negative control EPZ5676, and positive controls thalidomide and lenalidomide. The eGFP-mCherry reporting cell line can report the degradation well in 24 hours. Exemplary compound JQ-DD6 showed the strongest signal for degradation of DOT1L.

Figure 27:
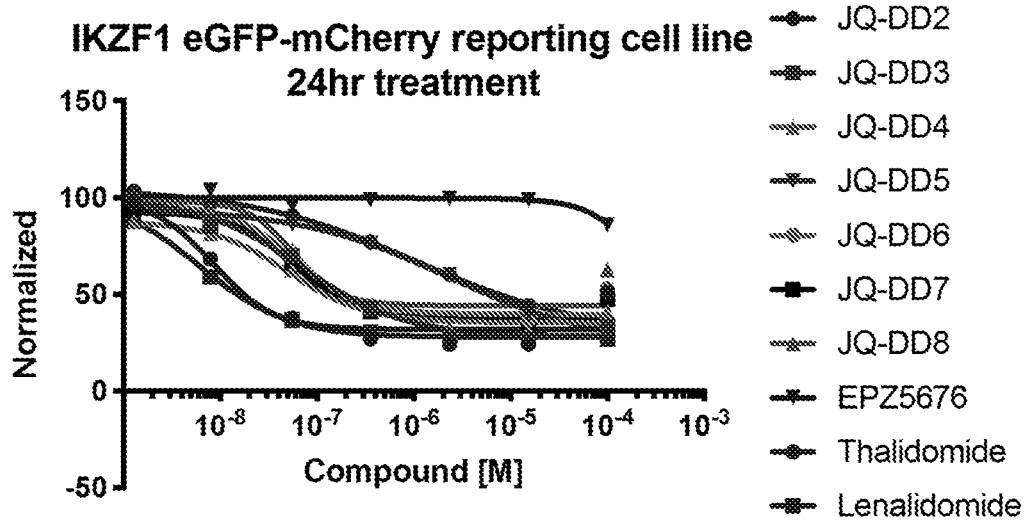

FIG. 27 shows an IKZF-degradation using eGFP-mCherry reporting cell line assay of tested exemplary DOT1L degrader compounds, and negative and positive control compounds at different concentrations [M], measured in [M] per mP upon the indicated 24 hour treatment. The tested compounds include exemplary DOT1L degrader compounds JQ-DD2, JQ-DD3, JQ-DD4, JQ-DD5, JQ-DD6, JQ-DD7, JQ-DD8, and negative control EPZ5676, and positive controls thalidomide and lenalidomide. The exemplary DOT1L degrader compounds also degrade the IKZF1, the neo substrate when immunomodulatory imide drugs (IMiDs) bind to CRBN.

Figure 28A:
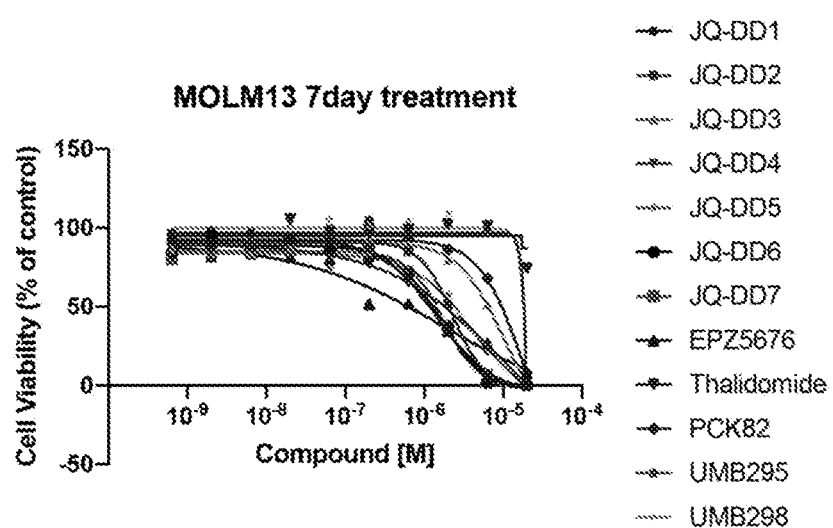
Figure 28B:
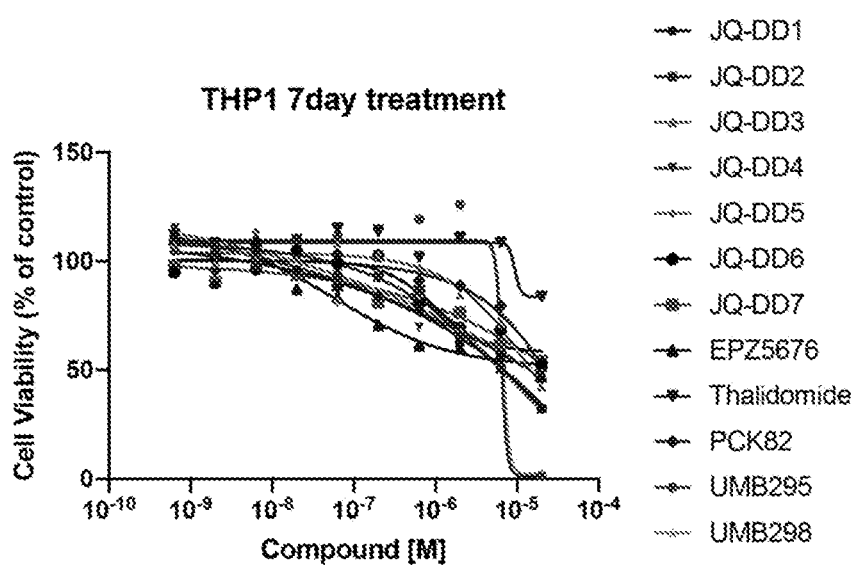

FIGS. 28A-28B show anti-proliferation effects of DOT1L degraders tested in MOLM13 and THP1 MLL-rearranged leukemia cell lines. FIG. 28A shows a MOLM13 7 day treatment assay of tested exemplary DOT1L degrader compounds, and positive control compounds at different concentrations [M], measured in [M] per mP. The tested compounds include exemplary DOT1L degrader compounds JQ-DD1, JQ-DD2, JQ-DD3, JQ-DD4, JQ-DD5, JQ-DD6, JQ-DD7, negative control EPZ5676, and positive control thalidomide. FIG. 28B shows a THP1 (human monocytic leukemia cells) 7 day treatment assay of tested exemplary DOT1L degrader compounds, and positive control compounds at different concentrations [M], measured in [M] per mP. The tested compounds include exemplary DOT1L degrader compounds JQ-DD1, JQ-DD2, JQ-DD3, JQ-DD4, JQ-DD5, JQ-DD6, JQ-DD7, negative control EPZ5676, and positive control thalidomide. The exemplary DOT1L degrader compounds show better anti-proliferative effects than inhibitor EPZ5676 in general. The exemplary DOT1L degrader compounds show better anti-proliferative effects than in the cell lines that rely on DOT1L but have no response with inhibitors. FIGS. 28A-28B show that DOT1L is deleted.

Figure 29A:
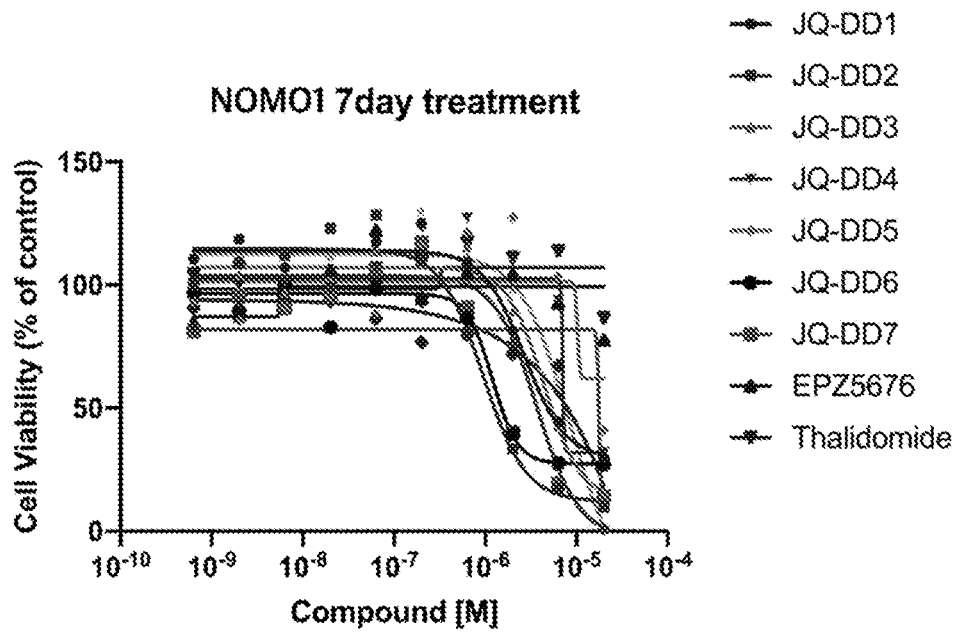
Figure 29B:
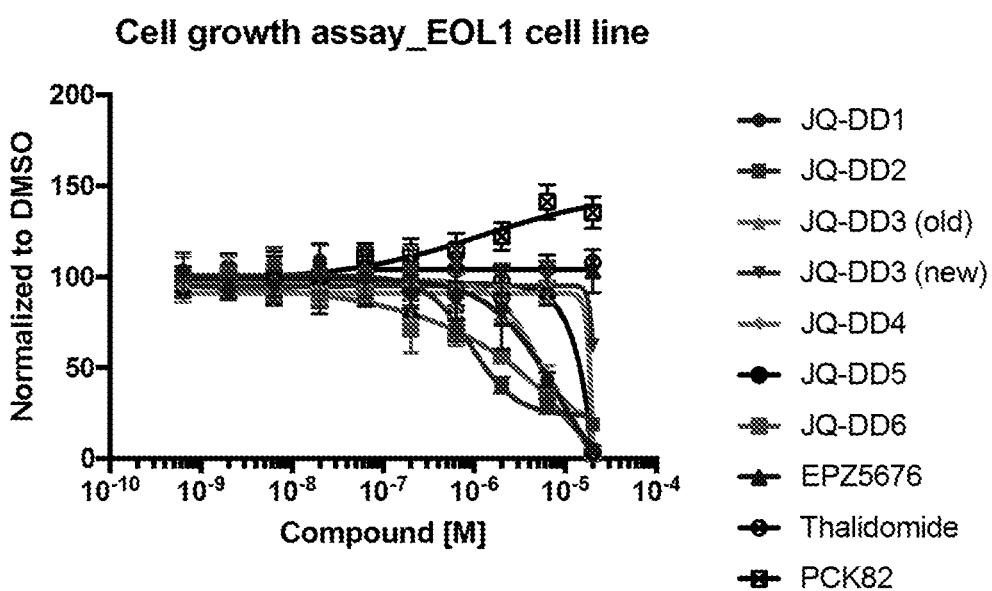

FIGS. 29A-29B show anti-proliferation effects of exemplary DOT1L degraders compared with inhibitors and iMiDs in different cell lines. FIG. 29A shows a NOMO1 (cancer cell line) 7 day treatment assay of tested exemplary DOT1L degrader compounds, inhibitors, and positive control iMiD compounds at different concentrations [M], measured in [M] per mP, and the percentage of viable cells following treatment over the indicated amount of time. The tested compounds include exemplary DOT1L degrader compounds JQ-DD1, JQ-DD2, JQ-DD3, JQ-DD4, JQ-DD5, JQ-DD6, JQ-DD7, negative control EPZ5676, and positive control thalidomide. FIG. 29B shows an EOL1 cell line cell growth assay of tested exemplary DOT1L degrader compounds, inhibitors, and positive control iMiD compounds at different concentrations [M], measured in [M] per mP, and the percentage of viable cells following treatment over the indicated amount of time. The tested compounds include exemplary DOT1L degrader compounds JQ-DD1, JQ-DD2, JQ-DD3 (old), JQ-DD3 (new), JQ-DD4, JQ-DD5, JQ-DD6, negative control EPZ5676, positive control thalidomide, and control PCK82.

Figure 30A:
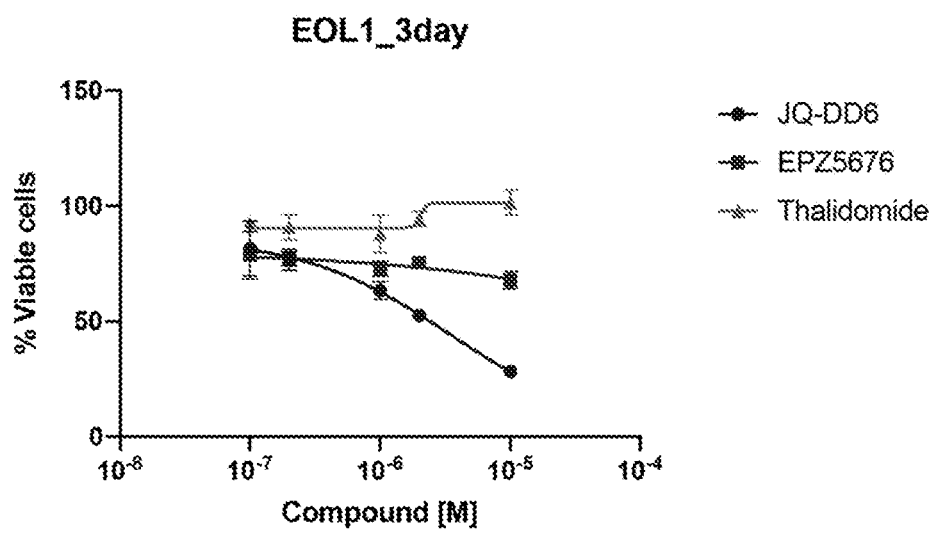
Figure 30B:
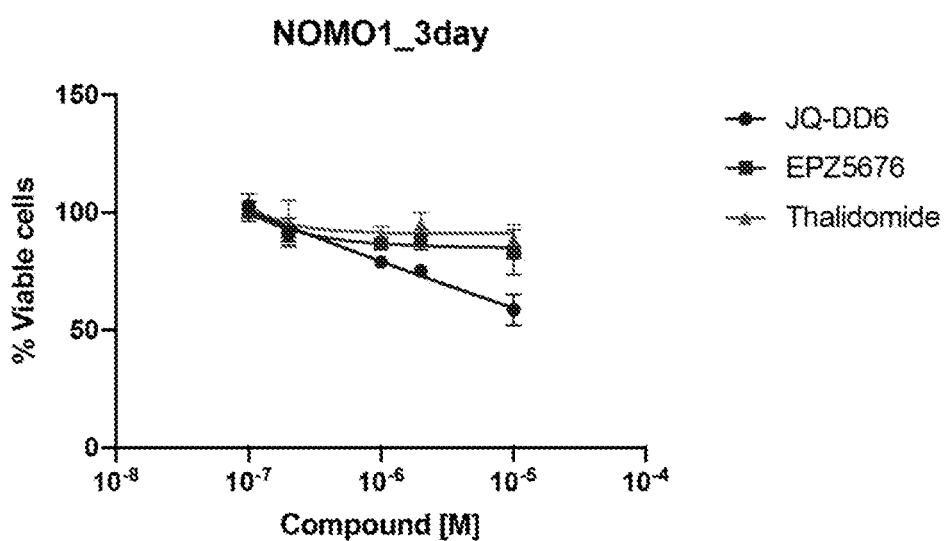
Figure 30C:
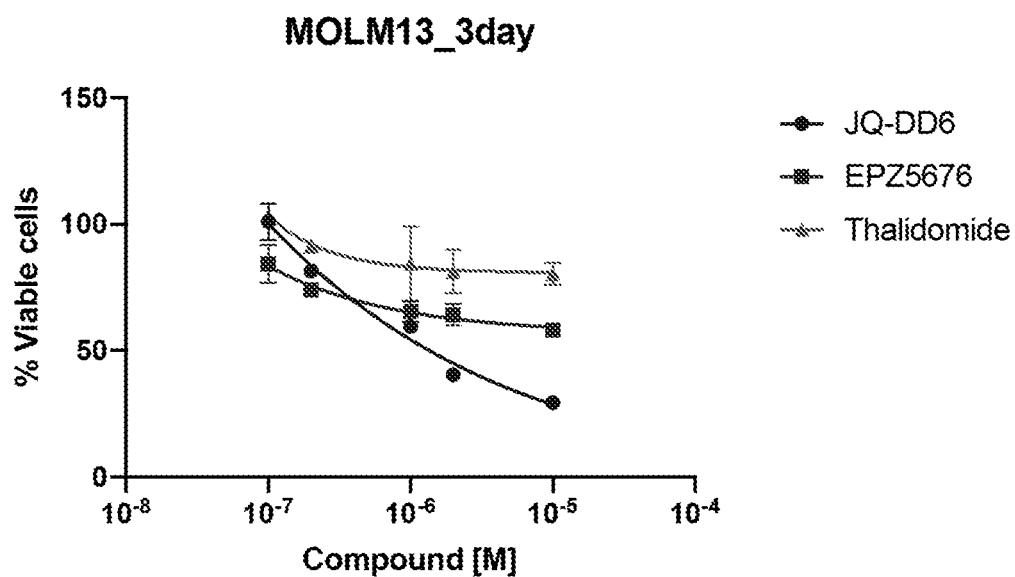
Figure 30D:
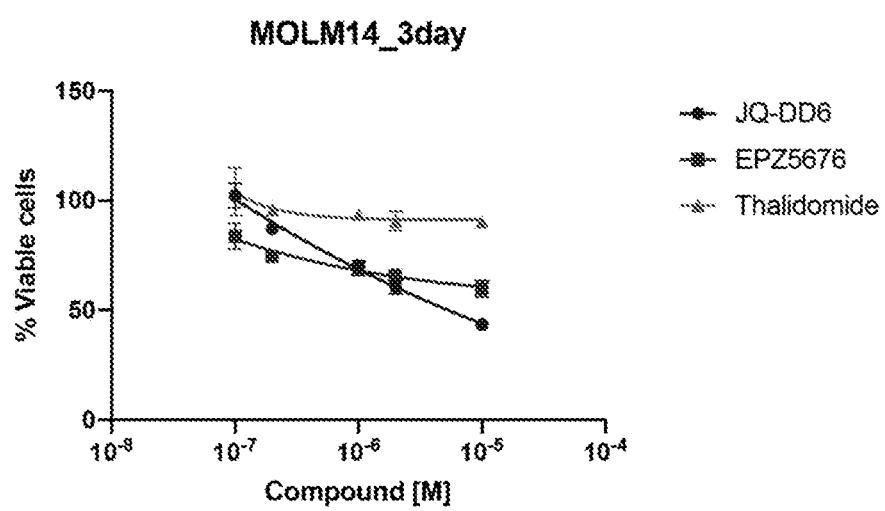
Figure 30E:
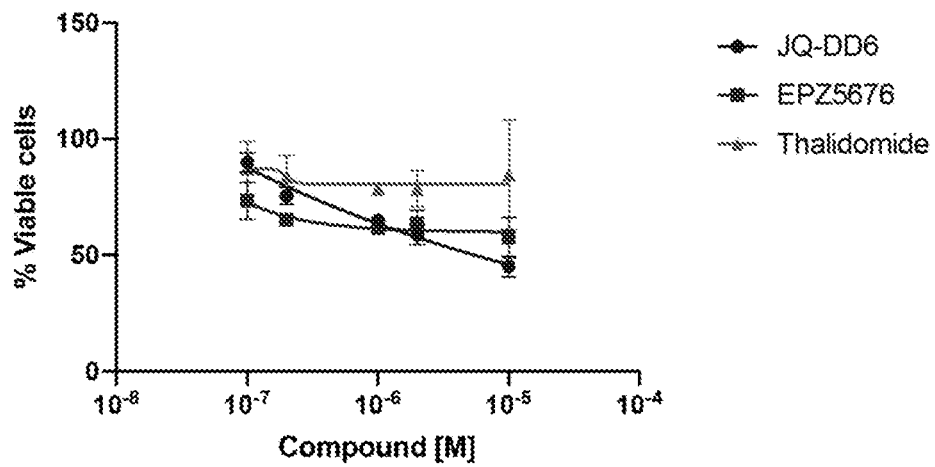

FIGS. 30A-30E show the percentage (%) of viable cells (in the indicated cancer cell lines), as indicated by the treatment with exemplary DOT1L degraders JQ-DD6, EPZ5676, and thalidomide on EOL1 cells, NOMO1 cells, MOLM13 cells, MOLM14 (human acute myeloid leukemia cell) cells, and MOLM14 crbnKO cell concentrations for 3 days. FIG. 30A shows the results in EOL1 cells. FIG. 30B shows the results in NOMO1 cells. FIG. 30C shows the results in MOLM13 cells. FIG. 30D shows the results in MOLM14 cells. FIG. 30E shows the results in MOLM14 crbnKO (CRBN knockout) cells.

Figure 31A:
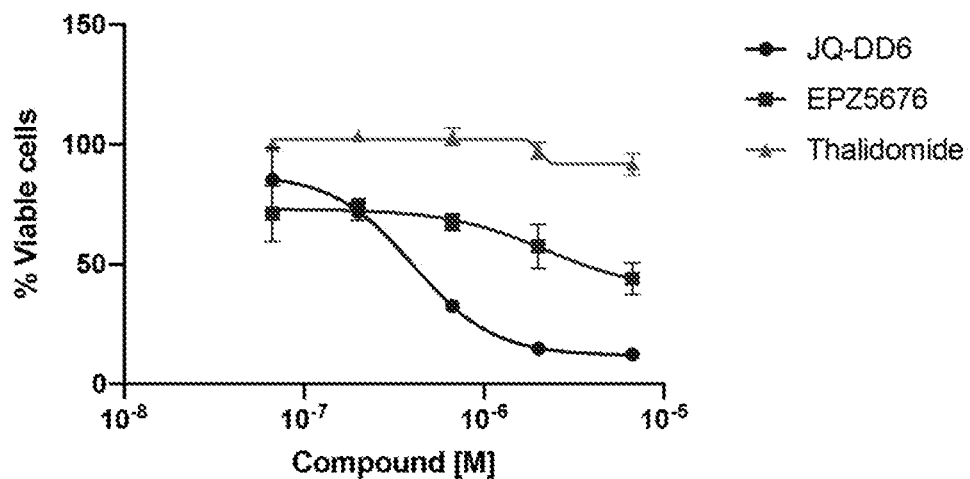
Figure 31B:
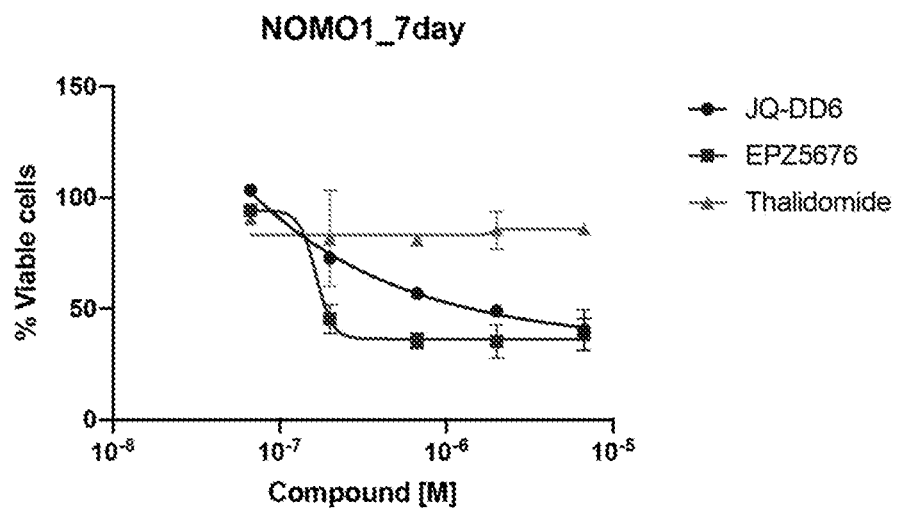
Figure 31C:
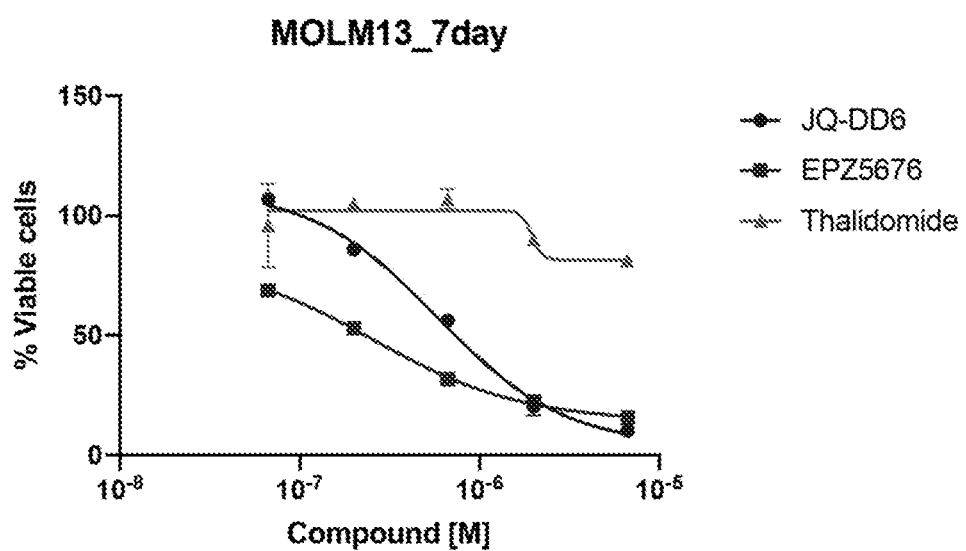
Figure 31D:
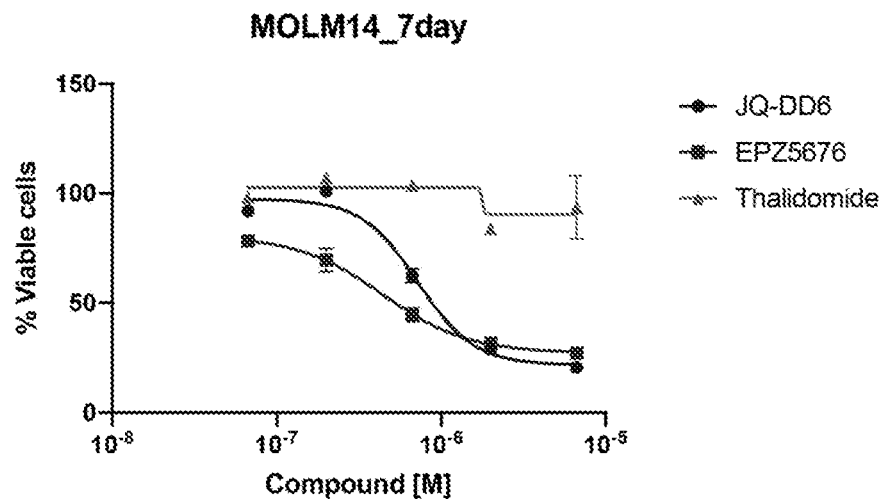
Figure 31E:
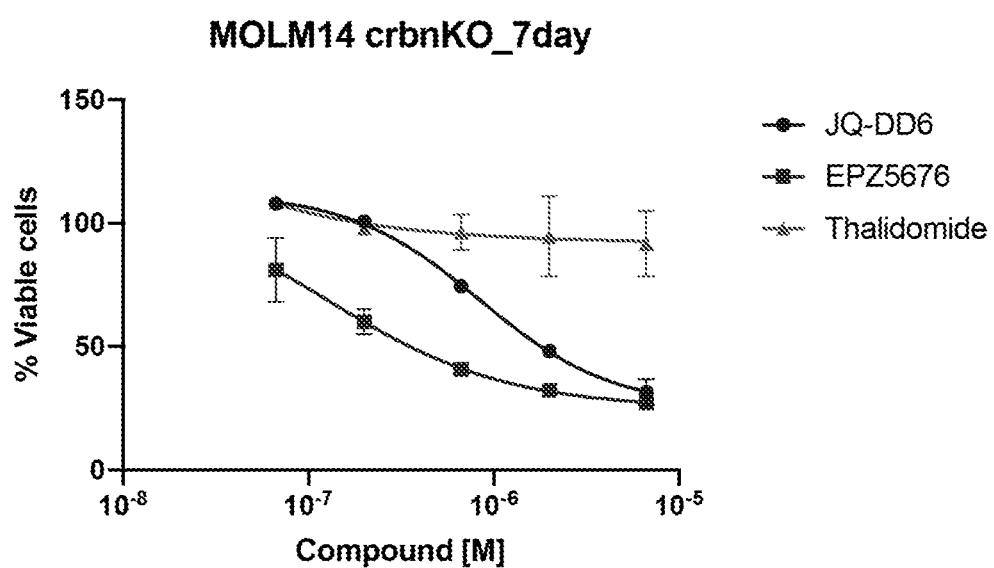

FIGS. 31A-31E show the (%) viable cells of acute myeloid leukemia cells, as indicated by the treatment with exemplary DOT1L degraders JQ-DD6, EPZ5676, and Thalidomide on EOL1 cells, NOMO1 cells, MOLM13 cells, MOLM14 cells, and MOLM14 crbnKO cells concentrations for 7 days. FIG. 31A shows the results in EOL1 cells. FIG. 31B shows the results in NOMO1 cells. FIG. 31C shows the results in MOLM13 cells. FIG. 31D shows the results in MOLM14 cells. FIG. 31E shows the results in MOLM14 crbnKO cells.

DETAILED DESCRIPTION OF CERTAIN EMBODIMENTS OF THE INVENTION

The bifunctional compounds described herein interact with an E3 ubiquitin ligase and the target protein DOT1L. As described herein, without wishing to be bound by any particular theory, the therapeutic effect may be the result of degradation, modulation, or binding of an E3 ubiquitin ligase (e.g., Cereblon) and the target protein DOT1L by a compound described herein. For example, the therapeutic effect may be a result of recruitment of an E3 ubiquitin ligase (e.g., Cereblon) by modulation, targeting, binding, or modification of the E3 ubiquitin ligase, which induces the ubiquitination of the target protein DOT1L, and its subsequent degradation by the proteasome. In certain embodiments, the therapeutic effect results from binding or modification of the E3 ubiquitin ligase, which induces the ubiquitination of the target protein DOT1L, and subsequent degradation of DOT1L.

A compound may be provided for use in any composition, kit, or method described herein as a pharmaceutically acceptable salt, co-crystal, tautomer, stereoisomer, solvate, hydrate, polymorph, isotopically enriched derivative, or prodrug thereof.

In certain embodiments, the E3 ubiquitin ligase binding moiety of the bifunctional compounds of Formula (I') is an E3 ubiquitin ligase binding moiety (based on an immunomodulatory imide drug (e.g., derivatives of lenalidomide or thalidomide, or lenalidomide or thalidomide) of the bifunctional compounds described in U.S. patent application U.S. Ser. No. 15/148,253, filed May 6, 2016, U.S. Ser. No. 14/707,930, filed May 8, 2015, U.S. Ser. No. 62/096,318, filed Dec. 23, 2014, U.S. Ser. No. 62/128,457, filed Mar. 4, 2015, and U.S. Ser. No. 62/149,170, filed Apr. 17, 2015, each of which is incorporated herein by reference.

In one aspect, disclosed are compounds of Formula (I'):

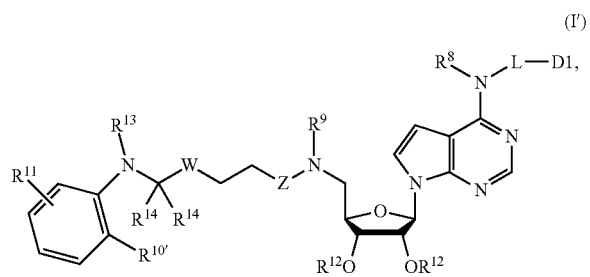

(I')

or a pharmaceutically acceptable salt, solvate, hydrate, tautomer, or stereoisomer thereof, wherein:

$R^8$ is hydrogen, optionally substituted alkyl, or a nitrogen protecting group;

$R^9$ is hydrogen, optionally substituted alkyl, or a nitrogen protecting group;

$R^{10'}$ is hydrogen, optionally substituted alkyl, or $-N(R^{10A})_2$;

each instance of $R^{10A}$ is independently hydrogen, optionally substituted alkyl, or a nitrogen protecting group;

$R^{11}$ is halogen or optionally substituted alkyl;

each instance of $R^{12}$ is independently hydrogen or an oxygen protecting group;

$R^{13}$ is hydrogen, optionally substituted alkyl, or a nitrogen protecting group; each instance of $R^{14}$ is independently hydrogen, halogen, or optionally substituted alkyl;

or, optionally wherein one instance of $R^{14}$ and one instance of $R^{10'}$ are taken together with their intervening atoms to form a substituted or unsubstituted heterocyclic or substituted or unsubstituted heteroaryl ring;

or, optionally wherein one instance of $R^{14}$ and one instance of $R^{10A}$ are taken together with their intervening atoms to form a substituted or unsubstituted heterocyclic or substituted or unsubstituted heteroaryl ring;

or, optionally wherein the moiety

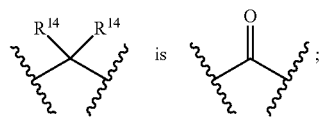

W is optionally substituted $-CH_2-$ or $-N(R^W)-$, wherein $R^W$ is hydrogen, optionally substituted alkyl, or a nitrogen protecting group;

Z is -(optionally substituted carbocyclyl)- or optionally substituted $-CH_2-$;

L is a linker; and

D1 is an E3 ubiquitin ligase binding moiety.

In certain embodiments, for a compound of Formula (I'):

$R^8$ is hydrogen, optionally substituted alkyl, or a nitrogen protecting group;

$R^9$ is hydrogen, optionally substituted alkyl, or a nitrogen protecting group;

$R^{10'}$ is hydrogen, optionally substituted alkyl, or $-N(R^{10A})_2$;

each instance of $R^{10A}$ is independently hydrogen, optionally substituted alkyl, or a nitrogen protecting group;

$R^{11}$ is halogen or optionally substituted alkyl;

each instance of $R^{12}$ is independently hydrogen or an oxygen protecting group;

$R^{13}$ is hydrogen, optionally substituted alkyl, or a nitrogen protecting group;

each instance of $R^{14}$ is independently hydrogen, halogen, or optionally substituted alkyl;

or, optionally wherein one instance of $R^{14}$ and one instance of $R^{10A}$ are taken together with their intervening atoms to form a substituted or unsubstituted heterocyclic or substituted or unsubstituted heteroaryl ring;

or, optionally wherein the moiety

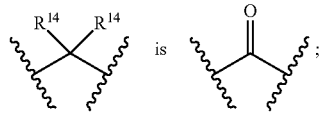

W is $-CH_2-$ or $-N(R^W)-$, wherein $R^W$ is hydrogen, optionally substituted alkyl, or a nitrogen protecting group;

Z is -(optionally substituted carbocyclyl)- or $-CH_2-$;

L is a linker; and

D1 is an E3 ubiquitin ligase binding moiety.

In certain embodiments, a compound of Formula (I') is a compound of Formula (I).

In one aspect, disclosed are compounds of Formula (I):

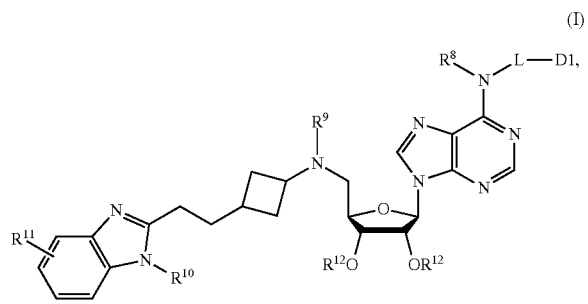

or a pharmaceutically acceptable salt, solvate, hydrate, tautomer, or stereoisomer thereof, wherein:

$R^8$ is hydrogen, optionally substituted alkyl, or a nitrogen protecting group;

$R^9$ is hydrogen, optionally substituted alkyl, or a nitrogen protecting group;

$R^{10}$ is hydrogen, optionally substituted alkyl, or a nitrogen protecting group;

$R^{11}$ is halogen or optionally substituted alkyl;

each instance of $R^{12}$ is independently hydrogen or an oxygen protecting group;

L is a linker; and

D1 is an E3 ubiquitin ligase binding moiety.

Group D

In certain embodiments, D1 is an E3 ubiquitin ligase binding moiety. D1 is inclusive of all moieties that bind, or can bind, any E3 ubiquitin ligase. For example, in certain embodiments, D1 is capable of binding an E3 ubiquitin ligase, such as Cereblon. In certain embodiments, D1 is capable of binding to multiple different E3 ubiquitin ligases. In certain embodiments, D1 binds to Cereblon. In certain embodiments, D1 is based on an immunomodulatory imide drug. In certain embodiments, D1 is derived from lenalidomide. In certain embodiments, D1 is derived from thalidomide.

Human Cereblon (CRBN) is a protein of 442 amino acids with an apparent molecular weight of ~51 kDa (GenBank: AAH17419). (For the CRBN protein sequence, see: Higgins et al., *Neurology.* 2004, 63, 1927-31. For additional information related to the CRBN structure see Hartmann et al., *PLoS One.* 2015, 10, e0128342.) Human CRBN contains the N-terminal part (237-amino acids from 81 to 317) of ATP-dependent Lon protease domain without the conserved Walker A and Walker B motifs, 11 casein kinase II phosphorylation sites, 4 protein kinase C phosphorylation sites, 1 N-linked glycosylation site, and 2 myristoylation sites. CRBN is widely expressed in testis, spleen, prostate, liver, pancreas, placenta, kidney, lung, skeletal muscle, ovary, small intestine, peripheral blood leukocyte, colon, brain, and retina. CRBN is located in the cytoplasm, nucleus, and peripheral membrane. (Chang et al., *Int. J. Biochem. Mol. Biol.* 2011, 2, 287-94.)

Cereblon is an E3 ubiquitin ligase, and it forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, Cereblon ubiquitination of target proteins results in increased levels of fibroblast growth factor 8 (FGF8) and fibroblast growth factor 10 (FGF10). FGF8, in turn, regulates a number of developmental processes, such as limb and auditory vesicle formation.

In certain embodiments, D1 is a modulator, binder, inhibitor, or ligand of Cereblon. In certain embodiments, D1 is a modulator of Cereblon. In certain embodiments, D1 is a binder of Cereblon. In certain embodiments, D1 is an inhibitor of Cereblon. In certain embodiments, D1 is a ligand of Cereblon. In certain embodiments, D1 is any modulator, binder, inhibitor, or ligand of Cereblon disclosed in U.S. patent application U.S. Ser. No. 14/792,414, filed Jul. 6, 2015, U.S. patent application U.S. Ser. No. 14/707,930, filed May 8, 2015, and International Patent Application, PCT/US2013/054663, filed Aug. 13, 2013, each of which is incorporated herein by reference. In certain embodiments, D1 is a modulator, binder, inhibitor, or ligand of a Cereblon variant. In certain embodiments, D1 is a modulator, binder, inhibitor, or ligand of a Cereblon isoform.

In certain embodiments, D1 comprises a heteroaryl ring. In certain embodiments, D1 comprises a fused bicyclic heteroaryl ring. In certain embodiments, D1 comprises a fused bicyclic heteroaryl ring and a heterocyclic ring. In certain embodiments, D1 comprises a fused bicyclic heteroaryl ring and a heterocyclic ring, where the heterocyclic ring contains at least one nitrogen. In certain embodiments, D1 comprises a fused bicyclic heteroaryl ring and a heterocyclic ring, where the fused bicyclic heteroaryl ring and heterocyclic ring each contain at least one nitrogen. In certain embodiments, D1 comprises a fused bicyclic heteroaryl ring and a heterocyclic ring, where the fused bicyclic heteroaryl ring and heterocyclic ring each contain one nitrogen. In certain embodiments, D1 comprises a phthalimido group, or an analogue or derivative thereof. In certain embodiments, D1 comprises a phthalimido-glutarimide group, or an analogue or derivative thereof.

In certain embodiments, D1 is of Formula (E-I):

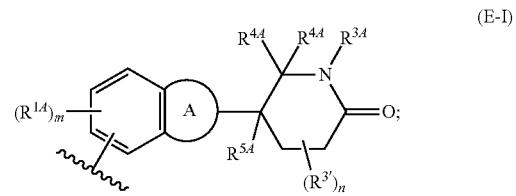

wherein:

Ring A is a substituted or unsubstituted heterocyclyl, or substituted or unsubstituted heteroaryl ring;

each $R^{1A}$ is, independently, halogen, —OH, $C_1$-$C_6$ alkyl, or $C_1$-$C_6$ alkoxy;

each $R^{3A}$ is, independently, H or $C_1$-$C_3$ alkyl;

each $R^Y$ is, independently, $C_1$-$C_3$ alkyl;

each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;

$R^{5A}$ is H, $C_1$-$C_3$ alkyl, F, or Cl;

m is 0, 1, 2, or 3; and n is 1 or 2.

In certain embodiments, Formula (E-I) is derived from an immunomodulatory imide drug (e.g., derived from lenalidomide or thalidomide). In certain embodiments, Formula (E-I) is of Formula (IA) or Formula (IB).

In certain embodiments, D1 is of Formula (IA):

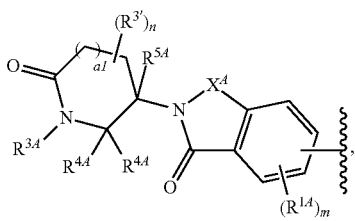

(IA)

wherein:
X$^A$ is C(O) or C(R$^3$)$_2$;
each R$^{1A}$ is independently halogen, OH, C$_1$-C$_6$ alkyl or C$_1$-C$_6$ alkoxy;
R$^{3A}$ is H or C$_1$-C$_3$ alkyl;
each R$^{3'}$ is independently C$_1$-C$_3$ alkyl;
each R$^{4A}$ is independently H or C$_1$-C$_3$ alkyl; or two R$^{4A}$, together with the carbon atom to which they are attached, form a C(O), C$_3$-C$_6$ carbocycle, or a 4-, 5-, or 6-membered heterocycle comprising 1 or 2 heteroatoms selected from N and O;
R$^{5A}$ is H, C$_1$-C$_3$ alkyl, or halogen;
m is 0, 1, 2, or 3;
n is 0, 1 or 2; and
a1 is 0 or 1.

In certain embodiments, D1 is of Formula (IA-a):

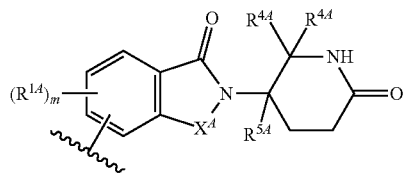

(IA-a)

wherein:
X$^A$ is C(O) or C(R$^{3A}$)$_2$;
each R$^{1A}$ is, independently, halogen, OH, C$_1$-C$_6$ alkyl, or C$_1$-C$_6$ alkoxy;
each R$^{4A}$ is, independently, H or C$_1$-C$_3$ alkyl; or two R$^{4A}$, together with the carbon atom to which they are attached, form a C(O), C$_3$-C$_6$ carbocycle, or a 4-, 5-, or 6-membered heterocycle comprising 1 or 2 heteroatoms selected from N and O;
R$^{5A}$ is H, C$_1$-C$_3$ alkyl, F, or Cl; and
m is 0, 1, 2, or 3.

In certain embodiments, D1 is of Formula (IA-b):

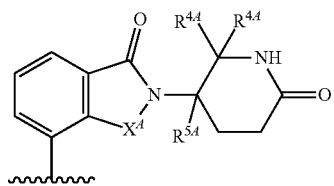

(IA-b)

wherein:
X$^A$ is C(O) or C(R$^{3A}$)$_2$;
each R$^{4A}$ is, independently, H or C$_1$-C$_3$ alkyl; or two R$^{4A}$, together with the carbon atom to which they are attached, form a C(O), C$_3$-C$_6$ carbocycle, or a 4-, 5-, or 6-membered heterocycle comprising 1 or 2 heteroatoms selected from N and O; and
R$^{5A}$ is H, C$_1$-C$_3$ alkyl, F, or Cl.

In certain embodiments, D1 is of Formula (IA-c):

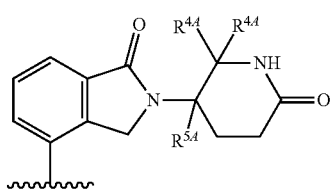

(IA-c)

wherein:
each R$^{4A}$ is, independently, H or C$_1$-C$_3$ alkyl; or two R$^{4A}$, together with the carbon atom to which they are attached, form a C(O), C$_3$-C$_6$ carbocycle, or a 4-, 5-, or 6-membered heterocycle comprising 1 or 2 heteroatoms selected from N and O; and
R$^{5A}$ is H, C$_1$-C$_3$ alkyl, F, or Cl.

In certain embodiments, D1 is of Formula (IA-d):

(IA-d)

wherein:
each R$^{4A}$ is, independently, H or C$_1$-C$_3$ alkyl; or two R$^{4A}$, together with the carbon atom to which they are attached, form a C(O), C$_3$-C$_6$ carbocycle, or a 4-, 5-, or 6-membered heterocycle comprising 1 or 2 heteroatoms selected from N and O; and
R$^{5A}$ is H, C$_1$-C$_3$ alkyl, F, or Cl.

In certain embodiments, D1 is of Formula (IB):

(IB)

wherein:
—X$^1$—X$^2$— is C(R$^{3A}$)═N or C(R$^{3A}$)$_2$—C(R$^{3A}$)$_2$;
each R$^{1A}$ is independently halogen, OH, C$_1$-C$_6$ alkyl, or C$_1$-C$_6$ alkoxy;
R$^{3A}$ is H or C$_1$-C$_3$ alkyl;
each R$^{3'}$ is independently C$_1$-C$_3$ alkyl;
each R$^{4A}$ is independently H or C$_1$-C$_3$ alkyl; or two R$^{4A}$, together with the carbon atom to which they are attached, form a C(O), C$_3$-C$_6$ carbocycle, or a 4-, 5-, or 6-membered heterocycle comprising 1 or 2 heteroators selected from N and O;
R$^{5A}$ is H, C$_1$-C$_3$ alkyl, or halogen:
m is 0, 1, 2, or 3;

n is 0, 1, or 2; and
a1 is 0 or 1.

In certain embodiments, D1 is of Formula (IB-a):

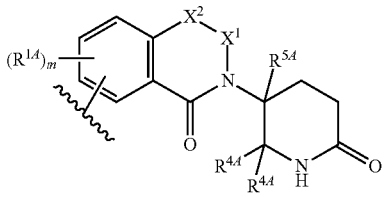

(IB-a)

wherein:
$X^1$—$X^2$ is $C(R^{3A})$=N or $C(R^{3A})_2$—$C(R^{3A})_2$;
each $R^{1A}$ is, independently, halogen, —OH, $C_1$-$C_6$ alkyl, or $C_1$-$C_6$ alkoxy;
each $R^{3A}$ is, independently, H or $C_1$-$C_3$ alkyl;
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, $C_1$-$C_3$ alkyl, F, or Cl; and
m is 0, 1, 2, or 3.

In certain embodiments, D1 is of Formula (IB-b):

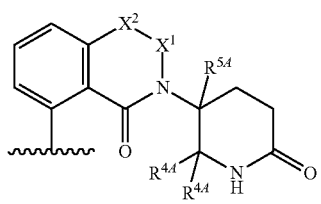

(IB-b)

wherein:
$X^1$—$X^2$ is $C(R^{3A})$=N or $C(R^{3A})_2$—$C(R^{3A})_2$;
each $R^{3A}$ is, independently, H or $C_1$-$C_3$ alkyl;
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, $C_1$-$C_3$ alkyl, F, or Cl.

In certain embodiments, D1 is of Formula (IB-c):

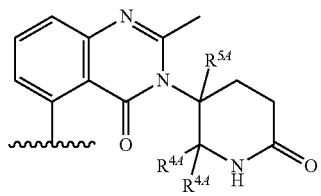

(IB-c)

wherein:
each $R^{4A}$ is, independently, H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, $C_1$-$C_3$ alkyl, F, or Cl.

Formulae (IA), (IA-a), and (IA-b) include substituent $X^A$. In certain embodiments, $X^A$ is C(O). In certain embodiments, $X^A$ is $C(R^{3A})_2$.

Formulae (IB), (IB-a), and (IB-b) include substituents —$X^1$—$X^2$—. In certain embodiments, —$X^1$—$X^2$— is $C(R^{3A})$=N. In certain embodiments, —$X^1$—$X^2$— is C(H)=N. In certain embodiments, —$X^1$—$X^2$— is $C(C_1$-$C_3$ alkyl)=N. In certain embodiments, —$X^1$—$X^2$— is $C(R^{3A})_2$—$C(R^{3A})_2$. In certain embodiments, —$X^1$—$X^2$— is $C(H)_2$—$C(H)_2$. In certain embodiments, —$X^1$—$X^2$— is $C(H)_2$—$C(C_1$-$C_3$ alkyl$)_2$. In certain embodiments, —$X^1$—$X^2$— is $C(H)_2$—$C(C_1$-$C_3$ alkyl$)_2$. In certain embodiments, —$X^1$—$X^2$— is $C(C_1$-$C_3$ alky$)_2$-$C(H)_2$—. In certain embodiments, —$X^1$—$X^2$— is $C(C_1$-$C_3$ alkyl$)_2$-$C(C_1$-$C_3$ alkyl$)_2$.

In Formulae (IB), (IB-a), and (IB-b), in certain embodiments, the moiety

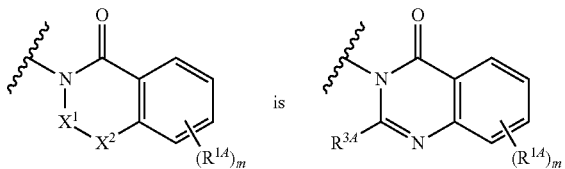

In certain embodiments, the moiety

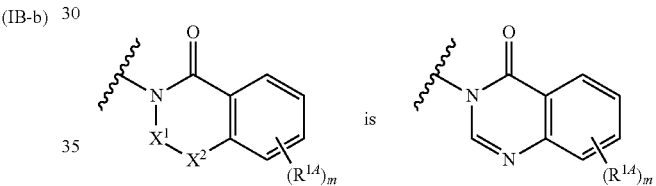

In certain embodiments, the moiety

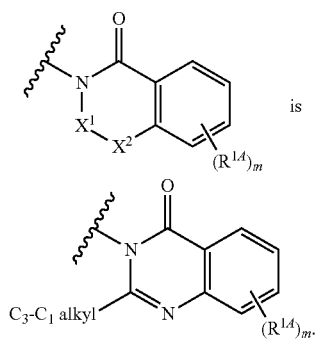

In certain embodiments, the moiety

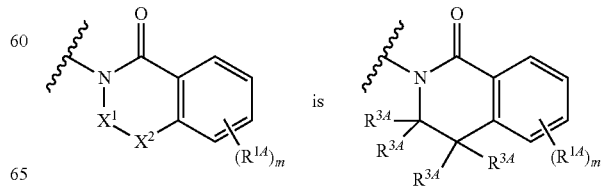

In certain embodiments, the moiety

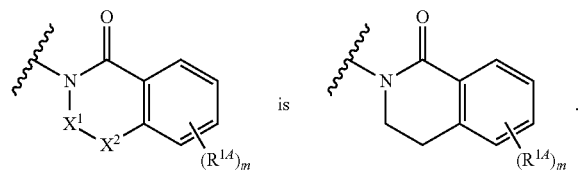

is

In certain embodiments, the moiety

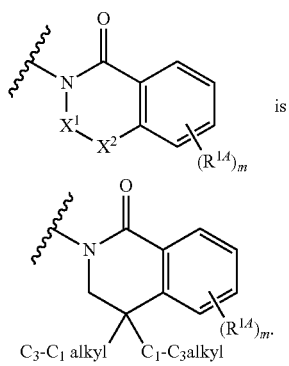

is

In certain embodiments, the moiety

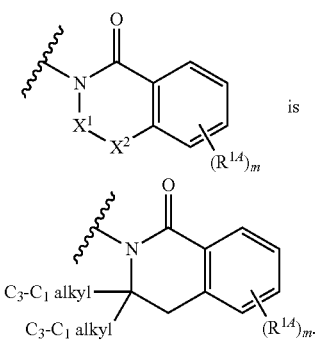

is

In certain embodiments, the moiety

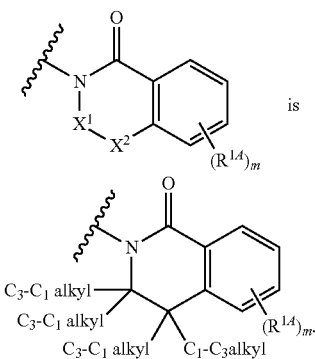

Formula (E-I) includes Ring A. In certain embodiments, Ring A is a substituted or unsubstituted heterocyclyl ring. In certain embodiments, Ring A is a substituted or unsubstituted heterocyclyl ring, which is a 3- to 10-membered non-aromatic ring system having ring carbon atoms and 1 to 4 ring heteroatoms, wherein each heteroatom is independently selected from nitrogen, oxygen, or sulfur. In certain embodiments, Ring A is a substituted or unsubstituted heteroaryl ring. In certain embodiments, Ring A is a substituted or unsubstituted heterocyclyl ring, which is a 5-10 membered monocyclic or bicyclic 4n+2 aromatic ring system having ring carbon atoms and 1-4 ring heteroatoms provided in the aromatic ring system, wherein each heteroatom is independently selected from the group consisting of nitrogen, oxygen, and sulfur. In certain embodiments, Ring A is a substituted or unsubstituted pyrrolidin-2-one. In certain embodiments, Ring A is a substituted or unsubstituted pyrrolidine-2,5-dione. In certain embodiments, Ring A is a substituted or unsubstituted 5,6-dihydropyrimidin-4(3H)-one. In certain embodiments, Ring A is a substituted or unsubstituted tetrahydropyrimidin-4(1H)-one.

Formulae (E-I), (IA-a), (IA), (IB), and (IB-a) include substituent $R^{1A}$. In certain embodiments, $R^{1A}$ is independently halogen, OH, $C_1$-$C_6$ alkyl, or $C_1$-$C_6$ alkoxy. In certain embodiments, at least one instance of $R^{1A}$ is halogen (e.g., F, Cl, Br, or I). In certain embodiments, at least one instance of $R^{1A}$ is OH. In certain embodiments, at least one instance of $R^{1A}$ is $C_1$-$C_6$ alkyl (e.g., methyl, ethyl). In certain embodiments, at least one instance of $R^{1A}$ is $C_1$-$C_6$ alkoxy (e.g., methoxy, ethoxy). In certain embodiments, m is 0. In certain embodiments, m is 1. In certain embodiments, m is 2. In certain embodiments, m is 3.

Formulae (E-I), (IA), (IB), (IB-a), and (IB-b) include substituent $R^{3A}$. In certain embodiments, $R^{3A}$ is H. In certain embodiments, $R^{3A}$ is $C_1$-$C_3$ alkyl (e.g. methyl, ethyl). In certain embodiments, at least one instance of $R^{3'}$ is $C_1$-$C_3$ alkyl (e.g., methyl, ethyl). In certain embodiments, at least one instance of $R^{3'}$ is methyl. In certain embodiments, at least one instance of RT is ethyl. In certain embodiments, n is 0. In certain embodiments, n is 1. In certain embodiments, n is 2.

Formulae (E-I), (IA-a), (IA-b), (IA-c), (IA-d), (IA), (IB), (IB-a), (IB-b), and (IB-c) include substituent $R^{5A}$. In certain embodiments, $R^{5A}$ is H. In certain embodiments, $R^{5A}$ is deuterium. In certain embodiments, $R^{5A}$ is $C_1$-$C_3$ alkyl. In certain embodiments, $R^{5A}$ is halogen (e.g., F, Cl, Br, or I).

In certain embodiments, a1 is 0. In certain embodiments, a1 is 1.

Formulae (E-I), (IA-a), (IA-b), (IA-c), (IA-d), (IA), (IB), (IB-a), (IB-b), and (IB-c) include substituent $R^{4A}$. In certain embodiments, at least one instance of $R^{4A}$ is H. In certain embodiments, at least one instance of $R^{4A}$ is $C_1$-$C_3$ alkyl (e.g., methyl, ethyl). In certain embodiments, two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O. In certain embodiments, two $R^{4A}$, together with the carbon atom to which they are attached, form a C(O).

In certain embodiments, m and n are both 0; $R^{3A}$ is H; two $R^{4A}$, together with the carbon atom to which they are attached, form a C(O); and $R^{5A}$ is H.

In certain embodiments, a1 is 1; m and n are both 0; $R^{3A}$ is H; two $R^{4A}$, together with the carbon atom to which they are attached, form a C(O); $R^{5A}$ is H; and $X^A$ is C(O). In certain embodiments, a1 is 1; m and n are both 0; $R^{3A}$ is H; two $R^{4A}$, together with the carbon atom to which they are attached, form a C(O); $R^{5A}$ is H; and $X^A$ is $C(R^{3A})_2$. In certain embodiments, two $R^{4A}$, together with the carbon atom to which they are attached, form a C(O); $R^{5A}$ is H; and $X^A$ is C(O). In certain embodiments, two $R^{4A}$, together with the carbon atom to which they are attached, form a C(O); $R^{5A}$ is H; and $X^A$ is $C(R^3)_2$. In certain embodiments, two $R^{4A}$, together with the carbon atom to which they are attached, form a C(O); and $R^{5A}$ is H. In certain embodiments, $X^A$ is C(O). In certain embodiments, $X^A$ is —CH$_2$—.

In certain embodiments, —$X^1$—$X^2$— is C($R^{3A}$)=N; $R^{3A}$ is H; and two $R^{4A}$, together with the carbon atom to which they are attached, form a C(O). In certain embodiments, —$X^1$—$X^2$— is C($R_{3A}$)$_2$—C($R^{3A}$)$_2$; $R^{3A}$ is H; and two $R^{4A}$, together with the carbon atom to which they are attached, form a C(O). In certain embodiments, —$X^1$—$X^2$— is C($R^{3A}$)=N; $R^{5A}$ is H; and two $R^{4A}$, together with the carbon atom to which they are attached, form a C(O). In certain embodiments, —$X^1$—$X^2$— is C($R_A$)$_2$—C($R^{3A}$)$_2$; $R^{5A}$ is H; and two $R^{4A}$, together with the carbon atom to which they are attached, form a C(O).

In certain embodiments, D1 is thalidomide, lenalidomide, pomalidomide, CC-885 (Matyskiela et al., *Nature* 2016, 535, 252-257), 3-(5-amino-2-methyl-4-oxoquinazolin-3 (4H)-yl)piperidine-2,6-dione, or an analogue or derivative thereof. In certain embodiments, D1 is thalidomide. In certain embodiments, D1 is lenalidomide.

In certain embodiments, D1 is:

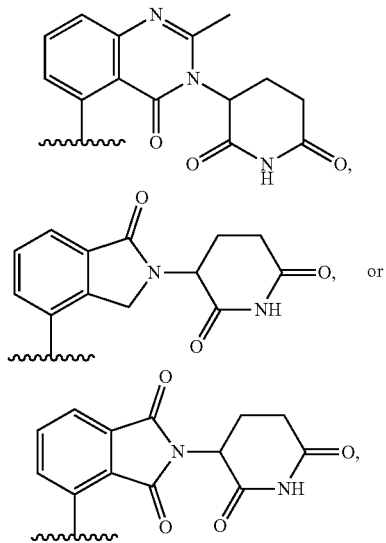

In certain embodiments, D1 is:

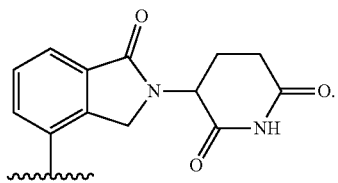 [SMILES: *c1cccc2c1CN(C1CCC(=O)NC1=O)C2=O]

In certain embodiments, D1 is

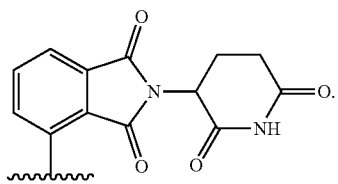 [SMILES: *c1cccc2c1C(=O)N(C1CCC(=O)NC1=O)C2=O]

In certain embodiments, D1 is of the formula:

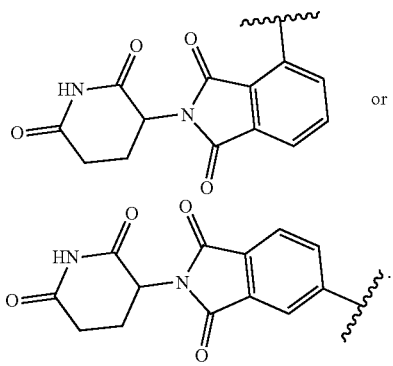

In certain embodiments, the E3 ligase binding moiety binds an E3 ubiquitin ligase with a $K_d$ of less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the E3 ligase binding moiety binds Cereblon with a $K_d$ of less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

In certain embodiments, the E3 ligase binding moiety selectively binds an E3 ubiquitin ligase as compared to another protein. In some embodiments, the E3 ligase binding moiety selectively binds Cereblon over another protein. In some embodiments, the E3 ligase binding moiety selectively binds Cereblon over another E3 ubiquitin ligase. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

Substituents $R^{10'}$, $R^{10A}$, $R^{13}$, and $R^{14}$

Compounds of Formula (I') are bifunctional compounds that bind to the target protein DOT1L and bind to E3 ligase. For compounds of Formula (I'), the DOT1L binding moiety includes substituents $R^8$, $R^9$, $R^{10'}$, $R^{10A}$, $R^{11}$, $R^{12}$, $R^{13}$, and $R^{14}$.

Substituents $R^8$, $R^9$, $R^{10}$, $R^{11}$, and $R^{12}$ are described below.

In certain embodiments, $R^{10'}$ is independently hydrogen, optionally substituted alkyl, or $-N(R^{10A})_2$; wherein each instance of $R^{10A}$ is independently hydrogen, optionally substituted alkyl, or a nitrogen protecting group. In certain embodiments, $R^{10'}$ is hydrogen. In certain embodiments, $R^{10'}$ is optionally substituted alkyl. In certain embodiments, $R^{10'}$ is $-N(R^{10A})_2$; and one instance of $R^{14}$ and one instance of $R^{10A}$ are taken together with their intervening atoms to form a substituted or unsubstituted heterocyclic or substituted or unsubstituted heteroaryl ring, and the other instance of $R^{10A}$ is hydrogen, optionally substituted alkyl, or a nitrogen protecting group. In certain embodiments, $R^{10'}$ is $-N(R^{10A})_2$; and one instance of $R^{14}$ and one instance of $R^{10A}$ are taken together with their intervening atoms to form a substituted or unsubstituted, 6-14 membered, heterocyclic or substituted or unsubstituted heteroaryl ring, and the other instance of $R^{10A}$ is hydrogen, optionally substituted alkyl, or a nitrogen protecting group. In certain embodiments, $R^{10'}$ is $-N(R^{10A})_2$; and one instance of $R^{14}$ and one instance of $R^{10A}$ are taken together with their intervening atoms to form a substituted or unsubstituted, 5-14 membered, heterocyclic or substituted or unsubstituted, 5-14 membered, heteroaryl ring. In certain embodiments, $R^{10'}$ is $-N(R^{14})_2$; and one instance of $R^{14}$ and one instance of $R^{10A}$ are taken together with their intervening atoms to form a substituted or unsubstituted, 5-6 membered, heterocyclic or substituted or unsubstituted, 5-6 membered, heteroaryl ring, wherein the heterocyclic or heteroaryl ring comprises 0-2 heteroatoms selected from the group consisting of N and O. In certain embodiments, one instance of $R^{14}$ and one instance of $R^{10'}$ are taken together with their intervening atoms to form a substituted or unsubstituted heterocyclic or substituted or unsubstituted heteroaryl ring. In certain embodiments, one instance of $R^{14}$ and one instance of $R^{10'}$ are taken together with their intervening atoms to form a substituted or unsubstituted, 5-14 membered, heterocyclic or substituted or unsubstituted, 5-14 membered, heteroaryl ring. In certain embodiments, one instance of $R^{14}$ and one instance of $R^{10'}$ are taken together with their intervening atoms to form a substituted or unsubstituted, 5-6 membered, heterocyclic or substituted or unsubstituted, 5-6 membered, heteroaryl ring.

In certain embodiments, $R^{10'}$ is $-N(R^{10A})_2$; and at least one instance of $R^{10A}$ is $R^{10}$ as described herein.

In certain embodiments, at least one instance of $R^{10A}$ is hydrogen. In certain embodiments, at least one instance of $R^{10A}$ is optionally substituted alkyl (e.g., optionally substituted $C_{1-6}$ alkyl). In certain embodiments, at least one instance of $R^{10A}$ is optionally substituted methyl or optionally substituted ethyl. In certain embodiments, at least one instance of $R^{10A}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, $R^{13}$ is hydrogen. In certain embodiments, $R^{13}$ is optionally substituted alkyl (e.g., optionally substituted $C_{1-6}$ alkyl). In certain embodiments, $R^{13}$ is optionally substituted methyl or optionally substituted ethyl. In certain embodiments, $R^{13}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, at least one instance of $R^{14}$ is hydrogen. In certain embodiments, both instances of $R^{14}$ are hydrogen. In certain embodiments, at least one instance of $R^{14}$ is optionally substituted alkyl (e.g., optionally substituted $C_{1-6}$ alkyl). In certain embodiments, at least one instance of $R^{14}$ is optionally substituted methyl or optionally substituted ethyl. In certain embodiments, at least one instance of $R^{14}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)). In certain embodiments, the moiety is

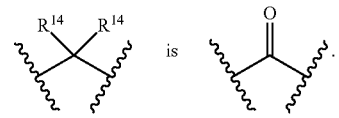

In certain embodiments, $R^{10'}$ is hydrogen, and the moiety

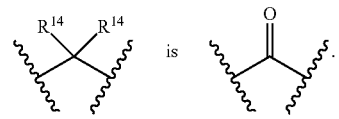

In certain embodiments, W is optionally substituted $-CH_2-$ or $-N(R^W)-$, wherein $R^W$ is hydrogen, optionally substituted alkyl, or a nitrogen protecting group. In certain embodiments, W is $-CH_2-$ or $-N(R^W)-$, wherein $R^W$ is hydrogen, optionally substituted alkyl, or a nitrogen protecting group. In certain embodiments, W is optionally substituted $-CH_2-$, optionally substituted with halogen, $-CN$, $-NO_2$, $-SO_2$, acyl (e.g., $-C(=O)$(alkyl)), or $-NH_2$). In certain embodiments, W is unsubstituted $-CH_2-$. In certain embodiments, W is $-N(R^W)-$, wherein $R^W$ is hydrogen, optionally substituted alkyl, or a nitrogen protecting group.

In certain embodiments, $R^{10'}$ is hydrogen, and the moiety

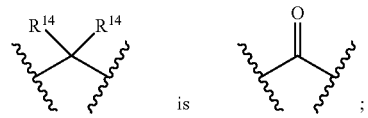

and W is $-N(R^W)-$, wherein $R^W$ is hydrogen, optionally substituted alkyl, or a nitrogen protecting group. In certain embodiments, $R^{10'}$ is hydrogen, and the moiety

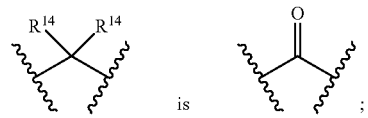

and W is $-NH-$.

In certain embodiments, Z is -(optionally substituted carbocyclyl)-. In certain embodiments, Z is -(optionally substituted $C_{3-10}$ carbocyclyl)-. In certain embodiments, Z is -(optionally substituted $C_{3-6}$ carbocyclyl)-. In certain embodiments, Z is -(optionally substituted cyclobutyl)-. In certain embodiments, Z is optionally substituted methylene (-optionally substituted $-CH_2-$). In certain embodiments, Z is optionally substituted $-CH_2-$, optionally substituted with halogen, $-CN$, $-NO_2$, $-SO_2$, acyl (e.g., $-C(=O)$ (alkyl)), or $-NH_2$). In certain embodiments, Z is unsubstituted $-CH_2-$. In certain embodiments, the moiety

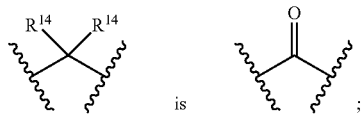

W is —NH—; and Z is —CH$_2$—.

Substituents R$^8$, R$^9$, R$^{10}$, R$^{11}$, and R$^{12}$

Compounds of Formula (I') and (I) are bifunctional compounds that bind to the target protein DOT1L and bind to E3 ligase. For compounds of Formula (I') and (I), the DOT1L binding moiety includes substituents R$^8$, R$^9$, R$^{10}$, R$^{11}$, and R$^{12}$.

In certain embodiments, R$^8$ is hydrogen. In certain embodiments, R$^8$ is optionally substituted alkyl (e.g., optionally substituted C$_{1-6}$ alkyl). In certain embodiments, R$^8$ is optionally substituted methyl or optionally substituted ethyl. In certain embodiments, R$^8$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, R$^9$ is hydrogen. In certain embodiments, R$^9$ is optionally substituted alkyl (e.g., optionally substituted C$_{1-6}$ alkyl). In certain embodiments, R$^9$ is optionally substituted methyl or optionally substituted ethyl. In certain embodiments, R$^9$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, R$^{10}$ is hydrogen. In certain embodiments, R$^{10}$ is optionally substituted alkyl (e.g., optionally substituted C$_{1-6}$ alkyl). In certain embodiments, R$^{10}$ is optionally substituted methyl or optionally substituted ethyl. In certain embodiments, R$^9$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, R$^{10}$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, R$^{11}$ is halogen (e.g., F, Cl, Br, or I). In certain embodiments, R$^{11}$ is optionally substituted alkyl (e.g., optionally substituted C$_{1-6}$ alkyl). In certain embodiments, R$^{11}$ is optionally substituted C$_{1-6}$ alkyl. In certain embodiments, R$^{11}$ is optionally substituted methyl or optionally substituted ethyl. In certain embodiments, R$^{11}$ is optionally substituted propyl. In certain embodiments, R$^{11}$ is optionally substituted butyl. In certain embodiments, R$^{11}$ is optionally substituted t-butyl. In certain embodiments, R$^{11}$ is unsubstituted t-butyl.

In certain embodiments, at least one instance of R$^{12}$ is hydrogen. In certain embodiments, at least one instance of R$^{12}$ is an oxygen protecting group (e.g., methyl, methoxylmethyl (MOM), trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), methanesulfonate (mesylate), benzylsulfonate, and tosylate (Ts)). In certain embodiments, both instances of R$^{12}$ are hydrogen.

In certain embodiments, a compound of Formula (I') is of Formula (I).

In certain embodiments, a compound of Formula (I) is of formula:

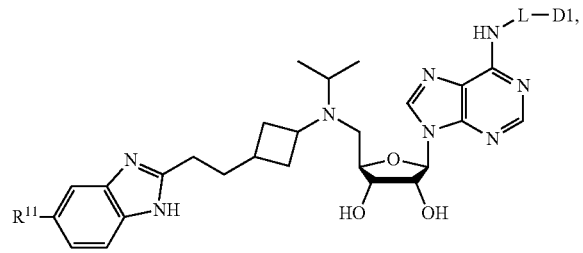

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of formula:

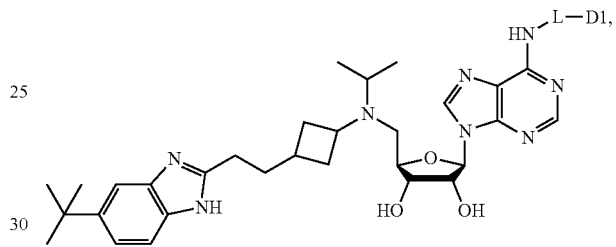

or a pharmaceutically acceptable salt, solvate, hydrate, polymorph, co-crystal, tautomer, stereoisomer, isotopically labeled derivative, or prodrug thereof.

In certain embodiments, a compound of Formula (I') is of formula:

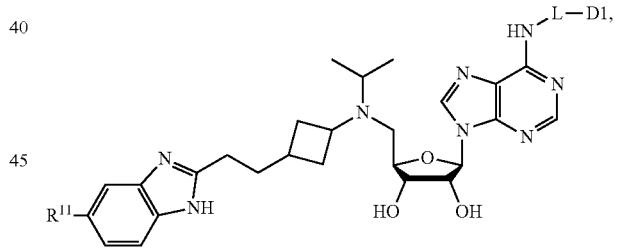

or a pharmaceutically acceptable salt, solvate, hydrate, polymorph, co-crystal, tautomer, stereoisomer, isotopically labeled derivative, or prodrug thereof.

In certain embodiments, a compound of Formula (I') is of formula:

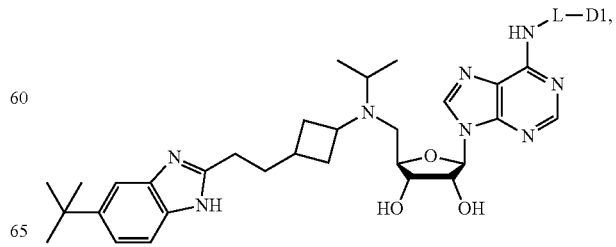

or a pharmaceutically acceptable salt, solvate, hydrate, polymorph, co-crystal, tautomer, stereoisomer, isotopically labeled derivative, or prodrug thereof.

In certain embodiments, the compound of Formula (I') is of formula:

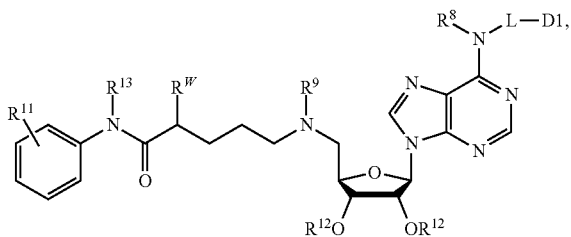

or a pharmaceutically acceptable salt, solvate, hydrate, tautomer, or stereoisomer thereof.

Linker L

In Formula (I), L is a divalent moiety linking the group D1 to the moiety of

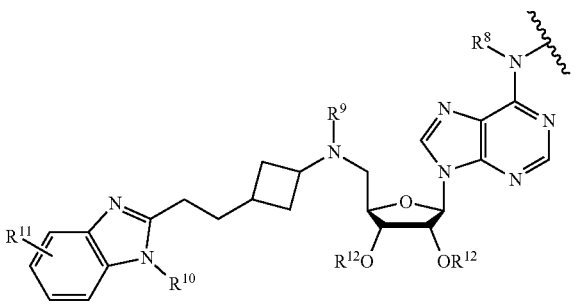

(i.e., the DOT1L binding moiety). In Formula (I), L covalently links the group D1 to the moiety of

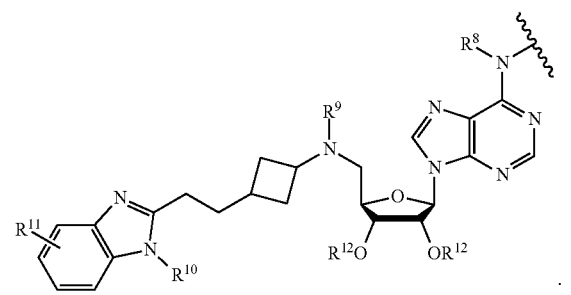

In Formula (I'), L is a divalent moiety linking the group D1 to the moiety of

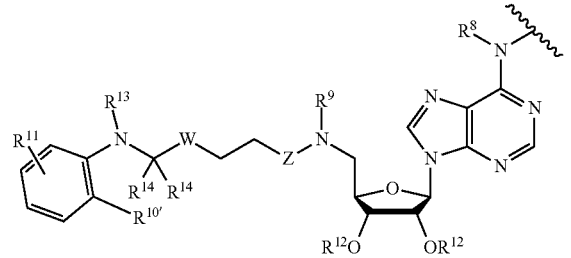

(i.e., the DOT1L binding moiety). In Formula (I), L covalently links the group D1 to the moiety of

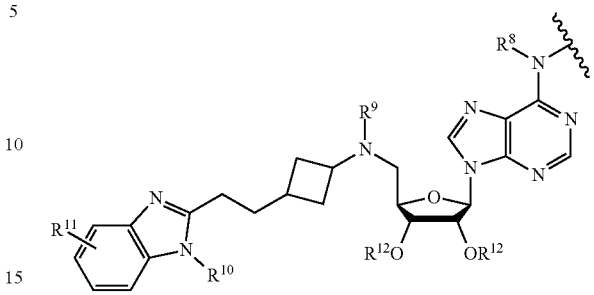

In Formula (I'), L is a divalent moiety. In certain embodiments, L is a substituted or unsubstituted $C_{1-50}$ hydrocarbon chain as the shortest path between D1 and the moiety of

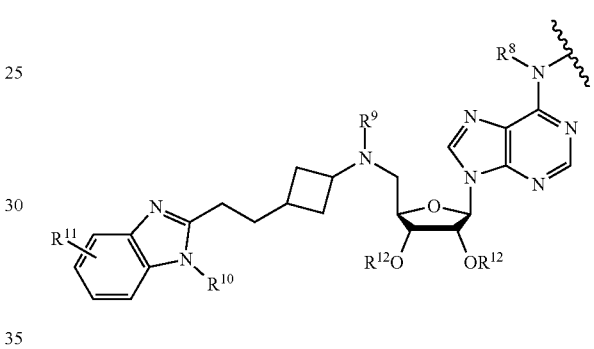

optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted $C_{1-6}$ alkyl, or a nitrogen protecting group. In certain embodiments, L is a substituted or unsubstituted $C_{1-50}$ hydrocarbon chain as the shortest path between D1 and the moiety of

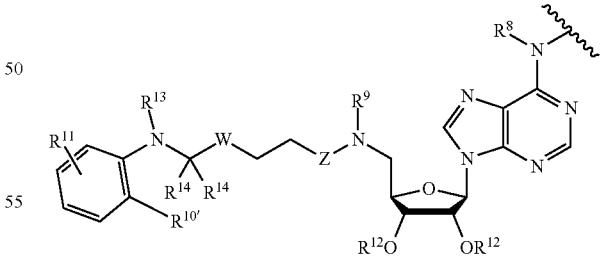

optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted $C_{1-6}$ alkyl, or a nitrogen protecting group. In certain embodiments, L is a substituted or unsubstituted $C_{1-50}$ linear hydrocarbon chain as the shortest path between D1 and the moiety of

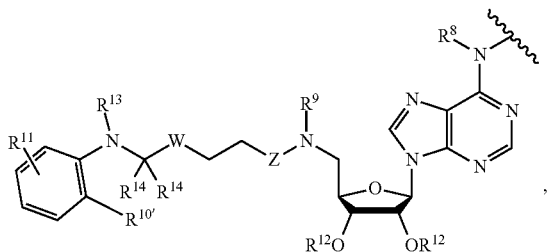

optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group. In certain embodiments, L is a substituted or unsubstituted C$_{1-50}$ linear hydrocarbon chain as the shortest path between D1 and the moiety of

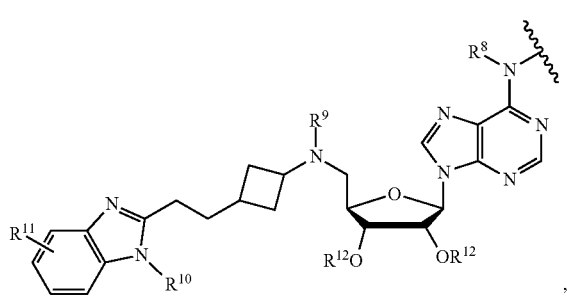

optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group. In certain embodiments. L is a substituted or unsubstituted C$_{1-6}$, linear hydrocarbon chain as the shortest path between D1 and the moiety of

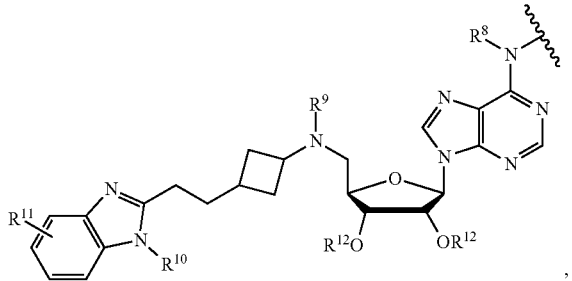

optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group.

In certain embodiments, L is a substituted or unsubstituted, linear C$_{1-30}$ hydrocarbon chain, optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group.

In certain embodiments, L is a substituted or unsubstituted C$_{1-30}$ hydrocarbon chain, optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group. In certain embodiments, L is an unsubstituted C$_{1-30}$ hydrocarbon chain, optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group. In certain embodiments, L is a substituted or unsubstituted C$_{1-26}$ hydrocarbon chain, optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group. In certain embodiments, L is an unsubstituted C$_{1-26}$ hydrocarbon chain, optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group. In certain embodiments, L is any "LO" group or "Linker" group recited in U.S. patent application U.S. Ser. No. 14/707,930, filed May 8, 2015, which is incorporated herein by reference. In certain embodiments, L is any "L" group recited in U.S. patent application U.S. Ser. No. 14/792,414, filed Jul. 6, 2015, which is incorporated herein by reference.

In certain embodiments, the chain of linker L comprises up to 50 consecutive covalently bonded atoms atoms in length as the shortest path between D1 and the moiety of

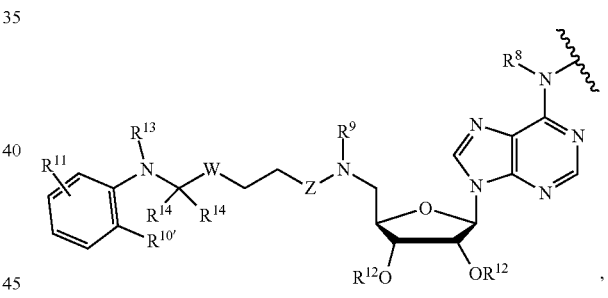

excluding hydrogen atoms and substituents.

In certain embodiments, the chain of linker L comprises up to 50 consecutive covalently bonded atoms atoms in length as the shortest path between D1 and the moiety of

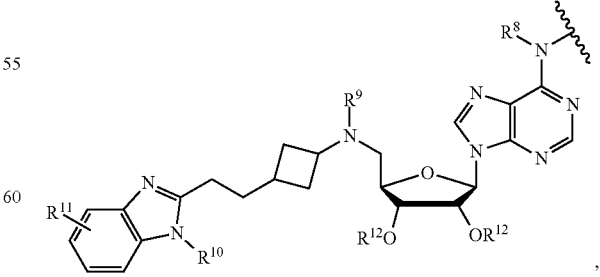

excluding hydrogen atoms and substituents.

In certain embodiments, the chain of linker L comprises up to 50 consecutive covalently bonded atoms atoms in length, excluding hydrogen atoms and substituents. In certain embodiments, L comprises up to 46 consecutive covalently bonded atoms atoms in length, excluding hydrogen atoms and substituents. In certain embodiments, L comprises up to 45 consecutive covalently bonded atoms atoms in length, excluding hydrogen atoms and substituents. In certain embodiments, L comprises up to 40 consecutive covalently bonded atoms atoms in length, excluding hydrogen atoms and substituents. In certain embodiments, L comprises up to 35 consecutive covalently bonded atoms atoms in length, excluding hydrogen atoms and substituents. In certain embodiments, L comprises up to 32 consecutive covalently bonded atoms atoms in length, excluding hydrogen atoms and substituents. In certain embodiments, L comprises up to 30 consecutive covalently bonded atoms atoms in length, excluding hydrogen atoms and substituents. In certain embodiments, L comprises up to 25 consecutive covalently bonded atoms atoms in length, excluding hydrogen atoms and substituents. In certain embodiments, L comprises up to 25 consecutive covalently bonded atoms atoms in length, excluding hydrogen atoms and substituents. In certain embodiments, L comprises up to 23 consecutive covalently bonded atoms atoms in length, excluding hydrogen atoms and substituents. In certain embodiments, L comprises up to 20 consecutive covalently bonded atoms atoms in length, excluding hydrogen atoms and substituents. In certain embodiments, L comprises up to 14 consecutive covalently bonded atoms atoms in length, excluding hydrogen atoms and substituents. In certain embodiments, L comprises up to 15 consecutive covalently bonded atoms atoms in length, excluding hydrogen atoms and substituents. In certain embodiments, L comprises up to 12 consecutive covalently bonded atoms atoms in length, excluding hydrogen atoms and substituents. In certain embodiments, L comprises up to 10 consecutive covalently bonded atoms atoms in length, excluding hydrogen atoms and substituents. In certain embodiments, L comprises up to 9 consecutive covalently bonded atoms atoms in length, excluding hydrogen atoms and substituents. In certain embodiments, L comprises up to 6 consecutive covalently bonded atoms atoms in length, excluding hydrogen atoms and substituents. In certain embodiments, L comprises up to 5 consecutive covalently bonded atoms atoms in length, excluding hydrogen atoms and substituents. In certain embodiments, L comprises up to 3 consecutive covalently bonded atoms atoms in length, excluding hydrogen atoms and substituents.

In certain embodiments, any of the atoms in L can be substituted. In certain embodiments, none of the atoms in the linker L are substituted. In certain embodiments, none of the carbon atoms in the linker are substituted.

In certain embodiments, L is a linker that contains an asymmetric carbon/stereocenter, i.e., an sp$^3$ hybridized carbon atom bearing 4 different groups attached thereto. In certain embodiments, the compound comprising such an L group is enantiomerically enriched or substantially enantiomerically enriched. In certain embodiments, the compound comprising such an L group is racemic.

In certain embodiments, L is substituted or unsubstituted carbocyclylene, substituted or unsubstituted heterocyclylene, substituted or unsubstituted arylene, substituted or unsubstituted heteroarylene, or substituted or unsubstituted heteroalkylene, or combinations thereof. In certain embodiments, L is substituted or unsubstituted carbocyclylene, substituted or unsubstituted heterocyclylene, substituted or unsubstituted arylene, substituted or unsubstituted heteroarylene, or substituted or unsubstituted heteroalkylene. In certain embodiments, L is a linker selected from the group consisting of the following divalent moieties: substituted and unsubstituted alkylene, substituted and unsubstituted alkenylene, substituted and unsubstituted alkynylene, substituted and unsubstituted heteroalkylene, substituted and unsubstituted heteroalkenylene, substituted and unsubstituted heteroalkynylene, substituted and unsubstituted heterocyclylene, substituted and unsubstituted carbocyclylene, substituted and unsubstituted arylene, substituted and unsubstituted heteroarylene, and combinations thereof.

Reference to L being a combination of at least two instances of the divalent moieties described herein refers to a linker consisting of at least one instance of a first divalent moiety and at least one instance of a second divalent moiety, wherein the first and second divalent moieties are the same or different and are within the scope of the divalent moieties described herein, and the instances of the first and second divalent moieties are consecutive covalently attached to each other. For example, when L is a combination of alkylene and heteroalkylene linkers -alkylene-heteroalkylene-, -alkylene-(heteroalkylene)$_2$-, and -heteroalkylene-alkylene-heteroalkylene- are all within the scope of L, wherein each instance of alkylene in any one of the linkers may be the same or different, and each instance of heteroalkylene in any one of the linkers may be the same or different.

In certain embodiments, L comprises at least one instance of substituted or unsubstituted alkylene, e.g., substituted or unsubstituted $C_{1-6}$alkylene, substituted or unsubstituted $C_{1-2}$alkylene, substituted or unsubstituted $C_{2-3}$alkylene, substituted or unsubstituted $C_{3-4}$alkylene, substituted or unsubstituted $C_{4-5}$alkylene, substituted or unsubstituted $C_{5-6}$alkylene, substituted or unsubstituted $C_{3-6}$alkylene, or substituted or unsubstituted $C_{4-6}$alkylene. Exemplary alkylene groups include unsubstituted alkylene groups such as methylene (—CH$_2$—), ethylene (—(CH$_2$)$_2$—), n-propylene (—(CH$_2$)$_3$—), n-butylene (—(CH$_2$)$_4$—), n-pentylene (—(CH$_2$)$_5$—), and n-hexylene (—(CH$_2$)$_6$—).

In certain embodiments, L comprises at least one instance of substituted or unsubstituted alkenylene, e.g., substituted or unsubstituted $C_{2-6}$alkenylene, substituted or unsubstituted $C_{2-3}$alkenylene, substituted or unsubstituted $C_{3-4}$alkenylene, substituted or unsubstituted $C_{4-5}$alkenylene, or substituted or unsubstituted $C_{5-6}$alkenylene.

In certain embodiments, L comprises at least one instance of substituted or unsubstituted alkynylene, e.g., substituted or unsubstituted $C_{2-6}$alkynylene, substituted or unsubstituted $C_{2-3}$alkynylene, substituted or unsubstituted $C_{3-4}$alkynylene, substituted or unsubstituted $C_{4-5}$alkynylene, or substituted or unsubstituted $C_{5-6}$alkynylene.

In certain embodiments, L comprises at least one instance of substituted or unsubstituted heteroalkylene, e.g., substituted or unsubstituted hetero$C_{1-6}$alkylene, substituted or unsubstituted hetero$C_{1-2}$alkylene, substituted or unsubstituted hetero$C_{2-3}$alkylene, substituted or unsubstituted hetero$C_{3-4}$alkylene, substituted or unsubstituted hetero$C_{4-5}$alkylene, or substituted or unsubstituted hetero$C_{5-6}$alkylene. Exemplary heteroalkylene groups include unsubstituted heteroalkylene groups such as —(CH$_2$)$_2$—O(CH$_2$)$_2$—, —OCH$_2$—, —CH$_2$O—, —O(CH$_2$)$_2$—, —(CH$_2$)$_2$O—, —O(CH$_2$)$_3$—, —(CH$_2$)$_3$O—, —O(CH$_2$)$_4$—, —(CH$_2$)$_4$—, —O(CH$_2$)$_5$—, —(CH$_2$)$_5$O—, —O(CH$_2$)$_6$—, and —O(CH$_2$)$_6$ O—, and amide groups (e.g., —NH—C(=O)— and —C(=O)NH—).

In certain embodiments, L comprises at least one instance of substituted or unsubstituted heteroalkenylene, e.g., substituted or unsubstituted hetero$C_{2-6}$alkenylene, substituted or unsubstituted heteroC$_{2-3}$alkenylene, substituted or unsubstituted heteroC$_{3-4}$alkenylene, substituted or unsubstituted heteroC$_{4-5}$alkenylene, or substituted or unsubstituted heteroC$_{5-6}$alkenylene.

In certain embodiments, L comprises at least one instance of substituted or unsubstituted heteroalkynylene, e.g., substituted or unsubstituted heteroC$_{2-6}$alkynylene, substituted or unsubstituted heteroC$_{2-3}$alkynylene, substituted or unsubstituted heteroC$_{3-4}$alkynylene, substituted or unsubstituted heteroC$_{4-5}$alkynylene, or substituted or unsubstituted heteroC$_{5-6}$alkynylene.

In certain embodiments, L comprises at least one instance of substituted or unsubstituted carbocyclylene, e.g., substituted or unsubstituted C$_{3-6}$carbocyclylene, substituted or unsubstituted C$_{3-4}$carbocyclylene, substituted or unsubstituted C$_{4-5}$ carbocyclylene, or substituted or unsubstituted C$_{5-6}$ carbocyclylene.

In certain embodiments, L comprises at least one instance of substituted or unsubstituted heterocyclylene, e.g., substituted or unsubstituted 3-6 membered heterocyclylene, substituted or unsubstituted 3-4 membered heterocyclylene, substituted or unsubstituted 4-5 membered heterocyclylene, or substituted or unsubstituted 5-6 membered heterocyclylene.

In certain embodiments, L comprises at least one instance of substituted or unsubstituted arylene, e.g., substituted or unsubstituted phenylene. In certain embodiments, L comprises at least one instance of substituted or unsubstituted heteroarylene, e.g., substituted or unsubstituted 5- to 6-membered heteroarylene.

In certain embodiments, each instance of R$^b$ is independently hydrogen, substituted or unsubstituted C$_{1-6}$ alkyl, or a nitrogen protecting group, or optionally two instances of R$^b$ are taken together with their intervening atoms to form a substituted or unsubstituted heterocyclic or substituted or unsubstituted heteroaryl ring. In certain embodiments, at least one instance of R$^b$ is hydrogen. In certain embodiments, at least one instance of R$^b$ is substituted or unsubstituted C$_{1-6}$ alkyl (e.g., substituted or unsubstituted methyl or ethyl). In certain embodiments, at least one instance of R$^b$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, L is an unsubstituted C$_{1-45}$ hydrocarbon chain as the shortest path between D1 and the moiety of

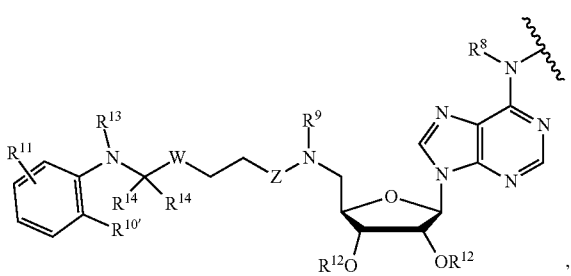

excluding hydrogen atoms and substituents, optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group.

In certain embodiments, L is an unsubstituted C$_{1-45}$ hydrocarbon chain as the shortest path between D1 and the moiety of

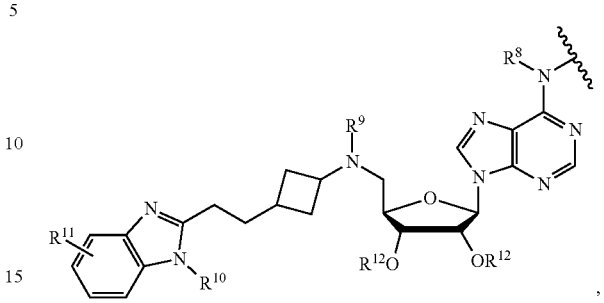

excluding hydrogen atoms and substituents, optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group.

In certain embodiments, L is an unsubstituted C$_{1-30}$ hydrocarbon chain, wherein one or more chain atoms of the hydrocarbon chain are independently replaced with —O— or —NR$^b$—. In certain embodiments, L is an unsubstituted C$_{1-30}$ hydrocarbon chain, wherein at least one chain atom of the hydrocarbon chain is independently replaced with —O—. In certain embodiments, L is an unsubstituted C$_{1-26}$ hydrocarbon chain, wherein one or more chain atoms of the hydrocarbon chain are independently replaced with —O— or —NR$^b$—. In certain embodiments, L is an unsubstituted C$_{5-26}$ hydrocarbon chain, wherein one or more chain atoms of the hydrocarbon chain are independently replaced with —O— or —NR$^b$—. In certain embodiments, L is an unsubstituted C$_{5-20}$ hydrocarbon chain, wherein one or more chain atoms of the hydrocarbon chain are independently replaced with —O— or —NR$^b$—. In certain embodiments, L is an unsubstituted C$_{5-15}$ hydrocarbon chain, wherein one or more chain atoms of the hydrocarbon chain are independently replaced with —O— or —NR$^b$—. In certain embodiments, L is an unsubstituted C$_{15-20}$ hydrocarbon chain, wherein one or more chain atoms of the hydrocarbon chain are independently replaced with —O— or —NR$^b$—. In certain embodiments, L is an unsubstituted C$_{20-25}$ hydrocarbon chain, wherein one or more chain atoms of the hydrocarbon chain are independently replaced with —O— or —NR$^b$—. In certain embodiments, L is a substituted or unsubstituted C$_{1-45}$ hydrocarbon chain. In certain embodiments, L is a substituted or unsubstituted C$_{5-40}$ hydrocarbon chain. In certain embodiments, one or more chain atoms of the hydrocarbon chain of L are independently replaced with —C(=O)—, —O—, —S—, —NR$^b$—, —N=, or =N—. In certain embodiments, one or more chain atoms of the hydrocarbon chain of L are independently replaced with —C(=O)—, —O—, or —NR$^b$—, wherein R$^b$ is independently hydrogen, substituted or unsubstituted C$_{1-6}$ alkyl, or a nitrogen protecting group. In certain embodiments, L is an unsubstituted C$_{1-26}$ hydrocarbon chain, wherein at least one chain atom of the hydrocarbon chain is independently replaced with —O—.

In certain embodiments, L is an all-carbon, substituted or unsubstituted C$_{1-45}$ hydrocarbon chain as the shortest path between D1 and the moiety of

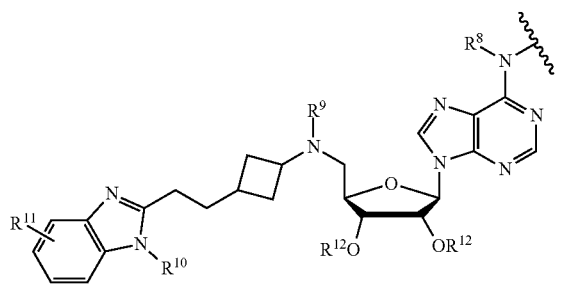

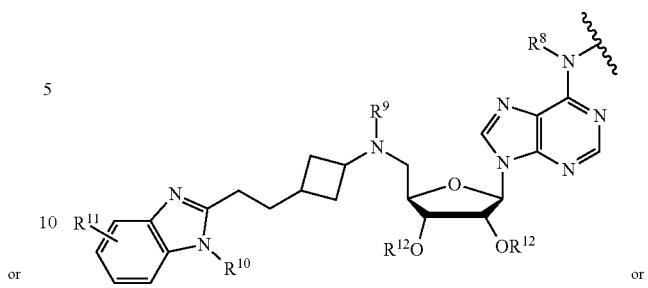

or

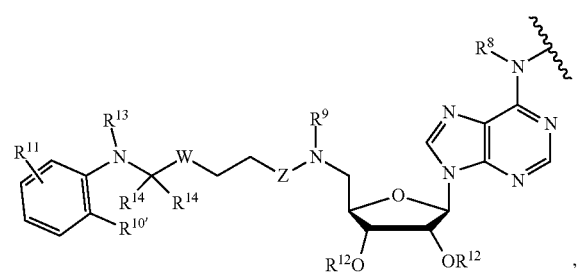

excluding hydrogen atoms and substituents. In certain embodiments, L is an all-carbon, substituted or unsubstituted $C_{1-30}$ hydrocarbon chain as the shortest path between D1 and the moiety of

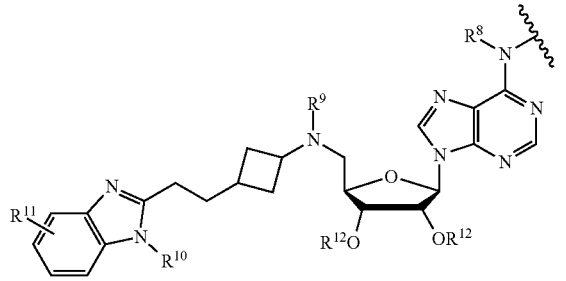

or excluding hydrogen atoms and substituents. In certain embodiments, L is an all-carbon, substituted or unsubstituted $C_{1-26}$ hydrocarbon chain as the shortest path between D1 and the moiety of excluding hydrogen atoms and substituents.

In certain embodiments, L is an all-carbon, substituted or unsubstituted $C_{1-45}$ hydrocarbon chain as the shortest path between D and the moiety of

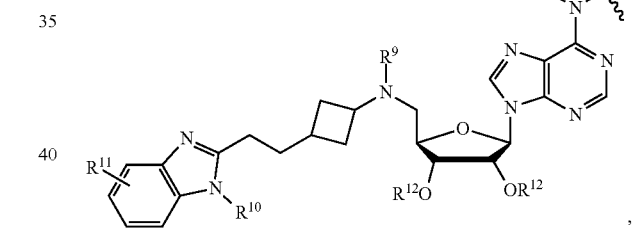

excluding hydrogen atoms and substituents. In certain embodiments, L is an all-carbon, substituted or unsubstituted $C_{1-30}$ hydrocarbon chain as the shortest path between D1 and the moiety of

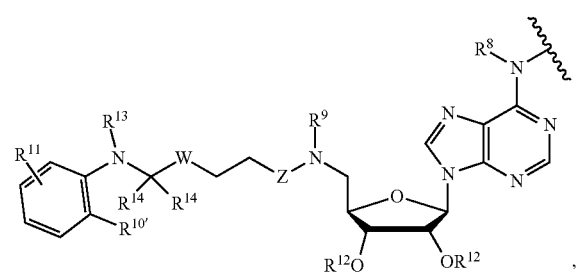

excluding hydrogen atoms and substituents. In certain embodiments, L is an all-carbon, substituted or unsubstituted $C_{1-26}$ hydrocarbon chain as the shortest path between D1 and the moiety of

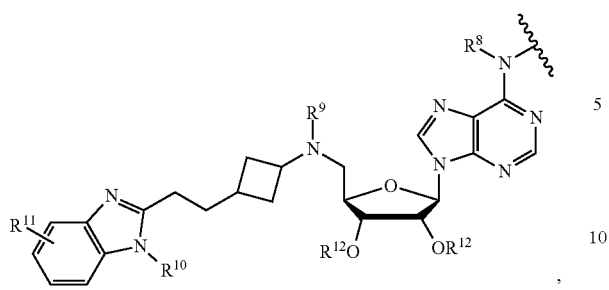

excluding hydrogen atoms and substituents.
In certain embodiments, L includes the moiety

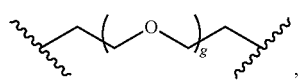

wherein g is 1, 2, 3, 4, 5, 6, 7, 8, 9, 10, 11, 12, 13, 14, or 15.
In certain embodiments, L includes the moiety

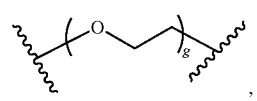

wherein g is 1, 2, 3, 4, 5, 6, 7, 8, 9, 10, 11, 12, 13, 14, or 15. In certain embodiments, L is a bond. In certain embodiments, g is 1. In certain embodiments, g is 2. In certain embodiments, g is 3. In certain embodiments, g is 4. In certain embodiments, g is 5. In certain embodiments, g is 6. In certain embodiments, g is 7. In certain embodiments, g is 8. In certain embodiments, g is 9. In certain embodiments, g is 10. In certain embodiments, g is 11. In certain embodiments, g is 12. In certain embodiments, g is 13. In certain embodiments, g is 14. In certain embodiments, g is 15. In certain embodiments, L includes the moiety —NHC(=O)—. In certain embodiments, L includes the moiety —NH—.
In certain embodiments, L is of the formula:

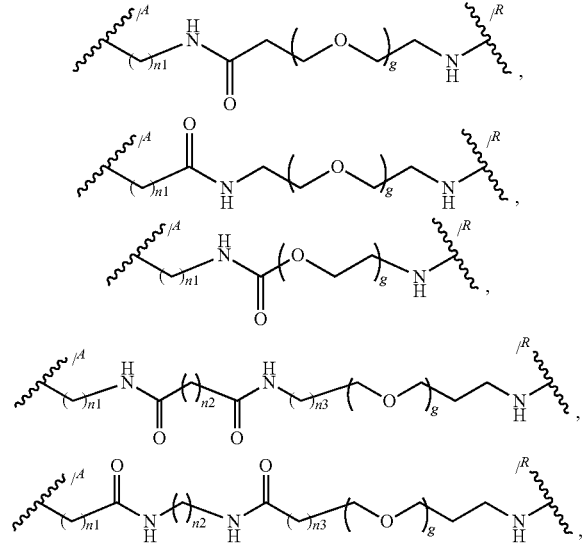

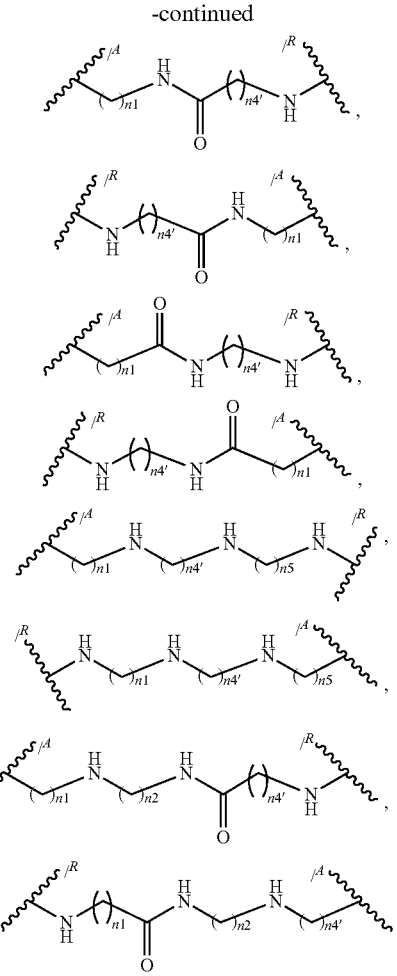

$l^R$ indicates the point of attachment to D1, and $l^A$ indicates the point of attachment to the moiety of formula

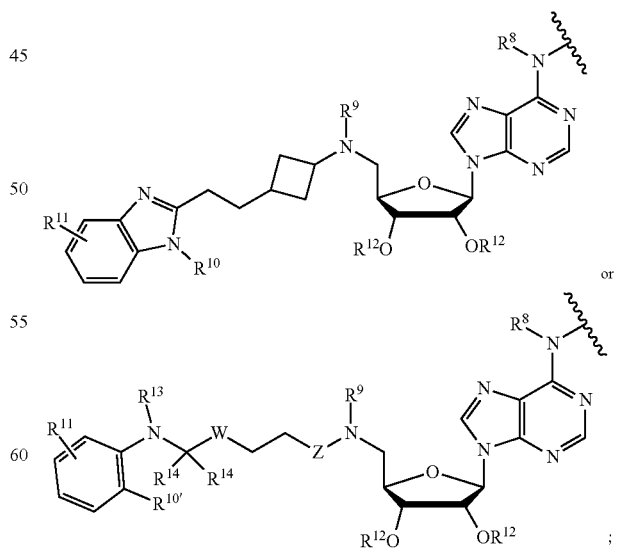

n1 is 1, 2, 3, 4, 5, or 6; n2 is 1, 2, 3, 4, 5, or 6; n3 is 1, 2, 3, 4, 5, or 6; n4' is 1, 2, 3, 4, 5, 6, 7, 8, 9, 10, 11, 12, 13, 14, 15, 16, 17, 18, 19, 20, 21, 22, 23, or 24; n5 is 1, 2, 3, 4, 5, 6, 7, 8, 9, 10, 11, or 12; and g is 1, 2, 3, 4, 5, 6, 7, 8, 9, 10, 11, 12, 13, 14, or 15.

In certain embodiments, L is of the formula:

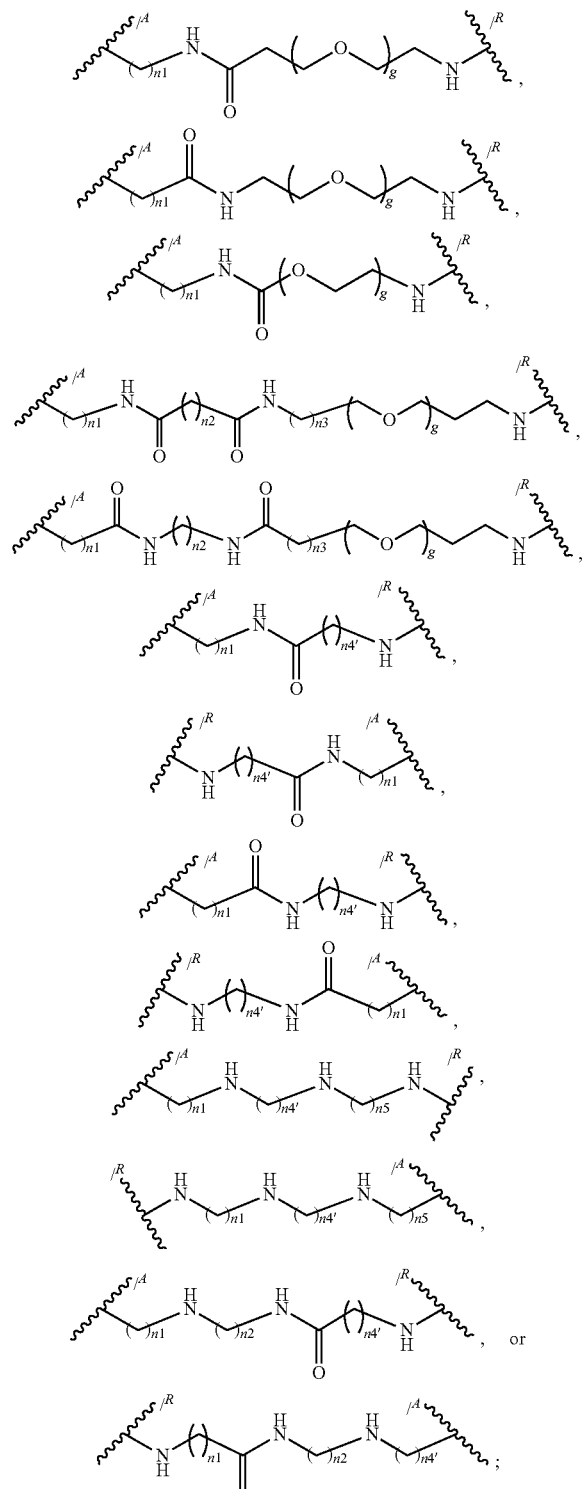

$l^R$ indicates the point of attachment to D1, and $l^A$ indicates the point of attachment to the moiety of formula

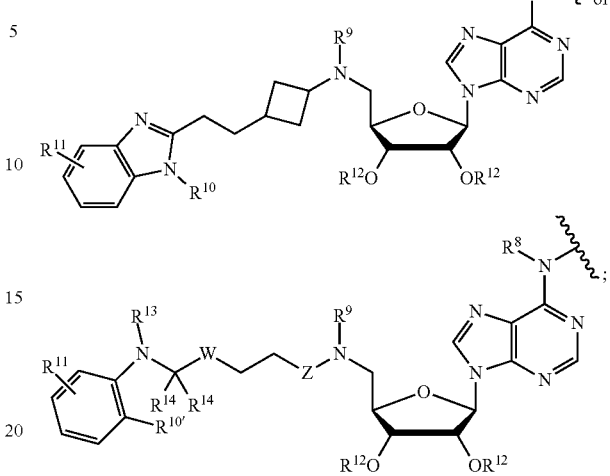

n1 is 1, 2, 3, 4, 5, or 6; n2 is 1, 2, 3, 4, 5, or 6; n3 is 1, 2, 3, 4, 5, or 6; n4' is 1, 2, 3, 4, 5, 6, 7, 8, 9, 10, 11, 12, 13, 14, 15, 16, 17, or 18; n5 is 1, 2, 3, 4, 5, 6, 7, 8, 9, 10, 11, or 12; and g is 1, 2, 3, 4, 5, 6, 7, 8, 9, 10, 11, 12, 13, 14, or 15.

In certain embodiments, n4' is 1, 2, 3, 4, 5, 6, 7, 8, 9, 10, 11, 12, 13, 14, 15, 16, 17, 18, 19, 20, 21, 22, 23, or 24. In certain embodiments, n4' is 1, 2, 3, 4, 5, 6, 7, 8, 9, 10, 11, 12, 13, 14, 15, 16, 17, or 18. In certain embodiments, n4' is n4. In certain embodiments, n4' is 1. In certain embodiments, n4' is 2. In certain embodiments, n4' is 3. In certain embodiments, n4' is 4. In certain embodiments, n4' is 5. In certain embodiments, n4' is 6. In certain embodiments, n4' is 7. In certain embodiments, n4' is 8. In certain embodiments, n4' is 9. In certain embodiments, n4' is 10. In certain embodiments, n4' is 11. In certain embodiments, n4' is 12. In certain embodiments, n4' is 13. In certain embodiments, n4' is 14. In certain embodiments, n4' is 15. In certain embodiments, n4' is 16. In certain embodiments, n4' is 17. In certain embodiments, n4' is 18. In certain embodiments, n4' is 19. In certain embodiments, n4' is 20. In certain embodiments, n4' is 21. In certain embodiments, n4' is 22. In certain embodiments, n4' is 23. In certain embodiments, n4' is 24.

In certain embodiments, L is of the formula:

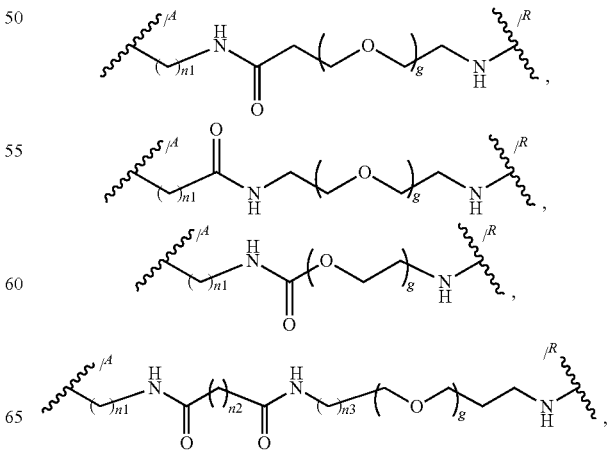

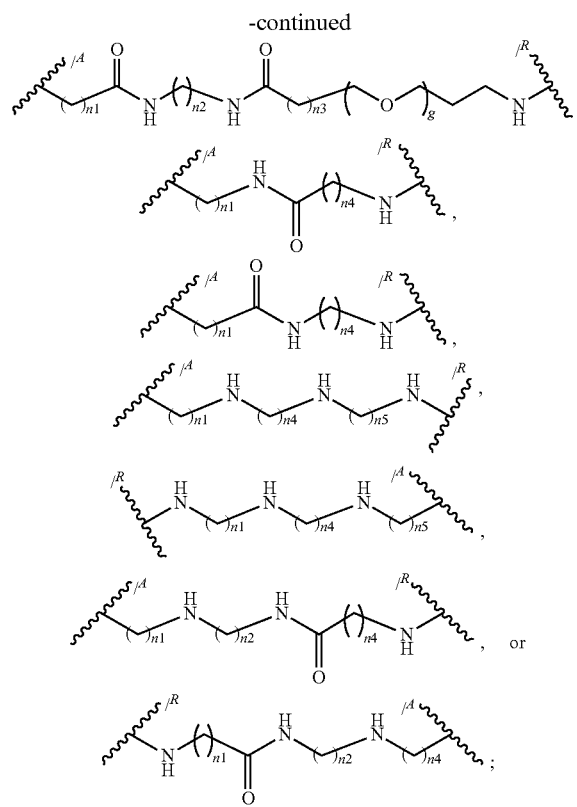

wherein:
$I^R$ indicates the point of attachment to D1, and $I^A$ indicates the point of attachment to the moiety of formula:

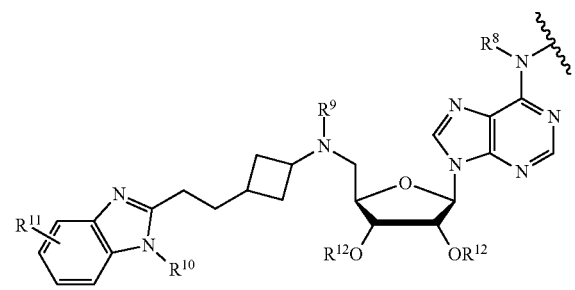

n1 is 1, 2, 3, 4, 5, or 6; n2 is 1, 2, 3, 4, 5, or 6; n3 is 1, 2, 3, 4, 5, or 6; n4 is 1, 2, 3, 4, 5, 6, 7, 8, 9, 10, 11, or 12; n5 is 1, 2, 3, 4, 5, 6, 7, 8, 9, 10, 11, or 12; and g is 1, 2, 3, 4, 5, 6, 7, 8, 9, 10, 11, 12, 13, 14, or 15. In certain embodiments, n1 is 1. In certain embodiments, n1 is 2. In certain embodiments, n1 is 3. In certain embodiments, n1 is 4. In certain embodiments, n1 is 5. In certain embodiments, n1 is 6. In certain embodiments, n2 is 1. In certain embodiments, n2 is 2. In certain embodiments, n2 is 3. In certain embodiments, n2 is 4. In certain embodiments, n2 is 5. In certain embodiments, n2 is 6. In certain embodiments, n4 is 1. In certain embodiments, n4 is 2. In certain embodiments, n4 is 3. In certain embodiments, n4 is 4. In certain embodiments, n4 is 5. In certain embodiments, n4 is 6. In certain embodiments, n4 is 7. In certain embodiments, n4 is 8. In certain embodiments, n4 is 9. In certain embodiments, n4 is 10. In certain embodiments, n4 is 11. In certain embodiments, n4 is 12. In certain embodiments, n5 is 1. In certain embodiments, n5 is 2. In certain embodiments, n5 is 3. In certain embodiments, n5 is 4. In certain embodiments, n5 is 5. In certain embodiments, n5 is 6. In certain embodiments, n5 is 7. In certain embodiments, n5 is 8. In certain embodiments, n5 is 9. In certain embodiments, n5 is 10. In certain embodiments, n5 is 11. In certain embodiments, n5 is 12. In certain embodiments, g is 1. In certain embodiments, g is 2. In certain embodiments, g is 3. In certain embodiments, g is 4. In certain embodiments, g is 5. In certain embodiments, g is 6. In certain embodiments, g is 7. In certain embodiments, g is 8. In certain embodiments, g is 9. In certain embodiments, g is 10. In certain embodiments, g is 11. In certain embodiments, g is 12. In certain embodiments, g is 13. In certain embodiments, g is 14. In certain embodiments, g is 15.

In certain embodiments, L is of the formula:

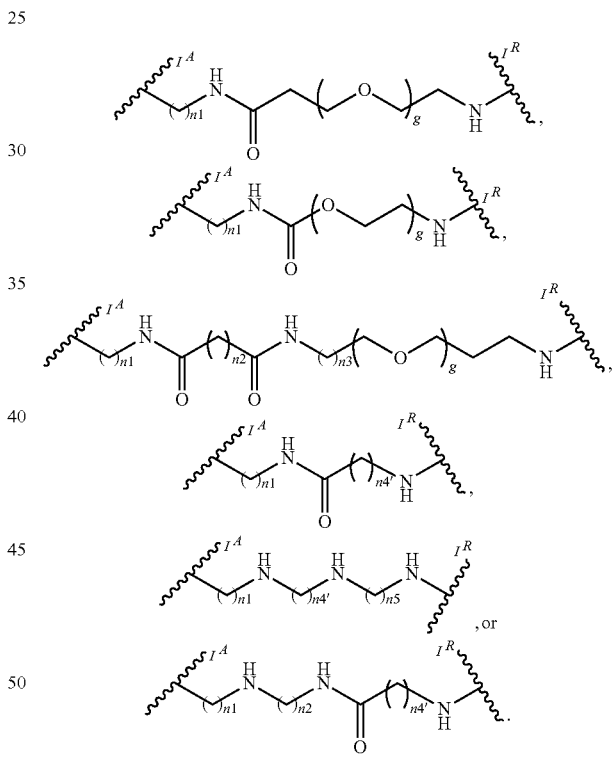

In certain embodiments, L is of the formula:

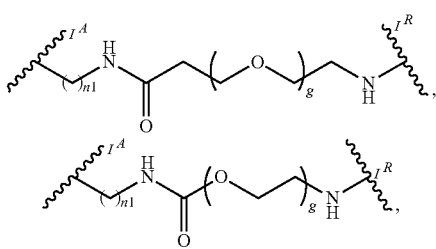

-continued

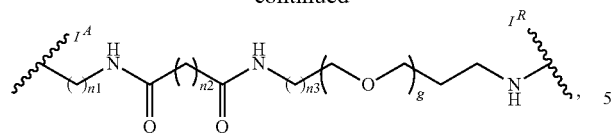

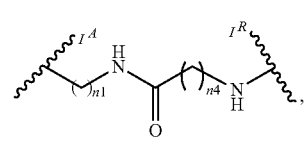

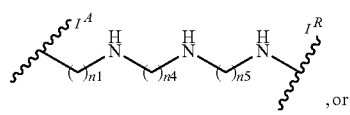, or

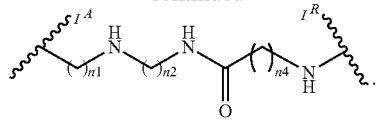

In certain embodiments, L is of the formula:

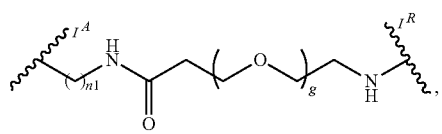

wherein:
n1 is 1, 2, 3, 4, 5, or 6; and g is 1, 2, 3, 4, 5, or 6. In certain embodiments, L is of the formula:

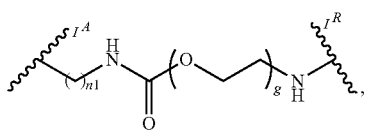

wherein: n1 is 1, 2, 3, 4, 5, or 6; and g is 1, 2, 3, 4, 5, 6, 7, 8, 9, 10, 11, 12, 13, 14, or 15. In certain embodiments, n1 is 4. In certain embodiments, n1 is 5. In certain embodiments, n1 is 6. In certain embodiments, g is 3. In certain embodiments, g is 5. In certain embodiments, g is 6. In certain embodiments, g is 12. In certain embodiments, g is 6. In certain embodiments, g is 13. In certain embodiments, L is of the formula:

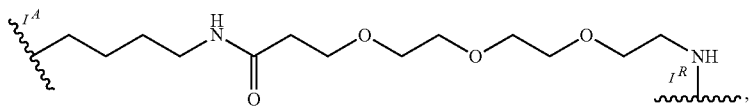

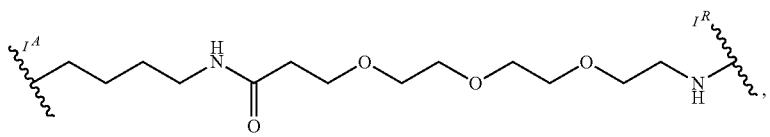

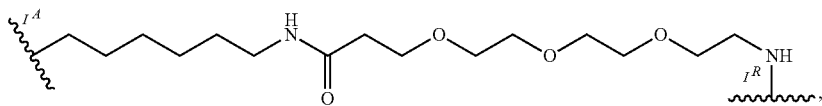

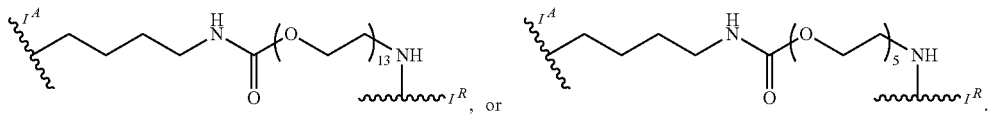

In certain embodiments, L is of the formula:

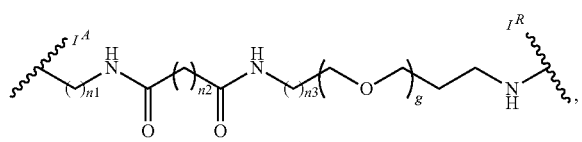

wherein: n1 is 1, 2, 3, 4, 5, or 6; n2 is 1, 2, 3, 4, 5, or 6; n3 is 1, 2, 3, 4, 5, or 6; and g is 1, 2, 3, 4, 5, 6, 7, 8, 9, 10, 11, 12, 13, or 14. In certain embodiments, n1 is 4. In certain embodiments, n1 is 5. In certain embodiments, n1 is 6. In certain embodiments, n2 is 3. In certain embodiments, n2 is 4. In certain embodiments, n2 is 5. In certain embodiments, n2 is 6. In certain embodiments. n2 is 2. In certain embodiments, n2 is 3. In certain embodiments. n2 is 4. In certain embodiments, g is 3. In certain embodiments, g is 5. In certain embodiments, g is 6.

In certain embodiments, L is of the formula:

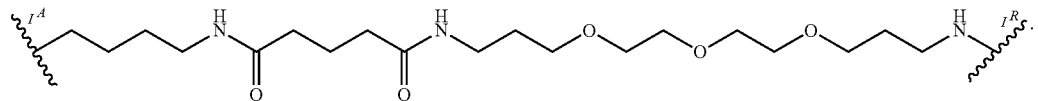

In certain embodiments, is of the formula:

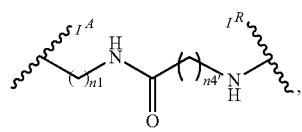

wherein: n1 is 1, 2, 3, 4, 5, or 6; and n4' is 1, 2, 3, 4, 5, 6, 7, 8, 9, 10, 11, 12, 13, 14, 15, 16, 17, or 18. In certain embodiments, n is 4. In certain embodiments, n1 is 5. In certain embodiments, n1 is 6. In certain embodiments, n4' is 3. In certain embodiments, n4' is 4. In certain embodiments, n4' is 5. In certain embodiments, n4' is 6. In certain embodiments, n4' is 7. In certain embodiments, n4' is 8. In certain embodiments, n4' is 9. In certain embodiments, n4' is 10. In certain embodiments, n4' is 11. In certain embodiments, n4' is 12. In certain embodiments, n4' is 13. In certain embodiments, n4' is 14. In certain embodiments, n4' is 15. In certain embodiments, n4' is 16. In certain embodiments, n4' is 17. In certain embodiments, n4' is 18.

In certain embodiments, L is of the formula:

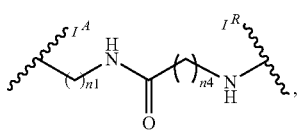

wherein: n1 is 1, 2, 3, 4, 5, or 6; and n4 is 1, 2, 3, 4, 5, 6, 7, 8, 9, 10, 11, or 12. In certain embodiments, n1 is 4. In certain embodiments, n1 is 5. In certain embodiments, n1 is 6. In certain embodiments, n4 is 8. In certain embodiments, n4 is 9. In certain embodiments, n4 is 10. In certain embodiments, n4 is 11. In certain embodiments, n4 is 12. In certain embodiments, L is of the formula:

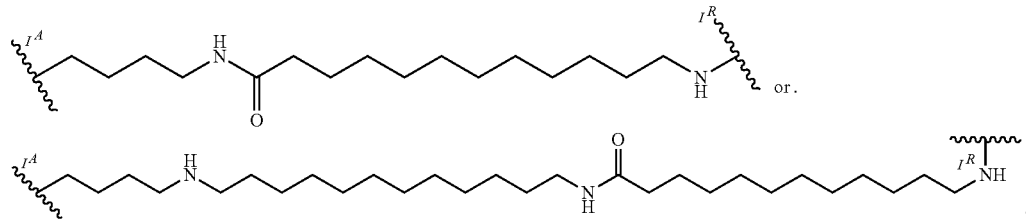

In certain embodiments, L is of the formula:

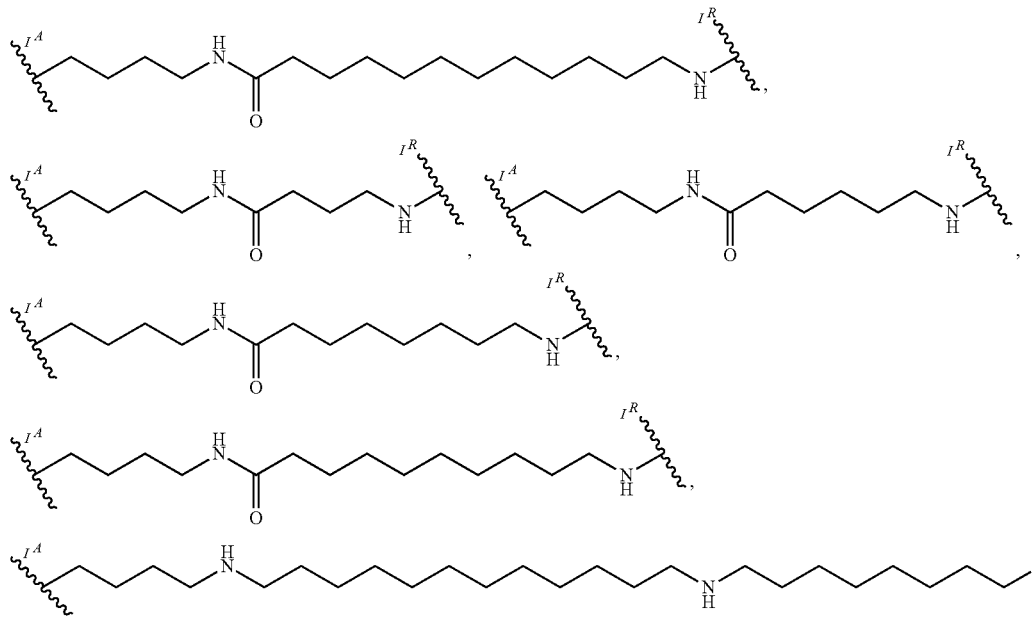

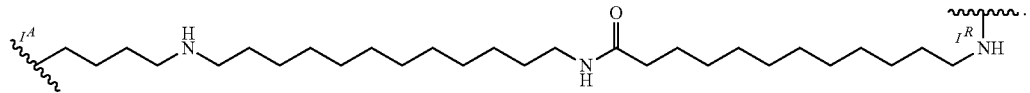

In certain embodiments, L is of the formula:

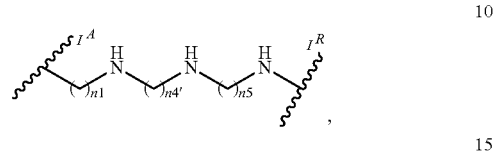

wherein: n1 is 1, 2, 3, 4, 5, or 6; n4' is 1, 2, 3, 4, 5, 6, 7, 8, 9, 10, 11, 12, 13, 14, 15, 16, 17, or 18; and n5 is 1, 2, 3, 4, 5, 6, 7, 8, 9, 10, 11, or 12. In certain embodiments, n5 is 1. In certain embodiments, n4 is 2. In certain embodiments, n5 is 3. In certain embodiments, n5 is 4. In certain embodiments, n5 is 5. In certain embodiments, n5 is 6. In certain embodiments, n5 is 7. In certain embodiments, n5 is 8. In certain embodiments, n5 is 9. In certain embodiments, n5 is 10. In certain embodiments, n5 is 11. In certain embodiments, n5 is 12. In certain embodiments, n is 4; n4' is 5, 6, 7, 8, 9, 10, 11, 12, 13, 14, 15, 16, 17, or 18; and n5 is 5, 6, 7, 8, 9, 10, 11, or 12. In certain embodiments, L is of the formula:

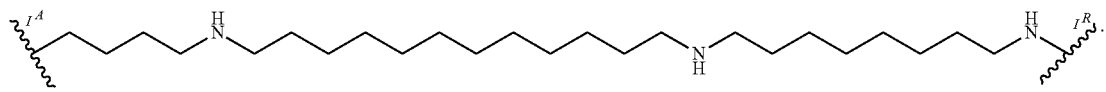

In certain embodiments, L is of the formula:

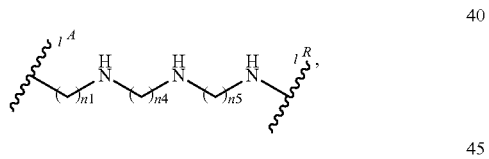

wherein: n1 is 1, 2, 3, 4, 5, or 6; n4 is 1, 2, 3, 4, 5, 6, 7, 8, 9, 10, 11, or 12; and n5 is 1, 2, 3, 4, 5, 6, 7, 8, 9, 10, 11, or 12. In certain embodiments, n5 is 1. In certain embodiments, n4 is 2. In certain embodiments, n5 is 3. In certain embodiments, n5 is 4. In certain embodiments, n5 is 5. In certain embodiments, n5 is 6. In certain embodiments, n5 is 7. In certain embodiments, n5 is 8. In certain embodiments, n5 is 9. In certain embodiments, n5 is 10. In certain embodiments, n5 is 11. In certain embodiments, n5 is 12. In certain embodiments, n is 4; n4 is 5, 6, 7, 8, 9, 10, 11, or 12; and n5 is 5, 6, 7, 8, 9, 10, 11, or 12. In certain embodiments L is of the formula:

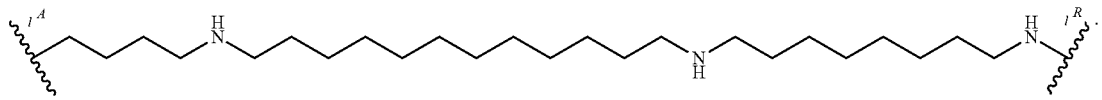

In certain embodiments, L is of the formula:

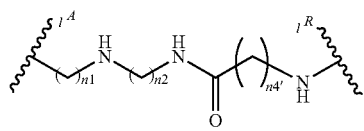

wherein: n1 is 1, 2, 3, 4, 5, or 6; n2 is 1, 2, 3, 4, 5, or 6; and n4' is 1, 2, 3, 4, 5, 6, 7, 8, 9, 10, 11, 12, 13, 14, 15, 16, 17, or 18. In certain embodiments, n1 is 4. In certain embodiments, n1 is 5. In certain embodiments, n1 is 6. In certain embodiments, n2 is 2. In certain embodiments, n1 is 3. In certain embodiments, n2 is 4. In certain embodiments, n2 is 5. In certain embodiments, n2 is 6. In certain embodiments, n4' is 3. In certain embodiments, n4' is 4. In certain embodiments, n4' is 5. In certain embodiments, n4' is 6. In certain embodiments, n4' is 7. In certain embodiments, n4' is 8. In certain embodiments, n4' is 9. In certain embodiments, n4' is 10. In certain embodiments, n4' is 11. In certain embodiments, n4' is 12. In certain embodiments, n4' is 13. In certain embodiments, n4' is 14. In certain embodiments, n4' is 15. In certain embodiments, n4' is 16. In certain embodiments, n4' is 17. In certain embodiments, n4' is 18.

In certain embodiments, L is of the formula:

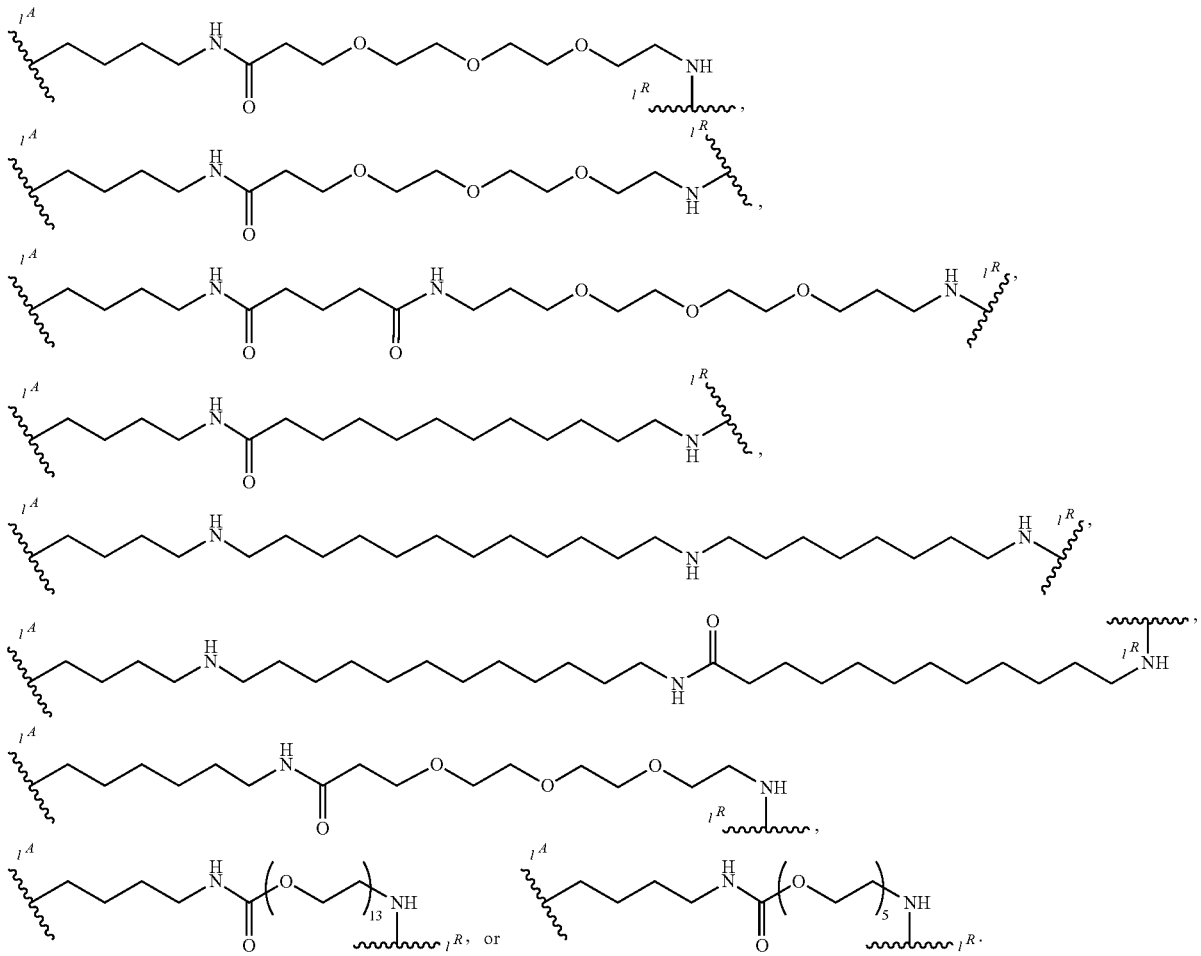

In certain embodiments, L is of the formula:

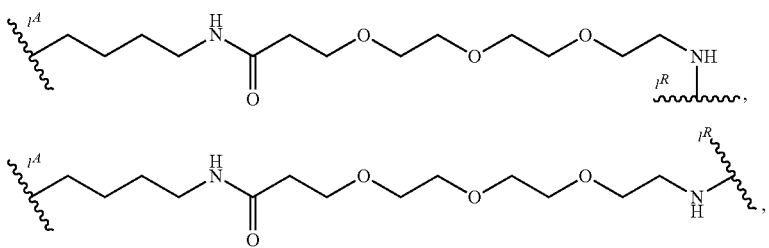

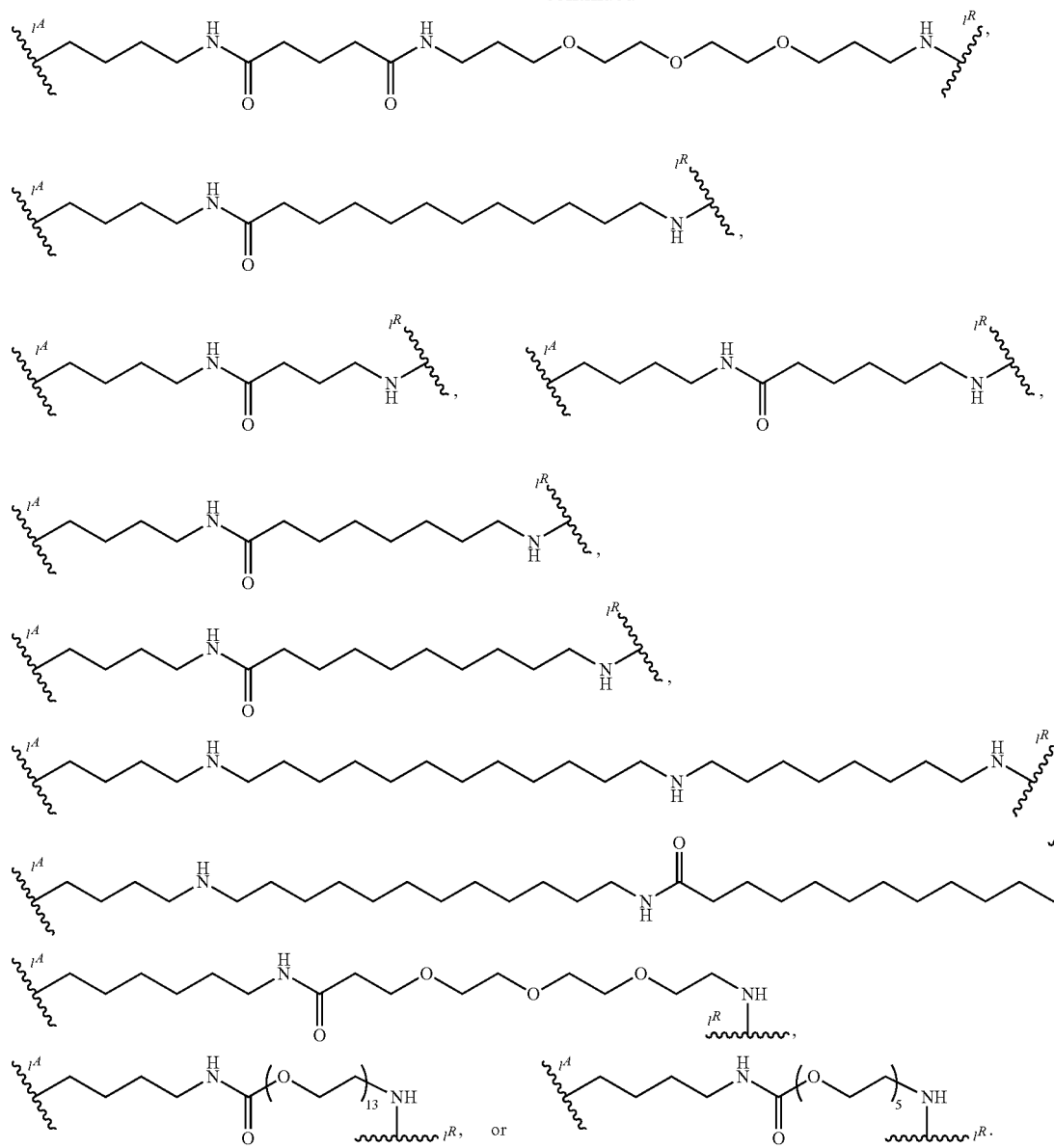
Compounds of Formula (I')
In certain embodiments, a compound of Formula (I') is of the formula:
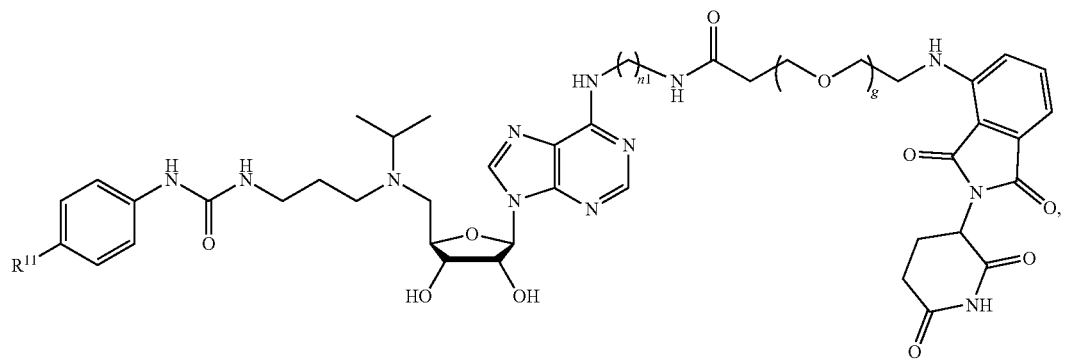

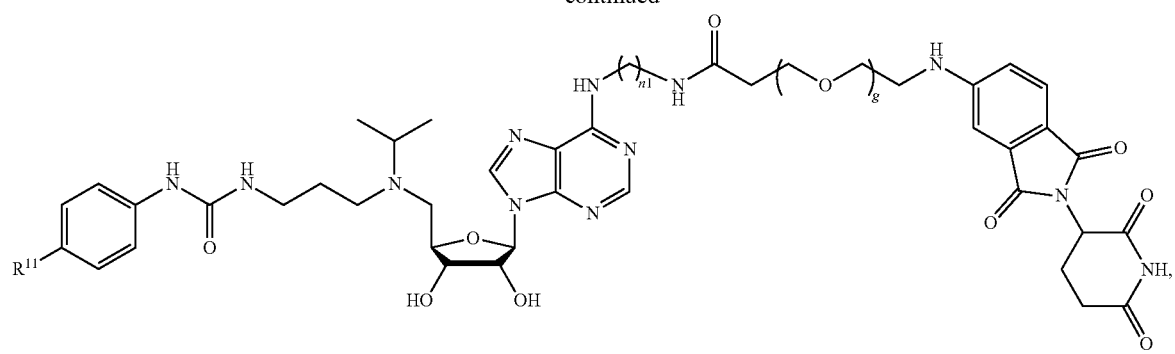
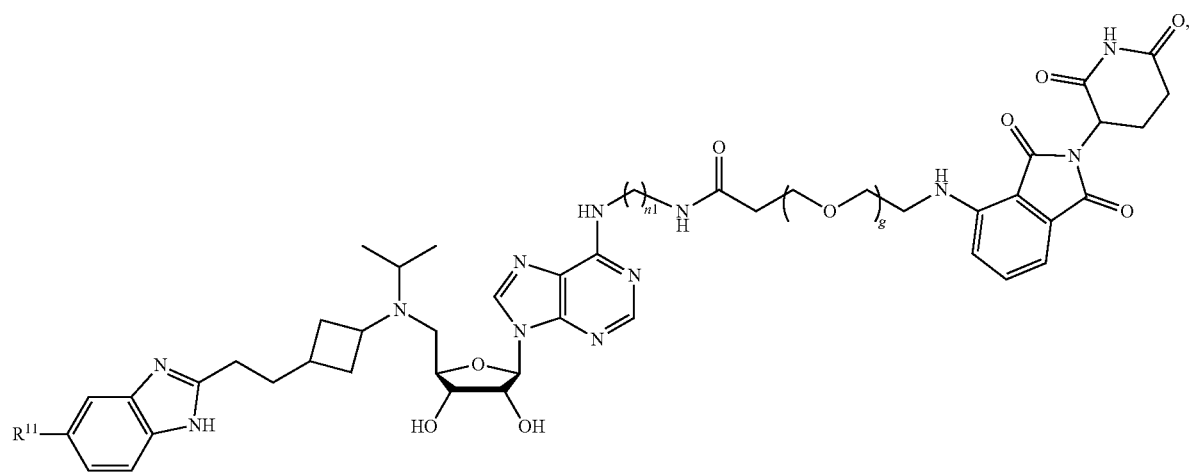
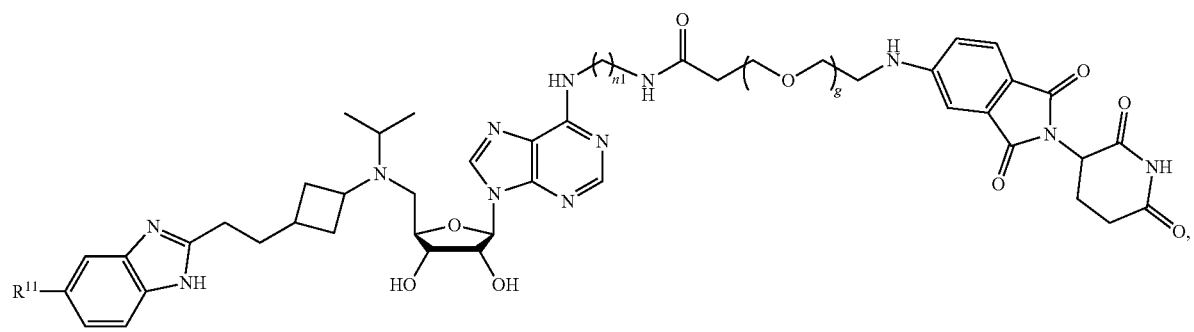
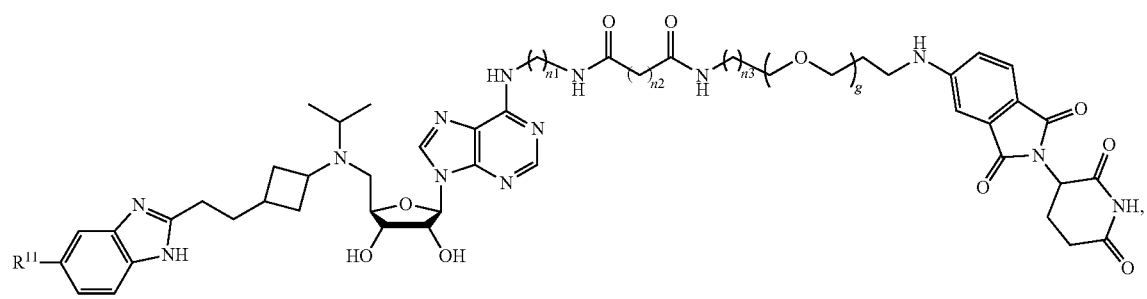

-continued
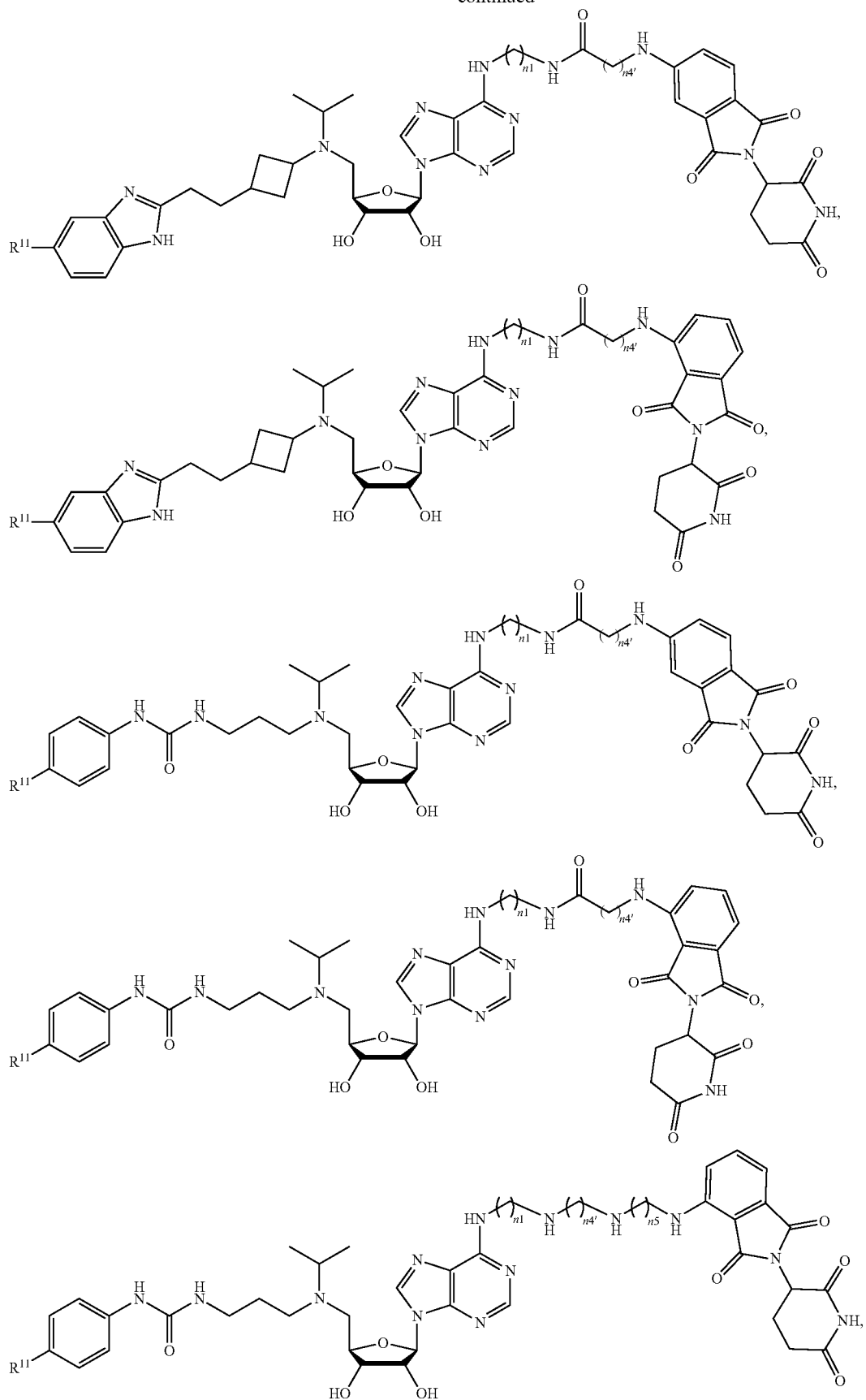

-continued
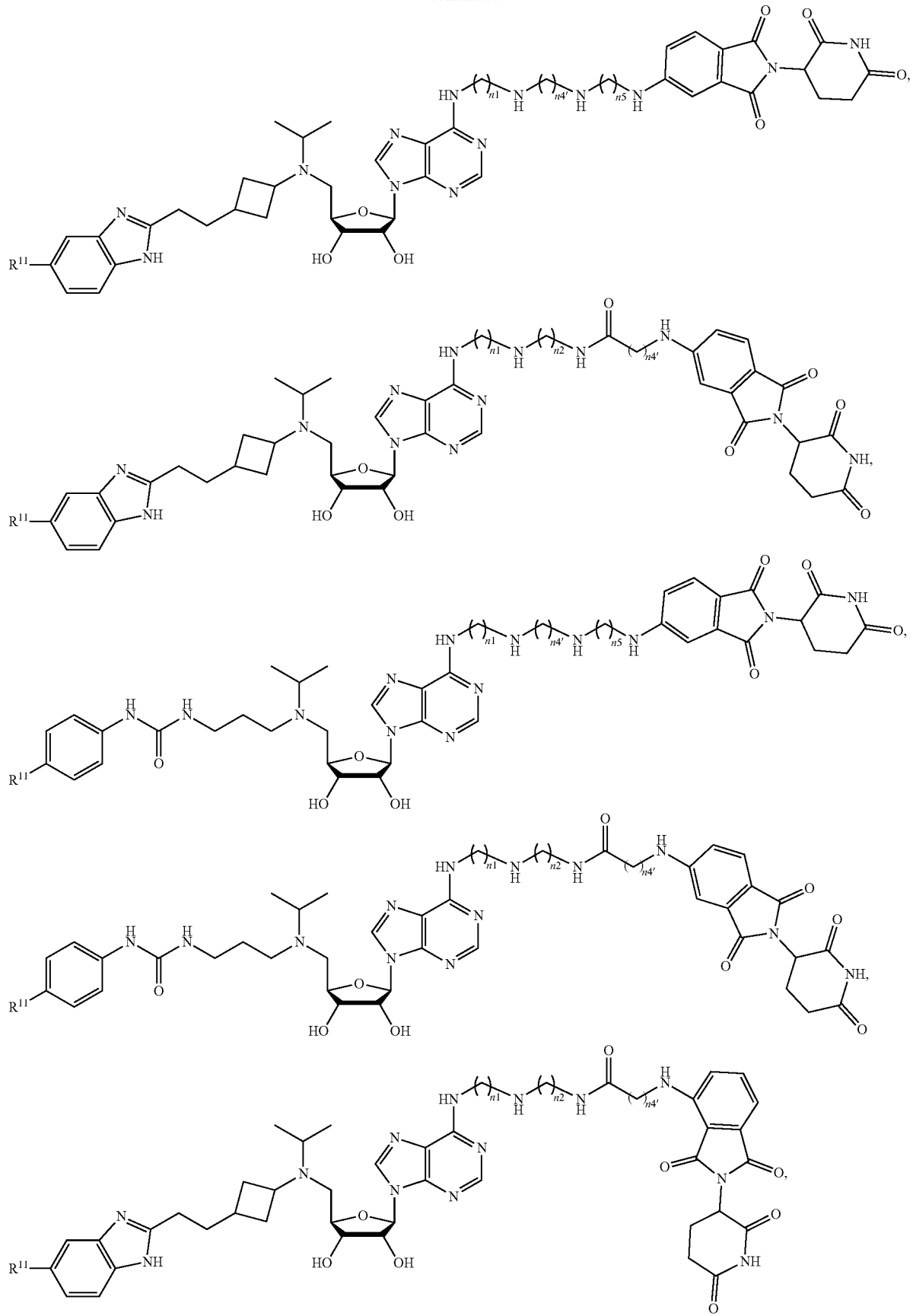

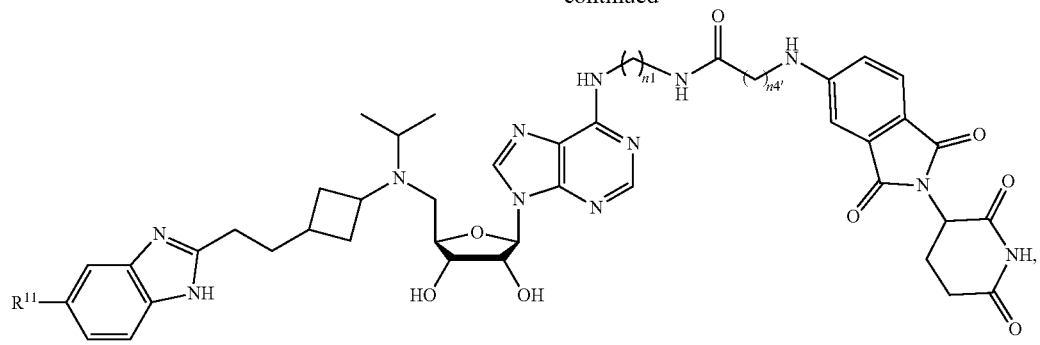
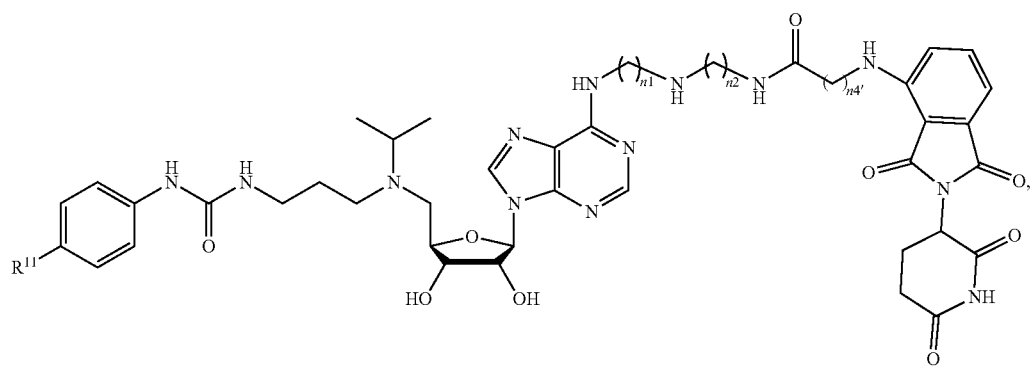
or a pharmaceutically acceptable salt, solvate, hydrate, tautomer, or stereoisomer thereof.
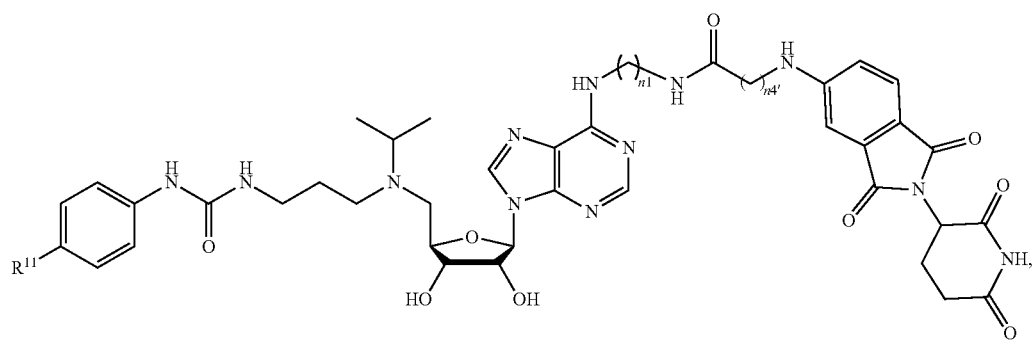
In certain embodiments, a compound of Formula (I') is of the formula:
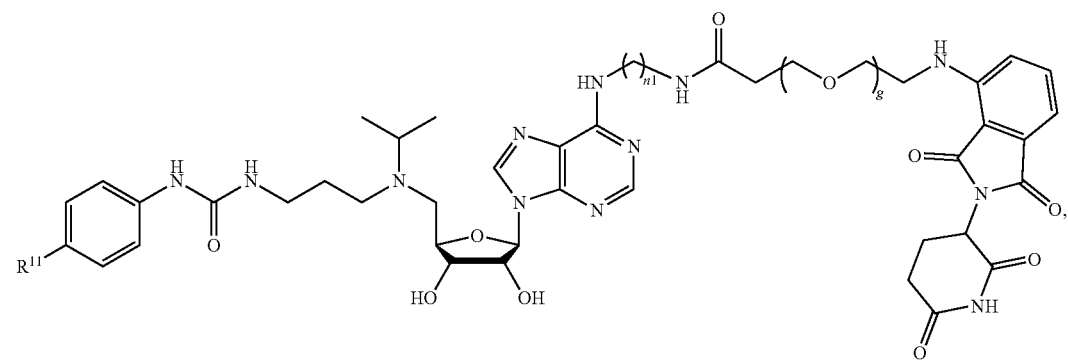

-continued
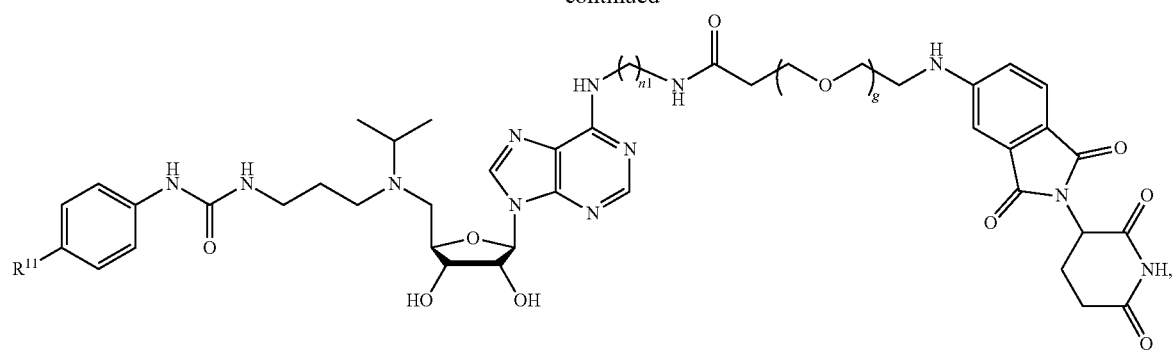
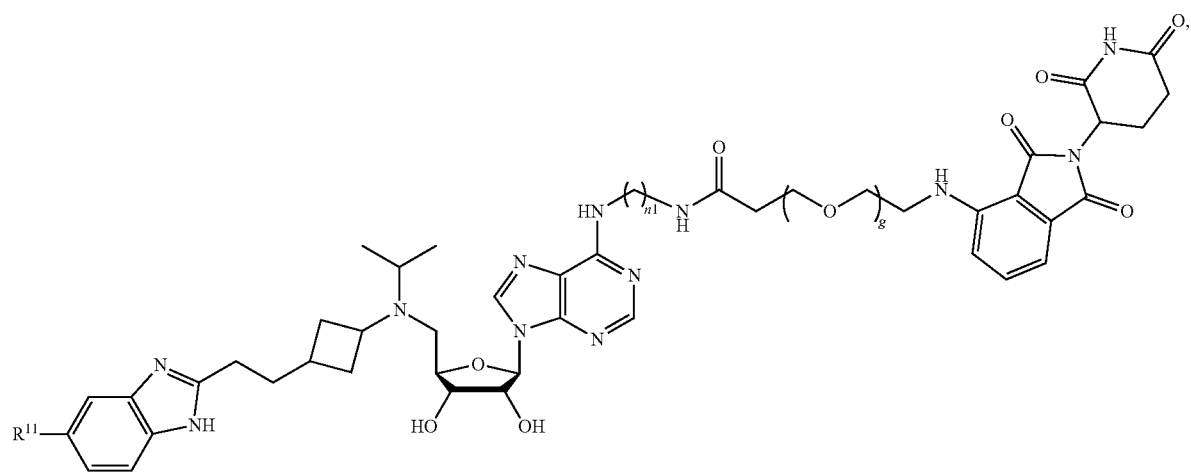
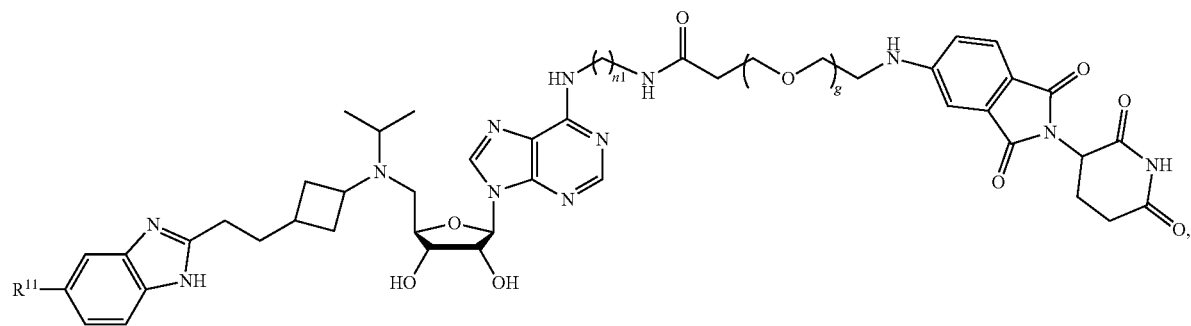
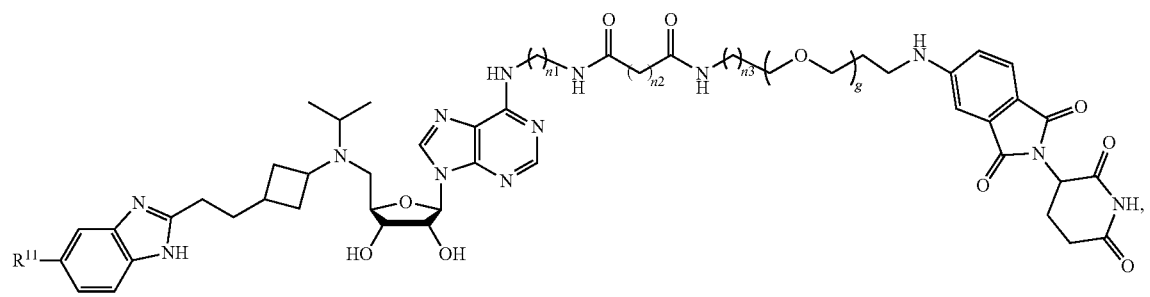

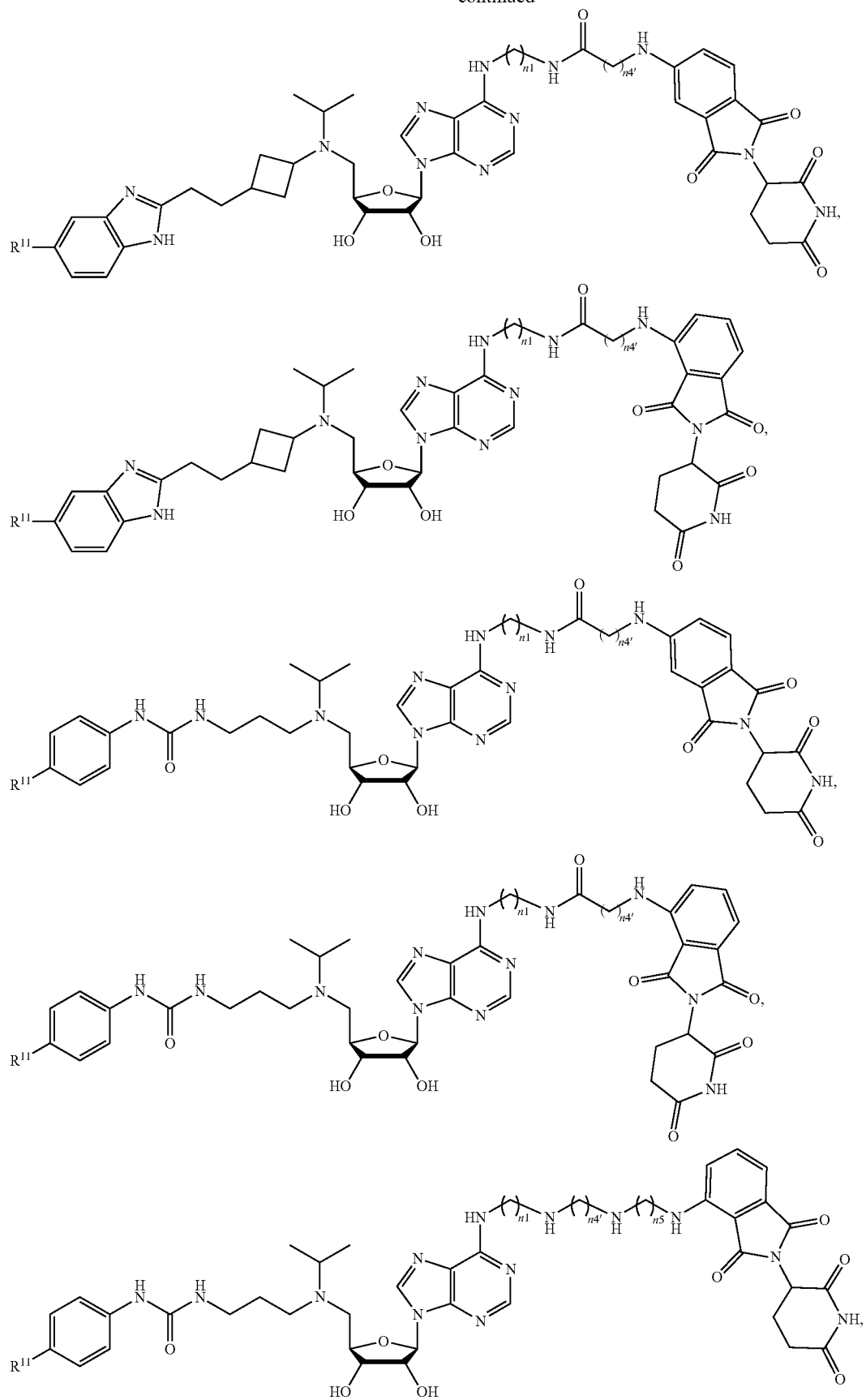

-continued
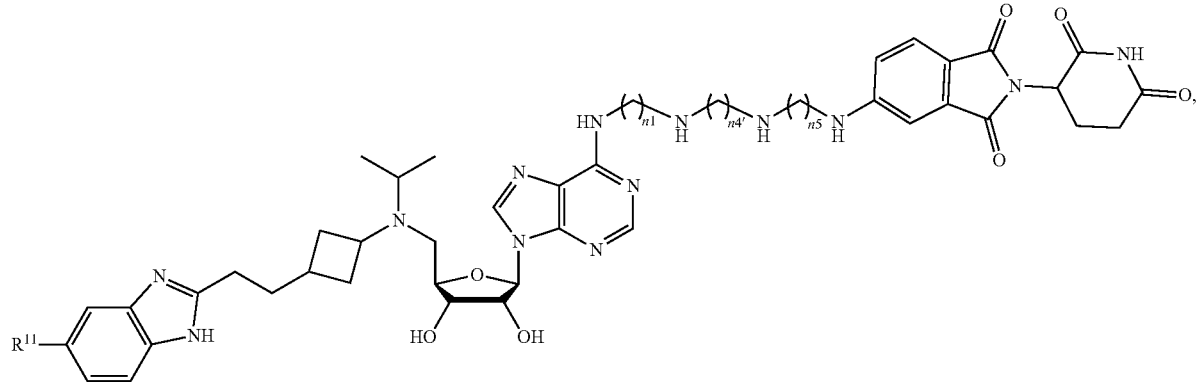
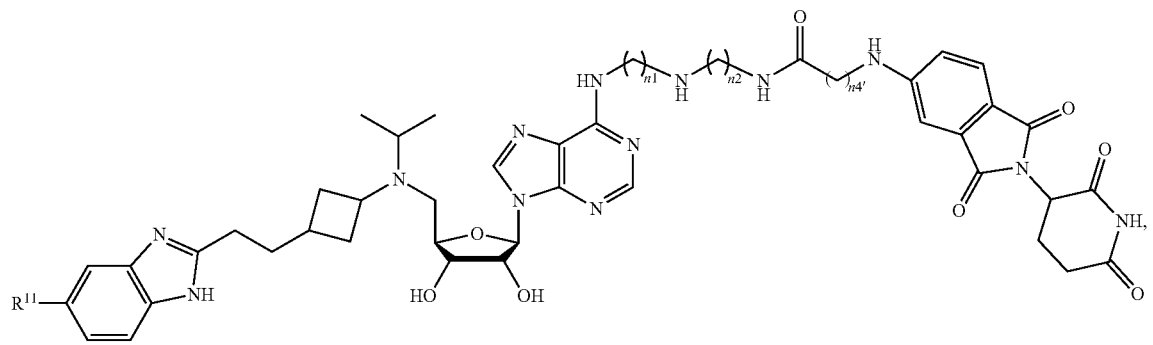
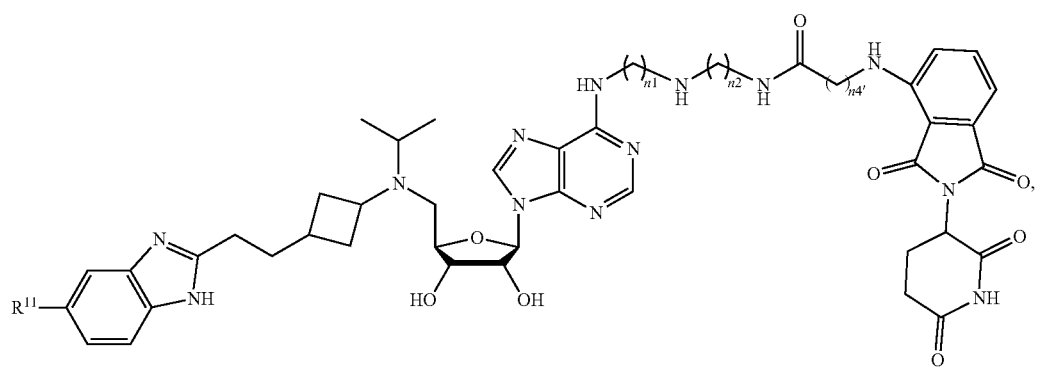
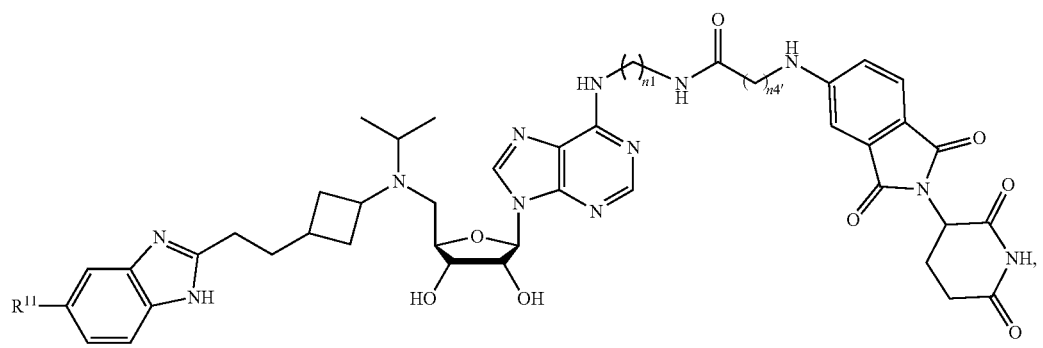

or a pharmaceutically acceptable salt, solvate, hydrate, tautomer, or stereoisomer thereof.
In certain embodiments, a compound of Formula (I') is of the formula:
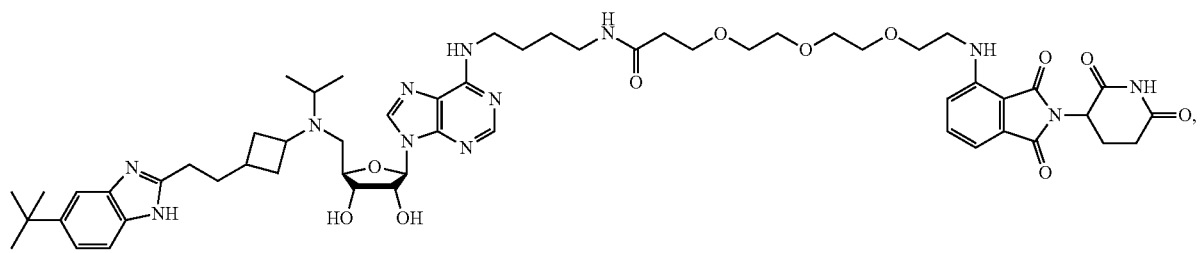
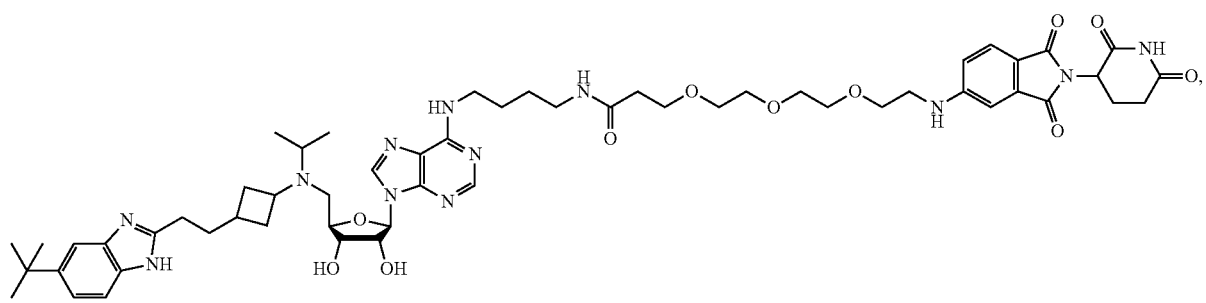
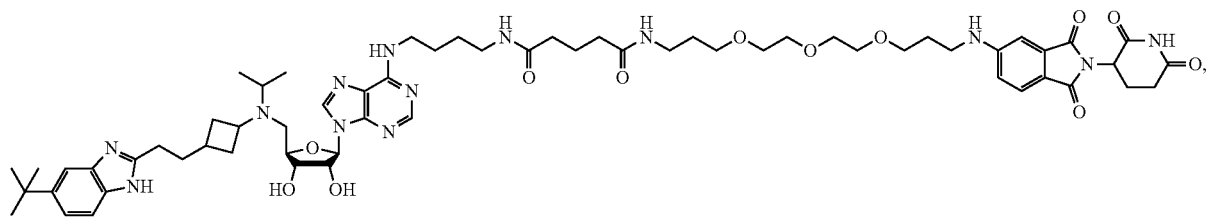
(JQ-DD1)
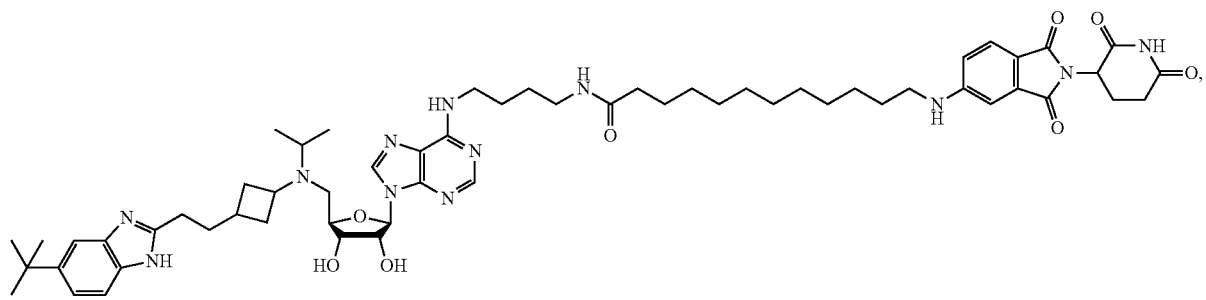
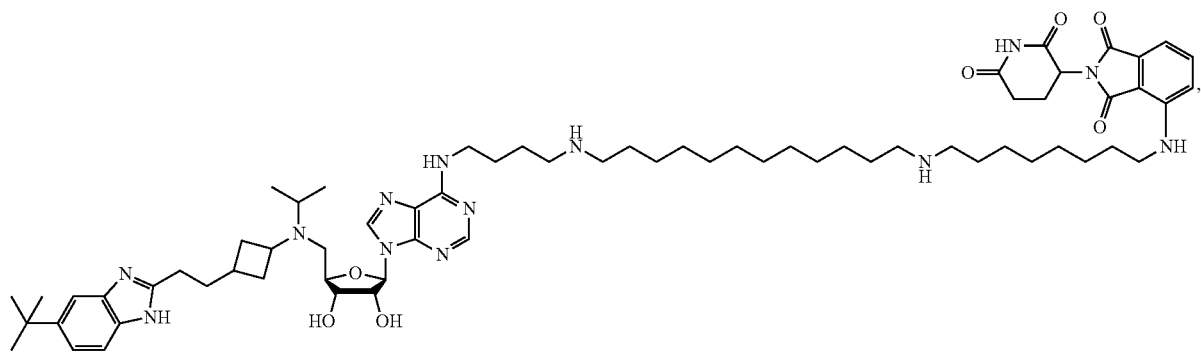

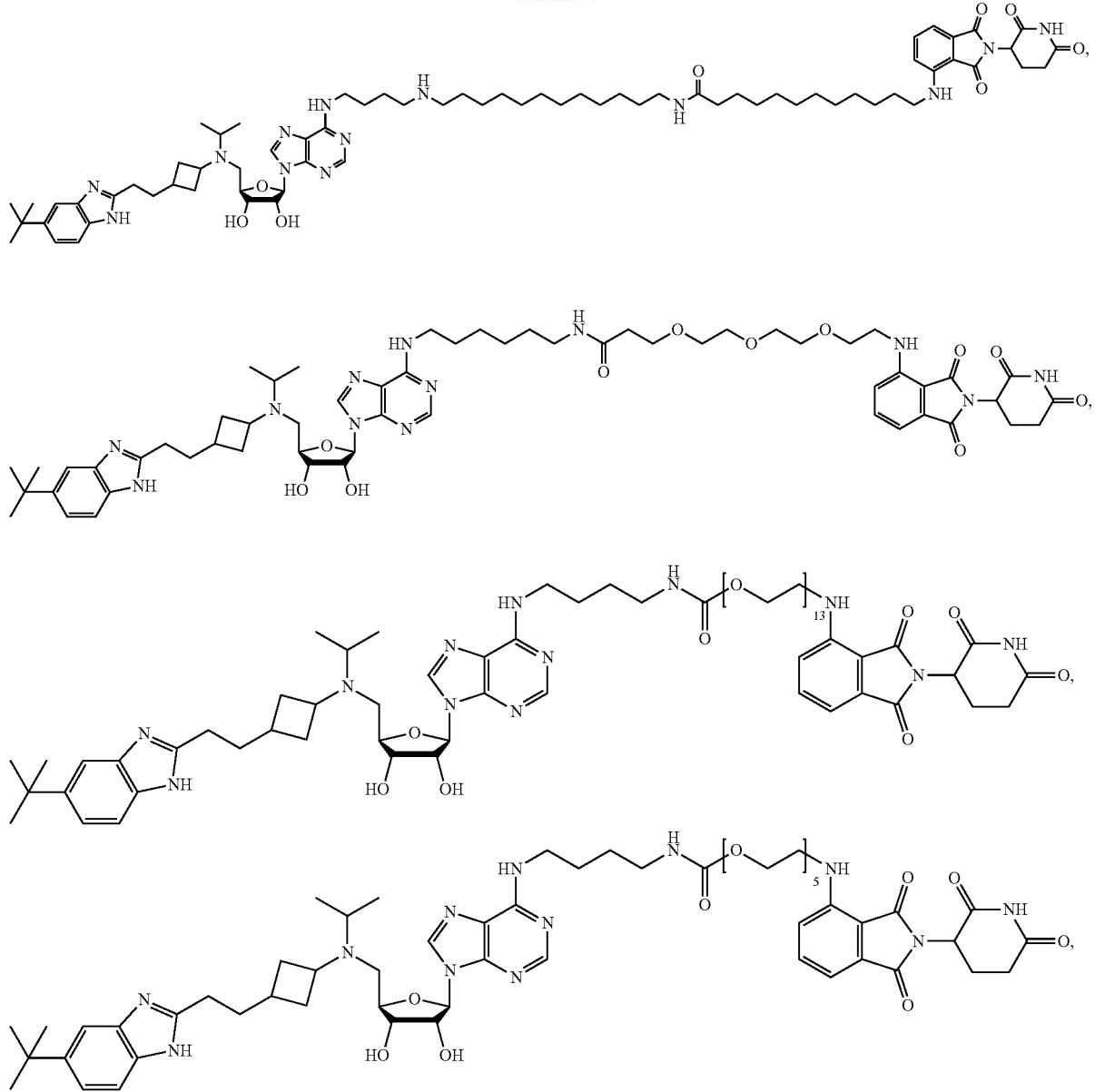
or a pharmaceutically acceptable salt, solvate, hydrate, tautomer, or stereoisomer thereof.
In certain embodiments, the compound of Formula (I') is of the formula:
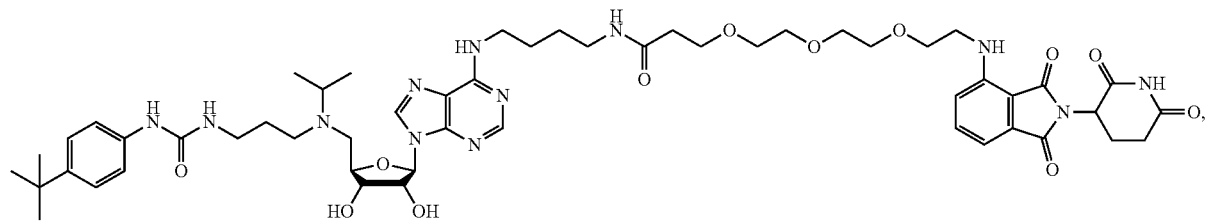
or a pharmaceutically acceptable salt, solvate, hydrate, tautomer, or stereoisomer thereof.

In certain embodiments, a compound of Formula (I') is of the formula:
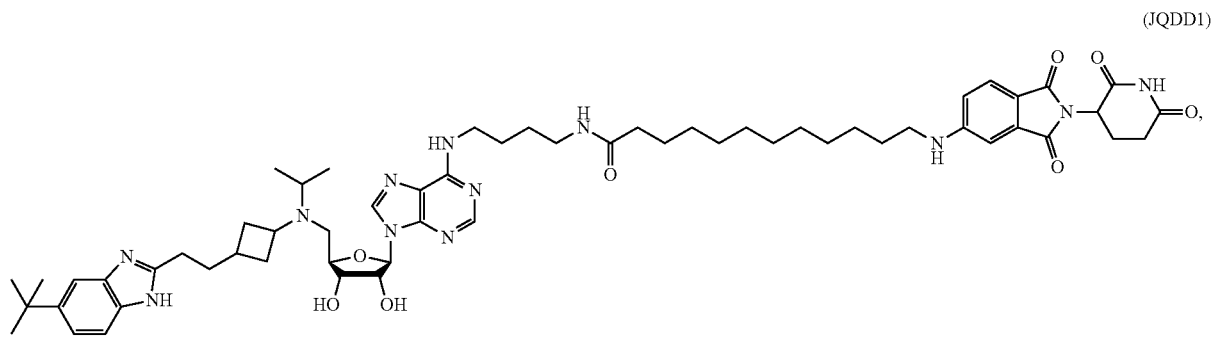
(JQDD1)
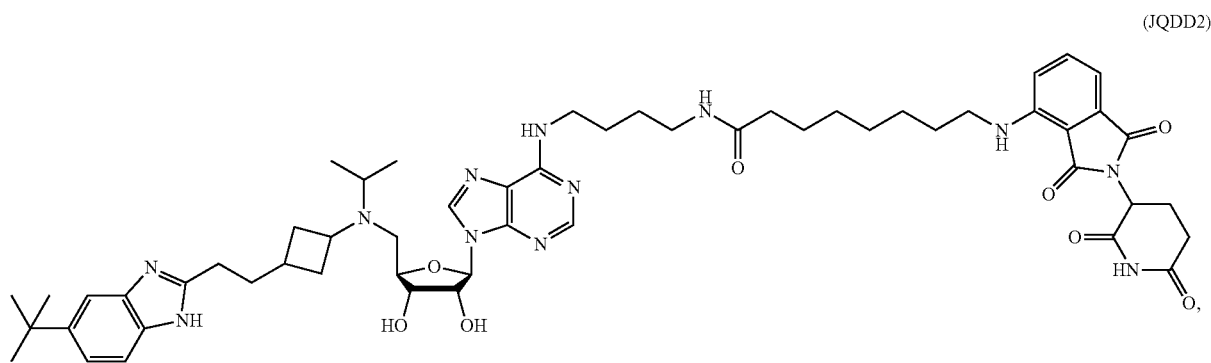
(JQDD2)
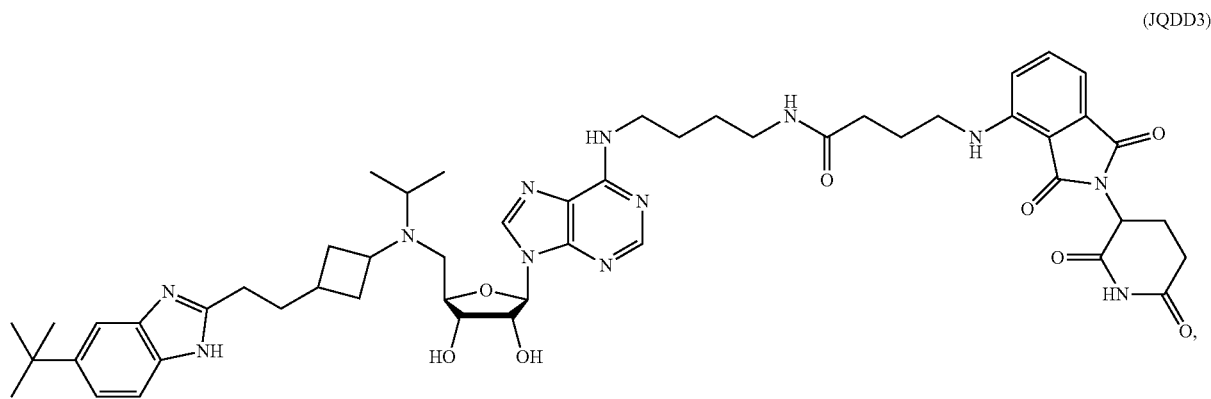
(JQDD3)
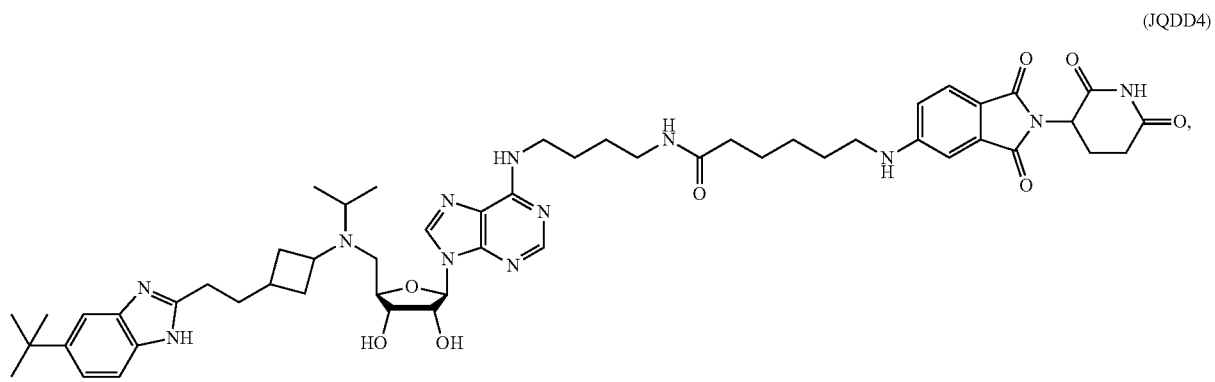
(JQDD4)

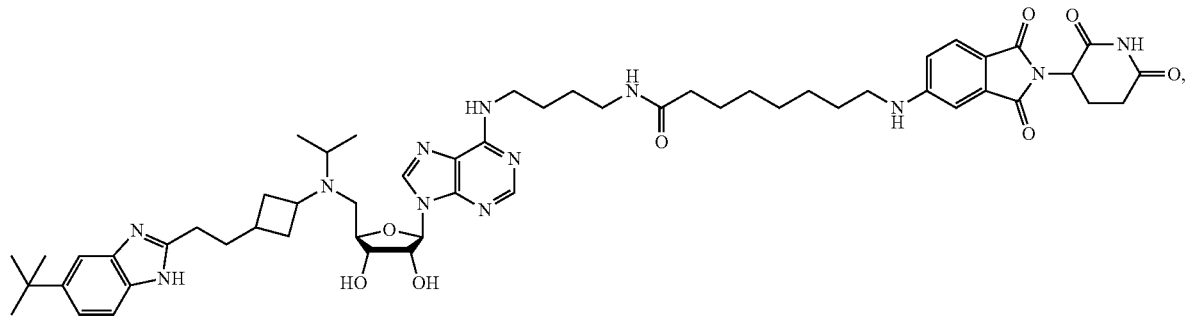

(JQDD5)

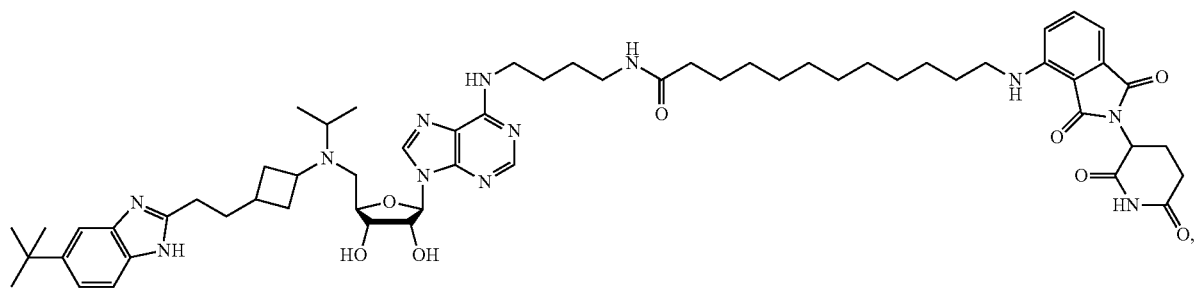

(JQDD6)

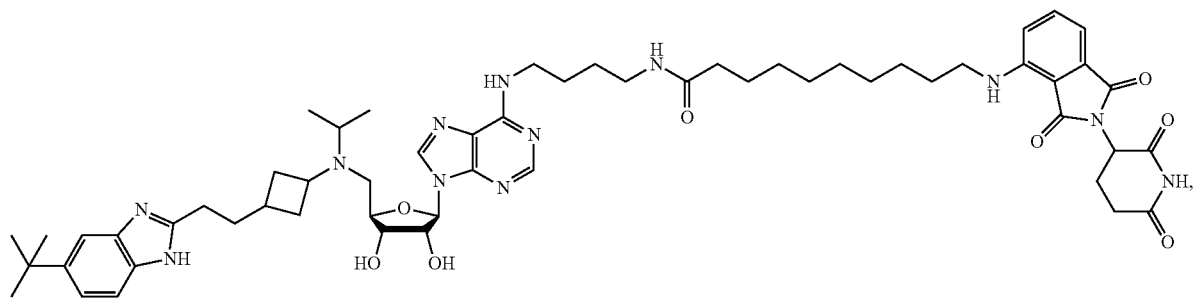

(JQDD7)

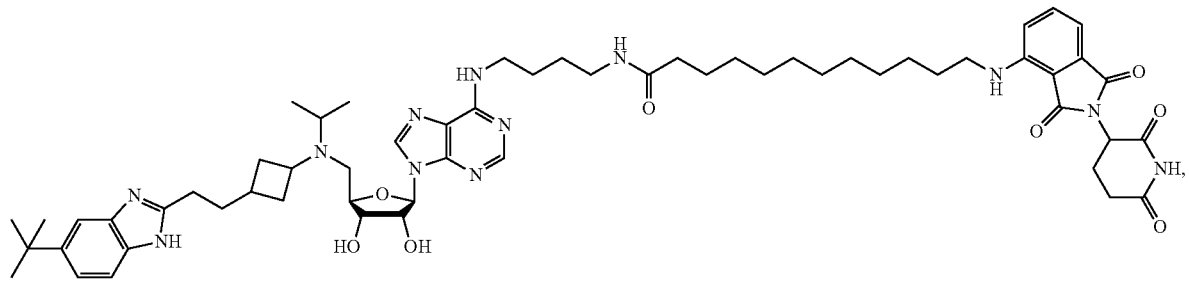

(JQDD8)

or a pharmaceutically acceptable salt, solvate, hydrate, tautomer, or stereoisomer thereof.

In certain embodiments, the compound of Formula (I') includes a pharmaceutically acceptable salt, solvate, hydrate, tautomer, or stereoisomer thereof. In certain embodiments, the compound of Formula (I') includes a pharmaceutically acceptable salt thereof. In some embodiments, the compound of Formula (I') selectively binds DOT1L over another protein. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In some embodiments, the compound of Formula (I') selectively degrades DOT1L over other proteins in the proteome. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In some embodiments, the compound of Formula (I') selectively binds E3 ligase over another protein. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In certain embodiments, the compound of Formula (I') induces the degradation of up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% of the target protein DOT1L at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

In certain embodiments, the compound of Formula (I') increases the rate of degradation of the target protein DOT1L up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

Pharmaceutical Compositions, Kits, and Administration

The present disclosure provides pharmaceutical compositions comprising a compound of Formula (I'), or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formula (I'), or a pharmaceutically acceptable salt thereof, and a pharmaceutically acceptable excipient.

In certain embodiments, the compound of Formula (I') is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a disease (e.g., a proliferative disease) in a subject in need thereof. In certain embodiments, the effective amount is an amount effective for preventing a disease (e.g., a proliferative disease) in a subject in need thereof. In certain embodiments, the effective amount is an amount effective for treating cancer in a subject in need thereof. In certain embodiments, the effective amount is an amount effective for preventing cancer in a subject in need thereof. In certain embodiments, the effective amount is an amount effective for reducing the risk of developing a disease (e.g., proliferative disease or cancer) in a subject in need thereof.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inducing the degradation of at least about 10%, at least about 15%, at least about 20%, at least about 25%, at least about 30%, at least about 35%, at least about 40%, at least about 42%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% of the target protein DOT1L in a cell. In certain embodiments, the effective amount is an amount effective for inducing the degradation of the target protein DOT1L in a cell by a range between a percentage described in this paragraph and another percentage described in this paragraph, inclusive.

The present disclosure provides pharmaceutical compositions comprising a compound that interacts with a E3 ubiquitin ligase (e.g., cereblon) and the target protein DOT1L for use in treating a disease (e.g., a proliferative disease) in a subject in need thereof.

In certain embodiments, the composition is for use in treating cancer. In certain embodiments, the composition is for use in treating multiple myeloma, lymphoma, leukemia (e.g., acute myelocytic leukemia (e.g., acute myelocytic leukemia with a mutation in the nucleophosmin (NPM1) gene; acute myelocytic leukemia with a mutation in the DNMT3A gene), mixed-lineage leukemia (MLL) rearranged acute myelocytic leukemia), or a cancer resistant to proteasome inhibitors. In certain embodiments, the composition is for use in treating multiple myeloma. In certain embodiments, the composition is for use in treating lymphoma. In certain embodiments, the composition is for use in treating leukemia. In certain embodiments, the composition is for use in treating acute myelocytic leukemia. In certain embodiments, the composition is for use in treating acute myelocytic leukemia with a mutation in the nucleophosmin (NPM1) gene. In certain embodiments, the composition is for use in treating acute myelocytic leukemia with a mutation in the DNMT3A gene. In certain embodiments, the composition is for use in treating mixed-lineage leukemia (MLL) rearranged acute myelocytic leukemia). In certain embodiments, the composition is for use in treating acute myeloid eosinophilic leukemia. In certain embodiments, the composition is for use in treating cancer resistant to proteasome inhibitors. In certain embodiments, the composition is for use in treating cancer resistant to bortezomib. In certain embodiments, the composition is for use in treating cancer resistant to carfilzomib. In certain embodiments, the composition is for use in treating multiple myeloma.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol*), sucrose fatty acid esters, polyethylene glycol fatty acid esters (e.g., Cremophor), polyoxyethylene ethers, (e.g., polyoxyethylene lauryl ether (Brij© 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum©), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip©, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner.

Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inducing the degradation of a target protein, and/or in reducing the risk to develop a disease in a subject in need thereof), improve bioavailability, improve their ability to cross the blood-brain barrier, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-proliferative agents, anti-cancer agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is an anti-leukemia agent. In certain embodiments, the additional pharmaceutical agent is an anti-lymphoma agent. In certain embodiments, the additional pharmaceutical agent is an anti-multiple myeloma agent. In certain embodiments, the additional pharmaceutical agent is ABITREXATE (methotrexate), ADE, Adriamycin RDF (doxorubicin hydrochloride), Ambochlorin (chlorambucil), ARRANON (nelarabine), ARZERRA (ofatumumab), BOSULIF (bosutinib), BUSULFEX (busulfan), CAMPATH (alemtuzumab), CERUBIDINE (daunorubicin hydrochloride), CLAFEN (cyclophosphamide), CLOFAREX (clofarabine), CLOLAR (clofarabine), CVP, CYTOSAR-U (cytarabine), CYTOXAN (cyclophosphamide), ERWINAZE (Asparaginase Erwinia Chrysanthemi), FLUDARA (fludarabine phosphate), FOLEX (methotrexate), FOLEX PFS (methotrexate), GAZYVA (obinutuzumab), GLEEVEC (imatinib mesylate), Hyper-CVAD, ICLUSIG (ponatinib hydrochloride), IMBRUVICA (ibrutinib), LEUKERAN (chlorambucil), LINFOLIZIN (chlorambucil), MARQIBO (vincristine sulfate liposome), METHOTREXATE LPF (methorexate), MEXATE (methotrexate), MEXATE-AQ (methotrexate), mitoxantrone hydrochloride, MUSTARGEN (mechlorethamine hydrochloride), MYLERAN (busulfan), NEOSAR (cyclophosphamide), ONCASPAR (Pegaspargase), PURINETHOL (mercaptopurine), PURIXAN (mercaptopurine), Rubidomycin (daunorubicin hydrochloride), SPRYCEL (dasatinib), SYNRIBO (omacetaxine mepesuccinate), TARABINE PFS (cytarabine), TASIGNA (nilotinib), TREANDA (bendamustine hydrochloride), TRISENOX (arsenic trioxide), VINCASAR PFS (vincristine sulfate), ZYDELIG (idelalisib), or a combination thereof. In certain embodiments, the additional pharmaceutical agent is an anti-lymphoma agent. In certain embodiments, the additional pharmaceutical agent is ABITREXATE (methotrexate), ABVD, ABVE, ABVE-PC, ADCETRIS (brentuximab vedotin), ADRIAMYCIN PFS (doxorubicin hydrochloride), ADRIAMYCIN RDF (doxorubicin hydrochloride), AMBOCHLORIN (chlorambucil), AMBOCLORIN (chlorambucil), ARRANON (nelarabine), BEACOPP, BECENUM (carmustine), BELEODAQ (belinostat), BEXXAR (tositumomab and iodine 1131 tositumomab), BICNU (carmustine), BLENOXANE (bleomycin), CARMUBRIS (carmustine), CHOP, CLAFEN (cyclophosphamide), COPP, COPP-ABV, CVP, CYTOXAN (cyclophosphamide), DEPOCYT (liposomal cytarabine), DTIC-DOME (dacarbazine), EPOCH, FOLEX (methotrexate), FOLEX PFS (methotrexate), FOLOTYN (pralatrexate), HYPER-CVAD, ICE, IMBRUVICA (ibrutinib), INTRON A (recombinant interferon alfa-2b), ISTODAX (romidepsin), LEUKERAN (chlorambucil), LINFOLIZIN (chlorambucil), Lomustine, MATULANE (procarbazine hydrochloride), METHOTREXATE LPF (methotrexate), MEXATE (methotrexate), MEXATE-AQ (methotrexate), MOPP, MOZOBIL (plerixafor), MUSTARGEN (mechlorethamine hydrochloride), NEOSAR (cyclophosphamide), OEPA, ONTAK (denileukin diftitox), OPPA, R-CHOP, REVLIMID (lenalidomide), RITUXAN (rituximab), STANFORD V, TREANDA (bendamustine hydrochloride), VAMP, VELBAN (vinblastine sulfate), VELCADE (bortezomib), VELSAR (vinblastine sulfate), VINCASAR PFS (vincristine sulfate), ZEVALIN (ibritumomab tiuxetan), ZOLINZA (vorinostat), ZYDELIG (idelalisib), or a combination thereof. In certain embodiments, the additional pharmaceutical agent is REVLIMID (lenalidomide), DACOGEN (decitabine), VIDAZA (azacitidine), CYTOSAR-U (cytarabine), IDAMYCIN (idarubicin), CERUBIDINE (daunorubicin), LEUKERAN (chlorambucil), NEOSAR (cyclophosphamide), FLUDARA (fludarabine), LEUSTATIN (cladribine), or a combination thereof. In certain embodiments, the additional pharmaceutical agent is ABITREXATE (methotrexate), ABRAXANE (paclitaxel albumin-stabilized nanoparticle formulation), AC, AC-T, ADE, ADRIAMYCIN PFS (doxorubicin hydrochloride), ADRUCIL (fluorouracil), AFINITOR (everolimus), AFINITOR DISPERZ (everolimus), ALDARA (imiquimod), ALIMTA (pemetrexed disodium), AREDIA (pamidronate disodium), ARIMIDEX (anastrozole), AROMASIN (exemestane), AVASTIN (bevacizumab), BECENUM (carmustine), BEP, BICNU (carmustine), BLENOXANE (bleomycin), CAF, CAMPTOSAR (irinotecan hydrochloride), CAPOX, CAPRELSA (vandetanib), CARBOPLATIN-TAXOL, CARMUBRIS (carmustine), CASODEX (bicalutamide), CEENU (lomustine), CERUBIDINE (daunorubicin hydrochloride), CERVARIX (recombinant HPV bivalent vaccine), CLAFEN (cyclophosphamide), CMF, COMETRIQ (cabozantinib-s-malate), COSMEGEN (dactinomycin), CYFOS (ifosfamide), CYRAMZA (ramucirumab), CYTOSAR-U (cytarabine), CYTOXAN (cyclophosphamide), DACOGEN (decitabine), DEGARELIX, DOXIL (doxorubicin hydrochloride liposome), DOXORUBICIN HYDROCHLORIDE, DOX-SL (doxorubicin hydrochloride liposome), DTIC-DOME (dacarbazine), EFUDEX (fluorouracil), ELLENCE (epirubicin hydrochloride), ELOXATIN (oxaliplatin), ERBITUX (cetuximab), ERIVEDGE (vismodegib), ETOPOPHOS (etoposide phosphate), EVACET (doxorubicin hydrochloride liposome), FARESTON (toremifene), FASLODEX (fulvestrant), FEC, FEMARA (letrozole), FLUOROPLEX (fluorouracil), FOLEX (methotrexate), FOLEX PFS (methotrexate), FOLFIRI, FOLFIRI-BEVACIZUMAB, FOLFIRI-CETUXIMAB, FOLFIRINOX, FOLFOX, FU-LV, GARDASIL (recombinant human papillomavirus (HPV) quadrivalent vaccine), GEMCITABINE-CISPLATIN, GEMCITABINE-OXALIPLATIN, GEMZAR (gemcitabine hydrochloride), GILOTRIF (afatinib dimaleate), GLEEVEC (imatinib mesylate), GLIADEL (carmustine implant), GLIADEL WAFER (carmustine implant), HERCEPTIN (trastuzumab), HYCAMTIN (topotecan hydrochloride), IFEX (ifosfamide), IFOSFAMIDUM (ifosfamide), INLYTA (axitinib), INTRON A (recombinant interferon alfa-2b), IRESSA (gefitinib), IXEMPRA (ixabepilone), JAKAFI (ruxolitinib phosphate), JEVTANA (cabazitaxel), KADCYLA (ado-trastuzumab emtansine), KEYTRUDA (pembrolizumab), KYPROLIS (carfilzomib), LIPODOX (doxorubicin hydrochloride liposome), LUPRON (leuprolide acetate), LUPRON DEPOT (leuprolide acetate), LUPRON DEPOT-3 MONTH (leuprolide acetate), LUPRON DEPOT-4 MONTH (leuprolide acetate), LUPRON DEPOT-PED (leuprolide acetate), MEGACE (megestrol acetate), MEKINIST (trametinib), METHAZOLASTONE (temozolomide), METHOTREXATE LPF (methotrexate), MEXATE (methotrexate), MEXATE-AQ (methotrexate), MITOXANTRONE HYDROCHLORIDE, MITOZYTREX (mitomycin c), MOZOBIL (plerixafor), MUSTARGEN (mechlorethamine hydrochloride), MUTAMYCIN (mitomycin c), MYLOSAR (azacitidine), NAVELBINE (vinorelbine tartrate), NEOSAR (cyclophosphamide), NEXAVAR (sorafenib tosylate), NOLVADEX (tamoxifen citrate), NOVALDEX (tamoxifen citrate), OFF, PAD, PARAPLAT (carboplatin), PARAPLATIN (carboplatin), PEG-INTRON (peginterferon alfa-2b), PEMETREXED DISODIUM, PERJETA (pertuzumab), PLATINOL (cisplatin), PLATINOL-AQ (cisplatin), POMALYST (pomalidomide), prednisone, PROLEUKIN (aldesleukin), PROLIA (denosumab), PROVENGE (sipuleucel-t), REVLIMID (lenalidomide), RUBIDOMYCIN (daunorubicin hydrochloride), SPRYCEL (dasatinib), STIVARGA (regorafenib), SUTENT (sunitinib malate), SYLATRON (peginterferon alfa-2b), SYLVANT (siltuximab), SYNOVIR (thalidomide), TAC, TAFINLAR (dabrafenib), TARABINE PFS (cytarabine), TARCEVA (erlotinib hydrochloride), TASIGNA (nilotinib), TAXOL (paclitaxel), TAXOTERE (docetaxel), TEMODAR (temozolomide), THALOMID (thalidomide), TOPOSAR (etoposide), TORISEL (temsirolimus), TPF, TRISENOX (arsenic trioxide), TYKERB (lapatinib ditosylate), VECTIBIX (panitumumab), VEIP, VELBAN (vinblastine sulfate), VELCADE (bortezomib), VELSAR (vinblastine sulfate), VEPESID (etoposide), VIADUR (leuprolide acetate), VIDAZA (azacitidine), VINCASAR PFS (vincristine sulfate), VOTRIENT (pazopanib hydrochloride), WELLCOVORIN (leucovorin calcium), XALKORI (crizotinib), XELODA (capecitabine), XELOX, XGEVA (denosumab), XOFIGO (radium 223 dichloride), XTANDI (enzalutamide), YERVOY (ipilimumab), ZALTRAP (ziv-aflibercept), ZELBORAF (vemurafenib), ZOLADEX (goserelin acetate), ZOMETA (zoledronic acid), ZYKADIA (ceritinib), ZYTIGA (abiraterone acetate), ENMD-2076, PCI-32765, AC220, dovitinib lactate (TK1258, CHIR-258), BIBW 2992 (TOVOK™) SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is a protein kinase inhibitor (e.g., tyrosine protein kinase inhibitor). In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease) in a subject in need thereof. In certain embodiments, the kits are useful for preventing a disease (e.g., proliferative disease) in a subject in need thereof.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease) in a subject in need thereof. In certain embodiments, the kits and instructions provide for preventing a disease (e.g., proliferative disease) in a subject in need thereof. In certain embodiments, the kits and instructions provide for inducing the degradation of target protein DOT1L in a subject, biological sample, tissue, or cell. A kit described herein may include one or more additional pharmaceutical agents described herein as a separate composition.

Methods of Treatment and Uses

The compounds described herein are capable of binding (e.g., reversibly binding or irreversibly binding) an E3 ubiquitin ligase (e.g., Cereblon) and the target protein DOT1L and inducing the degradation of the target protein DOT1L. The present disclosure thus also provides methods of inducing the degradation of the target protein DOT1L in a subject, biological sample, tissue, or cell. The present disclosure further provides methods for the treatment of diseases, such as proliferative diseases in a subject in need thereof.

In certain embodiments, the application provides a method of binding an ubiquitin receptor RPN13 and promoting the degradation of the target protein DOT1L. In another aspect, the present disclosure provides methods of inducing the degradation of the target protein DOT1L in a subject in need thereof, the methods comprise administering to the subject an effective amount of a compound or pharmaceutical composition described herein.

In another aspect, the present disclosure provides methods of inducing the degradation of the target protein DOT1L in a biological sample, tissue, or cell, the methods comprise contacting the biological sample, tissue, or cell with an effective amount of a compound or pharmaceutical composition described herein.

In certain embodiments, the application provides a method of binding an E3 ubiquitin ligase (e.g., Cereblon) and the target protein DOT1L and inducing the degradation of the target protein DOT1L. In certain embodiments, the binder of the target protein DOT1L is of the formula:

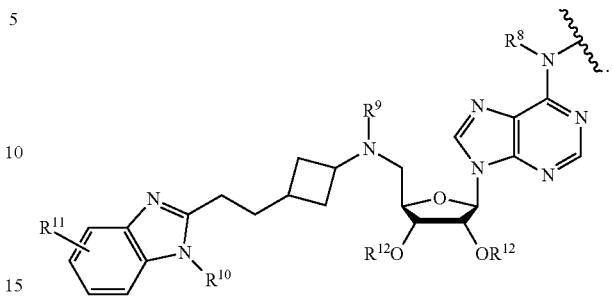

In certain embodiments, the binder of the target protein DOT1L is of the formula:

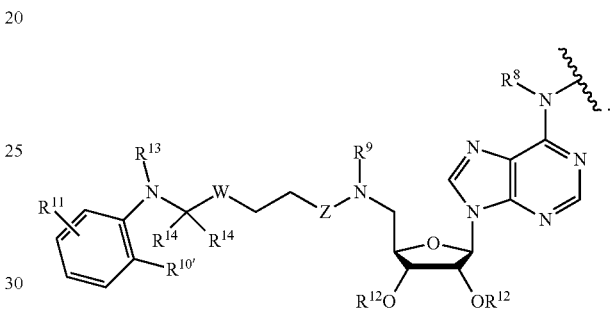

Use of a bifunctional compound that binds an E3 ubiquitin ligase (e.g., Cereblon) and the target protein DOT1L provides a strategy for treating diseases associated with DOT1L (e.g. proliferative diseases), as research tools for studying the role of DOT1L in the cell, or as research tools for studying diseases associated with DOT1L (e.g. proliferative diseases).

The present disclosure also provides a compound of Formula (I'), or a pharmaceutically acceptable salt, co-crystal, tautomer, stereoisomer, solvate, hydrate, polymorph, isotopically enriched derivative, or prodrug, or composition thereof, for use in the treatment of diseases, such as proliferative diseases, in a subject in need thereof.

The present disclosure also provides uses of a compound of Formula (I'), or a pharmaceutically acceptable salt, co-crystal, tautomer, stereoisomer, solvate, hydrate, polymorph, isotopically enriched derivative, or prodrug, or composition thereof, in the manufacture of a medicament for the treatment of diseases, such as proliferative diseases, in a subject in need thereof.

In certain embodiments, the methods of the disclosure comprise administering to the subject an effective amount of a compound of Formula (I'), or a pharmaceutically acceptable salt, co-crystal, tautomer, stereoisomer, solvate, hydrate, polymorph, isotopically enriched derivative, or prodrug, or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formula (I'), or at different times than the compound of Formula (I'). For example, the compound of Formula (I') and any additional pharmaceutical agent(s) may be on the same dosing schedule or different dosing schedules. All or some doses of the compound of Formula (I') may be administered before all or some doses of an additional pharmaceutical agent, after all or some does an additional pharmaceutical agent, within a dosing schedule of an additional pharmaceutical agent, or a combination thereof. The timing of administration of the compound of Formula (I') and additional pharmaceutical agents may be different for different additional pharmaceutical agents.

In certain embodiments, the additional pharmaceutical agent comprises an agent useful in the treatment of diseases, such as proliferative diseases, in a subject in need thereof. In certain embodiments, the additional pharmaceutical agent is useful in the treatment of a proliferative disease. In certain embodiments, the additional pharmaceutical agent is useful in the treatment of an inflammatory disease. In certain embodiments, the additional pharmaceutical agent is useful in the treatment of proliferative diseases. In certain embodiments, the additional pharmaceutical agent is useful in the treatment of multiple myeloma. In certain embodiments, the additional pharmaceutical agent is useful in the treatment of leukemia. In certain embodiments, the additional pharmaceutical agent is useful in the treatment of acute myelocytic leukemia. In certain embodiments, the additional pharmaceutical agent is useful in the treatment of mixed-lineage leukemia (MLL) rearranged acute myelocytic leukemia. In certain embodiments, the additional pharmaceutical agent is useful in the treatment of acute myelocytic leukemia with a mutation in the nucleophosmin (NPM1) gene. In certain embodiments, the additional pharmaceutical agent is useful in the treatment of acute myelocytic leukemia with a mutation in the DNMT3A gene. In certain embodiments, the additional pharmaceutical agent is useful in the treatment of lymphoma. In certain embodiments, the additional pharmaceutical agent is useful in the treatment of a non-Hodgkin's lymphoma. In certain embodiments, the additional pharmaceutical agent is useful in the treatment of cancer resistant to proteasome inhibitors (e.g., resistant to bortezomib).

In another aspect, the present disclosure provides methods for inducing the degradation of DOT1L, the method comprising administering to the subject a compound of Formula (I'), or a pharmaceutically acceptable salt, co-crystal, tautomer, stereoisomer, solvate, hydrate, polymorph, isotopically enriched derivative, or prodrug, or composition thereof.

In another aspect, the present disclosure provides methods for binding an E3 ubiquitin ligase and promoting the degradation and/or ubiquitination of DOT1L, the method comprising administering to the subject a compound of Formula (I'), or a pharmaceutically acceptable salt, co-crystal, tautomer, stereoisomer, solvate, hydrate, polymorph, isotopically enriched derivative, or prodrug, or composition thereof. In certain embodiments, provided are methods of treating cancers resistant to standard cancer treatment. In certain embodiments, provided are methods of treating cancers resistant to proteasome inhibitors. In certain embodiments, provided are methods of treating diseases, such as proliferative diseases, in a subject in need thereof. In certain embodiments, the disease is a proliferative disease. In certain embodiments, the disease is an inflammatory disease. In certain embodiments, the proliferative disease is cancer. In certain embodiments, the cancer is multiple myeloma. In certain embodiments, the cancer is leukemia. In certain embodiments, the leukemia is acute myelocytic leukemia. In certain embodiments, the leukemia is mixed-lineage leukemia (MLL) rearranged acute myelocytic leukemia. In certain embodiments, the leukemia is acute myelocytic leukemia with a mutation in the nucleophosmin (NPM1) gene. In certain embodiments, the leukemia is acute myelocytic leukemia with a mutation in the DNMT3A gene. In certain embodiments, the leukemia is acute myeloid eosinophilic leukemia. In certain embodiments, the cancer is lymphoma. In certain embodiments, the lymphoma is non-Hodgkin's lymphoma. In certain embodiments, the cancer treated is resistant to proteasome inhibitors (e.g., resistant to bortezomib). In certain embodiments, provided are methods of treating cancers resistant to proteasome inhibitors (e.g., resistant to bortezomib).

In still another aspect, the present disclosure provides the pharmaceutical compositions described herein for use in binding an E3 ubiquitin ligase and DOT1L and promoting the degradation of DOT1L; inducing the ubiquitination of DOT1L in a subject, biological sample, tissue, or cell; and treating and/or preventing proliferative diseases.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

The compounds provided herein can be prepared from readily available starting materials using the following general methods and procedures or methods known in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Compounds of Formula (I') or (I) may be prepared using the synthetic schemes and procedures described in detail below.

Example 1. Experimental Procedures for Synthesis of Exemplary Compounds

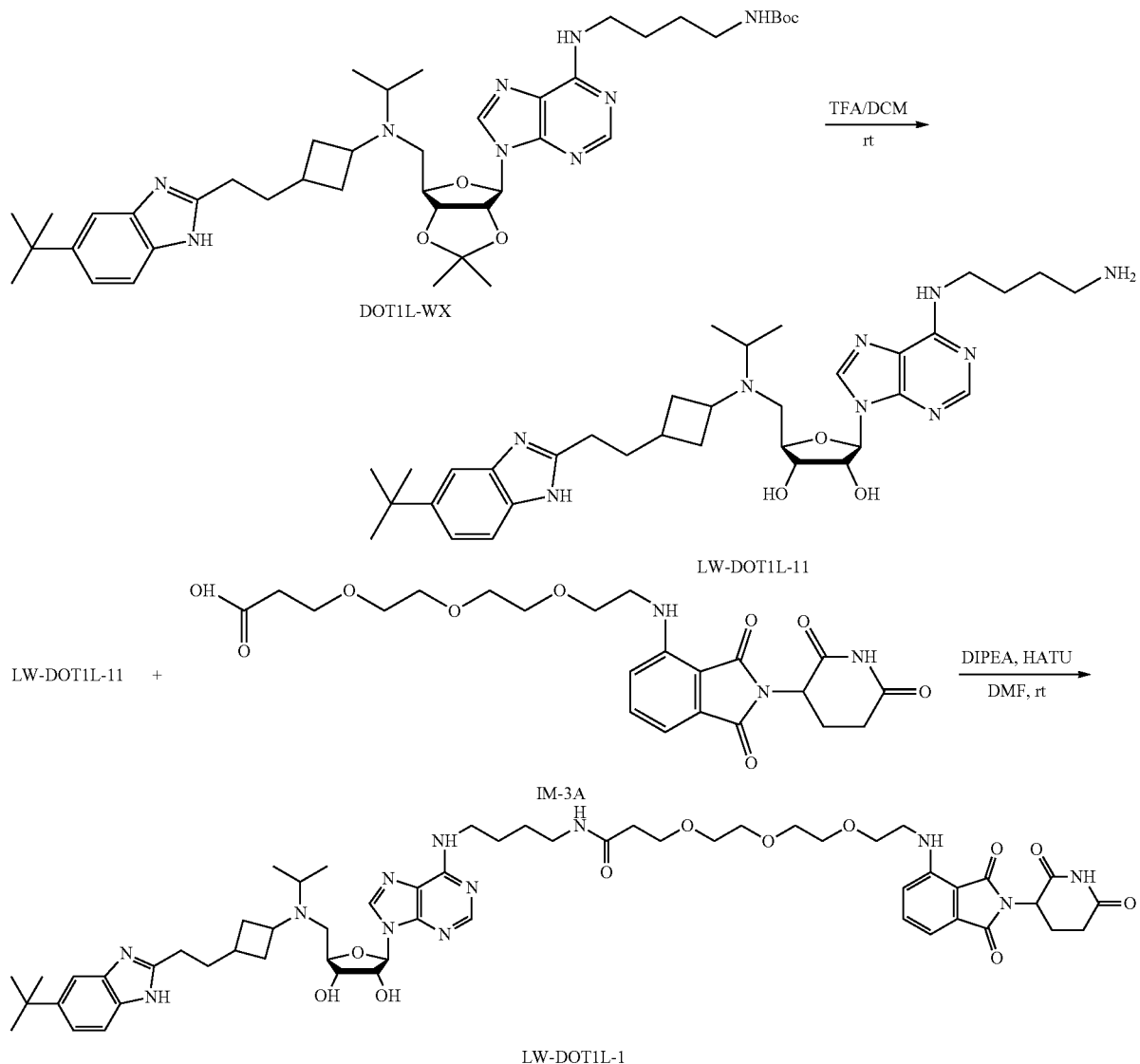

1) (2R,3R,4S,5R)-2-(6-((4-aminobutyl)amino)-9H-purin-9-yl)-5-(((3-(2-(5-(tert-butyl)-1H-benzo[d]imidazol-2-yl)ethyl)cyclobutyl)(isopropyl)amino)methyl)tetrahydrofuran-3,4-diol To a solution of DOT1L-WX (15 mg, 0.019 mmol) in DCM (0.4 mL) was added TFA (0.1 mL). The reaction mixture was stirred at room temperature overnight, concentrated and dried in vacuo to afford the crude LW-DOT1L-11, which was used in the next steps without further purification.

(2) N-(4-((9-((2R,3R,4S,5R)-5-(((3-(2-(5-(tert-butyl)-1H-benzo[d]imidazol-2-yl)ethyl)cyclobutyl)(isopropyl)amino)methyl)-3,4-dihydroxytetrahydrofuran-2-yl)-9H-purin-6-yl)amino)butyl)-3-(2-(2-(2-((2-(2,6-dioxopiperidin-3-yl)-1,3-dioxoisoindolin-4-yl)amino)ethoxy)ethoxy)ethoxy)propenamide To a solution of IM-3A (2.38 mg, 0.0050 mmol) and HATU (2.09 mg, 0.0055 nnol) in DMF (0.1 mL) was added DIPEA (3.23 mg, 0.0250 mmol) at room temperature. To a solution of LW-DOT1L-11 (0.0050 mmol) in DMF (0.1 mL) was added DIPEA (3.23 mg, 0.0250 mmol) at room temperature. The latter was added to the former, and the combined reaction mixture was stirred for 30 minutes, which was purified via HPLC (0.1% TFA/MeCN) to afford LW-DOT1L-1 (2.13 mg) as a white solid.

Example 2. Biological Assays of Exemplary Compounds with DOT1L

DOT1L Fluorescence Polarization (FP) Displacement Assay

Figure 1:
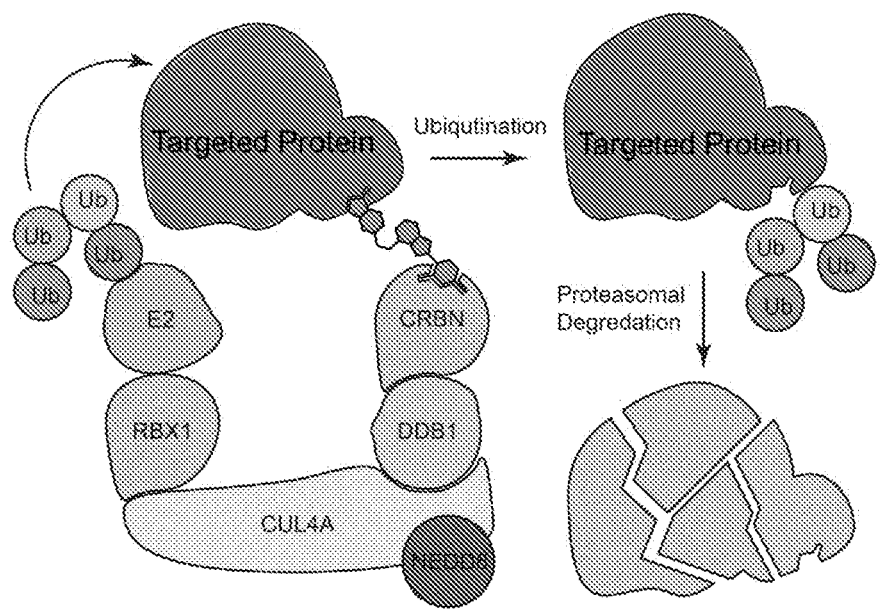
FIG. 1 shows CRBN-induced degradation of a targeted protein, in which protein ubiquitination occurs, followed by proteasomal degradation.
Figure 2A:
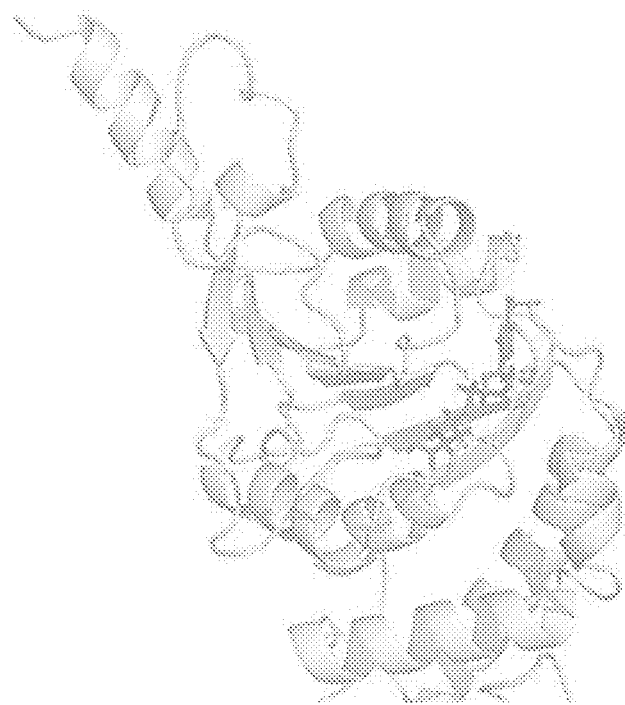
FIGS. 2A-2C show the degradation of DOT1L using an exemplary DOT1L degrader compound.
Figure 2B:
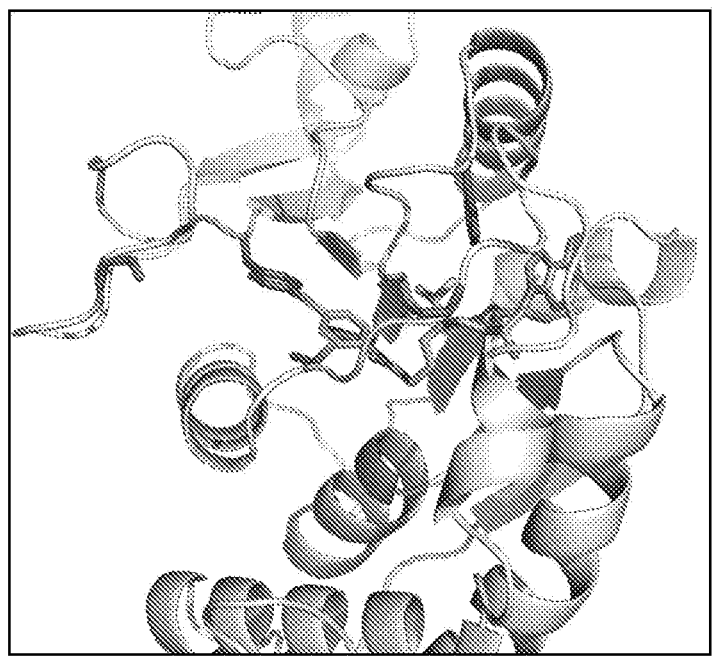
Figure 2C:
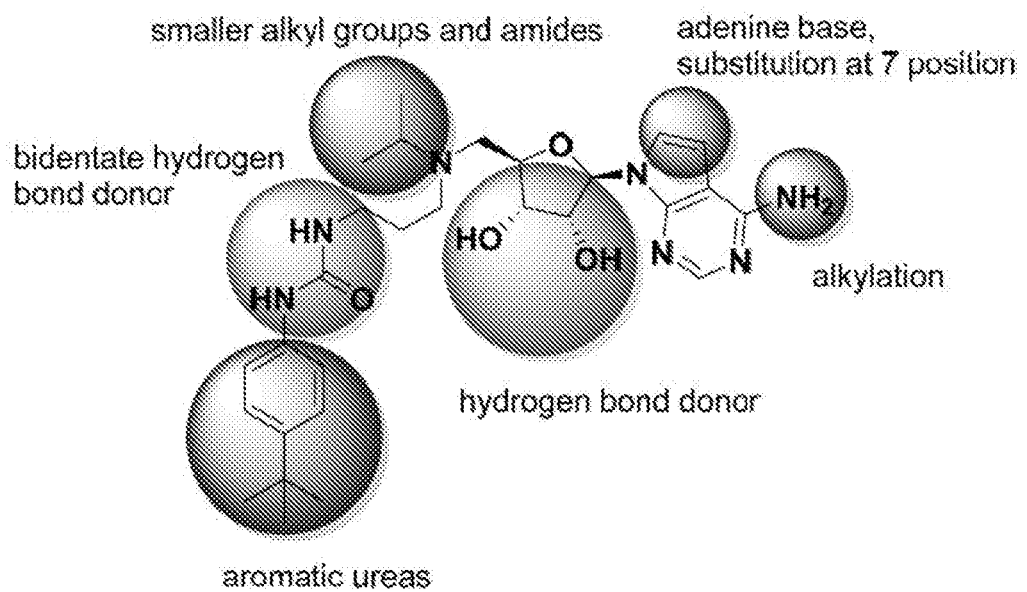
Figure 3:
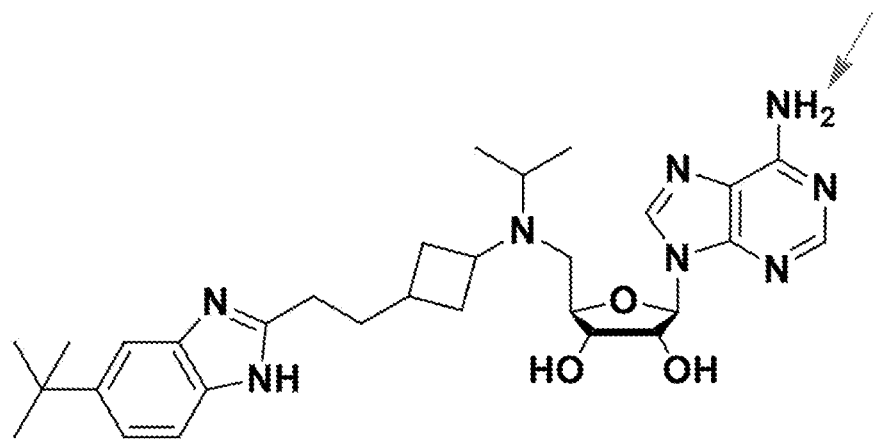
FIG. 3 shows the design principles behind CRBN-based exemplary DOT1L degrader compounds.
Figure 3:
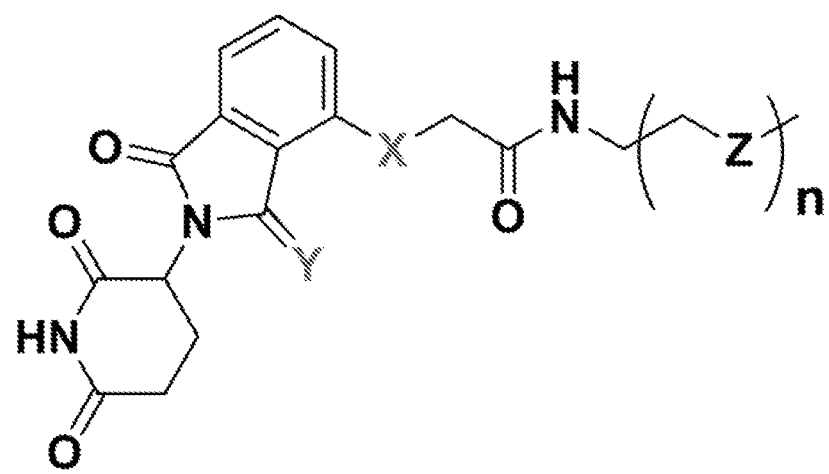
Figure 4C:
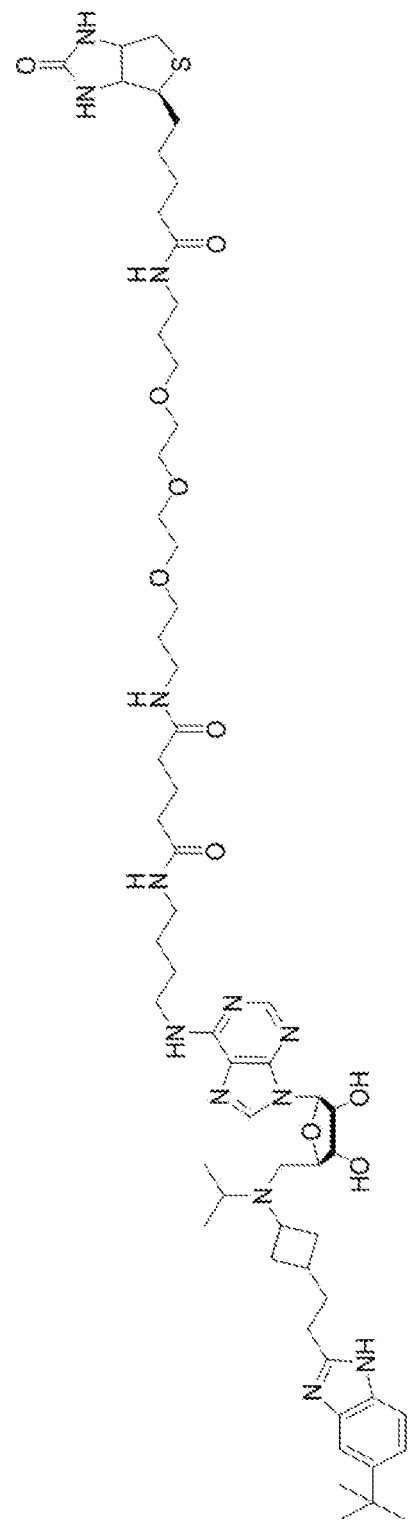
Figure 4D:
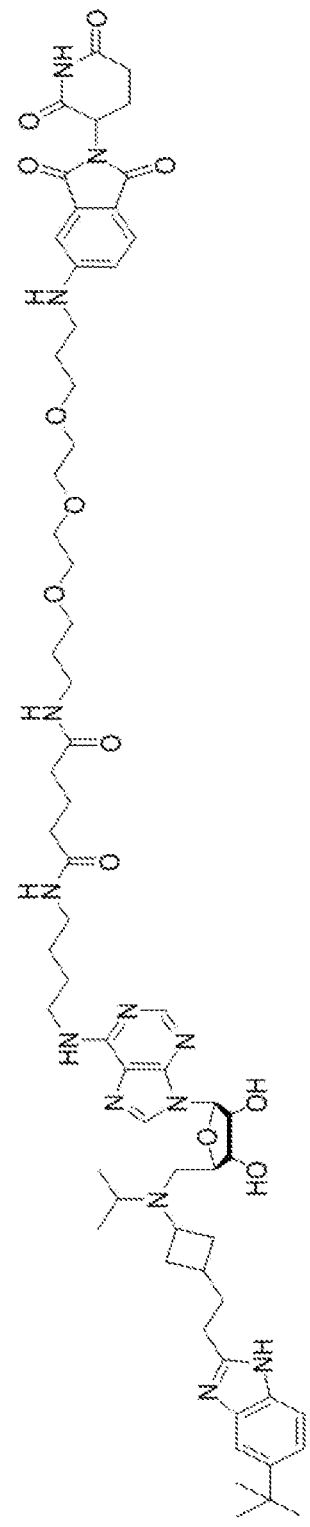
Figure 4E:
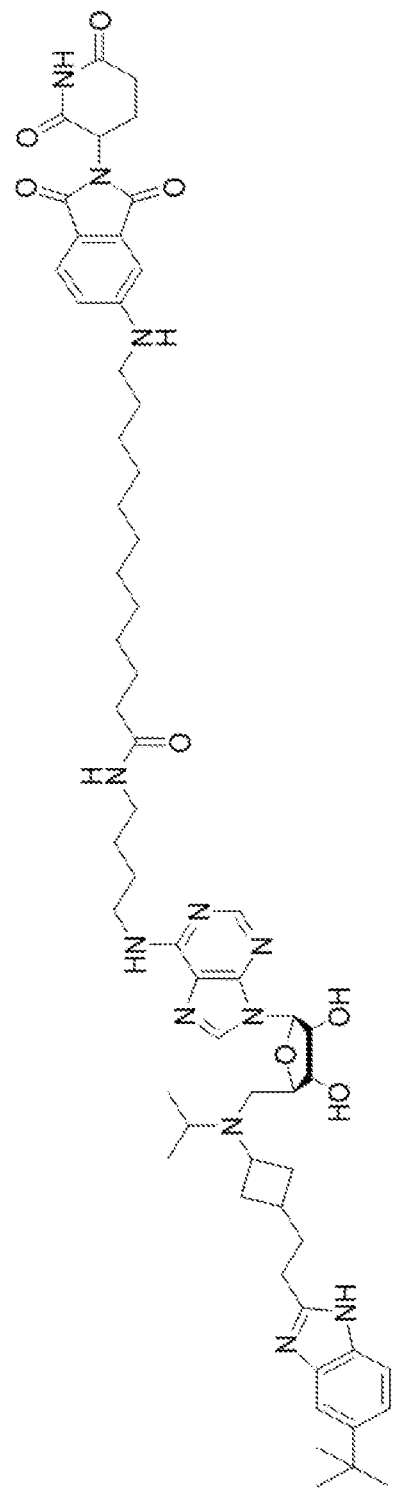
Figure 4F:
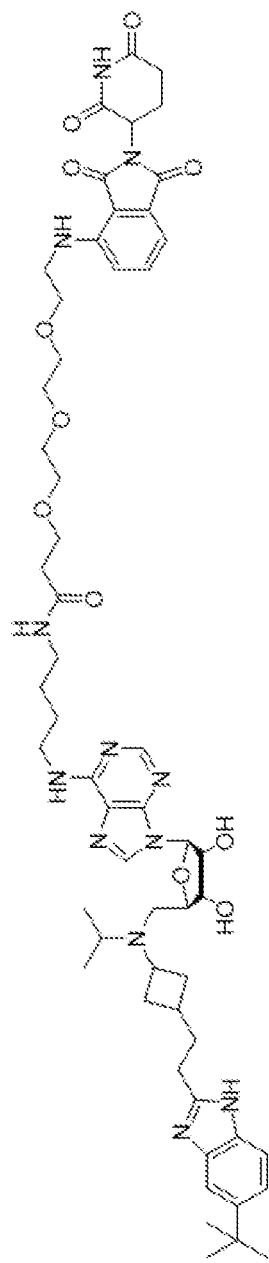
Figure 5:
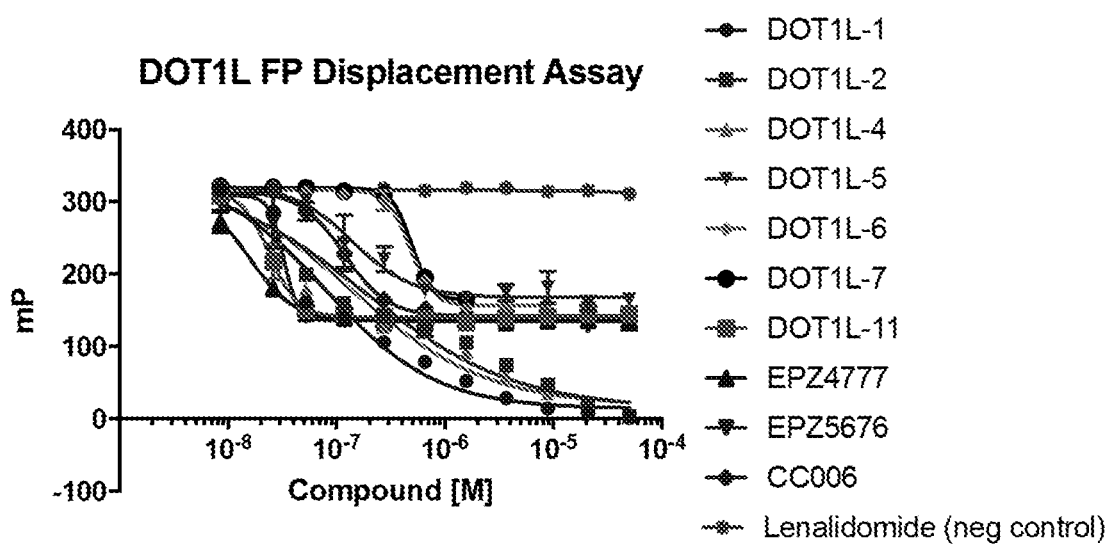
FIG. 5 shows a DOT1L Fluorescence Polarization (FP) displacement assay of tested exemplary DOT1L degrader compounds, a derivative of an inhibitor, and negative and positive control compounds at different concentrations [M], measured in [M] per mP. The tested compounds include exemplary DOT1L degrader compounds DOT1L-1, DOT1L-2, DOT1L-4, DOT1L-5, DOT1L-6, DOT1L-7, a derivative of an inhibitor (DOT1L-11), negative control compounds EPZ4777, EPZ5676, and CC006, and positive control Lenalidomide. The compounds EPZ4777, EPZ5676, and CC006 have the structures depicted as follows.

DOT1L Fluorescence Polarization (FP) Displacement assays were conducted for exemplary DOT1L degrader compounds, a derivative of an inhibitor, and negative and positive control compounds at different concentrations [M], measured in [M] per mP. The tested compounds include exemplary DOT1L degrader compounds DOT1L-1, DOT1L-2, DOT1L-4, DOT1L-5, DOT1L-6, DOT1L-7, a derivative of an inhibitor (DOT1L-11), negative control compounds EPZ4777. EPZ5676, and CC006, and positive control Lenalidomide. The results of the assay are indicated in FIG. 5.

DOT1L Fluorescence Polarization (FP) Displacement assays were conducted for exemplary DOT1L degrader compounds, and control compounds at different concentrations [M], measured in [M] per mP. The tested compounds include exemplary DOT1L degrader compounds JQ-DD1, JQ-DD2, JQ-DD3, JD-DD4, JD-DD5, JD-DD6, and positive controls Thalidomide and EPZ5676. The exemplary compounds show binding to each of DOT1L and CRBN. The results of the assay are indicated in FIG. 18.

CRBN Binding Assay

CRBN binding assays were conducted for exemplary DOT1L degrader compounds, a derivative of an inhibitor, negative control compounds, and positive control compounds at different concentrations [M], as indicated in concentration [M] versus mP. The compounds include exemplary DOT1L degrader compounds DOT1L-1, DOT1L-2, DOTL-4, DOT1L-5, DOT1L-6, and DOT1L-7; a derivative of an inhibitor (DOT1L-11); and positive control Lenalidomide. The results of the assay are indicated in FIG. 6.

CRBN binding assays were conducted for exemplary DOT1L degrader compounds, negative control compounds, and positive control compounds at different concentrations [M], as indicated in concentration [M] versus mP. The compounds include exemplary DOT1L degrader compounds JQ-DD1, JQ-DD2, JQ-DD3, JQ-DD4, JQ-DD5; JQ-DD6; and controls Thalidomide and EPZ5676. The results of the assay are indicated in FIG. 19.

DOTL eGFP-mCherry Reporting Cell Line Assay

A new DOT1L degradation reporting cell line was developed with DOT1L tagged GFP and mcherry. This reporting cell line can directly report the targeted protein degradation. (See Sievers et al., *Science*, 2018). DOT1L degradation using eGFP-mCherry reporting cell line assays were conducted for exemplary DOT1L degrader compounds, and control compounds at different concentrations [M], measured in [M] per mP. The tested compounds include exemplary DOT1L degrader compounds JQ-DD2, JQ-DD3, JQ-DD4, JQ-DD5, JQ-DD6, JQ-DD7, JQ-DD8, and controls EPZ5676, Thalidomide, and Lenalidomide. The results of the assay are indicated in FIG. 26.

IKZF-GFP Degradation Assay

IKZF-GFP degradation assays were conducted on exemplary DOT1L degrader compounds, a derivative of an inhibitor, negative control compounds, and positive control compounds at different concentrations [M], as indicated as concentration of the compounds versus normalized levels. The exemplary compounds include exemplary DOT1L degrader compounds DOT1L-1, DOT1L-2, DOT1L-4, DOT1L-5, DOT1L-6, DOT1L-7; a derivative of an inhibitor DOT1L-11; negative control compounds EPZ4777, EPZ5676, and CC006; and positive control Lenalidomide. The results of the assay are indicated in FIG. 8.

IKZF-GFP degradation using eGFP-mCherry reporting cell line assays were conducted for exemplary DOT1L degrader compounds, and control compounds at different concentrations [M], measured in [M] per mP. The tested compounds include exemplary DOT1L degrader compounds JQ-DD2, JQ-DD3, JQ-DD4, JQ-DD5, JQ-DD6, JQ-DD7, JQ-DD8, and controls EPZ5676, Thalidomide, and Lenalidomide. The exemplary DOT1L degrader compounds degrade DOT1L as well as IKZF1, the neo substrate when immunomodulatory imide drugs (IMiDs) bind to CRBN. The results of the assay are indicated in FIG. 27.

Degradation by dDOT1L-1 in Molm13 PA Cell Line

Molm13PA (acute myeloid leukemia) cells were treated with dDOT1L-1 at 0 µM, 0.3 µM, 1 µM, 3.3 µM, and 10 µM for 24 hours and 48 hours. Cell lysates were loaded on SDS-PAGE, then immunoblotted with DOT1L (D402T), actin, H3K79me2, total H3. Repeat treatment was performed at 24 hours, 48 hours and 72 hours at the same concentrations of dDOT1L-1. The blots show that dDOT1L-1 inhibits acute myeloid leukemia cells (Molm13 PA). (see FIGS. 9A-9B). FIG. 9A shows the cells were treated with DOT1L-1 at the indicated concentration (0 µM, 0.3 µM, 1 µM, 3.3 µM, and 10 µM) for the indicated amount of time (24 hours and 48 hours). FIG. 9B shows a repeat treatment where the cells were treated with DOT1L-1 at the indicated concentration (0 µM, 0.3 µM, 1 µM, 3.3 µM, and 10 µM) for the indicated amount of time (24 hours, 48 hours, and 72 hours).

Degradation by dDOT1L-1 in Mouse MLL-AF9 PA Cell Line

Mouse MLL-AF9 PA (Mixed-lineage leukemia (MLL)-AF9 leukemia) cells were treated with DOT1L-1 at 0 µM, 0.3 µM, 1 µM, 3.3 µM, and 10 µM for 24 hours, 48 hours, and 72 hours. Cell lysates were loaded on SDS-PAGE, then immunoblotted with DOT1L (D402T), actin, H3K79me2, and total H3. A second treatment was performed with DOT1L-1 concentrations of 0 µM, 0.01 µM, 0.1 µM, 0.3 µM, 1 µM, 3.3 µM, and 10 µM, at 24 hours and 48 hours. The blots show that exemplary DOT1L degrader compound DOT1L-1 degrades Mouse MLL-AF9 PA (Mixed-lineage leukemia (MLL)-AF9 leukemia) cells (see FIGS. 10A-10B). FIG. 10A shows Experiment 1 where the cells were treated with DOT1L-1 at the indicated concentration (0 µM, 0.3 µM, 1 µM, 3.3 µM, and 10 µM) for the indicated amount of time (24 hours, 48 hours, and 72 hours). FIG. 10B shows Experiment 2 where the cells were treated with DOT1L-1 at the indicated concentration (0 µM, 0.3 µM, 1 µM, 3.3 µM, and 10 µM) for the indicated amount of time (24 hours and 48 hours).

Degradation by dDOT1L-4 in Molm13 PA Cell Line

Molm13PA (acute myeloid leukemia) cells were treated with DOT1L-4 at 0 µM, 0.3 µM, 1 µM, 3.3 µM, and 10 µM for 24 hours, 48 hours, and 72 hours. Cell lysates were loaded on SDS-PAGE, then immunoblotted with DOT1L (D402T), actin, H3K79me2, total H3. The blots show that DOT1L-4 degrades (Mixed-lineage leukemia (MLL)-AF9 leukemia) cells (see FIG. 11).

Degradation by JQ-DD1-8 in EOL1 Cell Lines

EOL1 (acute myeloid (eosinophilic) leukemia cell line) cells were treated with exemplary DOT1L degrader compounds JQ-DD6, JQ-DD7, and JQ-DD8 at 0.5 µM, 1 µM, 3 µM, 5 µM, and 10 µM for 24 hours. Cell lysates were loaded on SDS-PAGE, then immunoblotted with DOT1L, Myc, H3K79me2, and actin. (see FIG. 21).

EOL1 cells were treated with exemplary DOT1L degrader compounds JQ-DD2, JQ-DD4, and JQ-DD6, JQ-DD7, and JQ-DD8 at 1 µM, 5 µM, and 10M for 48 hours. Cell lysates were immunoblotted with DOT1L, H3K79me2, Myc, actin, and H3 at the indicated concentrations for 48 hours. (see FIG. 22).

EOL1 cells were treated with exemplary DOT1L degrader compounds JQ-DD2, JQ-DD4, and JQ-DD6, JQ-DD7, and JQ-DD8 at 1 µM and 10M for 2, 4, 8, 16, and 24 hours. Cell lysates were immunoblotted with DOT1L, Myc, H3K79me2, and actin at the indicated concentrations for the indicated times. (see FIG. 23).

EOL1 cells were treated with exemplary DOT1L degrader compounds JQ-DD6, JQ-DD7, and JQ-DD8 at 1 µM and 10M for 24 and 48 hours. Cell lysates were immunoblotted with DOT1L, Myc, H3K79me2, and actin at the indicated concentrations for the indicated times. (see FIG. 24).

Relative Cell Growth in the Presence of Exemplary Thalidomide-Based, DOT1L Degrader Compounds Molm13 PA (acute myeloid leukemia), Molm13 RE (acute myeloid leukemia), and HL60 (human leukemia) cells were treated with exemplary thalidomide-based, DOT1L degrader compounds DOT1L-1, DOT1L-2, DOT1L-4, DOT1L-5 and negative control compound EPZ5676 at various concentrations between 0 and 10 µM. The relative cell growth of the Molm13 PA, Molm13 RE, and HL60 cells was measured after 10 days. The results show that there was reduced cell growth for the Molm13 leukemia cells and HL60 (human leukemia) cells that were treated with exemplary DOT1L degrader compounds, with increased concentration of the exemplary DOT1L degrader compounds (see FIGS. 12A-12E).

Example 3. Dimerization Assay

Biochemical Dimerization Assay

A biochemical assay was completed to determine the dimerization of CRBN with DOT1L induced by the degraders. This assay checks if the exemplary compounds can dimerize CRBN and DOT1L in a biochemical assay setting. FIG. 20 shows that exemplary compounds can bind to both proteins simultaneously. The JQ-DD6 gave the strongest signal. The results of the assay are indicated in FIG. 20.

Example 4. Antiproliferation Effects of DOT1L Degraders

MOLM13 7 day treatment assays were conducted for exemplary DOT1L degrader compounds, and control compounds at different concentrations [M], measured in [M] per mP. The tested compounds include exemplary DOT1L degrader compounds JQ-DD1, JQ-DD2, JQ-DD3, JQ-DD4, JQ-DD5, JQ-DD6, JQ-DD7, and controls EPZ5676 and Thalidomide. (see FIG. 28A).

THP1 7 day treatment assays were conducted for exemplary DOT1L degrader compounds, and positive control compounds at different concentrations [M], measured in [M] per mP. The tested compounds include exemplary DOT1L degrader compounds JQ-DD1, JQ-DD2, JQ-DD3, JQ-DD4, JQ-DD5, JQ-DD6, JQ-DD7, and controls EPZ5676 and Thalidomide. (see FIG. 28B).

NOMO1 7 day treatment assays were conducted for exemplary DOT1L degrader compounds, and control compounds at different concentrations [M], measured in [M] per mP. The tested compounds include exemplary DOT1L degrader compounds JQ-DD1, JQ-DD2, JQ-DD3, JQ-DD4, JQ-DD5, JQ-DD6, JQ-DD7, and controls EPZ5676 and Thalidomide. (see FIG. 29A).

EOL1 cell line cell growth assays were conducted for exemplary DOT1L degrader compounds, and control compounds at different concentrations [M], measured in [M] per mP. The tested compounds include exemplary DOT1L degrader compounds JQ-DD1, JQ-DD2, JQ-DD3 (old), JQ-DD3 (new), JQ-DD4, JQ-DD5, JQ-DD6, and controls EPZ5676, Thalidomide, and PCK82. (see FIG. 29B).

The percentage (%) of viable Cells of exemplary cancer cells (e.g., acute myeloid leukemia cells) were checked following the treatment of these cells with exemplary DOT1L degraders JQ-DD6, EPZ5676, and Thalidomide on EOL1 cells, NOMO1 cells, MOLM13 cells, MOLM14 cells, and MOLM14 crbnKO cells concentrations for 3 days. The results of these assays are indicated in FIGS. 30A-30E.

(The percentage (%) of viable Cells of exemplary cancer cells (e.g., acute myeloid leukemia cells) were checked following the treatment of these cells with exemplary DOT1L degraders JQ-DD6, EPZ5676, and Thalidomide on EOL1 cells, NOMO1 cells, MOLM13 cells, MOLM14 cells, and MOLM14 crbnKO cells concentrations for 7 days. The results of these assays are indicated in FIGS. 31A-31E.

Example 5. Exemplary DOT1L Degraders

Exemplary DOT1L degraders are shown in Table 1 below. The compounds of Table 1 below were synthesized according to the exemplary procedures shown in the synthetic schemes of Example 1.

TABLE 1
Exemplary DOT1L degraders
| Compound Number | Structure |
|---|---|
| JQDD1 (IQ-DD1) | 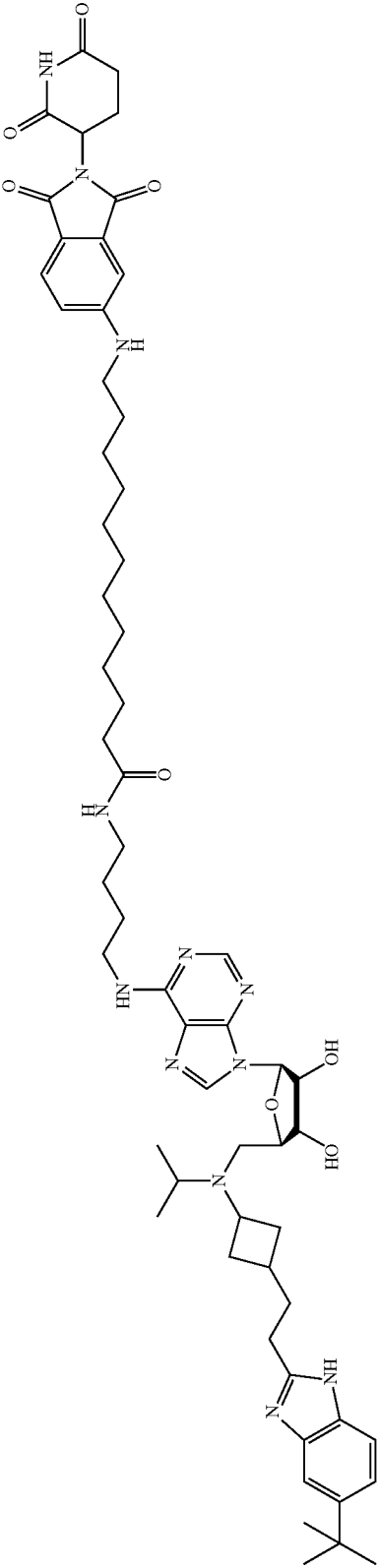 |
| JQDD2 (IQ-DD2) | 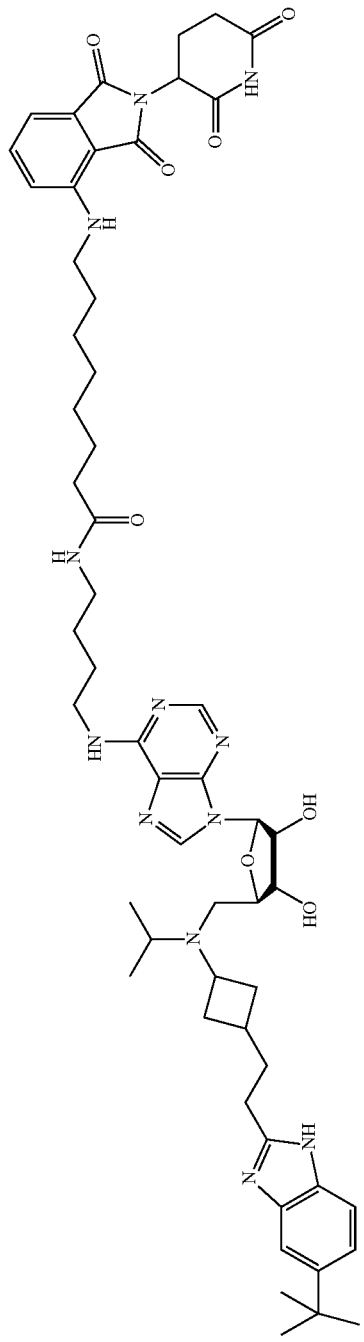 |

TABLE 1-continued
Exemplary DOT1L degraders
| Compound Number | Structure |
|---|---|
| JQDD3 (JQ-DD3) | 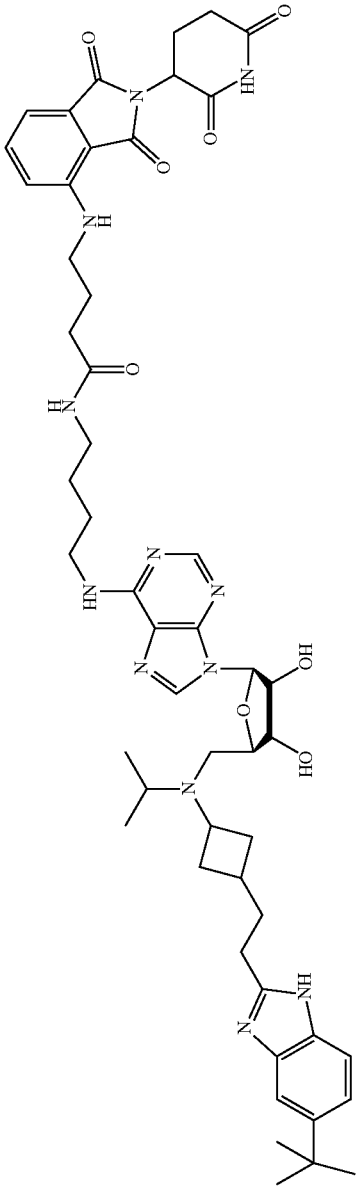 |
| JQDD4 (JQ-DD4) | 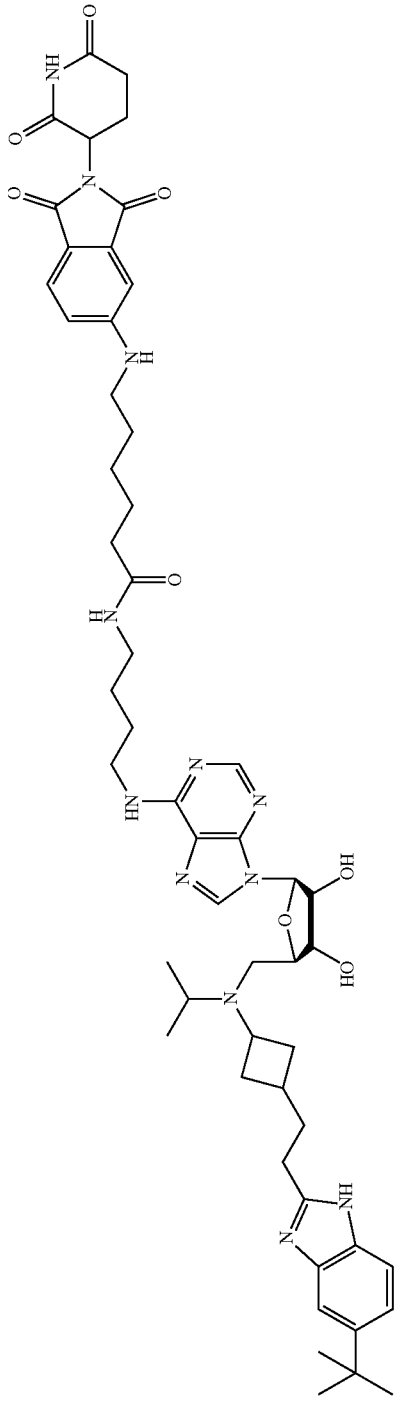 |

TABLE 1-continued

Exemplary DOT1L degraders

| Compound Number | Structure |
|---|---|
| JQDD5 (IQ-DD5) | |
| JQDD6 (IQ-DD6) | |

TABLE 1-continued
Exemplary DOT1L degraders
| Compound Number | Structure |
|---|---|
| JQDD7 (IQ-DD7) | 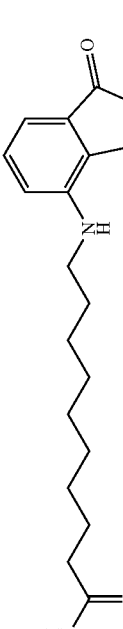 |
| JQDD8 (IQ-DD8) | 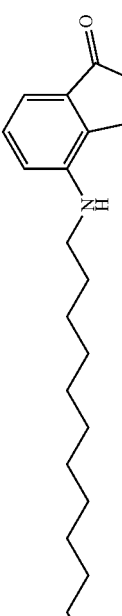 |

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound of Formula (I') or (I):

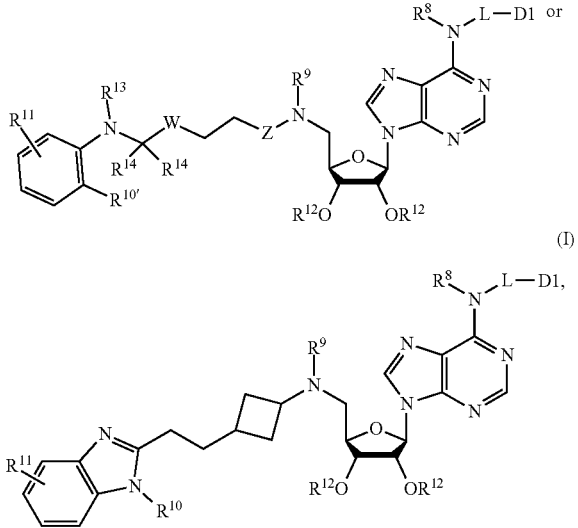

or a pharmaceutically acceptable salt, solvate, hydrate, tautomer, or stereoisomer thereof, wherein:

$R^8$ is hydrogen, optionally substituted alkyl, or a nitrogen protecting group;

$R^9$ is hydrogen, optionally substituted alkyl, or a nitrogen protecting group;

$R^{10}$ is hydrogen, optionally substituted alkyl, or a nitrogen protecting group;

$R^{10'}$ is hydrogen, optionally substituted alkyl, or $-N(R^{10A})_2$;

each instance of $R^{10A}$ is independently hydrogen, optionally substituted alkyl, or a nitrogen protecting group;

$R^{11}$ is halogen or optionally substituted alkyl;

each instance of $R^{12}$ is independently hydrogen or an oxygen protecting group;

$R^{13}$ is hydrogen, optionally substituted alkyl, or a nitrogen protecting group;

each instance of $R^{14}$ is independently hydrogen, or optionally substituted alkyl;

or, optionally wherein one instance of $R^{14}$ and one instance of $R^{10'}$ are taken together with their intervening atoms to form a substituted or unsubstituted 3-10 membered heterocyclic or substituted or unsubstituted 5-10 membered heteroaryl ring, wherein the heterocyclic or heteroaryl comprises 1 to 4 heteroatoms independently selected from nitrogen, oxygen, and sulfur;

or, optionally wherein one instance of $R^{14}$ and one instance of $R^{10A}$ are taken together with their intervening atoms to form a substituted or unsubstituted 3-10 membered heterocyclic or substituted or unsubstituted 5-10 membered heteroaryl ring, wherein the heterocyclic or heteroaryl comprises 1 to 4 heteroatoms independently selected from nitrogen, oxygen, and sulfur;

or, optionally wherein the moiety

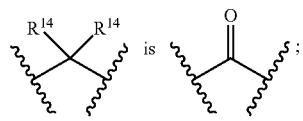

W is optionally substituted $-CH_2-$ or $-N(R^W)-$, wherein $R^W$ is hydrogen, optionally substituted alkyl, or a nitrogen protecting group;

Z is -(optionally substituted carbocyclyl)- or optionally substituted $-CH_2-$;

L is a linker, which has any one of structures:

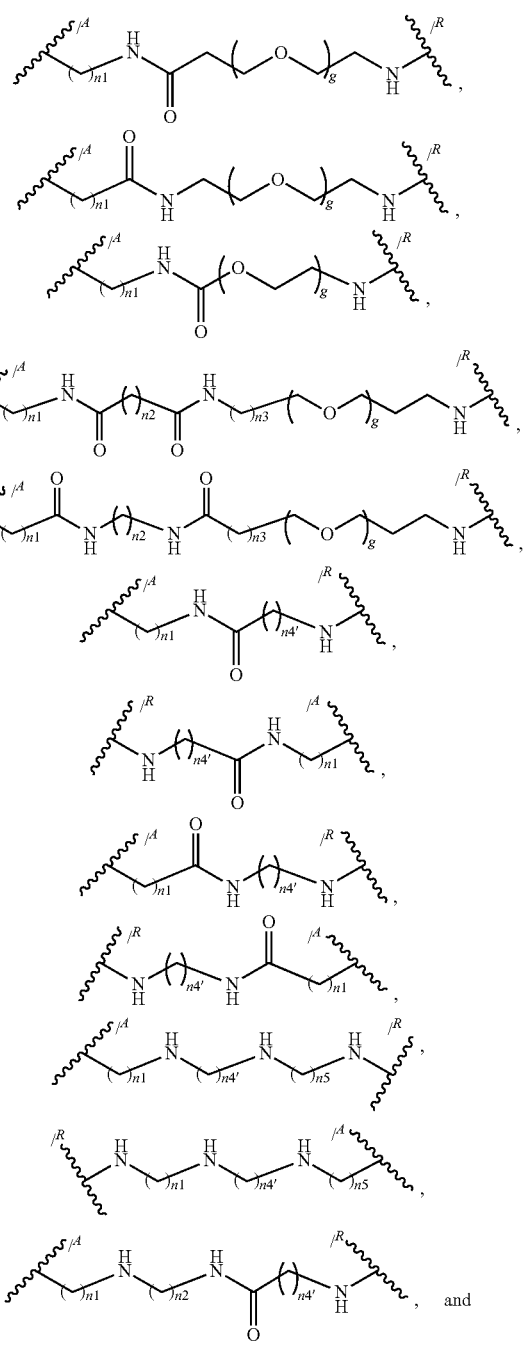

and

-continued

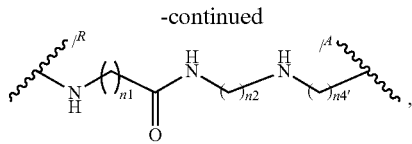

wherein $1^R$ indicates the point of attachment to D1, and $1^A$ indicates the point of attachment to the moiety

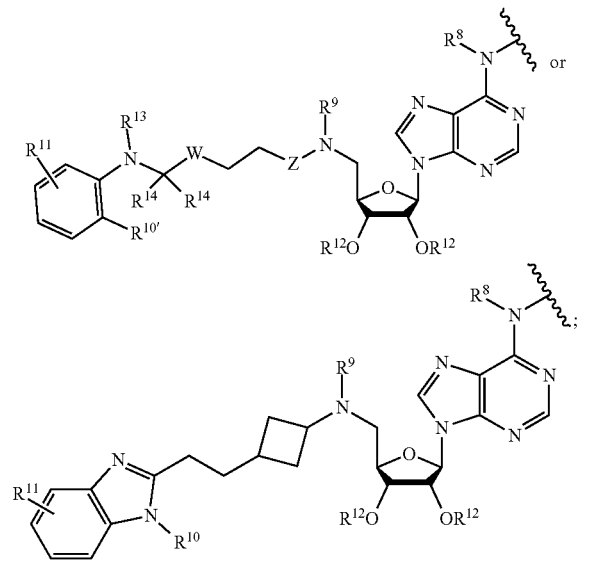

n1 is 1, 2, 3, 4, 5, or 6;
n2 is 1, 2, 3, 4, 5, or 6;
n3 is 1, 2, 3, 4, 5, or 6;
n4' is 1, 2, 3, 4, 5, 6, 7, 8, 9, 10, 11, 12, 13, 14, 15, 16, 17, 18, 19, 20, 21, 22, 23, or 24;
n5 is 1, 2, 3, 4, 5, 6, 7, 8, 9, 10, 11, or 12; and
g is 1, 2, 3, 4, 5, 6, 7, 8, 9, 10, 11, 12, 13, 14, or 15; and
D1 is an E3 ubiquitin ligase binding moiety and is of formula IA or IB:

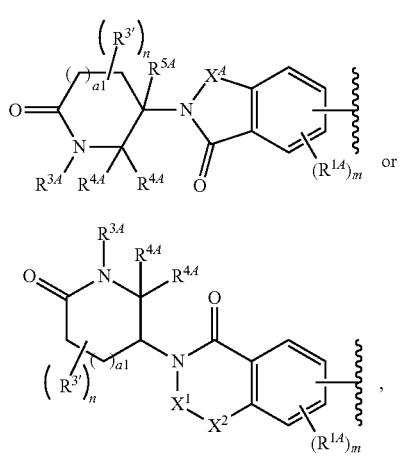

wherein:
$X^A$ is C(O) or $C(R^{3A})_2$;
$-X^1-X^2-$ is $C(R^{3A})=N$ or $C(R_{3A})_2-C(R^{3A})_2$;
each $R^{1A}$ is independently halogen, OH, $C_1$-$C_6$ alkyl, or $C_1$-$C_6$ alkoxy;
each $R^{3A}$ is independently H or $C_1$-$C_3$ alkyl;
each $R^{3'}$ is independently $C_1$-$C_3$ alkyl;
each $R^{4A}$ is independently H or $C_1$-$C_3$ alkyl; or two $R^{4A}$, together with the carbon atom to which they are attached, form a C(O), $C_3$-$C_6$ carbocycle, or a 4-, 5-, or 6-membered heterocycle comprising 1 or 2 heteroatoms selected from N and O;
$R^{5A}$ is H, $C_1$-$C_3$ alkyl, or halogen;
m is 0, 1, 2 or 3;
n is 0, 1, or 2; and
a1 is 0 or 1,
wherein the alkyl, heterocyclic, heteroaryl, carbocyclyl, is optionally substituted with halogen, $-NO_2$, $-N_3$, $-SO_2H$, $-SO_3H$, $-C(=O)C_{1-10}$ alkyl, $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, 5-14 membered heteroaryl, branched $C_{1-10}$ alkyl, $-OH$, $-O(C_{1-10}$ alkyl), $-O(C_{2-10}$ alkenyl), $-O(C_{2-10}$ alkynyl), $-COOH$, $-COO(C_{1-10}$ alkyl), $-NH_2$, $-NH(C_{1-10}$ alkyl), $-N(C_{1-10}$ alkyl)$_2$, $-C(=O)N(C_{1-10}$ alkyl), urea, imide, $-CN$, or carbamate, wherein the heterocyclyl or heteroaryl comprises 1 to 4 heteroatoms independently selected from nitrogen, oxygen, and sulfur.

2. The compound of claim 1, wherein the compound is any one of formulas:

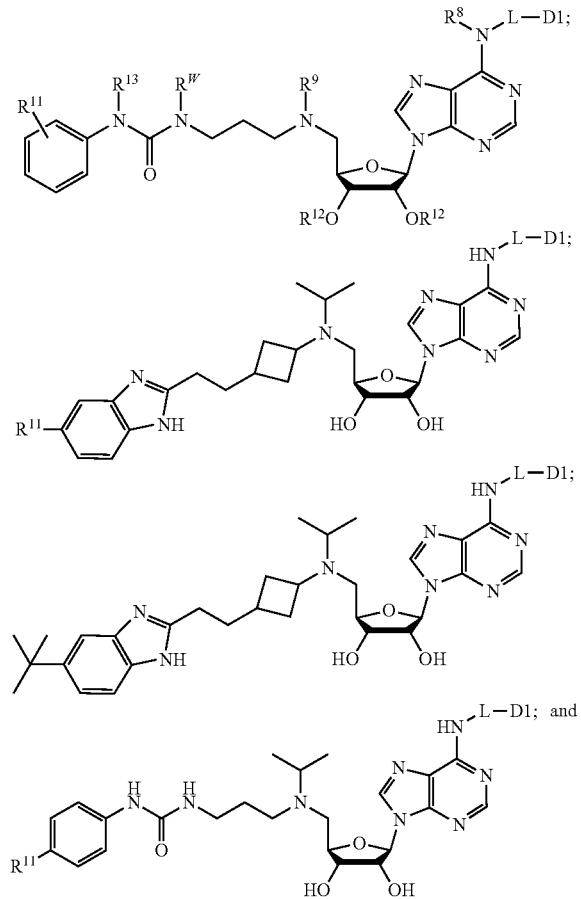

-continued

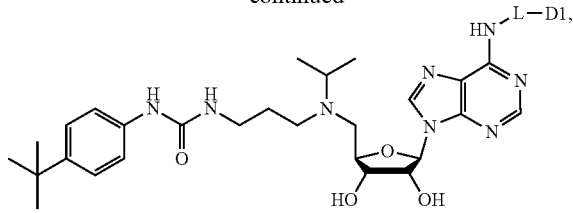

or a pharmaceutically acceptable salt, solvate, hydrate, tautomer, or stereoisomer thereof, wherein:

$R^8$ is hydrogen, optionally substituted alkyl, or a nitrogen protecting group;

$R^9$ is hydrogen, optionally substituted alkyl, or a nitrogen protecting group;

$R^{10}$ is hydrogen, optionally substituted alkyl, or a nitrogen protecting group;

$R^{11}$ is halogen or optionally substituted alkyl;

each instance of $R^{12}$ is independently hydrogen or an oxygen protecting group.

3. The compound of claim 1, wherein a1 is 1.

4. The compound of claim 1, wherein $R^{3A}$ is hydrogen.

5. The compound of claim 1, wherein two $R^{4A}$, together with the carbon atom to which they are attached, form a C(O).

6. The compound of claim 1, wherein $X^A$ is C(O) or —CH$_2$—.

7. The compound of claim 1, wherein m is 0.

8. The compound of claim 1, wherein n is 0.

9. The compound of claim 1, wherein D1 is of the formula:

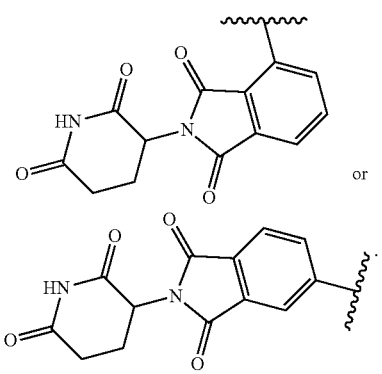

10. The compound of claim 1, wherein one of $R^8$, $R^9$, $R^{10}$, and $R^{13}$ is hydrogen.

11. The compound of claim 1, wherein $R^{10'}$ is $N(R^{10A})_2$; and one instance of $R^{14}$ and one instance of $R^{10A}$ are taken together with their intervening atoms to form a substituted or unsubstituted 6-14 membered heterocyclic or substituted or unsubstituted 5-10 membered heteroaryl ring, wherein the heterocyclic or heteroaryl comprises 1 to 4 heteroatoms independently selected from nitrogen, oxygen, and sulfur.

12. The compound of claim 1, wherein $R^{11}$ is optionally substituted $C_{1-6}$ alkyl or unsubstituted t-butyl.

13. The compound of claim 1, wherein both instances of $R^{12}$ are hydrogen.

14. The compound of claim 1, wherein the moiety

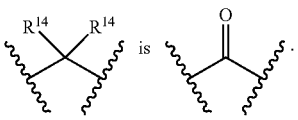

15. The compound of claim 1, wherein W is unsubstituted —CH$_2$— or —NH—.

16. The compound of claim 1, wherein Z is -(optionally substituted cyclobutyl)- or unsubstituted —CH$_2$—.

17. The compound of claim 1, wherein the moiety

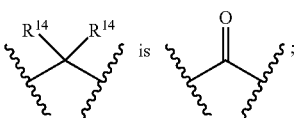

W is —NH—; and Z is —CH$_2$—.

18. The compound of claim 1, wherein L is of the formula:

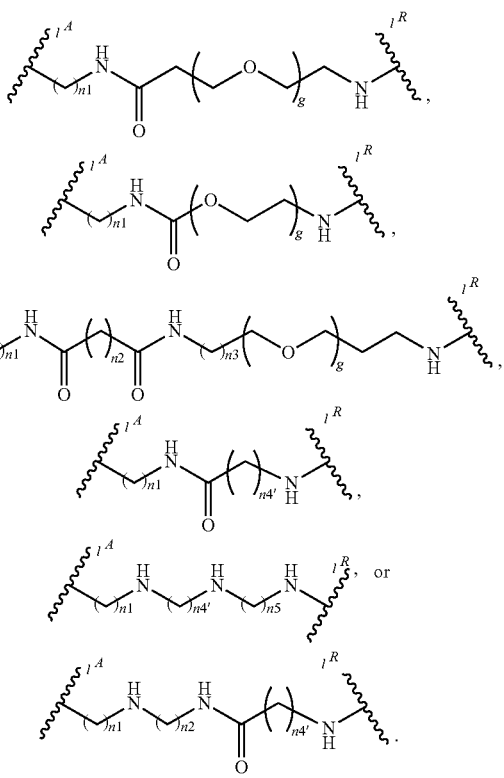

19. The compound of claim 1, wherein:

n1 is 4 or 6;

n2 is 2, 3, or 12;

n3 is 3;

n4 is 10, 11, or 12;

n4' is 3, 5, 6, 7, or 9;

n5 is 8; and g is 3, 5, or 13.

20. The compound of claim 1, wherein L is of the formula:
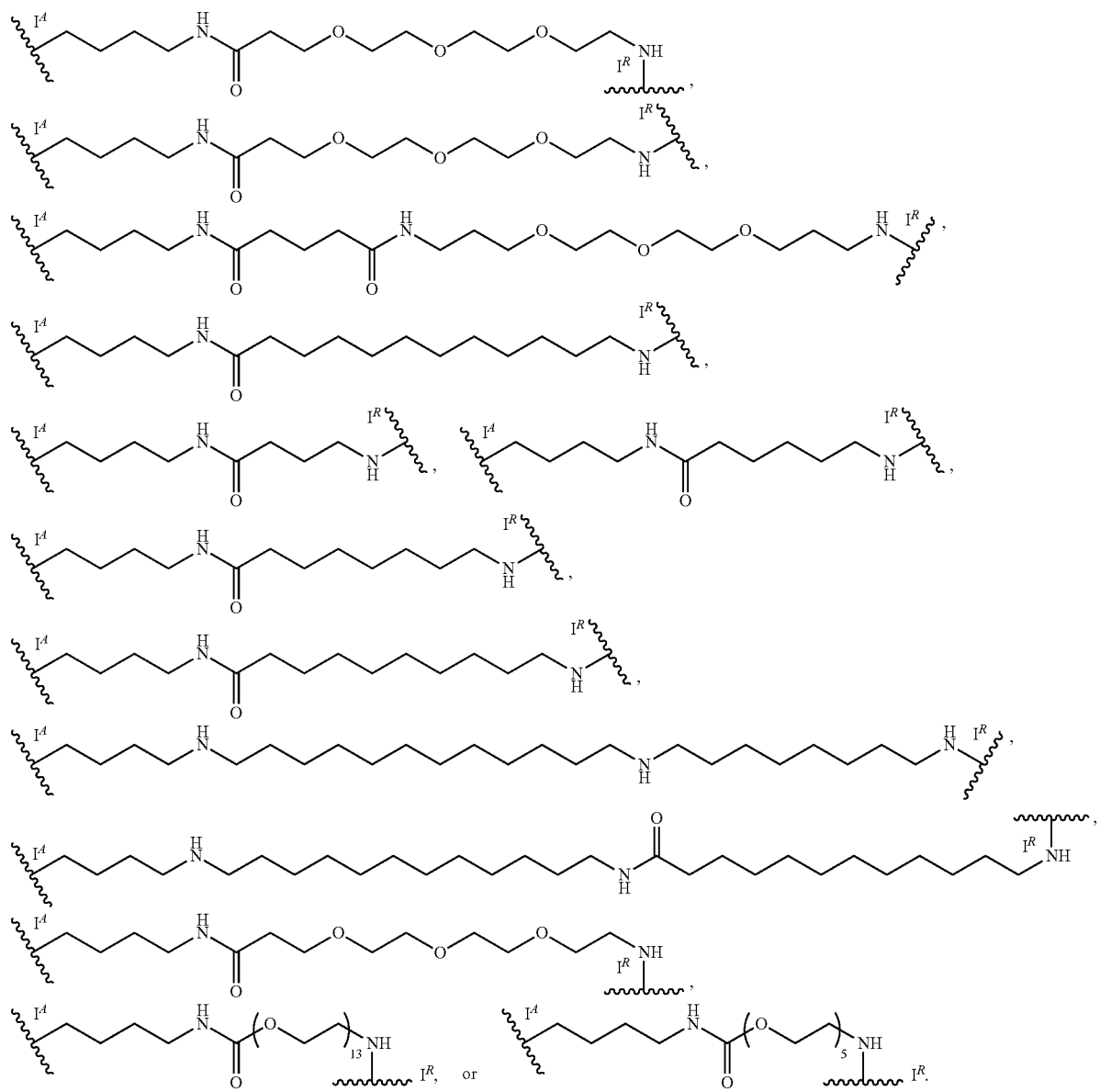
21. The compound of claim 1, wherein the compound is of the formula:
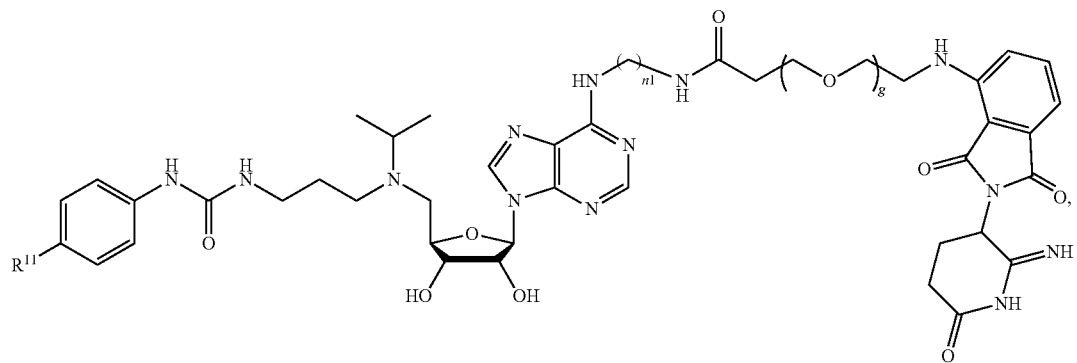

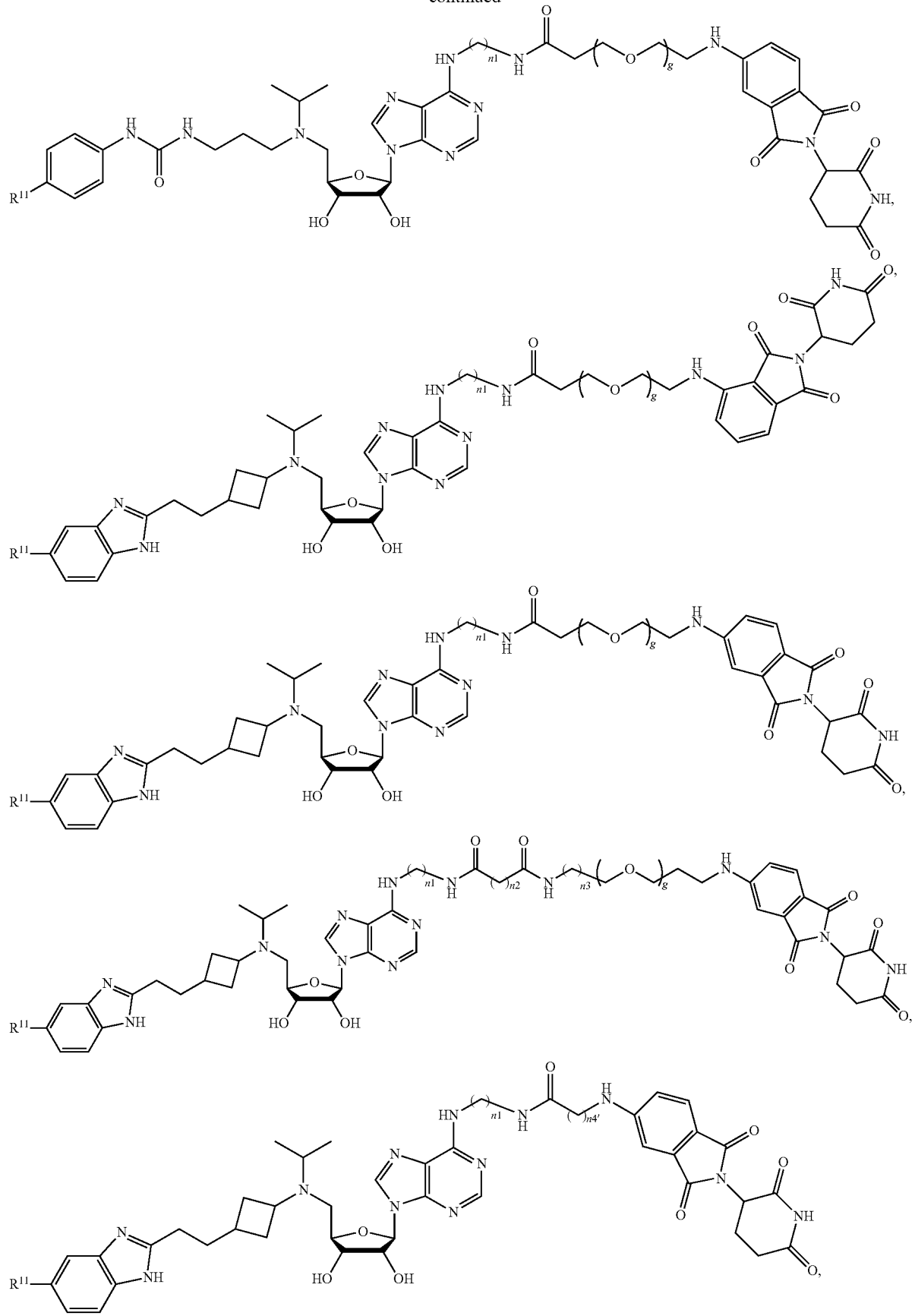

-continued
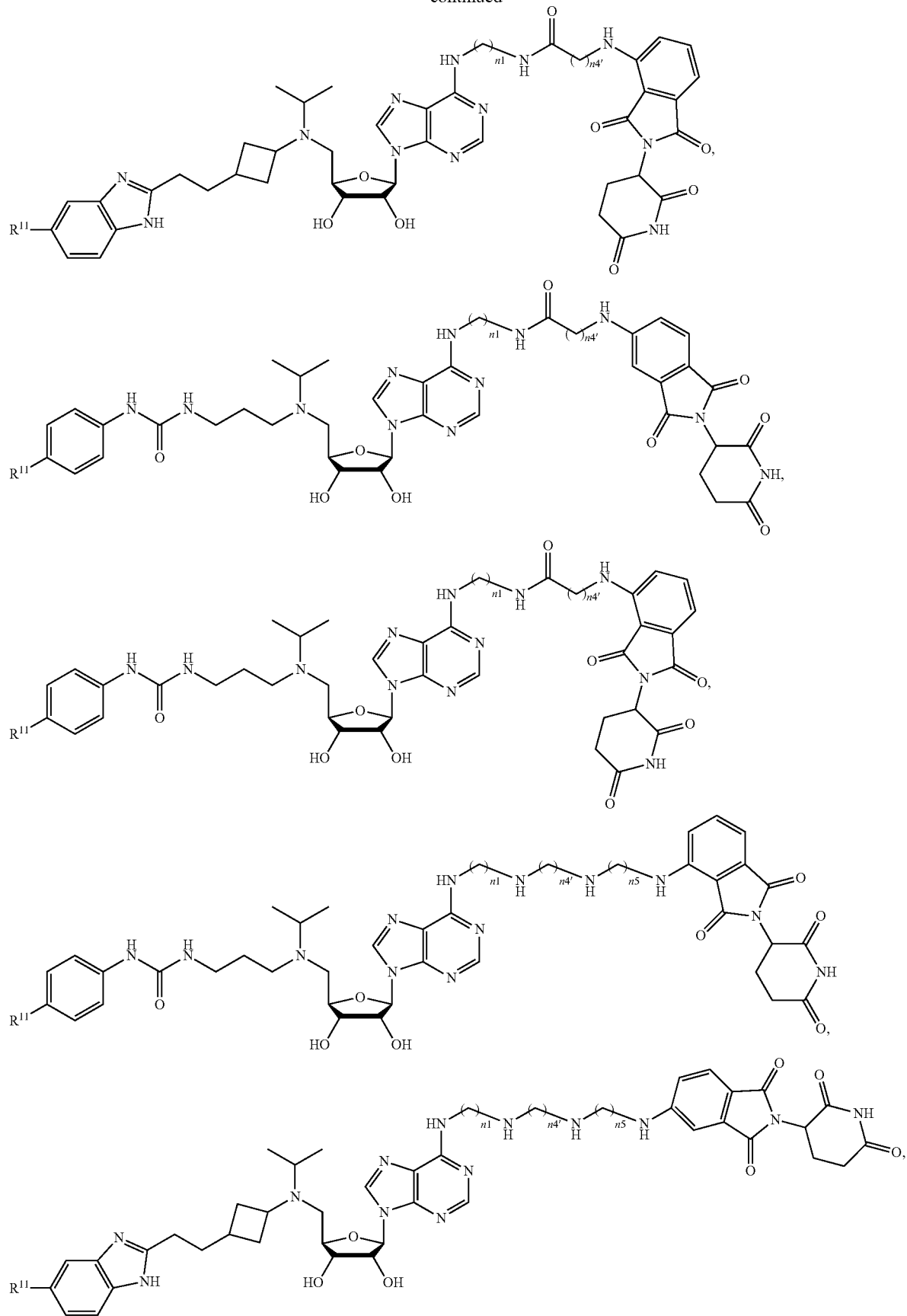

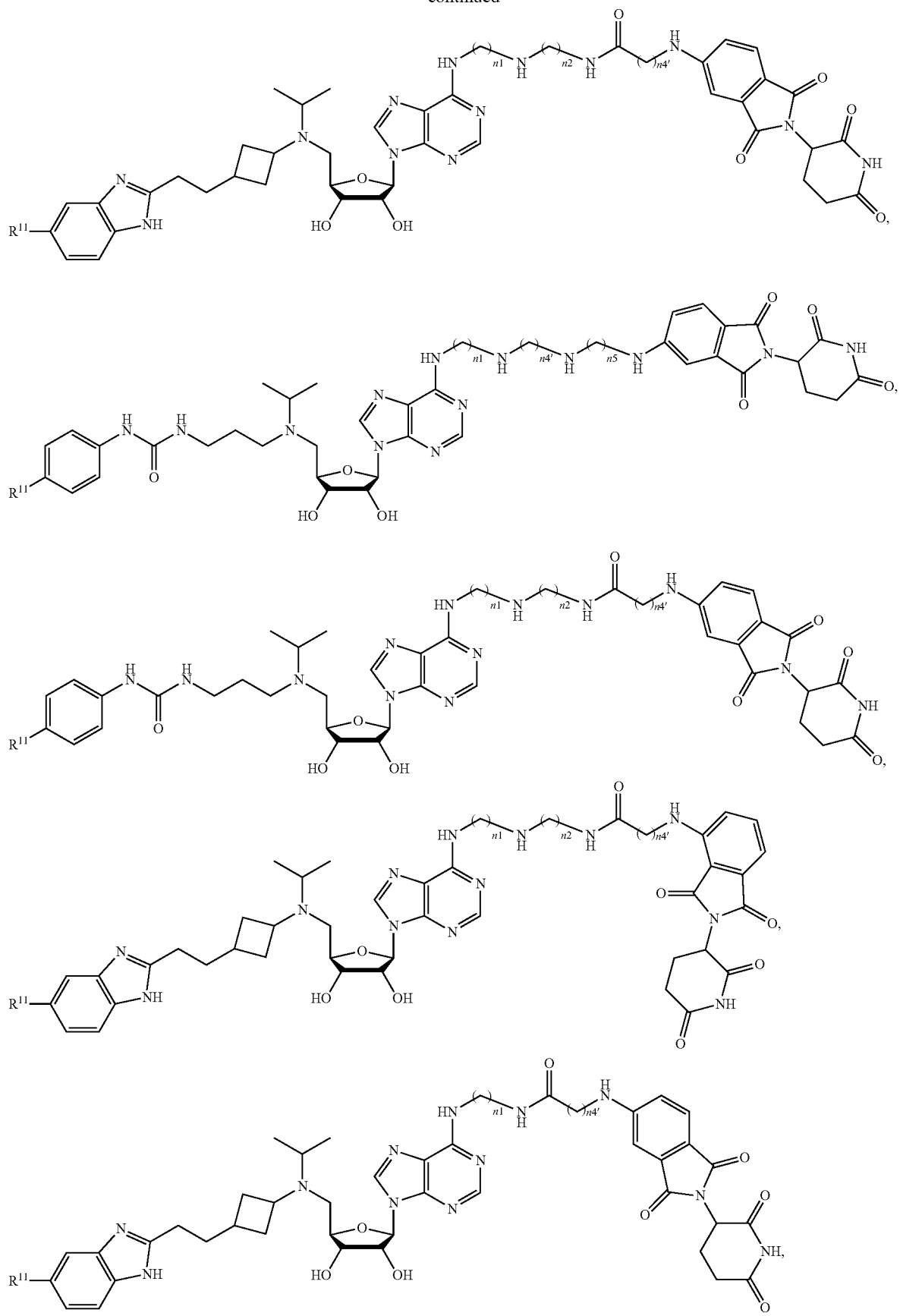

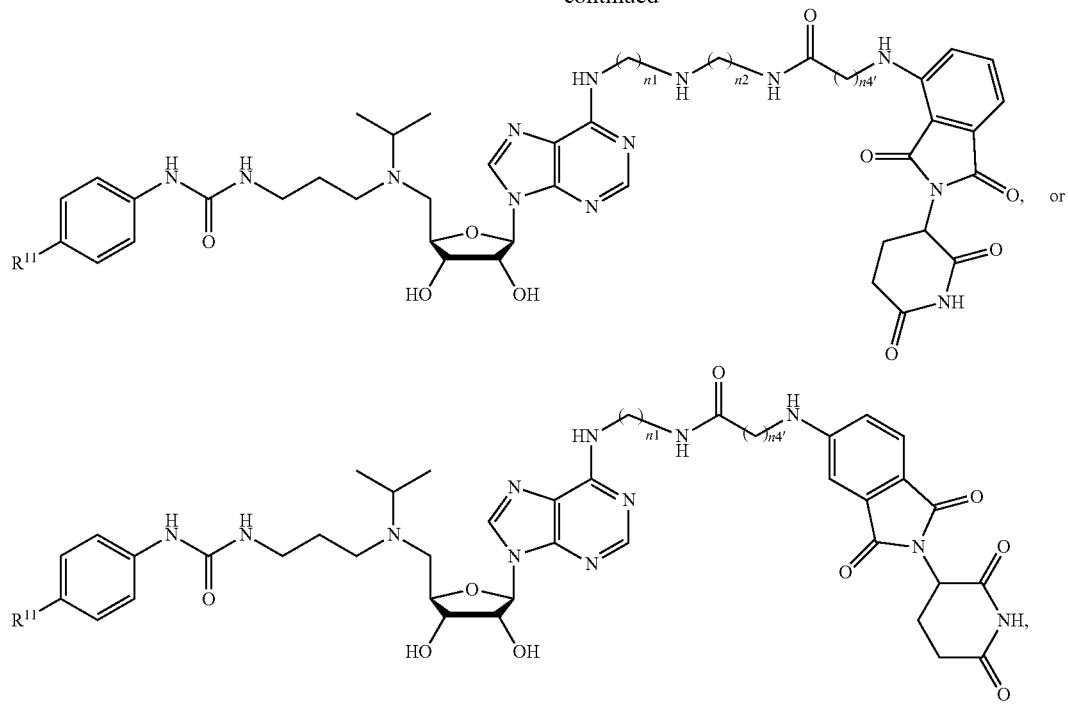
or a pharmaceutically acceptable salt, solvate, hydrate, tautomer, or stereoisomer thereof.
22. The compound of claim 1, wherein the compound is of the formula:
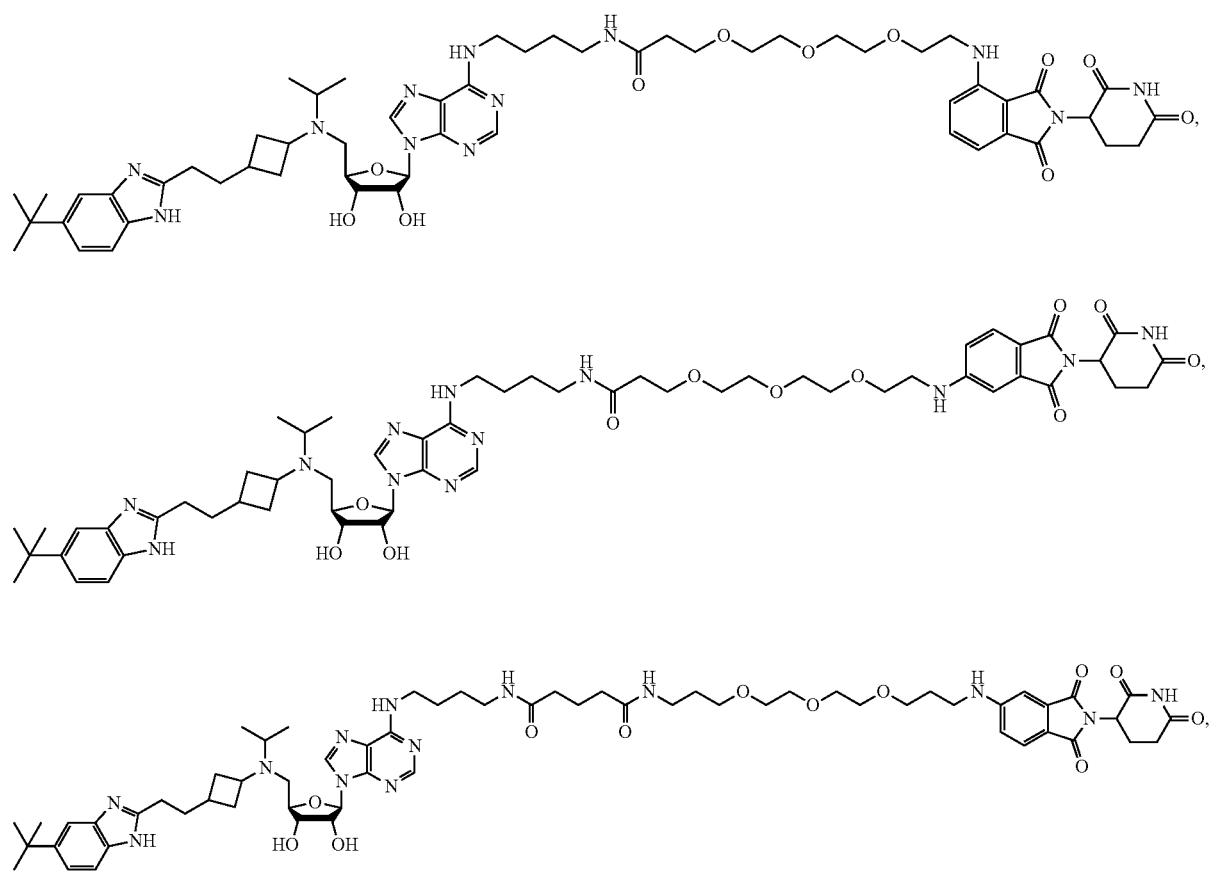

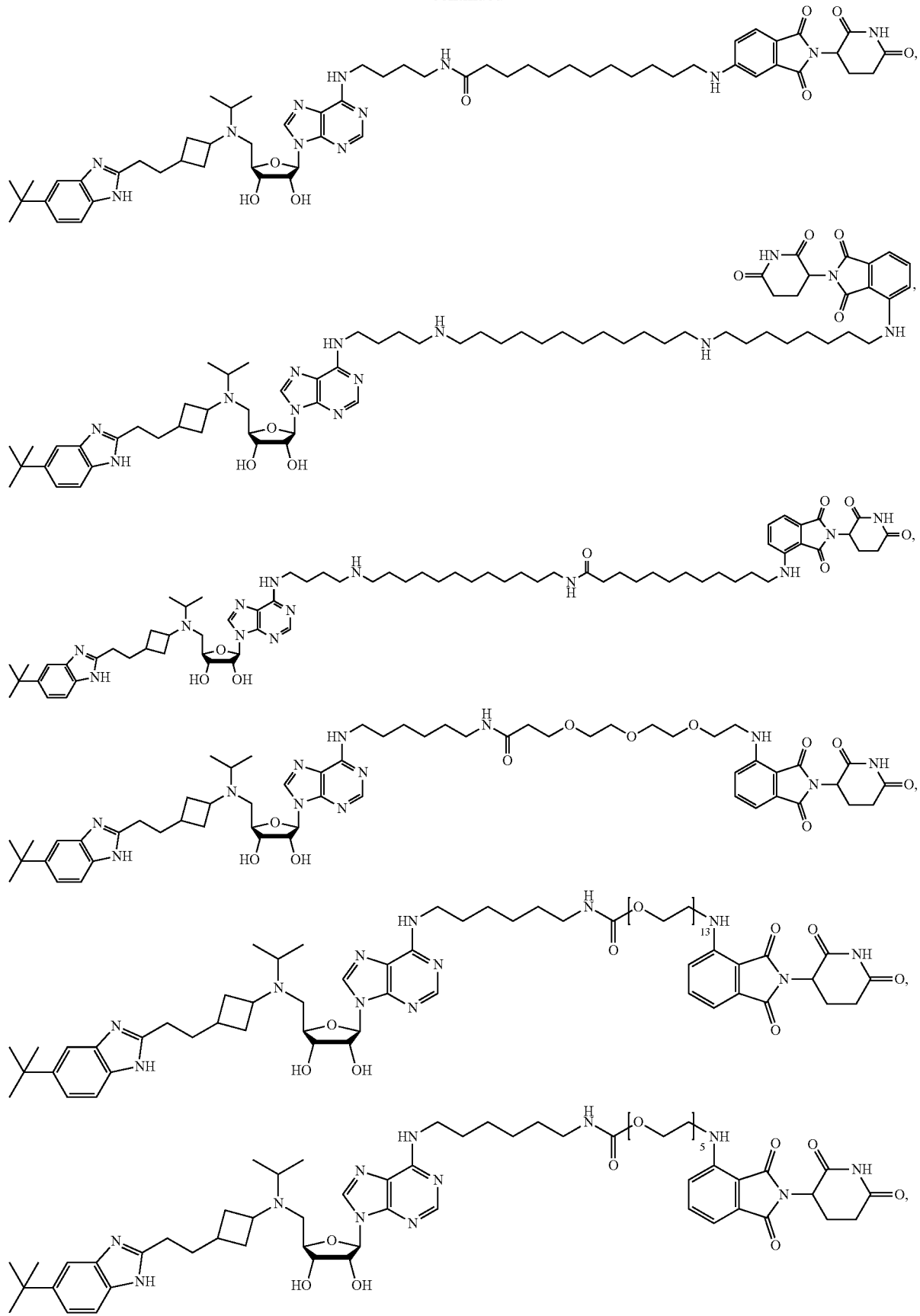

-continued
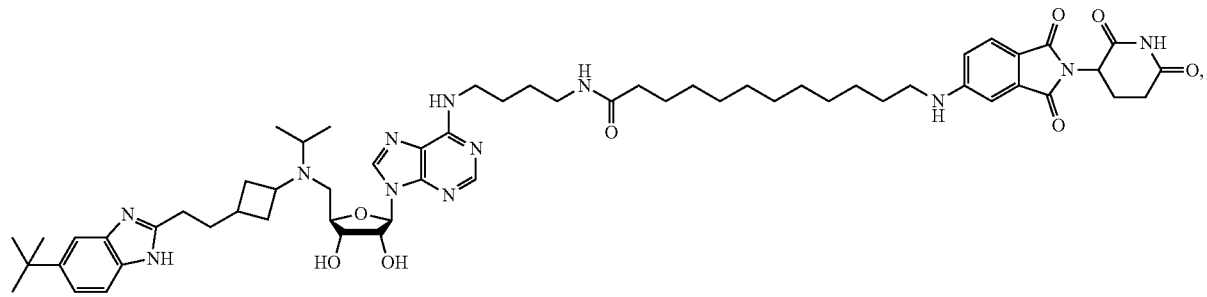
(JQDD1)
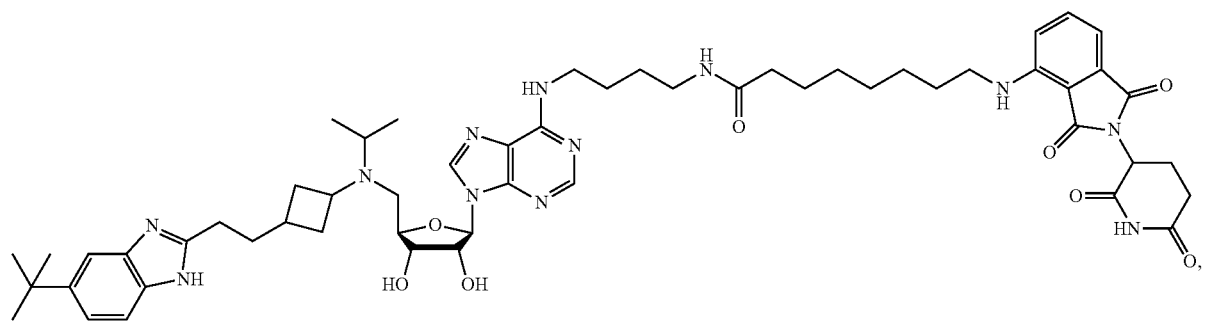
(JQDD2)
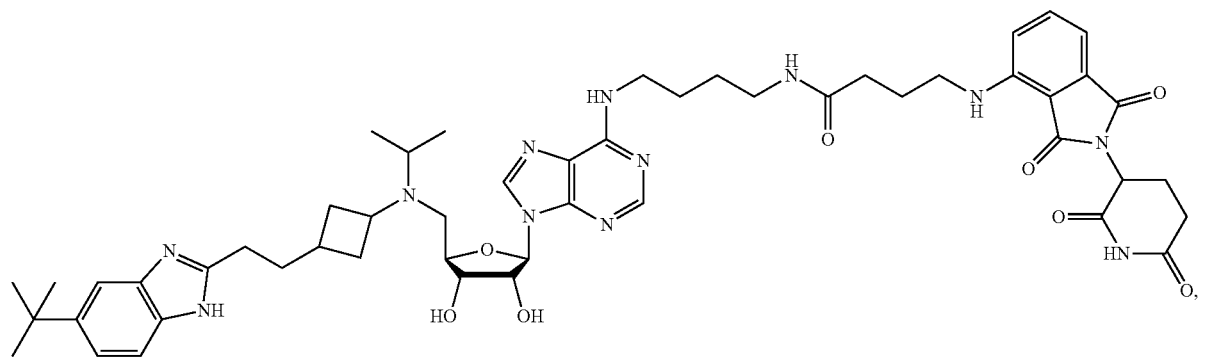
(JQDD3)
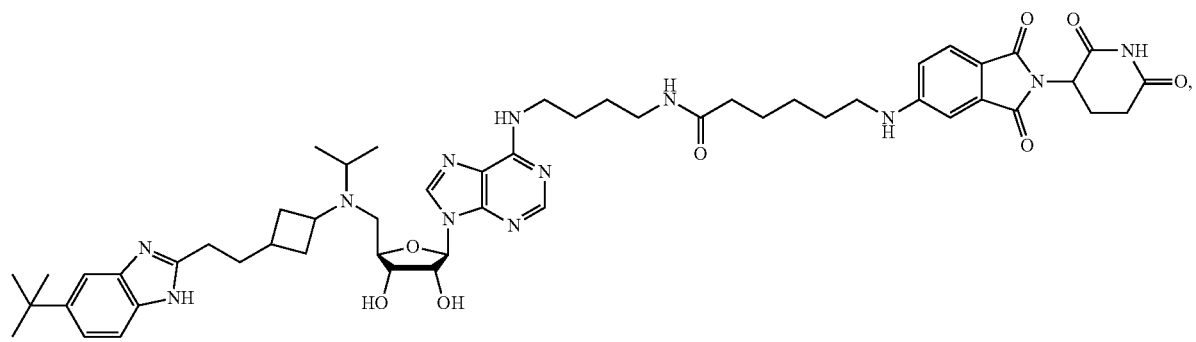
(JQDD4)

-continued
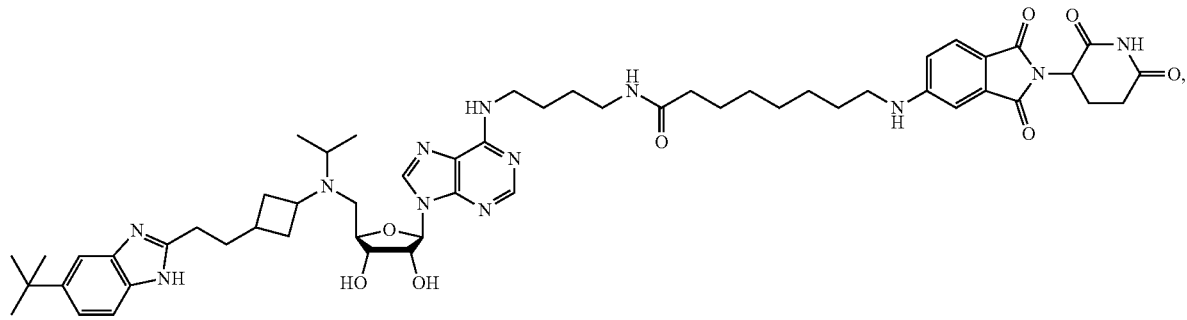
(JQDD5)
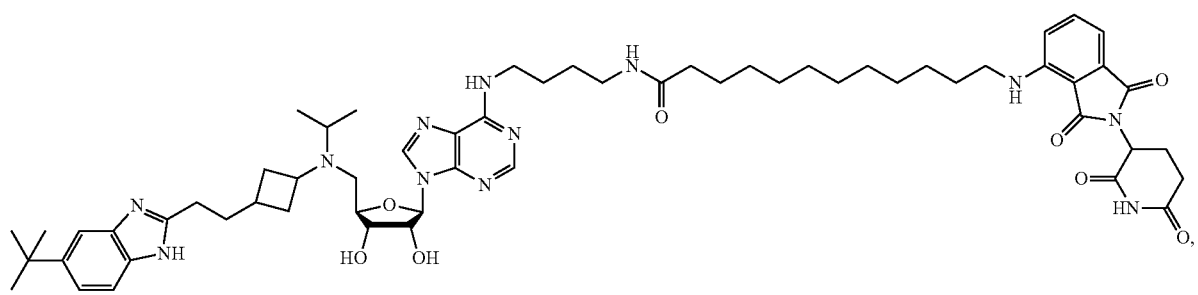
(JQDD6)
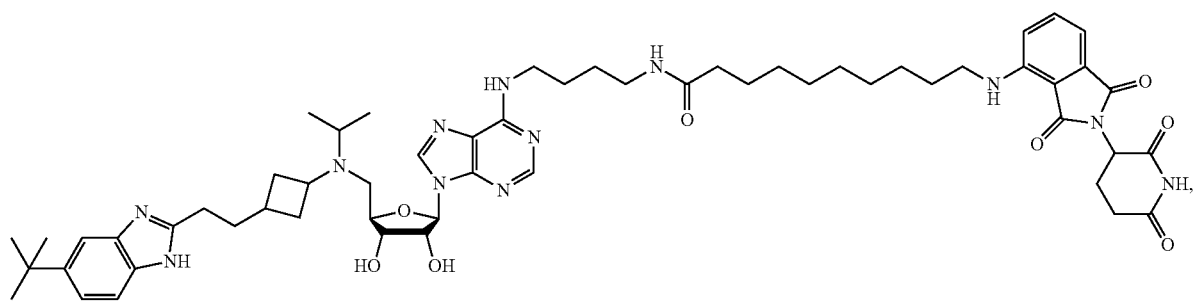
(JQDD7)
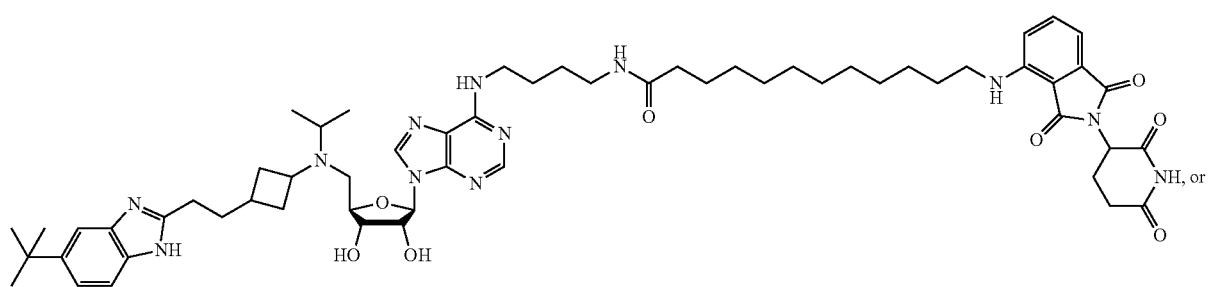
(JQDD8)
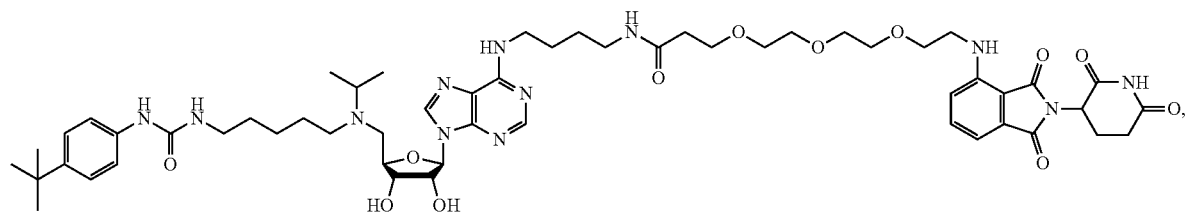
(LW-DOT1L-13)
or a pharmaceutically acceptable salt, solvate, hydrate, tautomer, or stereoisomer thereof.
23. The compound of claim 1, wherein the compound is of the formula:

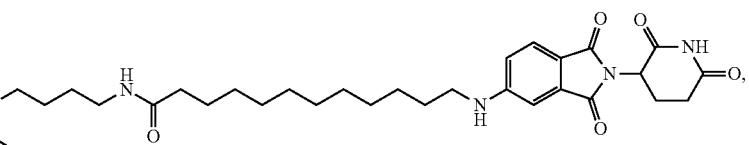
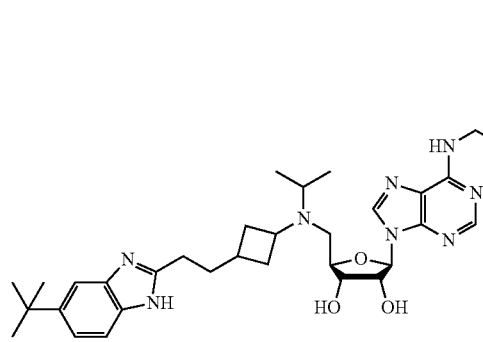
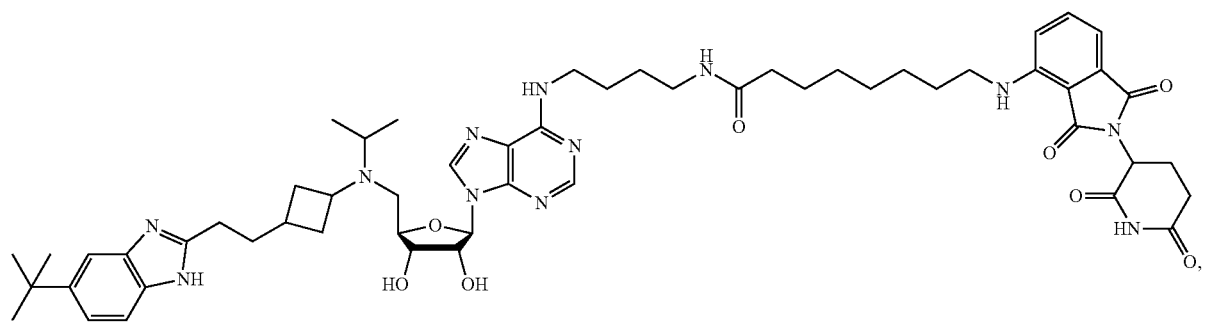
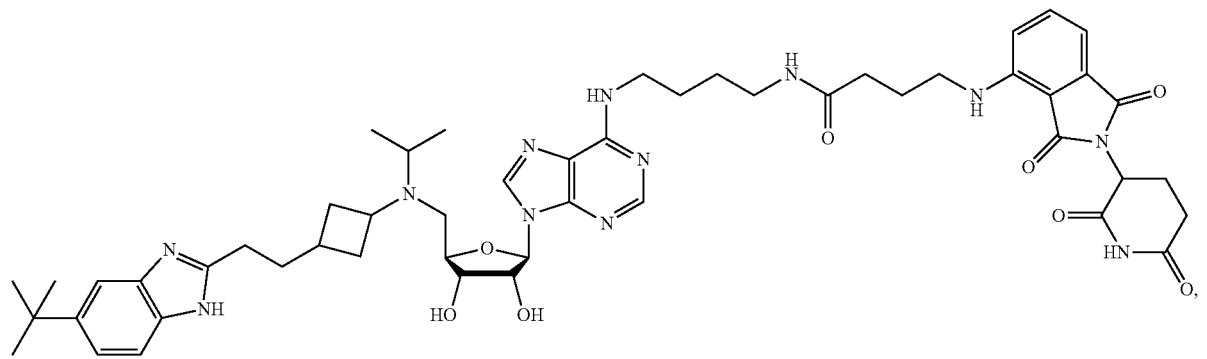
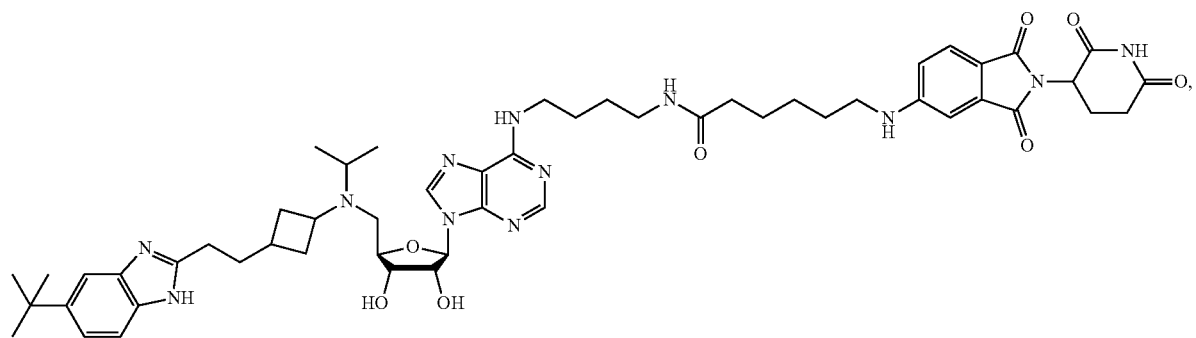

-continued

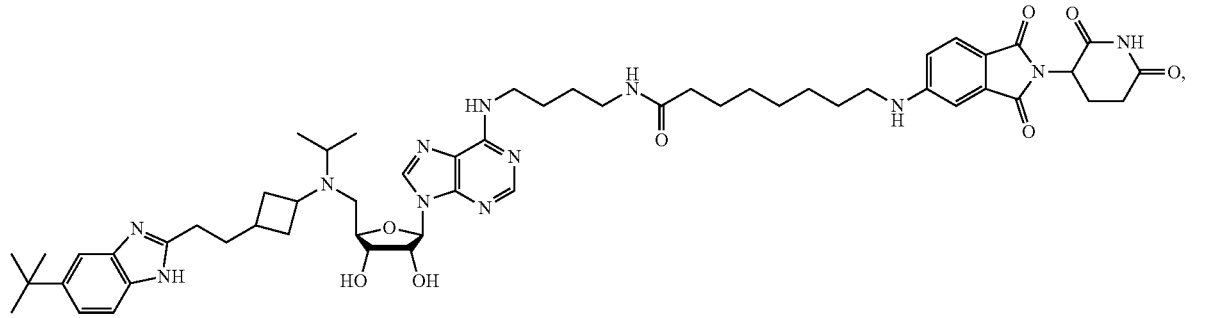
(JQDD5)

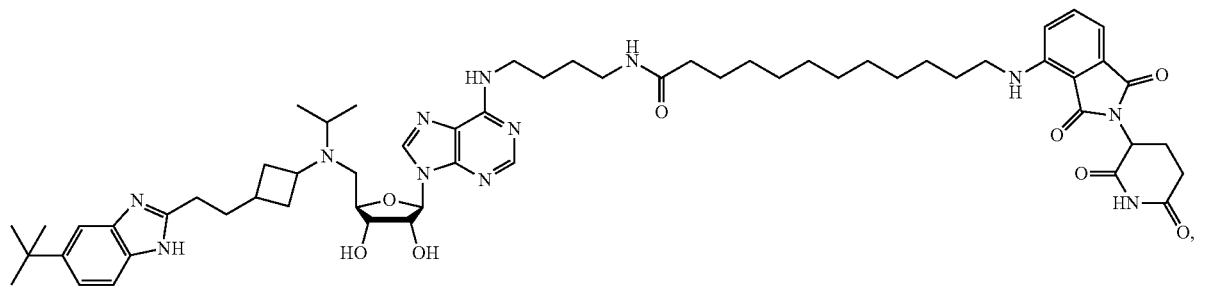
(JQDD6)

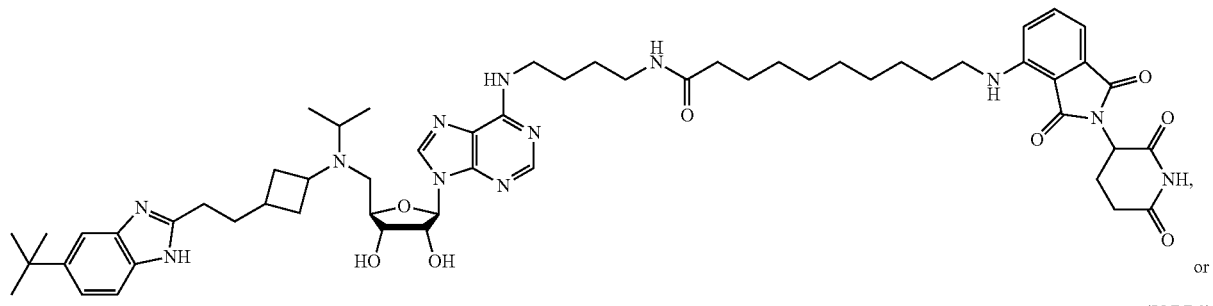
(JQDD7)

or

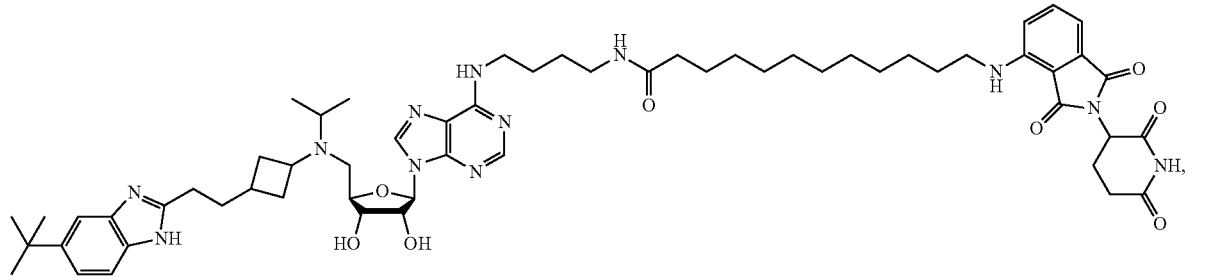
(JQDD8)

or a pharmaceutically acceptable salt, solvate, hydrate, tautomer, or stereoisomer thereof.

24. A pharmaceutical composition comprising a therapeutically effective amount of the compound or a pharmaceutically acceptable salt, solvate, hydrate, tautomer, or stereoisomer thereof of claim 9, and optionally a pharmaceutically acceptable excipient.

25. A method of treating a disease in which DOT1L plays a role, comprising administering to a subject in need thereof a therapeutically effective amount of the compound or a pharmaceutically acceptable salt, solvate, hydrate, tautomer, or stereoisomer thereof of claim 9, wherein the disease is a hematological cancer.

26. The method of claim 25, wherein the hematological cancer is selected from multiple myeloma, lymphoma, and leukemia.

27. The method of claim 26, wherein the leukemia is acute myelocytic leukemia, mixed-lineage leukemia (MLL) rearranged acute myelocytic leukemia, acute myelocytic leukemia with a mutation in the nucleophosmin (NPM1) gene, acute myelocytic leukemia with a mutation in the DNMT3A gene, or acute myeloid eosinophilic leukemia.

28. A method of inducing the degradation of DOT1L in a cell, tissue, or biological sample comprising contacting the cell, tissue, or biological sample with a therapeutically effective amount of the compound or a pharmaceutically acceptable salt, solvate, hydrate, tautomer, or stereoisomer thereof of claim 9.

\* \* \* \* \*